US010752676B2

(12) United States Patent
Humphreys et al.

(10) Patent No.: US 10,752,676 B2
(45) Date of Patent: Aug. 25, 2020

(54) **NEUTRALISING ANTIBODIES TO THE MAJOR EXOTOXINS TCDA AND TCDB OF *CLOSTRIDIUM DIFFICILE***

(75) Inventors: David Paul Humphreys, Slough (GB); Daniel John Lightwood, Slough (GB); Kerry Louise Tyson, Slough (GB); David Edward Ormonde Knight, Slough (GB); Karine Jeannine Madeleine Hervé, Slough (GB); Joanne Elizabeth Compson, Slough (GB); Matthew Jon Timothy Page, Slough (GB); Andrew Charles Payne, Slough (GB); Nicola Louise Fisher, Slough (GB); Brendon Mackenzie, Slough (GB); Matthew Cox, Slough (GB)

(73) Assignee: UCB Biopharma SPRL, Brussels (BE)

( * ) Notice: Subject to any disclaimer, the term of this patent is extended or adjusted under 35 U.S.C. 154(b) by 709 days.

(21) Appl. No.: 14/344,637

(22) PCT Filed: Sep. 10, 2012

(86) PCT No.: PCT/GB2012/052222
§ 371 (c)(1),
(2), (4) Date: Jan. 20, 2015

(87) PCT Pub. No.: WO2013/038156
PCT Pub. Date: Mar. 21, 2013

(65) Prior Publication Data
US 2014/0348844 A1 Nov. 27, 2014

Related U.S. Application Data

(60) Provisional application No. 61/535,532, filed on Sep. 16, 2011, provisional application No. 61/638,731, filed on Apr. 26, 2012.

(51) Int. Cl.
*C07K 16/12* (2006.01)
*A61K 39/40* (2006.01)
*A61K 45/06* (2006.01)
*A61K 39/00* (2006.01)
*G01N 33/569* (2006.01)
*G01N 33/573* (2006.01)
*G01N 33/68* (2006.01)

(52) U.S. Cl.
CPC ........ *C07K 16/1282* (2013.01); *A61K 39/40* (2013.01); *A61K 45/06* (2013.01); *G01N 33/56911* (2013.01); *G01N 33/573* (2013.01); *G01N 33/6854* (2013.01); *A61K 2039/505* (2013.01); *A61K 2039/507* (2013.01); *A61K 2039/545* (2013.01); *C07K 2317/76* (2013.01); *C07K 2317/92* (2013.01); *C07K 2317/94* (2013.01); *G01N 2333/91097* (2013.01)

(58) Field of Classification Search
None
See application file for complete search history.

(56) References Cited

U.S. PATENT DOCUMENTS

| 4,741,900 | A |  | 5/1988 | Alvarez et al. |
|---|---|---|---|---|
| 5,057,540 | A |  | 10/1991 | Kensil et al. |
| 5,219,996 | A |  | 6/1993 | Bodmer et al. |
| 5,585,089 | A |  | 12/1996 | Queen et al. |
| 5,677,425 | A |  | 10/1997 | Bodmer et al. |
| 6,005,099 | A |  | 12/1999 | Davies et al. |
| 7,625,559 | B2 |  | 12/2009 | Abrosino et al. |
| 9,828,438 | B2 | * | 11/2017 | Humphreys ............ C07K 16/00 |
| 9,873,735 | B2 | * | 1/2018 | Adams ............... C07K 16/2866 |
| 9,969,793 | B2 | * | 5/2018 | Grossman ............ A61K 39/155 |
| 10,100,130 | B2 | * | 10/2018 | Humphreys ............ C07K 16/00 |
| 2008/0107673 | A1 | * | 5/2008 | Ballard ............ G01N 33/56911 424/190.1 |
| 2013/0230537 | A1 | * | 9/2013 | Hussack ............ C07K 16/1282 424/167.1 |
| 2014/0348844 | A1 | * | 11/2014 | Humphreys ....... C07K 16/1282 424/139.1 |
| 2015/0175681 | A1 | * | 6/2015 | Ma ..................... C07K 16/1282 424/150.1 |
| 2015/0259402 | A1 | * | 9/2015 | Takada ............... C07K 16/1282 424/167.1 |
| 2016/0137724 | A1 | * | 5/2016 | Seeberger .......... C07K 16/1282 424/137.1 |
| 2016/0311930 | A1 | * | 10/2016 | Humphreys ........... C07K 16/00 |
| 2017/0198062 | A1 | * | 7/2017 | Bhatta ................. C07K 16/468 |

(Continued)

FOREIGN PATENT DOCUMENTS

| EP | 0362279 B1 | 4/1990 |
|---|---|---|
| EP | 0392745 A2 | 10/1990 |
| EP | 0468520 | 1/1992 |

(Continued)

OTHER PUBLICATIONS

Greenbaum et al, Journal of Molecular Recognition, 20(2):75-82, 2007.*

(Continued)

*Primary Examiner* — Nita M. Minnifield
(74) *Attorney, Agent, or Firm* — Saul Ewing Arnstein & Lehr LLP; Doreen Y. Trujillo

(57) ABSTRACT

This present invention describes the derivation and selection of antibodies capable of neutralising the major exotoxins; TcdA and TcdB of *Clostridium difficile*. The invention also describes novel neutralisation and antigen binding properties of individual Mabs and mixtures thereof.

43 Claims, 69 Drawing Sheets
Specification includes a Sequence Listing.

(56) References Cited

U.S. PATENT DOCUMENTS

2017/0204200 A1* 7/2017 Bhatta ............... C07K 16/468

FOREIGN PATENT DOCUMENTS

| EP | 0549074 B1 | 6/1993 |
|---|---|---|
| EP | 0689454 | 1/1996 |
| EP | 0729473 B1 | 9/1996 |
| EP | 0948544 B1 | 10/1999 |
| EP | 1090037 B1 | 11/2004 |
| GB | 2122204 B | 1/1984 |
| WO | WO1986/001533 A1 | 3/1986 |
| WO | WO1989/000195 A1 | 1/1989 |
| WO | WO1989/001476 A1 | 2/1989 |
| WO | WO1991/009967 A1 | 7/1991 |
| WO | WO1992/002551 A1 | 2/1992 |
| WO | WO1992/022583 A2 | 12/1992 |
| WO | WO1993/006231 A1 | 4/1993 |
| WO | WO1994/000153 | 1/1994 |
| WO | WO1995/017210 | 6/1995 |
| WO | WO1996/002555 | 2/1996 |
| WO | WO1996/011711 | 4/1996 |
| WO | WO1996/033739 | 10/1996 |
| WO | WO1998/015287 | 4/1998 |
| WO | WO1998/016247 | 4/1998 |
| WO | WO1998/025971 | 6/1998 |
| WO | WO1998/056414 | 12/1998 |
| WO | WO1999/010008 | 3/1999 |
| WO | WO1999/011241 | 3/1999 |
| WO | WO2003/031581 A2 | 4/2003 |
| WO | WO2004/051268 A1 | 6/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO2005/113605 A1 | 12/2005 |
| WO | WO2005/117984 A2 | 12/2005 |
| WO | WO2006/071877 | 7/2006 |
| WO | WO2006/121422 A2 | 11/2006 |
| WO | WO2008/038024 | 4/2008 |
| WO | WO2009/040562 A1 | 4/2009 |
| WO | WO2010/035012 A9 | 4/2010 |
| WO | WO 2012/055030 A1 * | 5/2012 |
| WO | WO 2013/038156 A1 * | 3/2013 |

OTHER PUBLICATIONS

Greenspan et al, Nature Biotechnology 17:936-937, 1999.*
Harlow et al In Antibodies A Laboratory Manual, Cold Spring Harbor Press, 1988, Chapter 3, pp. 23-35.*
Bendig (Methods: A Companion to Methods in Enzymology 1995; 8:83-93).*
Mariuzza et al, Ann. Rev. Biophys. Biophys. Chem., 1987, 16:139-159.*
Kim et al, Microbial Ecology in Health and Disease, 1989, 2:47-59.*
Ferrara et al, mAbs, Jan./Feb. 2015, vol. 7, Issue 1,pp. 32-41. (Year: 2015).*
Adair, J.R., & Lawson, A.D.G., "Therapeutic Antibodies," Drug Design Reviews—Online, vol. 2, No. 3, pp. 209 217, 2005.
Altschul, S.F. et al., "Basic Local Alignment Search Tool," J. Mol. Biol., vol. 215, pp. 403-410, 1990.
Altschul, S.F., et al., "Gapped BLAST and PSI-BLAST: A new generation of protein database search programs," Nucleic Acids Res., vol. 25, pp. 3389-3402, 1997.
Angal, S., et al. "A single amino acid substitution abolishes the heterogeneity of chimeric mouse/human (IgG4) antibody," Molecular Immunology, vol. 30, No. 1, pp. 105-108, 1993.
Babcock, G. J. et al, "Human monoclonal antibodies directed against toxins A and B prevent Clostridium difficile-induced mortality in hamster," Infect. Imm., vol. 74, No. 11, pp. 6339-6347 (2006).

Babcook, J. S. et al., "A novel strategy for generating monoclonal antibodies from single, isolated lymphocytes producing antibodies of defined specificities," Proc. Natl. Acad. Sci. U.S.A., vol. 93, No. 15, pp. 7843-7848 (1996).
Barbut et al, "Epidemiology of Recurrences or Reinfections of Clostridium difficile-Associated Diarrhea," J. Clin. Microbiol., vol. 38, No. 6, 2386-2388 (2000).
Bauer, M.P. et al., "Clostridium difficile infection in Europe: a hospital-based survey," Lancet, vol. 377, pp. 63-73 (2011).
Brazolot-Millan, C. et al., "CpG DNA can induce strong Th1 humoral and cell-mediated immune responses against hepatitis B surface antigen in young mice," Proc. Natl. Acad, Sci., U.S.A., vol. 95, No. 26, pp. 15553-15558 (1998).
Chapman, A., "PEGylated antibodies and antibody fragments for improved therapy: a review," Advanced Drug Delivery Reviews, vol. 54, pp. 531-545, 2002.
Chaves-Olarte, E. et al., "Toxins A and B from Clostridium difficile Differ with Respect to Enzymatic Potencies, Cellular Substrate Specificities, and Surface Binding to Cultured Cells," J. Clin. Invest., 100(7):1734-1741 (1997).
Chaves-Olarte, E., "A Novel Cytotoxin from Clostridium difficile Serogroup F Is a Functional Hybrid between Two Other Large Clostridial Cytotoxins," J.B.C., vol. 274, pp. 11046-11052 (1999).
Chothia, C. et al., "Canonical Structures for the Hypervariable Regions of Immunoglobulins," A.M. J. Mol. Biol., vol. 196, pp, 901-917 (1987).
Cohen, S. et al., "Clinical Practice Guidelines for Clostridium difficile Infection in Adults: 2010 Update by the Society for Healthcare Epidemiology of America (SHEA) and the Infectious Diseases Society of America (IDFS)," Infect. Cont. and Hosp. Epidem., vol. 31, No. 5, pp. 431-455 (2010).
Cole, S.P.C., et al., "The EBV-hybridoma technique and its application to human lung cancer," Monoclonal Antibodies and Cancer Therapy, pp. 77-96, Alan R. Liss, Inc., 1985.
Corthier et al., "Protection against Experimental Pseudomembranous Colitis in Gnotobiotic Mice by Use of Monoclonal Antibodies against Clostridium difficile Toxin A," Infect. Imm., vol. 59, No. 3, pp. 1192-1195 (1991).
Crameri, A. et al., "DNA Shuffling of a Family of Genes from Diverse Species Accelerated Directed Evolution," Nature, vol. 391, pp. 288-291, 1998.
Davies, A.H. et al., "Super toxins from a super bug: structure and function of Clostridium difficile toxins," Biochem. J., vol. 436, pp. 517-526 (2011).
Davies, K.A. et al., "A Study of In Vivo Immune Complex Formation and Clearance in Man," Journal of Immunology, vol. 144, No. 12, pp. 4613.4620 (1990).
Davies, N.L. et al., "A Mixture of Functionally Oligoclonal Humanized Monoclonal Antibodies That Neutralize Clostridium difficile TcdA and TcdB with High Levels of In Vitro Potency Shows In Vivo Protection in a Hampster Infection Model," Clin. Vaccine Immunol., 10(3):377-390 (2013).
Davis, H. et al., "CpG DNA Is a Potent Enhancer of Specific Immunity in Mice Immunized with Recombinant Hepatitis B Surface Antigen," J. Immunol., vol. 160, No. 2, pp. 870-876 (1998).
Demarest, S. et al., "Neutralization of Clostridium difficile toxin A using antibody combinations," mAbs, vol. 2, No. 2, pp. 190-198 (2010).
Du, T. and Alfa, M.J., "Translocation of Clostridium difficile toxin B across polarized Caco-2 cell monolayers is enhanced by toxin A," Can. J. Infect. Dis., vol. 15, No. 2, pp. 83-88 (2004).
Dubberke, E.R. et al., "Review of Current Literature on the Economic Burden of Clostridium difficile Infection," Infection Control and Hospital Epidemiology 30(1):57-66 (2009).
Dubowchik, G.M. et al., "Receptor-Mediated and Enzyme-Dependent Targeting of Cytotoxic Anticancer Drugs," Pharmacology and Therapeutics, vol. 83, pp. 67-123, 1999.
Eidhin, D.B., "Active immunization of hamsters against Clostridium difficile infection using surface-layer protein," Immunol. Med. Microbiol., vol. 52, pp. 207-218 (2008).
Flegel, W.A. et al., "Cytokine Response by Human Monocytes to Clostridium difficile Toxin A and Toxin B," Infection and Immunity 59(10): 3659-3666 (1991).

(56) References Cited

OTHER PUBLICATIONS

Forster, A.J. et al., "The effect of hospital-acquired infection with Clostridium difficile on length of stay in hospital," CMAJ 184(1): 37-42 (2012).
Garber, E. et al., "A broad range of Fab stabilities within a host of therapeutic IgGs," Biochemical and Biophysical Research Communications, vol. 355, pp. 751-757 (2007).
Giannasca, P.J. et al., "Serum Antitoxin Antibodies Mediate Systemic and Mucosal Protection from Clostridium difficile Disease in Hamsters," Infection and Immunity 67(2): 527-538 (1999).
Gish, W., et al., "Identification of protein coding regions by database similarity search," Nature Genet., vol. 3, pp. 266-272, 1993.
Goulding, D. et al., "Distinctive Profiles if Infection and Pathology in Hamsters Infected with Clostridium difficile Strains 630 and B1," Infection and Immunity 77(12): 5478-5485 (2009).
Harris, R.J., "Processing of C-terminal lysine and arginine residues of proteins isolated from mammalian cell culture," Journal of Chromatography, vol. 705, No. 1, pp. 129-134, 1995.
Hecht, G. et al., "Clostridium difficile Toxin B Disrupts the Barrier Function of $T_{84}$ Monolayers," Gastroenterology, 102: 416-423 (1992).
Hilgers, L. et al., "Synthetic sulpholipopolysaccharides: novel adjuvants for humoral immune reponses," Immunol., Vol, 60, No. 1, pp. 141-146 (1987).
Hilgers et al,, "Synergistic Effects of Synthetic Adjuvants on the Humoral Immune Response," Int. Arch. Allergy Immunol., vol. 79, No. 4, pp. 392-396 (1986).
Holliger, P., and Hudson, P.J., "Engineered antibody fragments and the rise of single domains," Nature Biotechnology, vol. 23, No. 9, pp. 1126-1136, 2005.
Hussack, G. et al., "Toxin-Specific Antibodies for the Treatment of Clostridium difficile: Current Status and Future Perspectives," Toxins, vol. 2, No. 5, pp. 998-1018 (2010).
Hussack, G. et al., "Neutralization of Clostridium difficile Toxin A with Single-domain Antibodies Targeting the Cell Receptor Binding Domain," Journal of Biological Chemistry, vol. 286, No. 11, pp. 8961-8976 (2011).
Jacob, S.S. et al., "Clostridium difficile and acute respiratory distress syndrome," Heart & Lung, vol. 33, No. 4, pp. 265-268 (2004).
Kabat, E. et al., "Sequences of Proteins of Immunological Interest," U.S. Dept. of Health and Health Services, NIH, USA (1983).
Kashmiri, S.V.S. et al., "SDR grafting—a new approach to antibody humanization," Methods, vol. 36, pp. 25-34, 2005.
Kelly, C.P. et al., "Anti-Clostridium difficile Bovine Immunoglobulin Concentrate Inhibits Cytotoxicity and Enterotoxicity of C. difficile Toxins," Antimicrobial Agents and Chemotherapy, vol. 40, No, 2, pp. 373-379 (1996).
Kensil, C. et al., "Separation and Characterization of Saponins with Adjuvant Activity from Quillaja saponaira Molina Cortex," J. Immunology, vol. 146, No. 2, pp. 431-437 (1991).
Kim, P. et al., "Immunization of Adult Hamsters against Clostridium diffcile-Associated Ileocecitis and Transfer of Protection to Infant Hamsters," Infect. Imm., vol. 55, No. 12, pp. 2984-2992 (1987).
Kink, J.A. and Williams, J.A., "Antibodies to Recombinant Clostridium difficile Toxins A and B Are an Effective Treatment and Prevent Relapse of C. difficile-Associated Disease in a Hamster Model of Infection," Infect. Imm., vol. 66, No. 5, pp, 2018-2025 (1998).
Kohler, G. & Milstein, C., "Continuous cultures of fused cells secreting antibody of predefined specificity," Nature, vol. 256, pp. 495-497, 1975.
Kotloff, K.L. et al., "Safety and Immunogenicity of Increasing Doses of a Clostridium difficile Toxoid Vaccine Administered to Healthy Adults," Infection and Immunity 69(2): 988-995 (2001).
Kovaiou, R.D. et al., "Age-related changes in immunity: implications for vaccination in the elderly," Expert Reviews in Molecular Medicine, vol. 9, No. 3, pp. 1-17, Cambridge University Press (2007).
Kozbor, D., et al., "The production of monoclonal antibodies from human lymphocytes," Immunology Today, vol. 4, No. 3, pp. 72-79, 1983.

Krieg, A. et al., "CpG motifs in bacterial DNA trigger direct B-cell activation," Nature, vol. 374, pp. 546-549 (1995).
Kuehne, S. et al., "The role of toxin A and toxin B in Clostridium difficile Infection," Nature, vol. 467, pp. 711-713 (2010).
Lacaille-Dubois, M. and Wagner, H., "A review of the biological and pharmacological activities of saponins," Phytomedicine, vol. 2, pp. 363-386 (1996).
Leav, B.A, et al., "Serum anti-toxin B antibody correlates with protection from recurrent Clostridium difficile infection (CDI)," Vaccine 28: 965-969 (2010).
Lee, B.Y. et al., "The potential value of Clostridium difficile vaccine: An economic computer simulation model," Vaccine, vol. 28, pp. 5245-5253 (2010).
Lima, A.A.M. et al., "Effects of Clostridium difficile Toxins A and B in Rabbit Small and Large Intestin In Vivo and on Cultured Cells In Vitro," Infection and Immunity, vol. 56, No. 3, pp. 582-588 (1988).
Linevsky, J.K. et al., "IL-8 release and neutrophil activation by Clostridium difficile toxin-exposed human monocytes," Am. J. Physiol.—Gastro. Liver Physiol. 273: 1333-1340 (1997).
Low, N.M., et al., "Mimicking somatic hypermutation: affinity maturation of antibodies displayed on bacteriophage using a bacterial mutator strain," J. Mol. Biol., vol. 260, pp. 359-368, 1996.
Lowy, I. et al., "Treatment with Monoclonal Antibodies against Clostridium difficile Toxins," NEJM, vol. 362, No. 3, pp. 197-205 (2010).
Lyerly, D.M. et al., "Characterization of Toxins A and B of Clostridium difficile with Monoclonal Antibodies," Infect. Imm., vol. 54, No. 1, pp. 70-76 (1986).
Lyerly, D.M. et al., "Effects of Clostridium difficile Toxins Given Intragastrically to Animals," Infection and Immunity 47(2): 349-352 (1985).
Lyerly, D.M. et al., "Nonspecific Binding of Mouse Monoclonal Antibodies to Clostridium difficile Toxins A and B," Current Microbiology 19: 303-306 (1989).
Lyerly, D.M. et al., "Passive Immunization of Hamsters against Disease Caused by Clostridium difficile by Use of Bovine Immunoglobulin G Concentrate," Infection and Immunity, vol. 59, No. 6, pp. 2215-2218 (1991).
Lyerly, D.M. et al., "Vaccination against Lethal Clostridium difficile Enterocolitis with a Nontoxic Recombinant Peptide of Toxin A," Current Microbiology, vol. 21, pp. 29-32 (1990).
Ma, D. et al., "Novel Monoclonal Antibodies for Treatment of Clostridium difficile-Associated Disease," Abstract No. 2979 related to ASM Poster May 27, 2010, ASM American Society for Microbiology, 110th General meeting, San Diego, CA, May 23-27, 2010.
Madden, T.L., et al., "Applications of Network BLAST Server," Meth. Enzymol., vol. 266, pp. 131-141, 1996.
Mannik, M. et al, "Elimination of Soluble Complexes from Rabbit Circulation," J. Exp. Med., vol. 133, pp. 713-739 (1971).
Marks, et al., "By-passing Immunization Human: Building High Affinity Human Antibodies by Chain Shuffling," Bio/Technology, vol. 10, pp. 779-783, 1992.
Marozsan, A. et al., "Protection Against Clostridium difficile Infection with Broadly Neutralizing Antitoxin Monoclonal Antibodies," Journal of Infectious Diseases 206: 706-713 (2012).
McCluskie, M. and Davis, H., "Cutting Edge: CpG DNA Is a Potent Enhancer of Systemic and Mucosal Immune Responses Against Hepatitis B Surface Antigen with Trananasal Administration to Mice," J. Immunol., vol. 161, No. 9, pp. 4463-4466 (1998).
Merck Sharp & Dohme Corp., "A Study of MK-3415, MK-6072, and MK-3415A in Participants Receiving Antibiotic Therapy for Clostridium Difficile Infection (MK-3415A-001)(MODIFY I)," ClinicalTrials.gov Identifier NCT01241552, Oct. 1, 2014, webpage URL: http://clinicaltrials.gov/ct2/show/NCT01241552, last accessed Dec. 15, 2015.
Merck Sharp & Dohme Corp., "A Study of MK-6072 and MK-3415A in Participants Receiving Antibiotic Therapy for Clostridium Difficile Infection (MK-3415A-002) (MODIFY II)," ClinicalTrials.gov Identifier NCT01513239, Nov. 19, 2014, webpage URL: http://clinicaltrials.gov/ct2/show/NCT01241552, last accessed Dec. 15, 2015.

(56) References Cited

OTHER PUBLICATIONS

Mitchell, T.J. et al., "Effect of toxin A and B of Clostridium difficile on rabbit ileum and colon," Gut 27: 78-95 (1986).

Miura, M. et al., "Identification of a Novel Virulence Factor in Clostridium difficile That Modulates Toxin Sensitivity of Cultured Epithelial Cells," Infection and Immunity 79(9): 3810-3820 (2011).

Nusrat, A. et al., "Clostridium difficile Toxins Disrupt Epithelial Barrier Function by Altering Membrane Microdomain Localization of Tight Junction Proteins," Infection and Immunity, vol. 69, No. 3, pp. 1329-1336 (2001).

Oake, N. et al., "The Effect of Hospital-Acquired Clostridium difficile Infection on In-Hospital Mortality," Arch Intern Med. 170(20): 1804-1810 (2010).

O'Brien, J.A. et al., "The Emerging Infectious Challenge of Clostridium difficile-Associated Disease in Massachusetts Hospitals: Clinical and Economic Consequences," Infection Control and Hospital Epidemiology 28(11): 1219-1227 (2007).

Patten, P., et al., "Applications of DNA shuffling to pharmaceuticals and vaccines," Curr. Opin. Biotechnol., vol. 8, No. 6, pp. 724-733, 1997.

Ravichandran, E. et al., "An Initial Assessment of the Systemic Pharmacokinetics of Botulinum Toxin," J. of Pharmacology and Experimental Therapeutics, vol. 318, No. 3, pp. 1343-1351 (2006).

Riechmann, L. et al., "Reshaping human antibodies for therapy," Nature, vol. 332, pp. 323-324, 1998.

Riegler, M. et al., "Clostridium difficile Toxin B is More Potent than Toxin A in Damaging Human Colonic Epithelium In Vitro," J. Clin. Invest. 95: 2004-2011 (1995).

Roberts, A. et al., "Development and Evaluation of an Ovine Antibody-Based Platform for Treatment of Clostridium difficile Infection," Infection and Immunity 180(2): 875-882 (2012).

Rothman, S. et al., "Differential Cytotoxic Effects of Toxins A and B Isolated from Clostridium difficile," Infect. Imm., vol. 46, No. 2, pp. 324-331 (1984).

Rupnik, M. et al., "New Types of Toxin A-Negative, Toxin B-Positive Strains among Clostridium difficile Isolates from Asia," J.C.M., vol. 41, No. 3, pp. 1118-1125 (2003).

Sanna, P.S. et al., "Synergistic Interactions of Antibodies in Rate of Virus Neutralization," Virology 270:386-396 (2000).

Savidge, T.C. et al., "Clostridium difficile Toxin B Is an Inflammatory Enterotoxin in Human Intestine," Gastroenterology 125(2): 413-420 (2003).

Seal, D. et al., "Treatment of Relapsing Clostridium difficile Diarrhoa by Administration of a Non-Toxigenic Strain," Eur. J.Clin. Microbiol., 6:51-53 (1987).

Shim, J.K. et al., "Primary symptomless colonization by Clostridium difficile and decreased risk of subsequent diarrhea," Lancet 351: 633-636 (1998).

Sougioultzis, S. et al., "Clostridium difficile Toxoid Vaccine in Recurrent C. difficile-Associated Diarrhea," Gastroenterology 128: 764-770 (2005).

Steele, J. et al., "Piglet Models for Acute or Chronic Clostridium difficile Illness (CDI)," J. Infect. Dis. 201(3): 428-434 (2010).

Sun, X. et al., "Mouse Relapse Model of Clostridium difficile Infection," Infection and Immunity 79(7): 2856-2864 (2011).

Takahashi, T. et al., "Localization of the Sites and Characterization of the Mechanisms by which Anti-Light Chain Antibodies Neutralize the Actions of the Botulinum Holotoxin," Vaccine, vol. 27, No. 19, pp. 2616-2619 (2009).

Taylor, N.S. et al., "Comparison of Two Toxins Produced by Clostridium difficile," Infection and Immunity 34(3): 1036-1043 (1981).

Taylor, C.P. et al., "Open-Label, Dose Escalation Phase I Study in Healthy Volunteers to Evaluate the Safety and Pharmacokinetics of a Human Monoclonal Antibody to Clostridium difficile Toxin A," Vaccine 26(27-28): 3404-3409 (2008).

Thompson, et al., "Affinity maturation of a high-affinity human monoclonal antibody against the third hypervariable loop of human immunodeficiency virus: use of phage display to improve affinity and broaden strain reactivity," J. Mol. Biol., vol. 256, No, 1, pp. 77-88, 1996.

Thorpe, P.E. et al., "The Preparation and Cytotoxic Properties of Antibody-Toxin Conjugates," Immunol. Rev., vol. 62, pp. 119-158, 1982.

Tickle et al., "High-Throughput Screening for High Affinity Antibodies," pp. 303-307 (2009).

Vaughan, et al., "Human antibodies by design," Nature Biotechnology, vol. 16, No. 6, pp. 535-539, 1998.

Verma, R., et al., "Antibody Engineering: Comparison of Bacterial, Yeast, Insect and Mammalian Expression Systems," Journal of Immunological Methods, vol. 216, Nos. 1-2, pp. 165-181, 1998.

Vernet, A. et al., "Relationship between Levels of Clostridium difficile Toxin a and Toxin B and Cecal Lesions in Gnotobiotic Mice," Infection and Immunity 57(7): 2123-2127 (1989).

Walker, W.A. et al., "Intestinal Update of Macromolecules: II, Effect of Parenteral Immunization," J. Immunol. 111(1): 221-226 (1973).

Wilcox, M. et al., "Recurrence of symptoms in Clostridium difficile infection—relapse or reinfection?" J. Hospital Infection, vol. 38, pp. 93-100 (1998).

Wu, A.L. et al., "Immunological Control Mechanism Against Cholera ToxinL Interference with Toxin Binding to Intestinal Receptors," Infection and Immunity 14(4): 1034-1042 (1976).

Wullt, M. et al., "A double-blind randomized controlled trial of fusidic acid and metronidazole for treatment of an initial episode of Clostridium difficile-associated diarrhoea," Journal of Antimicrobial Chemotherapy 54: 211-216 (2004).

Xu et al., "Vaccination with recombinant HBsAg-HBIG complex in healthy adults," Vaccine, vol. 23, pp. 2658-2664 (2005).

Yang, W.P, et al., "CDR walking mutagenesis for the affinity maturation of a potent human anti-HIV-1 antibody into the picomolar range", J. Mol. Biol., vol. 254, pp. 392-403, 1995.

Yoshida, M. et al., "Neonatal Fc receptor for IgG regulates mucosal immune responses to luminal bacteria," J. Clin. Invest., vol. 116, pp. 2142-2151 (2006).

Yousaf, N. et al., "Studies in cobra venom factor treated rats of antibody coated erythrocyte clearance by the spleen: differential influence of red blood cell antigen number on the inhibitory effects of immune complexes on Fc dependent clearance," Clin. Exp. Immunol., vol. 66, pp. 654-660 (1986).

Zhang, J., et al., "PowerBLAST: a new network BLAST application for interactive or automated sequence analysis and annotation," Genome Res., vol. 7, No. 6, pp. 649-656, 1997.

Zubler, R. H. et al., "Mutant EL-4 thymoma cells polyclonally activate murine and human B cells via direct cell interaction," J. Immunol., vol. 134, pp. 3662-3668 (1985).

International Search Report dated Feb. 12, 2013 based on International Application No. PCT/GB2012/052222.

Davies, Nicola L. et al., "A Mixture of Functionally Oligoclonal Humanized Monoclonal Antibodies That Neutralize Clostridium difficile TcdA and TcdB with High Levels of In Vitro Potency Shows In Vivo Protection in a Hamster Infection Model," Clinical and Vaccine Immunology, vol. 20, No. 3, Mar. 2013, pp. 377-390.

\* cited by examiner

Figure 1

SEQ ID NO: 8 polynucleotide sequence encoding anti-toxin A antibody 922.g1 VK (gL1)

GACCCTGTGA TGACCCAGAG TCCGAGCACT CTTTCTGCCT CCGTGGGAGA CCGCGTGACC
ATTACATGTC AGGCTTCACA AAGTATCTCC AATGCTCTGG CCTGGTATCA GCAGAAACCC
GGCAAAGCCC CTAAGCTGCT CATCTACTCT GCATCAAGCC TGGCTAGCGG CGTGCCAAGC
CGATTCAAGG GGAGCGGTTC TGGCACTGAG TTTACGCTGA CCATCAGTAG CTTGCAGCCT
GACGATTTTG CAACCTATTA CTGCCAGTAC ACACACTACT CCCATACATC TAAAAACCCA
TTCGGAGGGG GTACTAAGGT CGAAATAAAG

SEQ ID NO: 10 polynucleotide sequence encoding anti-toxin A antibody 922.g1 VH (gH1)

GAAGTGCAAT TGGTGGAAAG TGGCGGAGGA CTGGTGCAAC CCGGGGGTAG TCTGCGACTG
AGCTGTGCTG CCTCCGGCTT TACCATTAGC TCCTACTATA TGAGCTGGGT TCGACAGGCC
CCTGGAAAAG GACTCGAATG GATCGGCATC ATATCTTCCG GTGGGCATTT CACCTGGTAC
GCAAACTGGG CTAAGGGGAG ATTCACGATT AGCAGCGACT CCACAACCGT GTACCTGCAA
ATGAACAGCC TGAGGGATGA GGACACTGCC ACATATTTCT GCGCACGCGC TTACGTGAGC
GGAAGCTCAT TTAATGGCTA TGCACTGTGG GGGCAAGGAA CACTCGTGAC TGTCTCG

SEQ ID NO: 18 polynucleotide sequence encoding anti-toxin A antibody CA923.g1 gL1

GACGTCGTGATGACTCAGAGCCCATCTAGTCTGAGCGCTAGCGTCGGAGACCGAGTCACAATTACC
TGTCAAGCCTCCCAGAGCATCTCCAACTACCTGGCCTGGTACCAACAGAAACCTGGCAAGGTGCCC
AAGCTGCTGATCTATAGTGCTTCCACACTCGCAAGCGGCGTTCCGTCACGCTTTAAGGGATCTGGC
TCTGGCACTCAGTTCACCTTGACGATCTCAAGCCTGCAGCCAGAAGATGTGGCCACCTATTACTGC
CAGTATTCCCACTACGGGACTGGGGTGTTCGGTGCCTTTGGAGGTGGGACCAAAGTGGAGATAAAG

Figure 2

SEQ ID NO: 20 polynucleotide sequence encoding anti-toxin A antibody CA923.g1 gH1

GAAGTTCAACTTGTGGAATCTGGAGGCGGGCTCGTGCAGCCTGGTGGAAGCCTTAGACTGAGCTGC
GCTGCATCCGCATTTTCCCTGTCCAACTACTACATGAGCTGGGTGCGACAAGCACCAGGCAAGGGA
CTGGAATGGATTGGCATCATAAGCTCCGGTTCCAATGCCCTGAAATGGTACGCATCATGGCCGAAA
GGCCGCTTTACCATAAGCAAGGACTCCACCACCGTCTATCTGCAGATGAACTCATTGCGTGCCGAG
GACACTGCAACGTACTTCTGTGCTCGCAACTACGTGGGAAGCGGATCTTATTATGGCATGGATCTG
TGGGGACAAGGTACACTCGTGACCGTCTCG

SEQ ID NO: 28 polynucleotide sequence encoding anti-toxin A antibody CA993.g1 gL1

GATGTCGTGA TGACTCAGTC CCCCTCTACA TTGAGTGCCT CTGTCGGTGA TCGAGTTACC
ATCACCTGTC AAGCAAGCCA GAGCATCAGC TCCTACTTCT CTTGGTACCA GCAAAAGCCG
GGAAAAGCCC CTCAACTGCT GATTTATGGG GCCTCAACAC TGGCTTCTGG CGTGCCATCA
AGATTCAAGG GATCTGGCTC CGGCACTGAG CTTACACTGA CCATTAGCTC CCTGCAACCT
GACGATTTTG CTACCTACTA CTGCCAGTGC ACCGACTATA GTGGGATATA TTTCGGCGGA
TTTGGGGGAG GGACGAAAGT GGAAATCAAG

SEQ ID NO: 30 polynucleotide sequence encoding anti-toxin A antibody CA993.g1 gH1

GAAGTTCAGC TGGTCGAGAG CGGAGGCGGA CTGGTGCAAC CTGGTGGTAG CCTGAAACTC
TCTTGTACTG CCTCCGGGTT TTCCCTGAGC TCTTACTATA TGTCATGGGT GAGACAGGCT
CCCGGGAAAG GATTGGAATG GATCGGGATT ATCTCCTCCG GCTCTTCCAC CACTTTCACA
TGGTACGCCT CATGGGCAAA GGGGAGGTTT ACCATAAGCA AGACAAGCAC GACCGTGTAT
CTTCAGATGA ACTCCCTGAA GACGGAGGAT ACTGCCACCT ACTTTTGCGC TCGGGCCTAT
GTGGGCTCAA GCTCTTACTA TGGCTTCGAC CCATGGGGAC AGGGCACACT TGTGACCGTC
TCG

Figure 3

SEQ ID NO: 38 polynucleotide sequence encoding anti-toxin A antibody 995.g1 VL region
GACGTCGTGA TGACACAGAG CCCTTCAACA CTGTCTGCAA GCGTGGGCGA TAGGGTCACC
ATAACGTGCC AGGCCTCTCA ATCCATCAAC AACTATTTTA GCTGGTACCA GCAGAAGCCA
GGCAAGGCTC CGAAACTTCT GATCTACGGA GCTGCCAACC TGGCAAGTGG CGTGCCATCA
CGGTTCAAGG GATCCGGGAG CGGTACTGAG TATACCCTGA CCATTTCATC TCTCCAACCC
GACGATTTCG CCACCTACTC CTGCCAGAAT AATTACGGCG TGCACATCTA TGGAGCTGCC
TTTGGCGGTG GGACAAAAGT GGAAATTAAG

SEQ ID NO: 40 polynucleotide sequence encoding anti-toxin A antibody 995.g1 VH region
GAAGTTCAGC TGGTCGAGAG TGGGGGAGGG CTTGTGCAAC CTGGTGGCTC CCTCCGTCTG
AGCTGTACTG CTTCTGGATT CTCACTGAGC AATTACGACA TGATCTGGGT GCGACAGGCA
CCCGGCAAAG GACTGGAGTA CATTGGCTTC ATCAACACCG GGGTATAAC GTACTATGCC
TCATGGGCTA AGGGGCGCTT TACAATTAGT AGGGATTCCT CTACCGTGTA CCTGCAGATG
AACTCACTGA GAGCCGAGGA CACTGCCACA TATTTCTGCG CTCGGGTGGA TGACTATATC
GGGGCCTGGG GCGCCGGATT GTGGGCCAA GGAACACTGG TCACCGTCTC G

SEQ ID NO: 48 polynucleotide sequence encoding anti-toxin A antibody 997.g1 VL region
GCACTCGTGATGACACAGAGCCCGAGTAGCTTTAGTGCTTCAACCGGTGATAGGGTCACTATTACT
TGCCAAGCCTCTCAGAGTATATCTAGCTATCTGAGCTGGTACCAGCAAAAGCCCGGGAAGGCTCCT
AAACTGCTGATCTACCGGGCTTCCACATTGGCCTCCGGCGTTCCCTCACGCTTTAGCGGCTCCGGA
TCCGGAACCGAGTACACCCTGACTATCTCTTGCCTGCAATCTGAGGACTTCGCAACCTACTATTGT
CTGGGCGTCTACGGATATAGCAACGATGACGGGATCGCCTTCGGCGGCGGTACCAAAGTGGAAATT
AAG

Figure 4

SEQ ID NO: 50 polynucleotide sequence encoding anti-toxin A antibody 997.g1 VH region
GAGGTGCAACTTGTGGAAAGCGGGGGAGGACTGGTGCAGCCTGGGGGCTCATTGAGACTGAGCTGC
ACCGTTTCTGGTATTGACCTGAGCTCCCATCATATGTGCTGGGTGCGCCAGGCACCCGGAAAAGGA
CTGGAATACATCGGCGTCATATACCACTTTGGCTCTACATACTATGCCAACTGGGCAACTGGGCGA
TTCACAATTAGCAAGGACTCAACTACCGTTTACCTGCAAATGAATAGCCTGAGGGCTGAGGATACT
GCCACCTATTTCTGTGCCCGGGCTTCAATCGCCGGCTATTCTGCCTTTGATCCATGGGGGCAAGGA
ACACTCGTGACCGTCTCG

SEQ ID NO: 58 polynucleotide sequence encoding anti-toxin A antibody 1000.g1 VL region
GAAATCGTGA TGACGCAGTC ACCAAGCACA CTGAGCGCTT CTGTGGGAGA TCGGGTCACA
ATAACCTGTC AGGCCTCCCA GAGCATCTAC TCTTATCTGG CATGGTACCA GCAGAAGCCA
GGGAAAGCTC CCAAGCTGCT GATTTATGAC GCCAGCACTT TGGCTTCCGG TGTTCCTAGT
AGGTTCAAAG GCTCCGGAAG CGGTACCGAG TTTACCCTGA CCATCTCATC TCTGCAACCC
GATGACTTTG CCACATACTA TTGCCAGGGG AATGCCTACA CTTCCAACTC ACACGACAAC
GCATTCGGGG GAGGCACCAA AGTCGAAATT AAG

SEQ ID NO: 60 polynucleotide sequence encoding anti-toxin A antibody 1000.g1 VH region
GAAGTTCAGC TGGTCGAGAG CGGAGGGGGT TTGATTCAGC CCGGTGGCTC ACTTAGATTG
AGCTGCACCG TGTCCGGAAT CGATCTGTCA TCTGATGCCG TGGGCTGGGT GCGACAGGCA
CCTGGGAAAG GACTGGAGTA TATAGGGATC ATCGCCACCT TCGACTCCAC ATACTACGCT
AGCTGGGCAA AAGGGCGCTT TACGATTAGC AAGGCCTCCT CTACTACCGT GTACCTCCAA
ATGAACTCAC TGAGGGCCGA GGACACTGCC ACTTATTTCT GTGCTCGGAC CGGTAGCTGG
TACTACATCT CTGGCTGGGG CTCCTACTAT TATGGCATGG ACCTGTGGGG ACAGGGGACA
CTCGTGACCG TCTCG

Figure 5

SEQ ID NO: 68 polynucleotide sequence encoding anti-toxin B antibody 926.g1 VL region

GATACCGTGCTGACCCAGAGCCCTGCTACATTGTCACTGAGCCCCGGGGAGAGGGCCACATTGAGC
TGCCGGGCTTCAAAATCCGTGTCCACCCTCATGCACTGGTTTCAGCAAAAGCCCGGGCAGGCCCCA
AAACTGCTGATCTACCTCGCATCTAACCTTGAATCTGGCGTGCCGGCCCGCTTTAGTGGCTCCGGA
AGCGGAACCGACTTCACACTGACGATTAGCTCCCTGGAGCCTGAGGATTTCGCCGTGTACTATTGC
CAGCAAACTTGGAATGACCCTTGGACTTTCGGGGGCGGTACTAAGGTCGAAATAAAG

SEQ ID NO: 70 polynucleotide sequence encoding anti-toxin B antibody 926.g1 VH region

GAGGTGGAACTGCTCGAATCTGGTGGTGGGCTGGTGCAGCCCGGTGGATCTCTGAGATTGTCATGC
GAGGCATCCGGCTTTACCTTTTCCAACTACGGAATGGCCTGGGTGAGACAGGCCCCAACGAAGGGG
CTCGAATGGGTTACAAGCATCAGCTCTTCTGGGGGATCTACTTACTATCGCGATAGCGTCAAAGGC
CGGTTTACCATTAGCCGAGATAATGCCAAATCAAGCCTGTATCTGCAAATGAACAGCCTGAGGGCT
GAGGACACCGCCACATACTATTGTACAACCGTGATAAGGGGCTACGTGATGGACGCATGGGGACAG
GGGACATTGGTTACCGTCTCG

SEQ ID NO: 78 polynucleotide sequence encoding anti-toxin B antibody 927.g2 VL region

GACACACAGA TGACCCAGAG CCCATCCACT TTGTCTGCAT CCGTGGGCGA CCGAGTGACA
ATCACCTGTA GAGCAAGCGG TTCCGTGAGC ACACTGATGC ATTGGTACCA GCAGAAGCCT
GGGAAGGCTC CCAAGCTGCT GATCTACAAA GCCAGCAACC TTGCCTCCGG CGTTCCAAGC
CGGTTTAGCG GTTCCGGATC TGGAACCGAG TTCACCCTGA CCATATCAAG CCTGCAACCC
GACGACTTCG CCACCTACTA TTGCCACCAG AGCTGGAATA GCGACACGTT CGGGCAAGGC
ACAAGGCTGG AAATCAAA

SEQ ID NO: 80 polynucleotide sequence encoding anti-toxin B antibody 927.g2 VH region

GAGGTGCAAC TTGTGGAAAG CGGAGGGGGC GTGGTCCAAC CCGGAAGAAG TCTCCGTCTT
TCTTGCGCCG CAAGTGGCTT CACCTTTTCC AACTACGGAA TGGCCTGGGT TCGACAAGCT
CCTGGGAAAG GATTGGAGTG GGTGGCCACT ATCAACTATG ACGGACGCAC GACACACTAC
CGAGACTCTG TTAAGGGGCG CTTTACGATT TCCCGCGACA ATAGCAAGAG CACCCTCTAC
CTGCAAATGA ATAGCCTCCG GGCCGAGGAT ACTGCTGTGT ACTATTGTAC CTCCATCTCA
CGGAGCCACT ACTTCGATTG CTGGGGACAA GGCACACTCG TGACTGTCTCG

Figure 6

SEQ ID NO: 88 polynucleotide sequence encoding anti-toxin B antibody 1099.g2 VL region
GACGTCCAGC TCACTCAATC TCCCTCCTTT CTGTCTGCTT CTGTGGGCGA TCGCGTGACA
ATAACCTGCA AGGCCTCCAA ATCAATTAGC AACCATCTGG CATGGTATCA GGAGAAGCCT
GGCAAAGCCA ATAAGCTGCT GATCCACTCC GGCTCAACTC TGCAATCCGG TACCCCAAGC
CGATTTAGCG GATCTGGGAG CGGAACCGAG TTCACACTTA CCATTAGCTC CCTGCAACCG
GAGGACTTCG CCACCTATTA CTGCCAGCAA TACGACGAAT ACCCCTATAC GTTCGGCCAA
GGGACAAGAT TGGAAATCAA GCGTACG

SEQ ID NO: 90 polynucleotide sequence encoding anti-toxin B antibody 1099.g2 VH region
GAAGTTCAGC TGCAGGAATC TGGACCTGGC TTGGTGAAAC CAAGCGAGAC ACTTAGTCTC
ACTTGCACCG TTTCCGGCTT CTCCCTTCAA TCCTACACGA TCTCTTGGGT GCGGCAACCA
CCCGGGAAAG GACTGGAATG GATCGCAGCC ATTAGCGGGG GAGGGAGCAC CTATTACAAC
TTGCCTCTCA AGAGCCGCGT GACCATATCC CGTGACACAA GCAAGAGCCA GGTTTCCCTG
AAGCTGAGCT CCGTGACTGC TGCCGATACG GCTGTTTACT ATTGCACCCG ACCTCGCTGG
TATCCCCGTT CCTATTTCGA CTACTGGGGA AGAGGCACAC TGGTTACCGT CTCG

SEQ ID NO: 98 polynucleotide sequence encoding anti-toxin B antibody 1102.g4 VL region
AACATCGTGC TGACACAGTC TCCTGCAACC CTTTCACTGT CTCCAGGTGA ACGAGCAACC
CTGAGTTGTA GAGCCAGTCA GAGGATCTCC ACGAGCATTC ACTGGTATCA GCAAAAGCCT
GGGCAAGCTC CCAGACTCTT GATCAAGTAC GCCTCTCAGA GCATAAGTGG CATTCCAGCT
AGGTTTAGCG GCTCAGGCTC AGGAACAGAC TTCACTCTGA CCATCAGCTC CCTGGAACCG
GAGGACTTTG CCGTCTATTA CTGCCAGCAA TCCTACTCCA GTCTGTACAC CTTCGGGCAG
GGTACTAAAC TGGAGATAAA G

Figure 7

SEQ ID NO: 100 polynucleotide sequence encoding anti-toxin B antibody 1102.g4 VH region
GAAGTGCAGC TGGTCGAATC CGGGGGAGGT TTGGTGCAAC CAGGTGGCTC ACTGAGACTG
AGCTGTGCCG TTTCCGGCTT TACGTTCTCA GACAGTTATA TGGCCTGGGT GCGTCAAGCA
CCTGGAAAAG GGCTGGAGTG GATTGCCAGT ATCAGCTATG GTGGGACCAT AATCCAGTAC
GGCGATAGCG TCAAGGGCAG GTTTACTATC TCCAGGGACA ACGCCAAGTC AAGCCTTTAC
CTGCAGATGA ATTCTCTCCG CGCAGAGGAT ACCGCTGTGT ATTACTGCGC TAGACGGCAG
GGAACCTACG CTCGATACCT GGACTTCTGG GGTCAGGGAA CACTCGTTAC AGTCTCG

SEQ ID NO: 108 polynucleotide sequence encoding anti-toxin B antibody 1114.g2 VL region
GCGACGCAAA TGACTCAGTC GCCCTCATCG CTTAGCGCGT CCGTCGGAGA TAGAGTGACG
ATCACCTGCC GCGCATCAGA GTCGGTGTCC ACACTCCTCC ACTGGTATCA GCAGAAACCG
GGGAAGGCAC CAAAACTCTT GATCTACAAA GCCAGCAACC TTGCGTCCGG TGTCCCGTCA
AGGTTCTCCG GGAGCGGTTC GGGGACAGAC TTTACTTTGA CCATTTCGTC GCTTCAGCCG
GAGGACTTCG CCACCTATTA CTGTCATCAG TCATGGAACT CACCTCCCAC ATTTGGCCAG
GGAACGAAAC TCGAAATCAA G

SEQ ID NO: 110 polynucleotide sequence encoding anti-toxin B antibody 1114.g2 VH region
GAAGTACAAC TCGTAGAGTC AGGGGGTGGG CTGGTCCAAC CTGGCGGCTC CCTTCGGCTT
TCGTGTGCCG CCTCGGGATT CACGTTTAGC AATTACGGTA TGGCCTGGGT GAGGCAGGCA
CCAGGGAAGG GTCTTGAGTG GGTAGCGATC ATCAACTATG ATGCAAGCAC CACCCACTAC
AGGGATAGCG TCAAGGGACG CTTTACTATC AGCCGGGATA ATGCGAAATC CTCGCTCTAT
CTGCAGATGA ACTCCCTCAG AGCCGAGGAC ACCGCAGTGT ACTATTGCAC ACGATACGGA
CGCTCGCACT ATTTCGACTA TTGGGGACAG GGGACGCTCG TAACTGTCTC G

Figure 8

SEQ ID NO: 118 polynucleotide sequence encoding anti-toxin B antibody 1114.g8 VL region
```
GACACGGTCC TGACTCAGTC GCCCTCATCG CTTAGCGCGT CCGTCGGAGA TAGAGTGACG
ATCACCTGCC GCGCATCAGA GTCGGTGTCC ACACTCCTCC ACTGGTATCA GCAGAAACCG
GGGAAGGCAC CAAAACTCTT GATCTACAAA GCCAGCAACC TTGCGTCCGG TGTCCCGTCA
AGGTTCTCCG GGAGCGGTTC GGGGACAGAC TTTACTTTGA CCATTTCGTC GCTTCAGCCG
GAGGACTTCG CCACCTATTA CTGTCATCAG TCATGGAACT CACCTCCCAC ATTTGGCCAG
GGAACGAAAC TCGAAATCAA G
```
SEQ ID NO: 120 polynucleotide sequence encoding anti-toxin B antibody 1114.g8 VH region
```
GAAGTACAAC TCGTAGAGTC AGGGGGTGGG CTGGTCCAAC CTGGCGGCTC CCTTCGGCTT
TCGTGTGCCG CCTCGGGATT CACGTTTAGC AATTACGGTA TGGCCTGGGT GAGGCAGGCA
CCAGGGAAGG GTCTTGAGTG GGTAGCGATC ATCAACTATG ATGCAAGCAC CACCCACTAC
AGGGATAGCG TCAAGGGACG CTTTACTATC AGCCGGGATA ATGCGAAATC CTCGCTCTAT
CTGCAGATGA ACTCCCTCAG AGCCGAGGAC ACCGCAGTGT ACTATTGCAC ACGATACGGA
CGCTCGCACT ATTTCGACTA TTGGGGACAG GGGACGCTCG TAACTGTCTC G
```
SEQ ID NO: 128 polynucleotide sequence encoding anti-toxin B antibody 1125.g2 VL region
```
GATATACAAA TGACTCAGAG CCCTAGCTCA CTGAGCGCTT CTGTGGGCGA TCGTGTGACA
ATCACTTGCA AAGCAAGCCA GAACATCTAT ATGTACCTGA ATTGGTACCA GCAAAAACCG
GGAAAAGCTC CCAAGCGCCT GATTTACAAC ACCAATAAGC TGCATACCGG CGTGCCAAGC
CGTTTTAGCG GATCTGGCTC TGGAACCGAA TATACACTGA CCATAAGCTC CCTGCAACCG
GAAGACTTTG CAACTTACTA TTGCCTCCAG CACAAATCCT TCCCTATAC GTTCGGACAA
GGGACCAAAC TGGAAATCAA A
```
SEQ ID NO: 130 polynucleotide sequence encoding anti-toxin B antibody 1125.g2 VH region
```
GAAGTGCAGC TGGTCGAAAG CGGCGGAGGA TTGGTGCAAC CTGGTGGCTC TCTTCGCCTG
TCTTGCGCTG CAAGCGGCTT TACGTTCCGC GATAGCTTTA TGGCTTGGGT GCGACAAGCT
CCTGGGAAAG GGCTGGAATG GGTCGCTAGC ATAAGCTACG AAGGCGACAA GACTTACTAT
GGGGACTCTG TGAAAGGCCG ATTCACCATT AGCCGAGACA ACGCAAAGAA CTCCCTGTAC
CTGCAGATGA ACTCCCTGCG TGCCGAAGAT ACCGCCGTGT ACTATTGCGC TAGGCTGACG
ATCACTACAA GCGGAGATAG CTGGGGACAA GGGACAATGG TGACCGTCTC GAGC
```
SEQ ID NO: 138 polynucleotide sequence encoding anti-toxin B antibody 1129.g1 VL region
```
GACACCCAGA TGACTCAGTC TCCGTCAAGC CTTTCTGCCT CTGTTGGAGA TCGAGTCACA
ATTACGTGCA AGGCAAGCCA ACACGTGGGT ACCAACGTGG ACTGGTATCA ACAGAAGCCA
GGGAAGGTCC CCAAACTGCT GATCTACGGT GCCAGTATTC GCTATACCGG CGTGCCTGAT
CGCTTCACCG GAAGCGGGTC AGGGACCGAT TTCACACTGA CAATCAGCTC CCTGCAACCT
GAAGACGTGG CTACTTACTA CTGCCTGCAG TACAACTATA ATCCCTACAC CTTTGGCCAG
GGCACCAAAC TGGAGATAAA G
```

SEQ ID NO: 140 polynucleotide sequence encoding anti-toxin B antibody 1129.g1 VH region
```
GAGGTGCAAC TTGTGGAATC AGGAGGTGGC GTGGTTCAGC CCGGTAGATC ACTTCGTCTG
AGTTGTGCAA CAAGCGGCTT TATCTTCTCC AACTTCGGGA TGTCTTGGGT TAGACAGGCT
CCTGGTAAGG GCCTCGAATG GGTGGCTAGT ATTAGCCCAA GCGGGGGAAA CGCCTACTAT
AGGGACAGCG TGAAAGGACG CTTCACTATC AGCCGAGATA ACTCCAAGAC CACGCTGTAT
CTGCAGATGA ATAGTCTGAG GGCCGAGGAT ACCGCAGTGT ACTACTGCAC TCGACGGGCC
TATTCTTCCC CTTTTGCCTT TTGGGGACAG GGGACTCTGG TGACAGTCTC GAGC
```

Figure 9

SEQ ID NO: 148 polynucleotide sequence encoding anti-toxin B antibody 1134.g5 VL region
GACGTCCAGC TCACTCAATC TCCCTCCTTT CTGTCTGCTT CTGTGGGCGA TCGCGTGACA
ATAACCTGCA AGGCCTCCAA ATCAATTAGC AACCATCTGG CATGGTATCA GGAGAAGCCT
GGCAAAGCCA ATAAGCTGCT GATCCACTCC GGCTCAACTC TGCAACCCGG TACCCCAAGC
CGATTTAGCG GATCTGGGAG CGGAACCGAG TTCACACTTA CCATTAGCTC CCTGCAACCG
GAGGACTTCG CCACCTATTA CTGCCAGCAA TACGACGAAT ACCCCTATAC GTTCGGCCAA
GGGACAAGAT TGGAAATCAA G

SEQ ID NO: 150 polynucleotide sequence encoding anti-toxin B antibody 1134.g5 VH region
GAAGTTCAGC TGCAGGAATC TGGACCTGGC TTGGTGAAAC CAAGCGAGAC ACTTAGTCTC
ACTTGCACCG TTTCCGGCTT CTCCCTTAAT TCCTACACGA TCACTTGGGT GCGGCAACCA
CCCGGGAAAG GACTGGAATG GATCGCAGCC ATTAGCGGGG GAGGGAGCAC CTATTTCAAC
TCGGCTCTCA AGAGCCGCGT GACCATATCC CGTGACACAA GCAAGAGCCA GGTTTCCCTG
AAGCTGAGCT CCGTGACTGC TGCCGATACG GCTGTTTACT ATTGCACCCG ACCTCGCTGG
TATCCCCGTT CCTATTTCGA CTACTGGGGA AGAGGCACAC TGGTTACCGT CTCG

SEQ ID NO: 158 polynucleotide sequence encoding anti-toxin B antibody 1151.g4 VL region
GCGATTCAAA TGACTCAGTC GCCCTCATCG CTTAGCGCGT CCGTCGGAGA TAGAGTGACG
ATCACGTGCA AAGCATCACA AAATGTCGGG AACAATGTGG CATGGTATCA GCATAAACCG
GGGAAGGCAC CAAAACTCTT GATCTACTAC GCCAGCAACA GGTTTACTGG TGTCCCGTCA
AGGTTCACGG GAGGGGGTTA CGGGACAGAC TTTACTTTGA CCATTTCGTC GCTTCAGCCG
GAGGACTTCG CCACCTATTA CTGTCAGAGG GTCTACCAGT CAACGTGGAC ATTTGGCCAG
GGAACGAAAG TGGAAATCAA G

Figure 10

SEQ ID NO: 160 polynucleotide sequence encoding anti-toxin B antibody 1151.g4 VH region
GAAGTACAAC TCCAAGAGTC GGGGCCTGGT CTGGTCAAGC CGTCCGAAAC ACTTTCGCTG
ACGTGTACGG TATCAGGATT CTCACTTACA TCATACTACG TCCACTGGGT GAGGCAGCCA
CCCGGGAAGG GTCTTGAGTG GATGGGCTGC ATTAGAACCG GAGGGAATAC CGAGTACCAG
AGCGAATTTA AGAGCCGCGT CACTATCAGC CGGGATACGT CCAAAAACCA GGTGTCGCTC
AAATTGTCCT CCGTGACGGC CGCTGACACC GCAGTGTACT ATTGCGCGCG AGGAAACTAT
GGCTTTGCGT ATTGGGGACA GGGGACGCTC GTAACTGTCT CG

SEQ ID NO: 168 polynucleotide sequence encoding anti-toxin B antibody 1153.g8 VL region
GATATACAGA TGACTCAGTC CCCTTCTAGC CTTTCAGCTT CCGTGGGCGA TAGAGTGACT
ATCACGTGTA AGGCTAGTCA GAACATTAAC AAGTATCTGG ACTGGTACCA GCAGAAACCC
GGGAAGGTTC CCAAGCTGCT GATCTACAAC ATCCAGTCCC TGCATACAGG CATTCCTAGC
CGGTTTAGCG GATCTGGTTC AGGGACCGAC TTCACCCTGA CAATCAGCTC TCTGCAACCA
GAAGACGTGG CCACCTATTA CTGCTTCCAG CACAATAGTG GCTGGACTTT TGGACAAGGT
ACCAGGCTGG AGATCAAA

SEQ ID NO: 170 polynucleotide sequence encoding anti-toxin B antibody 1153.g8 VH region

GAGGTTCAGC TGGTGGAATC AGGAGGGGGT CTGGTGCAAC CAGGAGGCTC CCTGAAACTG
TCTTGCGCCG CAAGCGGCTT TACGTTTACC CAGGCCGCTA TGTTCTGGGT TAGGCAGGCC
AGTGGGAAGG GTCTTGAAGG CATCGCAAGA ATCAGCACCA AGAGCAACAA TTTCGCTACG
TACTATCCGG ACTCCGTGAA AGGCCGGTTT ACCATTTCTC GCGATGACAG CAAGAACACC
GTGTACCTGC AGATGAACAG TCTCAAGACC GAGGACACAG CCGTGTACTA TTGTACTGCT
CCCGCCTATT ATTACGATGG CACAGTGCCT TTCGCATACT GGGGACAGGG
TACTTTGGTG ACTGTCTCG

Sera titres from 4 rabbits immunised with TcdA toxoid and 5 rats immunised with TcdB binding domain (TcdB1234). ELISA data generated using TcdA toxin or TcdB binding domain coated on an ELISA plate Figure 12 Anti TcdA (Ribotype 003) in-vitro neutralization data for single Mabs (X axis conc. (ng/ml) and Y axis % Neutralization)
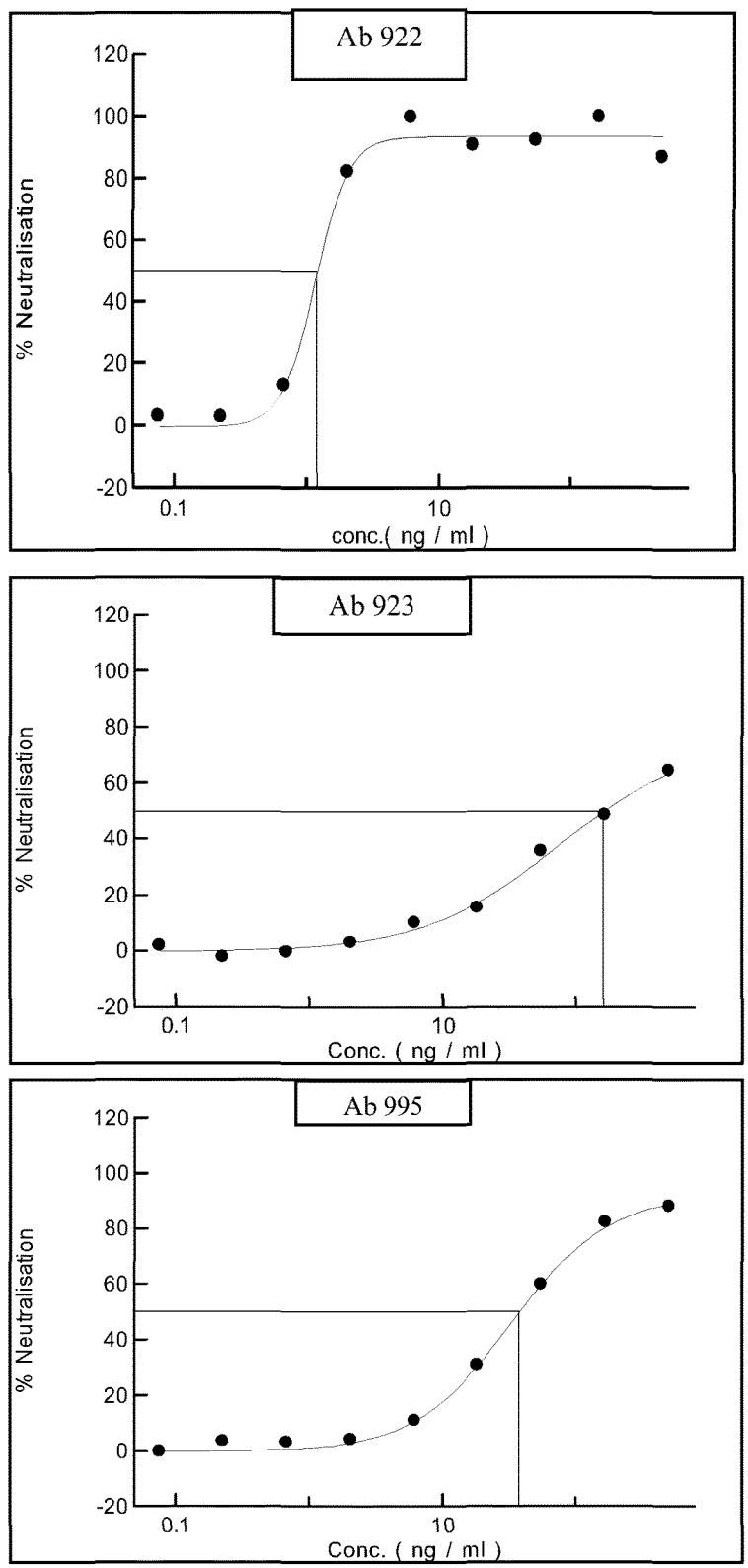

Figure 13 Anti TcdA (Ribotype 003) in-vitro neutralization data for single Mabs (X axis conc. (ng/ml) and Y axis % Neutralization)

Figure 14 Anti TcdA (Ribotype 003) in-vitro neutralization data for paired Mabs (X axis conc. (ng/ml) and Y axis % Neutralization)
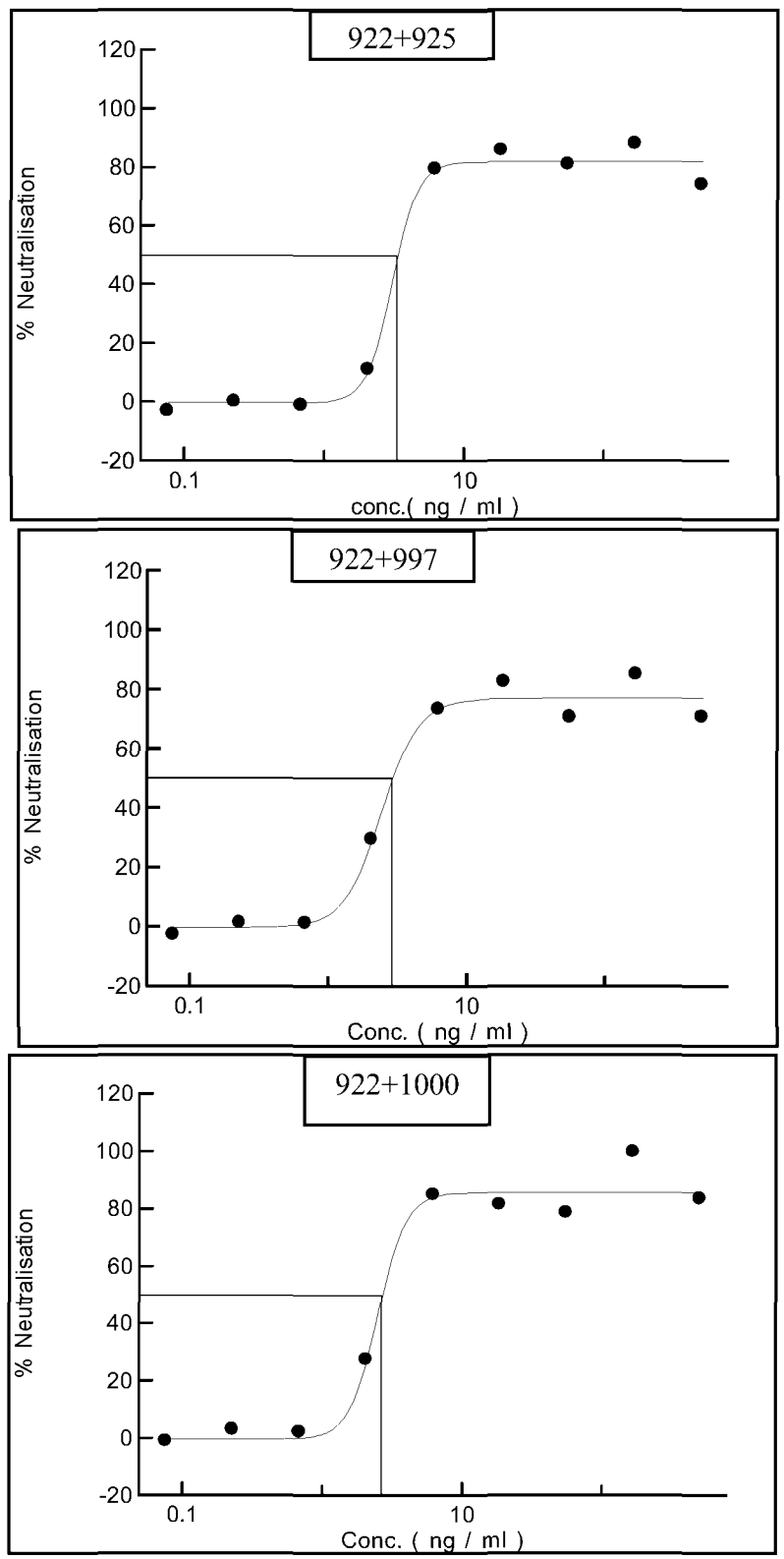

Figure 15 Anti TcdA (Ribotype 003) in-vitro neutralization data for paired Mabs (X axis conc. ( Figure 16 Anti TcdA (Ribotype 003) in-vitro neutralization data for three Mab mixtures (X axis conc. (ng/ml) and Y axis % Neutralization)

Figure 17 Anti TcdA (Ribotype 003) in-vitro neutralization data for three Mab mixtures (X axis conc. (ng/ml) and Y axis % Neutralization)

Figure 18 Anti TcdA (Ribotype 003) in-vitro neutralization data for three Mab mixtures (X axis conc. (ng/ml) and Y axis % Neutralization)

Figure 19 Anti TcdA (Ribotype 003) in-vitro neutralization data for four and five Mab mixtures (X axis conc. (ng/ml) and Y axis % Neutralization)

Figure 20 Anti TcdA (Ribotype 003) in-vitro neutralization data for four and five Mab mixtures (X axis conc. (ng/ml) and Y axis % Neutralization)
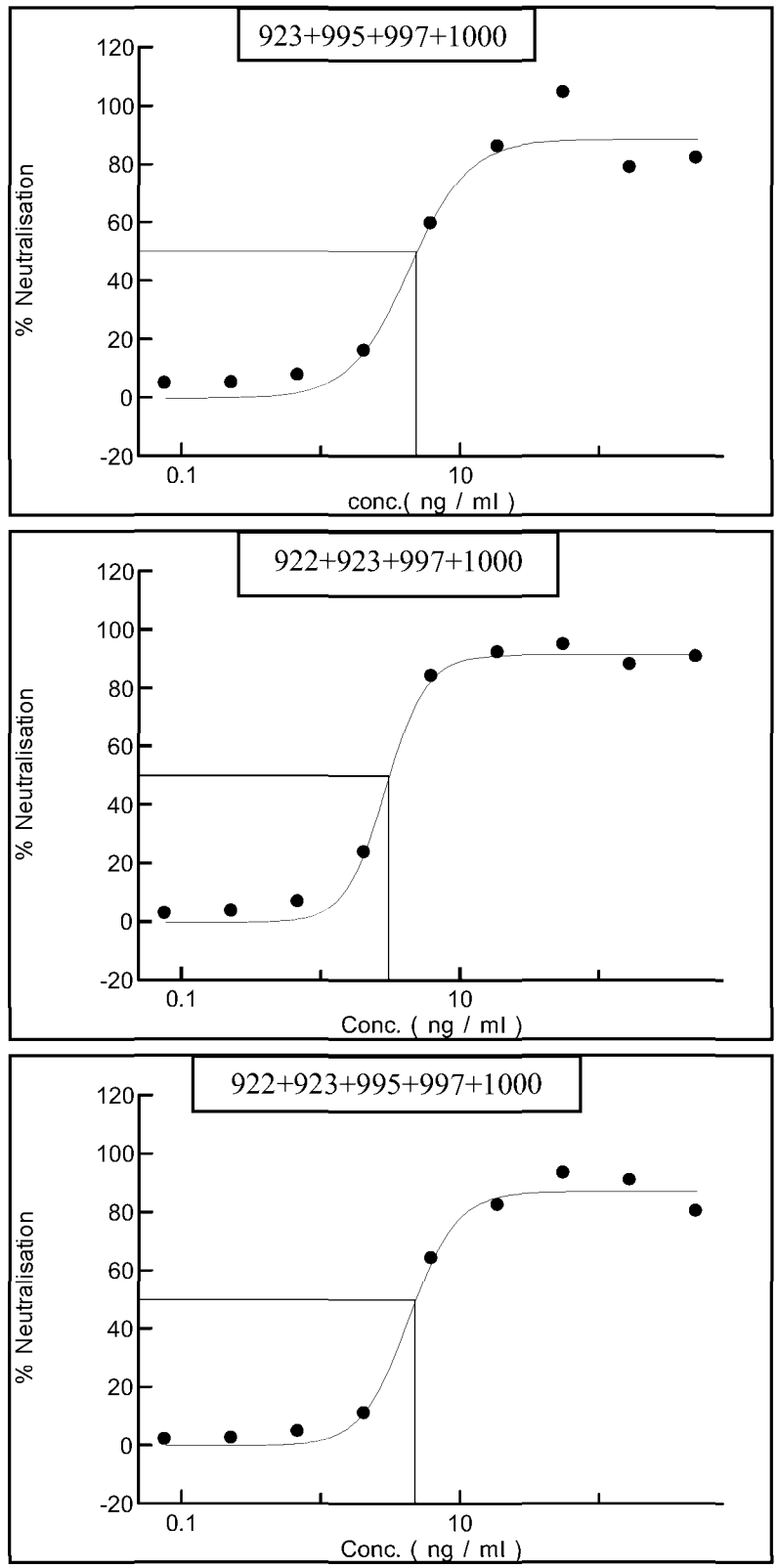

Figure 21 Anti TcdA (Ribotype 003) in-vitro neutralization data for single and paired Mabs at different TcdA concentrations (X axis is conc ng/ml)

Figure 22 Anti TcdA (Ribotype 003) in-vitro neutralization data for single and paired Mabs at different TcdA concentrations (X axis is conc. ng/ml)

Figure 23 Anti TcdA (Ribotype 003) in-vitro neutralization data for single and to five Mab mixtures at different TcdA concentrations (X axis conc. ng/ml)

Figure 24 Anti TcdA (Ribotype 003) in-vitro neutralization data for single and to five Mab mixtures at different TcdA concentrations (X axis is conc. ng/ml Figure 25 Anti TcdB (Ribotype 003) in-vitro neutralization data for single Mabs (Y axis neutralization X axis conc ng/ml for 1125.g2, 1134.g5 and 927.g2 respectively)

Figure 26 Anti TcdB (Ribotype 003) in-vitro neutralization data for single Mabs Y axis neutralization X axis conc ng/ml for1153.g8 and 1102.g4 respectively)

Figure 27 Anti TcdB (Ribotype 003) in-vitro neutralization data for paired Mabs
Y axis neutralization X axis conc ng/ml for combinations of 927+1099, 927+1102, 927+1114
respectively)
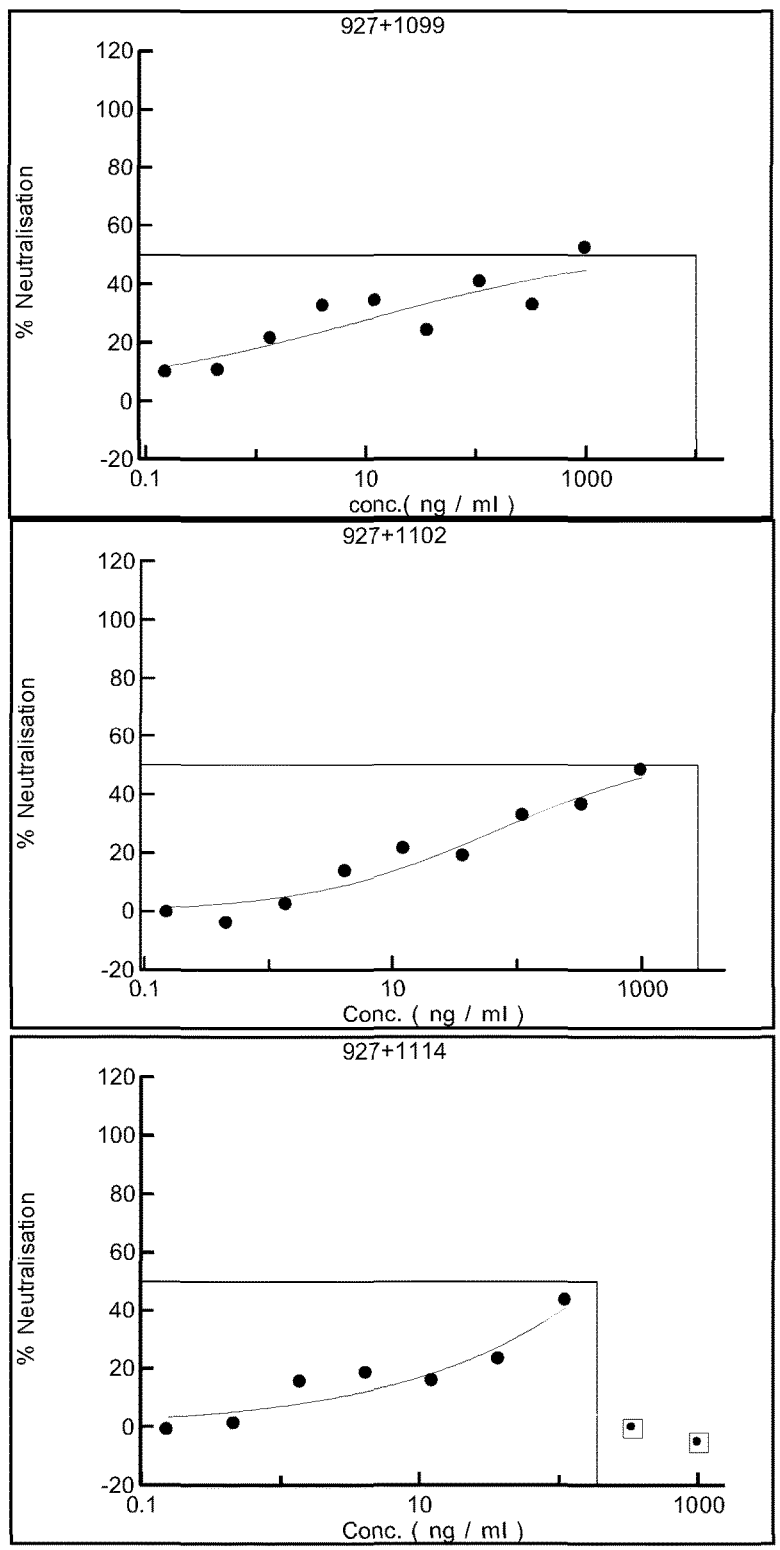

Figure 28 Anti TcdB (Ribotype 003) in-vitro neutralization data for paired Mabs (Y axis neutralization X axis conc ng/ml for combinations of 927+1125, 927+1134, 1099+1114 respectively)

Figure 29 Anti TcdB (Ribotype 003) in-vitro neutralization data for paired Mabs (Y axis neutralization X axis conc ng/ml for combinations of 1102+1114, 1102+1125, 1114+1134 respectively)
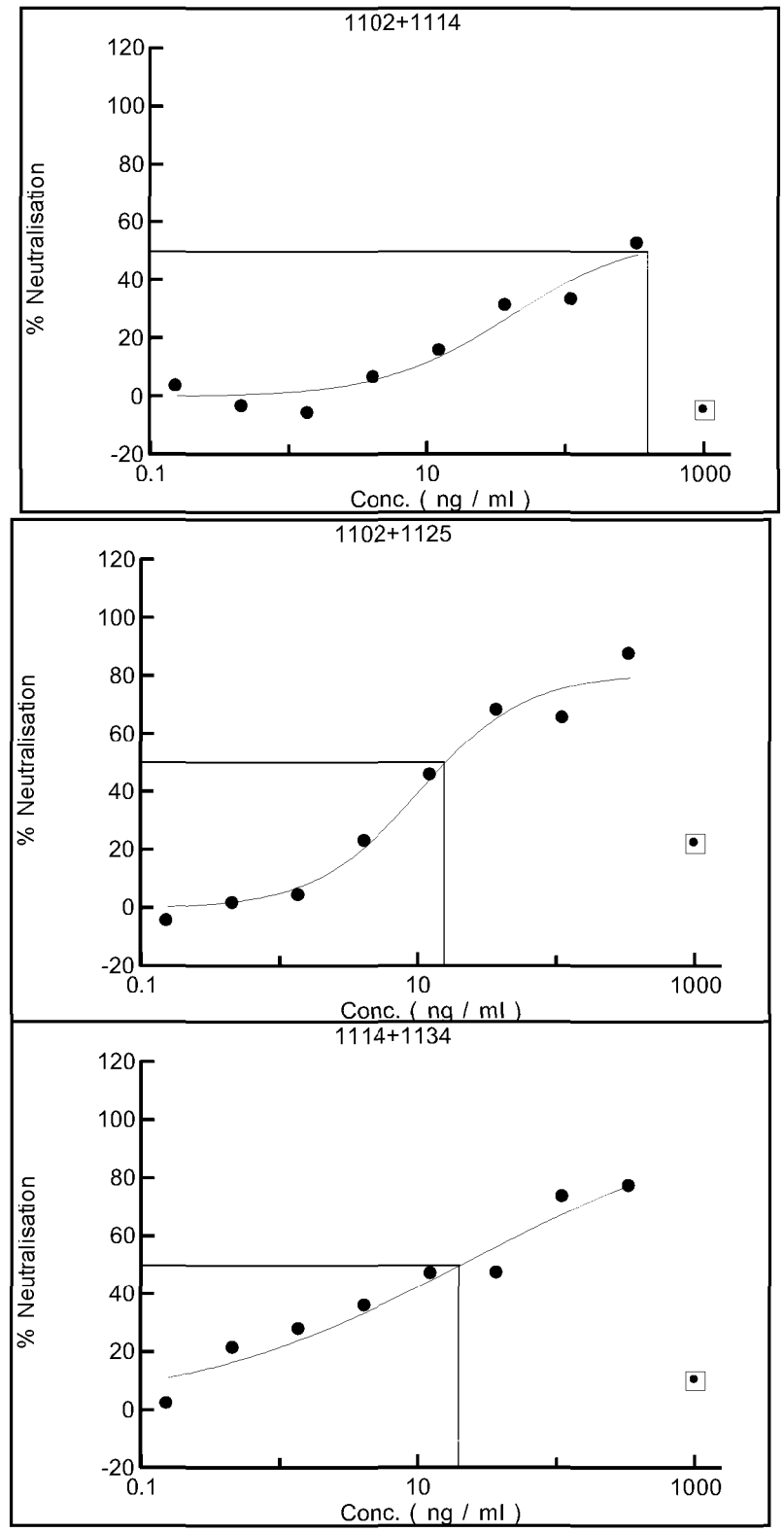

Figure 30 Anti TcdB (Ribotype 003) in-vitro neutralization data for paired Mabs (Y axis neutralization X axis conc ng/ml for combinations of 1114+1151, 1114+1153, 1125+1134 respectively)

Figure 31 Anti TcdB (Ribotype 003) in-vitro neutralization data for three Mab mixtures (Y axis neutralization X axis conc ng/ml for combinations of 1125+1134+1114, 1125+1134+927, 1125+1151+*1114* respectively)
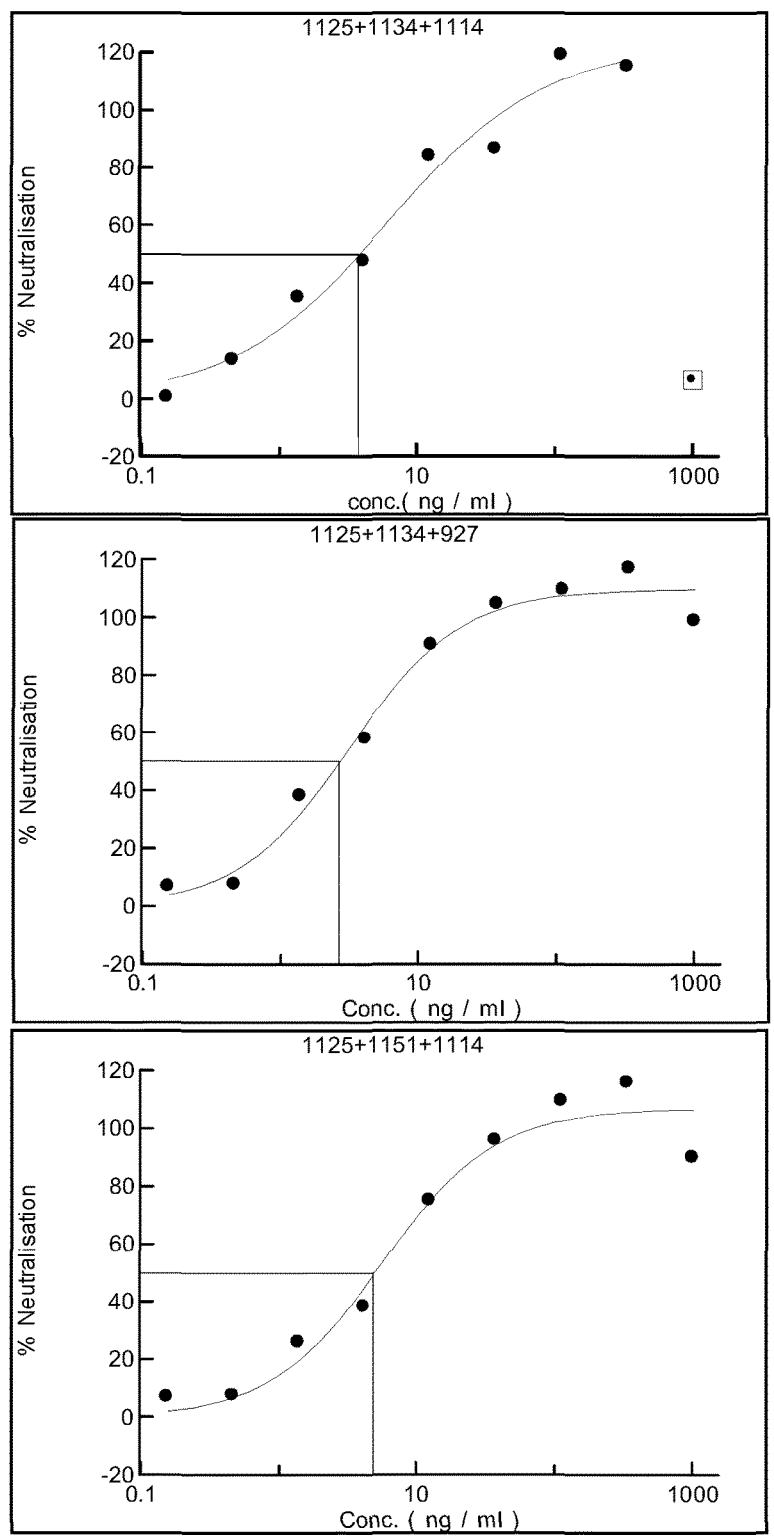

Figure 32 Anti TcdB (Ribotype 003) in-vitro neutralization data for three Mab mixtures (Y axis neutralization X axis conc ng/ml for 1125.+1151+927, 1125.g2+1134.g5+927.g2 respectively)
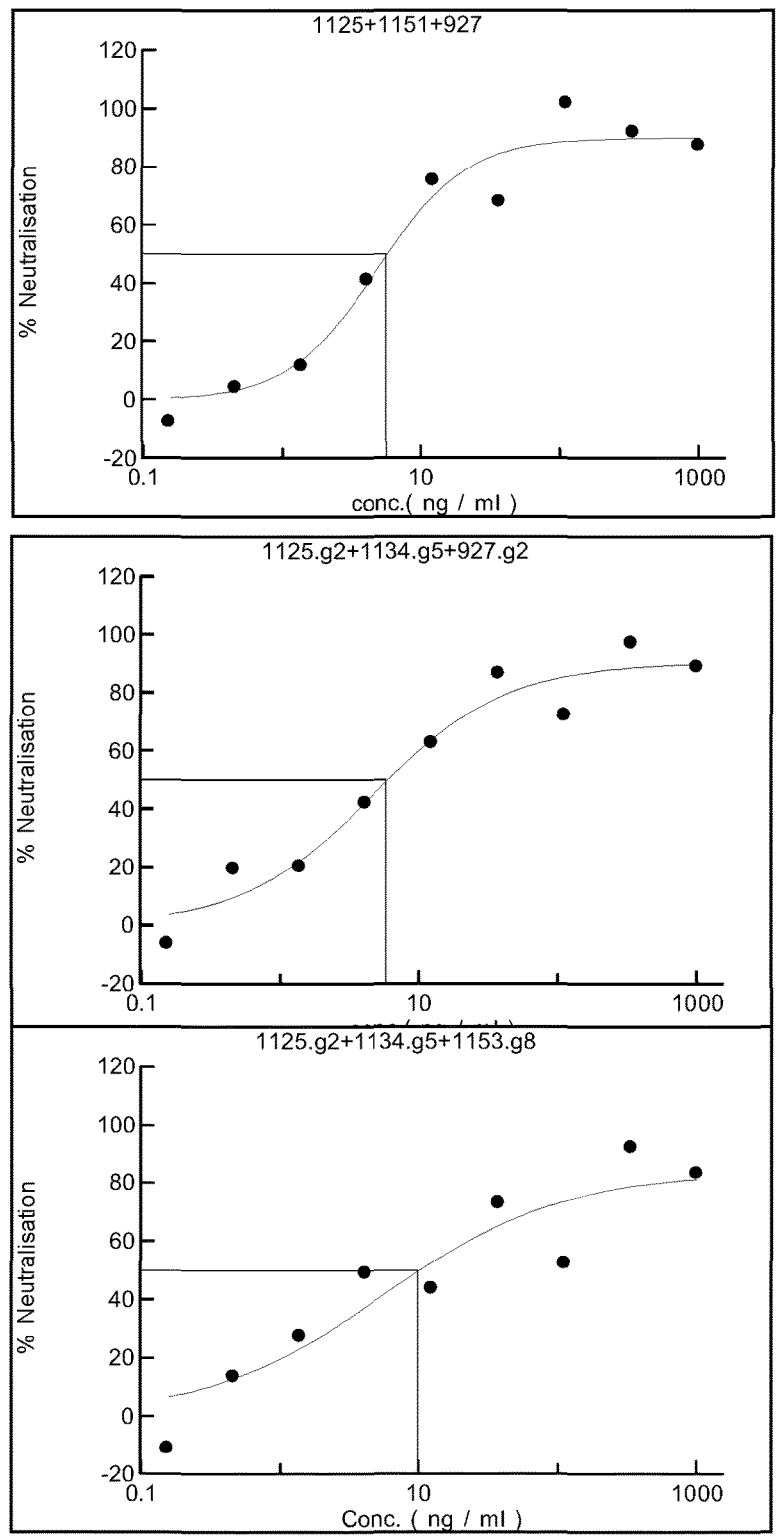

Figure 33 Anti TcdB (Ribotype 003) in-vitro neutralization data for three Mab mixtures Figure 34 Anti TcdB (Ribotype 003) in-vitro neutralization data for two Mab mixtures at different toxin concentrations
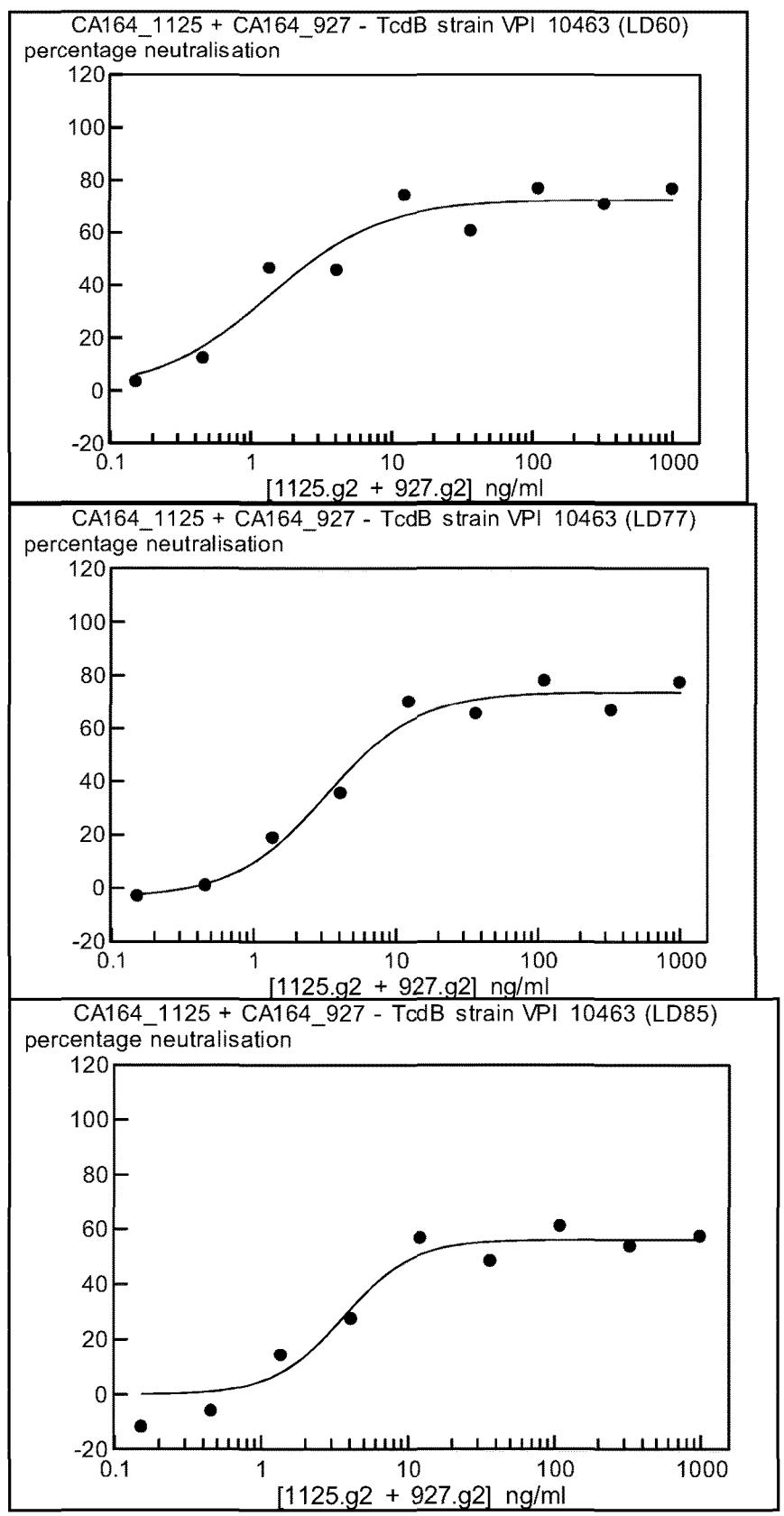

Figure 35 Anti TcdB (Ribotype 003) in-vitro neutralization data for two Mab mixtures at different toxin concentrations Figure 36 Anti TcdB (Ribotype 003) in-vitro neutralization data for two Mab mixtures at different toxin concentrations Figure 37 Anti TcdB (Ribotype 003) in-vitro neutralization data for two Mab mixtures at different toxin concentrations Figure 38 Anti TcdB (Ribotype 003) in-vitro neutralization data for two Mab mixtures at different toxin concentrations Figure 39 Anti TcdB (Ribotype 003) in-vitro neutralization data for two Mab mixtures at different toxin concentrations

Figure 40 Anti TcdB (Ribotype 003) in-vitro neutralization data for two Mab mixtures at different toxin concentrations Figure 41 Anti TcdB (Ribotype 003) in-vitro neutralization data for two Mab mixtures at different relative Mab ratios and different toxin concentrations
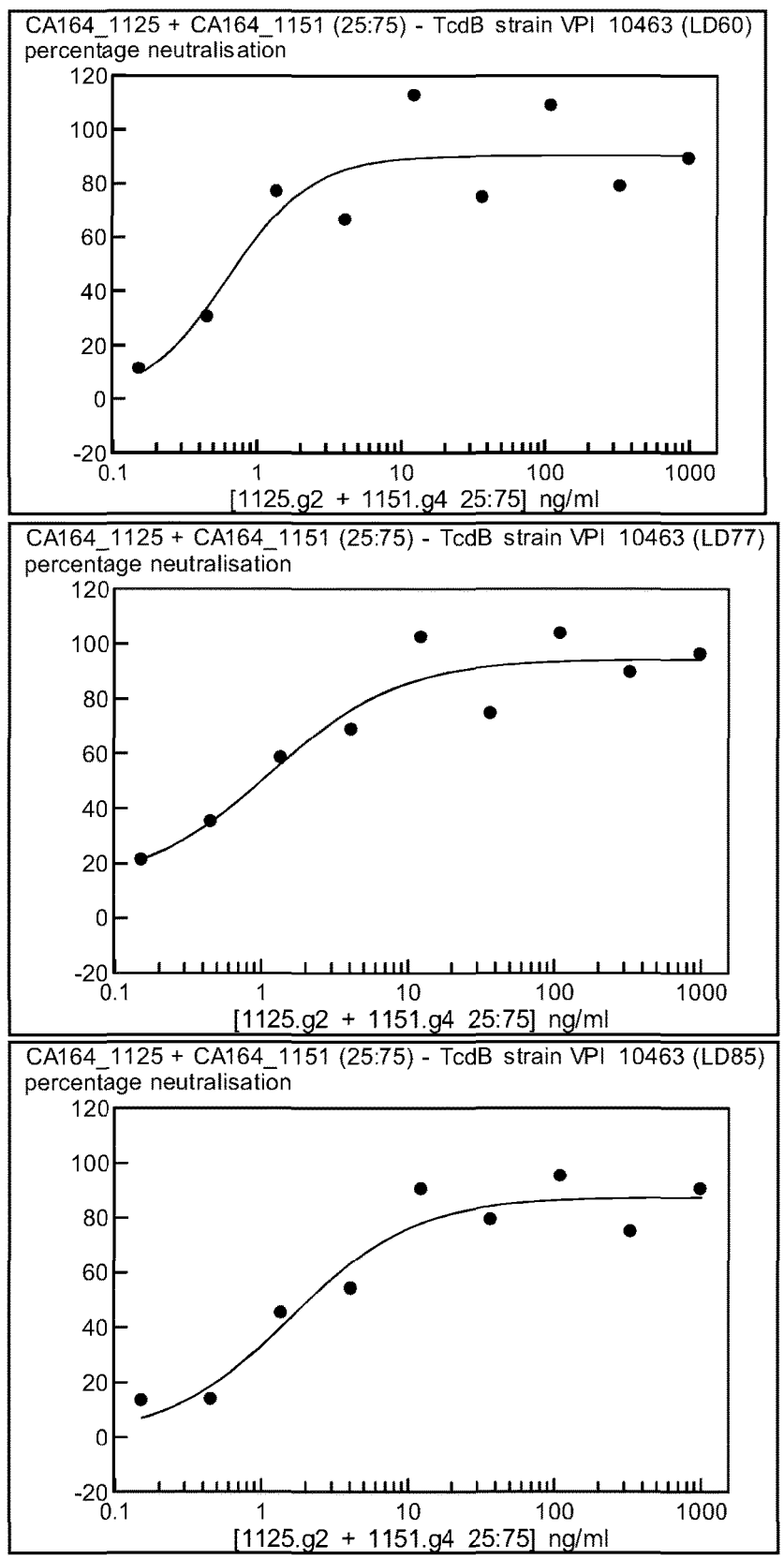

Figure 42 Anti TcdB (Ribotype 003) in-vitro neutralization data for two Mab mixtures at different relative Mab ratios and different toxin concentrations Figure 43 Anti TcdB (Ribotype 003) in-vitro neutralization data for two Mab mixtures at different relative Mab ratios and different toxin concentrations Figure 44 Anti TcdB (Ribotype 003) in-vitro neutralization data for two Mab mixtures at different relative Mab ratios and different toxin concentrations Figure 45 Anti TcdB (Ribotype 003) in-vitro neutralization data for two Mab mixtures at different relative Mab ratios and different toxin concentrations
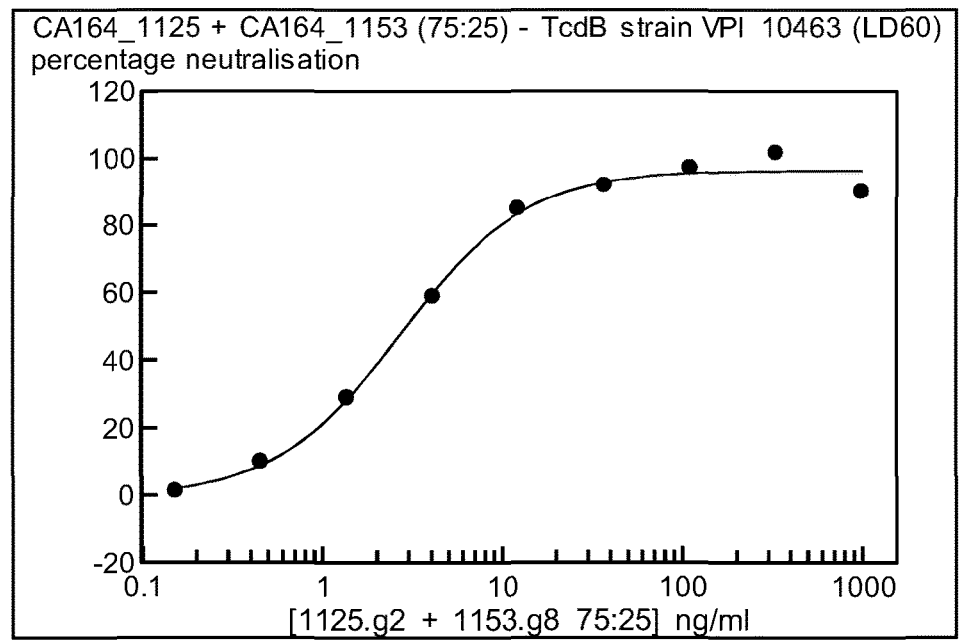
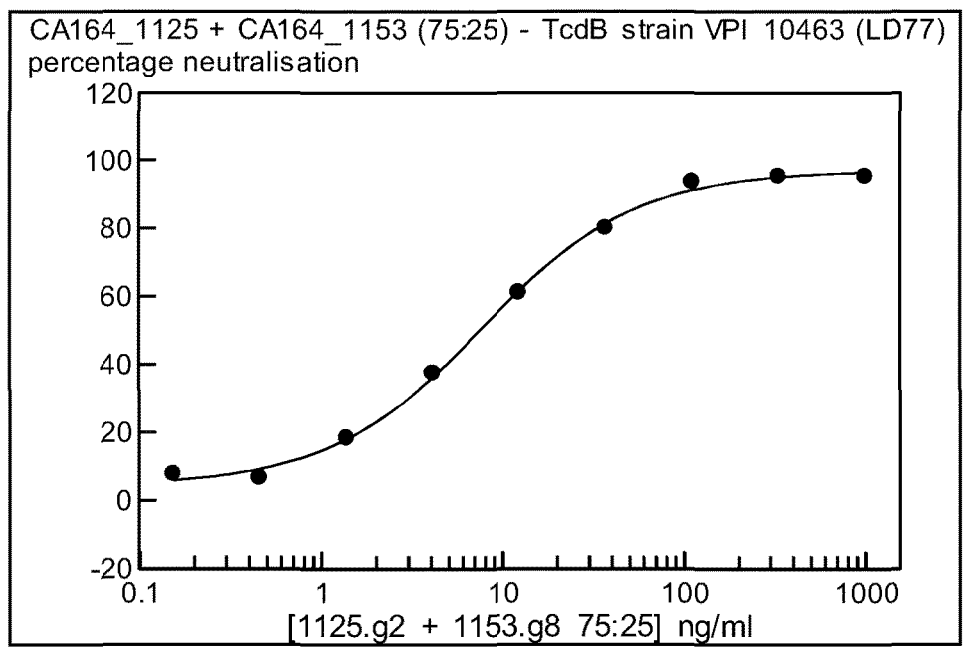

Figure 46 TcdB strain VPI 10463 neutralisation, Antibody singles and pairs, Constant toxin dose (LD80)

Figure 47 TcdB neutralisation, Antibody singles and pairs, Constant toxin dose (LD80)
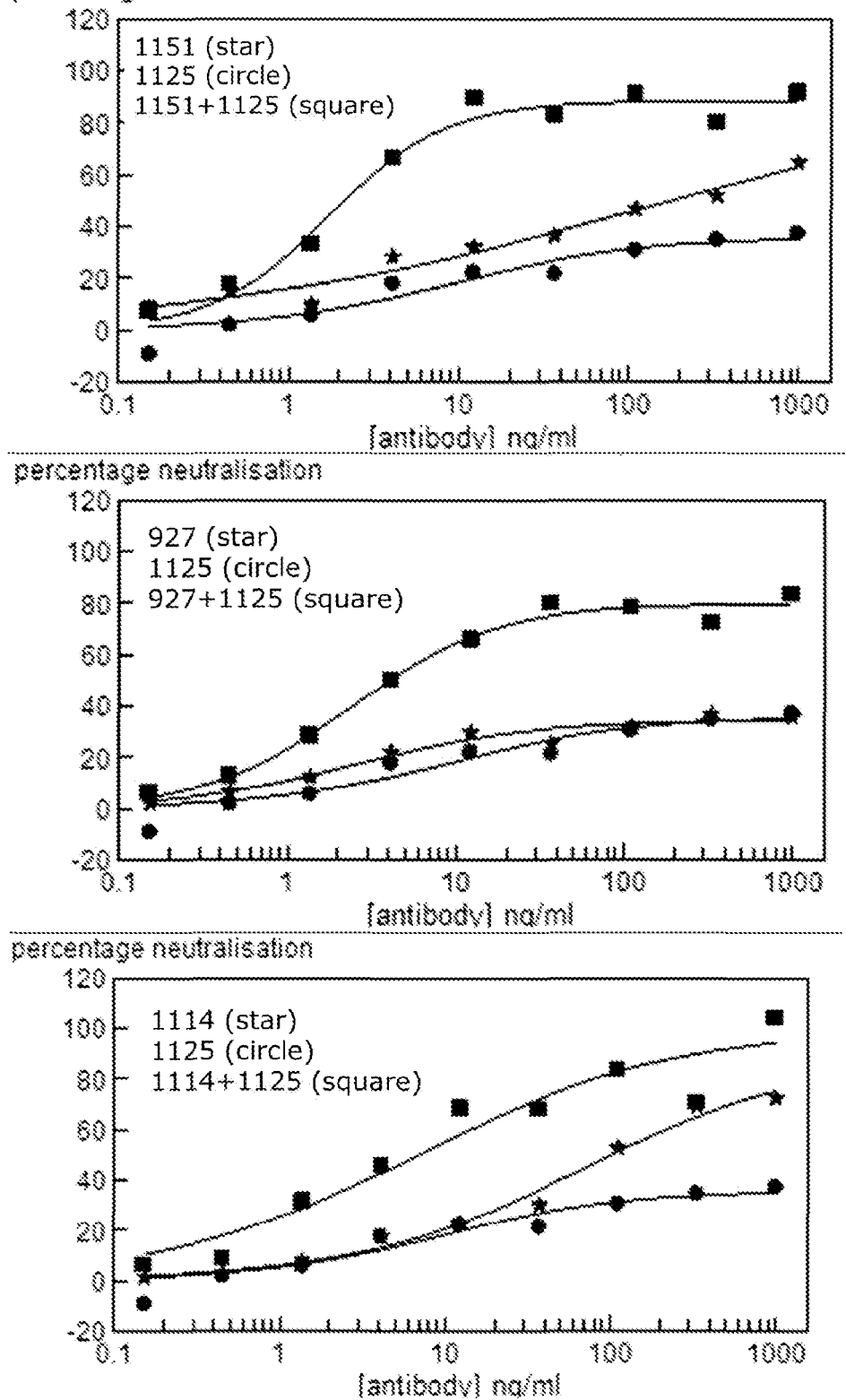

Figure 48 TcdB neutralisation, Antibody singles and pairs, Constant toxin dose (LD80)
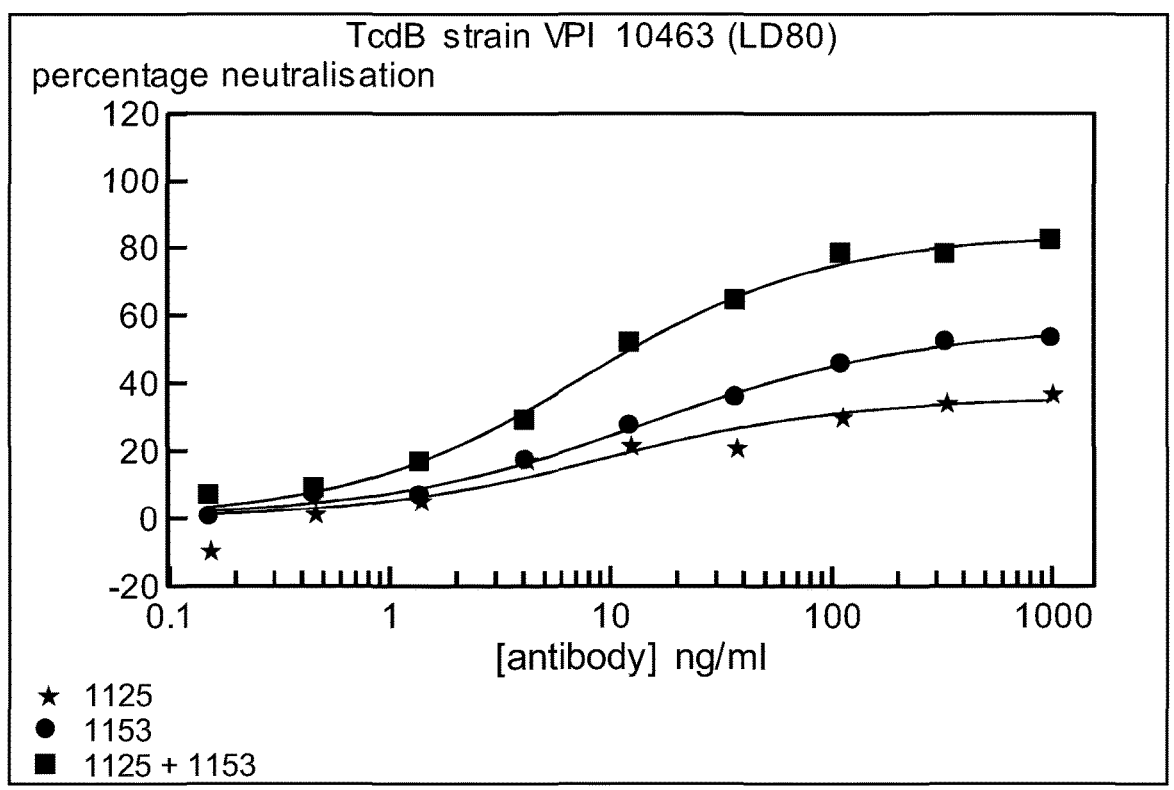

Figure 49 TcdB neutralisation, Antibody singles and pairs, Varying toxin dose (straddling)

Figure 50 TcdB neutralisation, Antibody singles and pairs, Varying toxin dose (straddling)
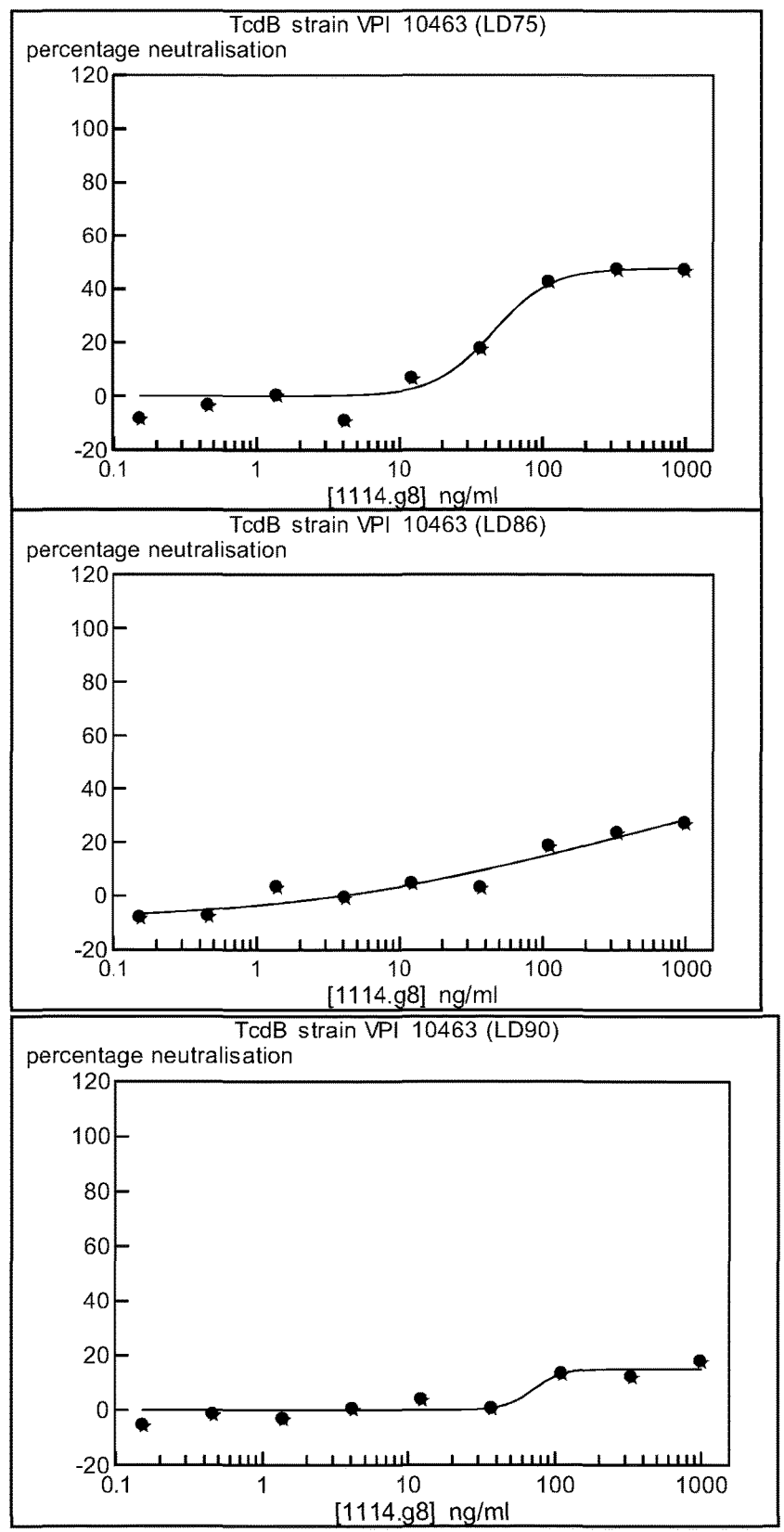

Figure 51 TcdB neutralisation, Antibody singles and pairs, Varying toxin dose (straddling)
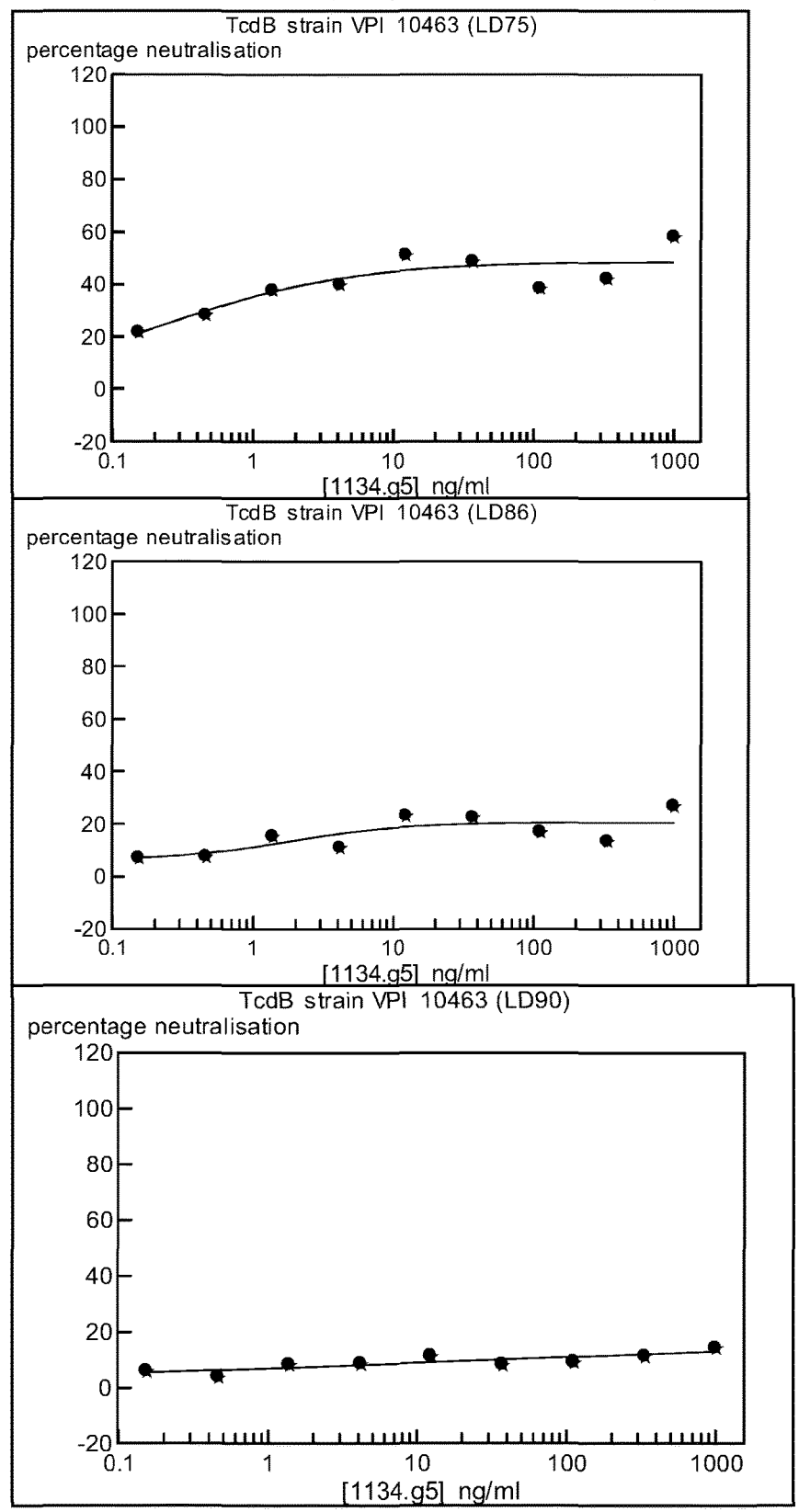

Figure 52 TcdB neutralisation, Antibody singles and pairs, Varying toxin dose (straddling)
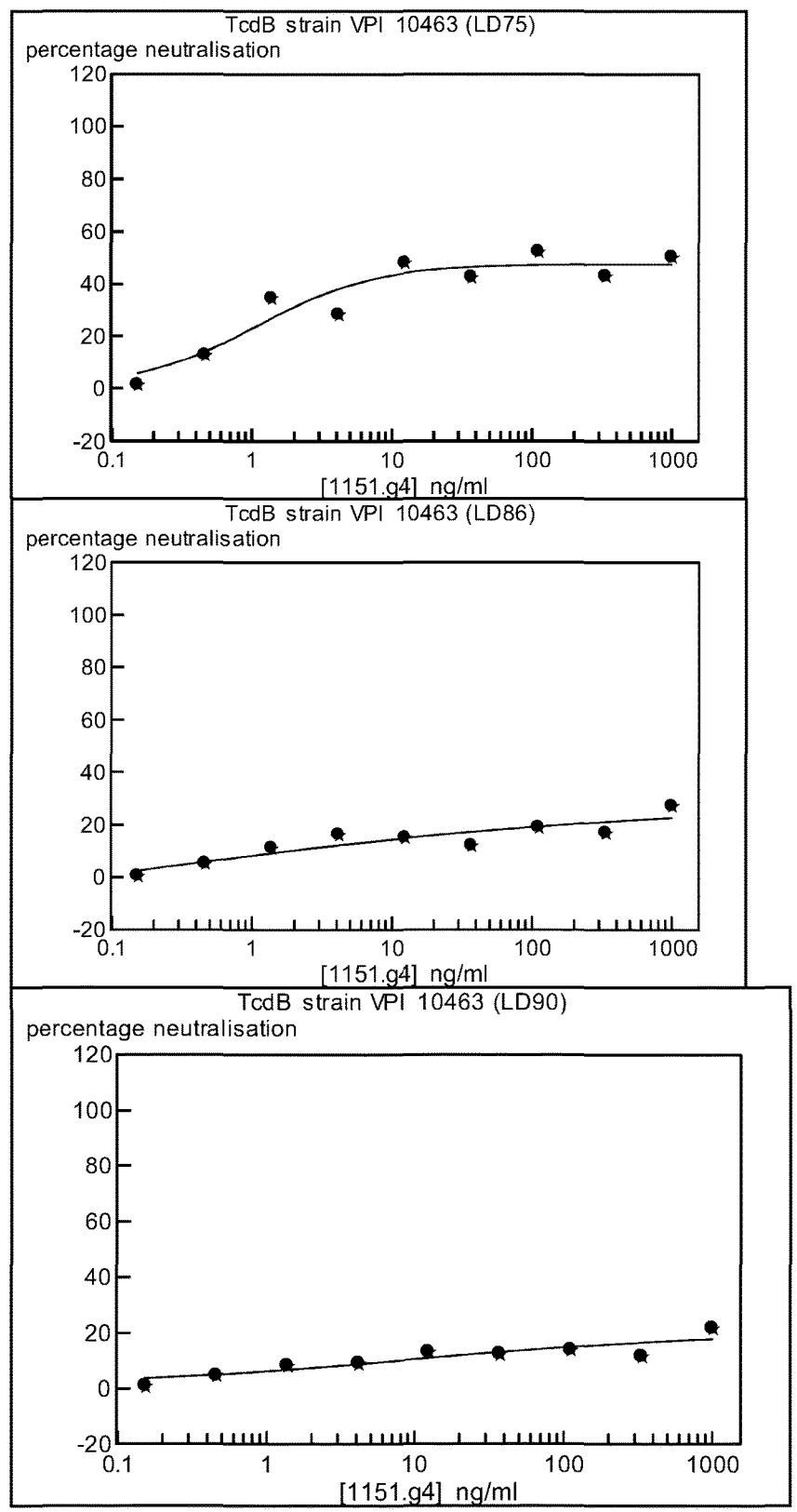

Figure 53 TcdB neutralisation, Antibody singles and pairs, Varying toxin dose (straddling)

Figure 54 TcdB neutralisation, Antibody singles and pairs, Varying toxin dose (straddling)

Figure 55 TcdB neutralisation, Antibody singles and pairs, Varying toxin dose (straddling)

Figure 56 TcdB neutralisation, Antibody singles and pairs, Varying toxin dose (straddling)

Figure 57 TcdB neutralisation, Antibody singles and pairs, Varying toxin dose (straddling)

Figure 58 TcdB neutralisation, Antibody singles and pairs, Varying toxin dose (straddling)

Figure 59 TcdB neutralisation, Antibody singles and pairs, Varying toxin dose (straddling)

Figure 60  Amino Acid sequence for TcdA SEQ ID NO: 171

```
MSLISKEELI KLAYSIRPRE NEYKTILTNL DEYNKLTTNN NENKYLQLKK LNESIDVFMN
KYKTSSRNRA LSNLKKDILK EVILIKNSNT SPVEKNLHFV WIGGEVSDIA LEYIKQWADI
NAEYNIKLWY DSEAFLVNTL KKAIVESSTT EALQLLEEEI QNPQFDNMKF YKKRMEFIYD
RQKRFINYYK SQINKPTVPT IDDIIKSHLV SEYNRDETVL ESYRTNSLRK INSNHGIDIR
ANSLFTEQEL LNIYSQELLN RGNLAAASDI VRLLALKNFG GVYLDVDMLP GIHSDLFKTI
SRPSSIGLDR WEMIKLEAIM KYKKYINNYT SENFDKLDQQ LKDNFKLIIE SKSEKSEIFS
KLENLNVSDL EIKIAFALGS VINQALISKQ GSYLTNLVIE QVKNRYQFLN QHLNPAIESD
NNFTDTTKIF HDSLFNSATA ENSMFLTKIA PYLQVGFMPE ARSTISLSGP GAYASAYYDF
INLQENTIEK TLKASDLIEF KFPENNLSQL TEQEINSLWS FDQASAKYQF EKYVRDYTGG
SLSEDNGVDF NKNTALDKNY LLNNKIPSNN VEEAGSKNYV HYIIQLQGDD ISYEATCNLF
SKNPKNSIII QRNMNESAKS YFLSDDGESI LELNKYRIPE RLKNKEKVKV TFIGHGKDEF
NTSEFARLSV DSLSNEISSF LDTIKLDISP KNVEVNLLGC NMFSYDFNVE ETYPGKLLLS
IMDKITSTLP DVNKNSITIG ANQYEVRINS EGRKELLAHS GKWINKEEAI MSDLSSKEYI
FFDSIDNKLK AKSKNIPGLA SISEDIKTLL LDASVSPDTK FILNNLKLNI ESSIGDYIYY
EKLEPVKNII HNSIDDLIDE FNLLENVSDE LYELKKLNNL DEKYLISFED ISKNNSTYSV
RFINKSNGES VYVETEKEIF SKYSEHITKE ISTIKNSIIT DVNGNLLDNI QLDHTSQVNT
LNAAFFIQSL IDYSSNKDVL NDLSTSVKVQ LYAQLFSTGL NTIYDSIQLV NLISNAVNDT

INVLPTITEG IPIVSTILDG INLGAAIKEL LDEHDPLLKK ELEAKVGVLA INMSLSIAAT
VASIVGIGAE VTIFLLPIAG ISAGIPSLVN NELILHDKAT SVVNYFNHLS ESKKYGPLKT
EDDKILVPID DLVISEIDFN NNSIKLGTCN ILAMEGGSGH TVTGNIDHFF SSPSISSHIP
SLSIYSAIGI ETENLDFSKK IMMLPNAPSR VFWWETGAVP GLRSLENDGT RLLDSIRDLY
PGKFYWRFYA FFDYAITTLK PVYEDTNIKI KLDKDTRNFI MPTITTNEIR NKLSYSFDGA
GGTYSLLLSS YPISTNINLS KDDLWIFNID NEVREISIEN GTIKKGKLIK DVLSKIDINK
NKLIIGNQTI DFSGDIDNKD RYIFLTCELD DKISLIIEIN LVAKSYSLLL SGDKNYLISN
LSNTIEKINT LGLDSKNIAY NYTDESNNKY FGAISKTSQK SIIHYKKDSK NILEFYNDST
LEFNSKDFIA EDINVFMKDD INTITGKYYV DNNTDKSIDF SISLVSKNQV KVNGLYLNES
VYSSYLDFVK NSDGHHNTSN FMNLFLDNIS FWKLFGFENI NFVIDKYFTL VGKTNLGYVE
FICDNNKNID IYFGEWKTSS SKSTIFSGNG RNVVVEPIYN PDTGEDISTS LDFSYEPLYG
IDRYINKVLI APDLYTSLIN INTNYYSNEY YPEIIVLNPN TFHKKVNINL DSSSFEYKWS
TEGSDFILVR YLEESNKKIL QKIRIKGILS NTQSFNKMSI DFKDIKKLSL GYIMSNFKSF
NSENELDRDH LGFKIIDNKT YYYDEDSKLV KGLININNSL FYFDPIEFNL VTGWQTINGK
KYYFDINTGA ALTSYKIING KHFYFNNDGV MQLGVFKGPD GFEYFAPANT QNNNIEGQAI
VYQSKFLTLN GKKYYFDNNS KAVTGWRIIN NEKYYFNPNN AIAAVGLQVI DNNKYYFNPD
TAIISKGWQT VNGSRYYFDT DTAIAFNGYK TIDGKHFYFD SDCVVKIGVF STSNGFEYFA
```

Figure 60 (cont.)

```
PANTYNNNIE GQAIVYQSKF LTLNGKKYYF DNNSKAVTGL QTIDSKKYYF NTNTAEAATG

WQTIDGKKYY FNTNTAEAAT GWQTIDGKKY YFNTNTAIAS TGYTIINGKH FYFNTDGIMQ
IGVFKGPNGF EYFAPANTDA NNIEGQAILY QNEFLTLNGK KYYFGSDSKA VTGWRIINNK
KYYFNPNNAI AAIHLCTINN DKYYFSYDGI LQNGYITIER NNFYFDANNE SKMVTGVFKG
PNGFEYFAPA NTHNNNIEGQ AIVYQNKFLT LNGKKYYFDN DSKAVTGWQT IDGKKYYFNL
NTAEAATGWQ TIDGKKYYFN LNTAEAATGW QTIDGKKYYF NTNTFIASTG YTSINGKHFY
FNTDGIMQIG VFKGPNGFEY FAPANTDANN IEGQAILYQN KFLTLNGKKY YFGSDSKAVT
GLRTIDGKKY YFNTNTAVAV TGWQTINGKK YYFNTNTSIA STGYTIISGK HFYFNTDGIM
QIGVFKGPDG FEYFAPANTD ANNIEGQAIR YQNRFLYLHD NIYYFGNNSK AATGWVTIDG
NRYYFEPNTA MGANGYKTID NKNFYFRNGL PQIGVFKGSN GFEYFAPANT DANNIEGQAI

RYQNRFLHLL GKIYYFGNNS KAVTGWQTIN GKVYYFMPDT AMAAAGGLFE IDGVIYFFGV
DGVKAPGIYG
```

Figure 61 Amino Acid sequence for TcdB SEQ ID NO: 172

```
MSLVNRKQLE KMANVRFRTQ EDEYVAILDA LEEYHNMSEN TVVEKYLKLK DINSLTDIYI
DTYKKSGRNK ALKKFKEYLV TEVLELKNNN LTPVEKNLHF VWIGGQINDT AINYINQWKD
VNSDYNVNVF YDSNAFLINT LKKTVVESAI NDTLESFREN LNDPRFDYNK FFRKRMEIIY
DKQKNFINYY KAQREENPEL IIDDIVKTYL SNEYSKEIDE LNTYIEESLN KITQNSGNDV
RNFEEFKNGE SFNLYEQELV ERWNLAAASD ILRISALKEI GGMYLDVDML PGIQPDLFES
IEKPSSVTVD FWEMTKLEAI MKYKEYIPEY TSEHFDMLDE EVQSSFESVL ASKSDKSEIF
SSLGDMEASP LEVKIAFNSK GIINQGLISV KDSYCSNLIV KQIENRYKIL NNSLNPAISE
DNDFNTTTNT FIDSIMAEAN ADNGRFMMEL GKYLRVGFFP DVKTTINLSG PEAYAAAYQD
LLMFKEGSMN IHLIEADLRN FEISKTNISQ STEQEMASLW SFDDARAKAQ FEEYKRNYFE
GSLGEDDNLD FSQNIVVDKE YLLEKISSLA RSSERGYIHY IVQLQGDKIS YEAACNLFAK
TPYDSVLFQK NIEDSEIAYY YNPGDGEIQE IDKYKIPSII SDRPKIKLTF IGHGKDEFNT
DIFAGFDVDS LSTEIEAAID LAKEDISPKS IEINLLGCNM FSYSINVEET YPGKLLLKVK

DKISELMPSI SQDSIIVSAN QYEVRINSEG RRELLDHSGE WINKEESIIK DISSKEYISF
NPKENKITVK SKNLPELSTL LQEIRNNSNS SDIELEEKVM LTECEINVIS NIDTQIVEER
IEEAKNLTSD SINYIKDEFK LIESISDALC DLKQQNELED SHFISFEDIS ETDEGFSIRF
INKETGESIF VETEKTIFSE YANHITEEIS KIKGTIFDTV NGKLVKKVNL DTTHEVNTLN
```

Figure 61 (cont.)

```
AAFFIQSLIE YNSSKESLSN LSVAMKVQVY AQLFSTGLNT ITDAAKVVEL VSTALDETID
LLPTLSEGLP IIATIIDGVS LGAAIKELSE TSDPLLRQEI EAKIGIMAVN LTTATTAIIT
SSLGIASGFS ILLVPLAGIS AGIPSLVNNE LVLRDKATKV VDYFKHVSLV ETEGVFTLLD

DKIMMPQDDL VISEIDFNNN SIVLGKCEIW RMEGGSGHTV TDDIDHFFSA PSITYREPHL
SIYDVLEVQK EELDLSKDLM VLPNAPNRVF AWETGWTPGL RSLENDGTKL LDRIRDNYEG
EFYWRYFAFI ADALITTLKP RYEDTNIRIN LDSNTRSFIV PIITTEYIRE KLSYSFYGSG
GTYALSLSQY NMGINIELSE SDVWIIDVDN VVRDVTIESD KIKKGDLIEG ILSTLSIEEN
KIILNSHEIN FSGEVNGSNG FVSLTFSILE GINAIIEVDL LSKSYKLLIS GELKILMLNS

NHIQQKIDYI GFNSELQKNI PYSFVDSEGK ENGFINGSTK EGLFVSELPD VVLISKVYMD
DSKPSFGYYS NNLKDVKVIT KDNVNILTGY YLKDDIKISL SLTLQDEKTI KLNSVHLDES
GVAEILKFMN RKGNTNTSDS LMSFLESMNI KSIFVNFLQS NIKFILDANF IISGTTSIGQ
FEFICDENDN IQPYFIKFNT LETNYTLYVG NRQNMIVEPN YDLDDSGDIS STVINFSQKY
LYGIDSCVNK VVISPNIYTD EINITPVYET NNTYPEVIVL DANYINEKIN VNINDLSIRY
VWSNDGNDFI LMSTSEENKV SQVKIRFVNV FKDKTLANKL SFNFSDKQDV PVSEIILSFT
PSYYEDGLIG YDLGLVSLYN EKFYINNFGM MVSGLIYIND SLYYFKPPVN NLITGFVTVG
DDKYYFNPIN GGAASIGETI IDDKNYYFNQ SGVLQTGVFS TEDGFKYFAP ANTLDENLEG
EAIDFTGKLI IDENIYYFDD NYRGAVEWKE LDGEMHYFSP ETGKAFKGLN QIGDYKYYFN
SDGVMQKGFV SINDNKHYFD DSGVMKVGYT EIDGKHFYFA ENGEMQIGVF NTEDGFKYFA
HHNEDLGNEE GEEISYSGIL NFNNKIYYFD DSFTAVVGWK DLEDGSKYYF DEDTAEAYIG
LSLINDGQYY FNDDGIMQVG FVTINDKVFY FSDSGIIESG VQNIDDNYFY IDDNGIVQIG
VFDTSDGYKY FAPANTVNDN IYGQAVEYSG LVRVGEDVYY FGETYTIETG WIYDMENESD
KYYFNPETKK ACKGINLIDD IKYYFDEKGI MRTGLISFEN NNYYFNENGE MQFGYINIED
KMFYFGEDGV MQIGVFNTPD GFKYFAHQNT LDENFEGESI NYTGWLDLDE KRYYFTDEYI
AATGSVIIDG EEYYFDPDTA QLVISE
```

Figure 62 Caco-2 monolayer (Trans-Epithelial Electrical Resistance) data – TcdA
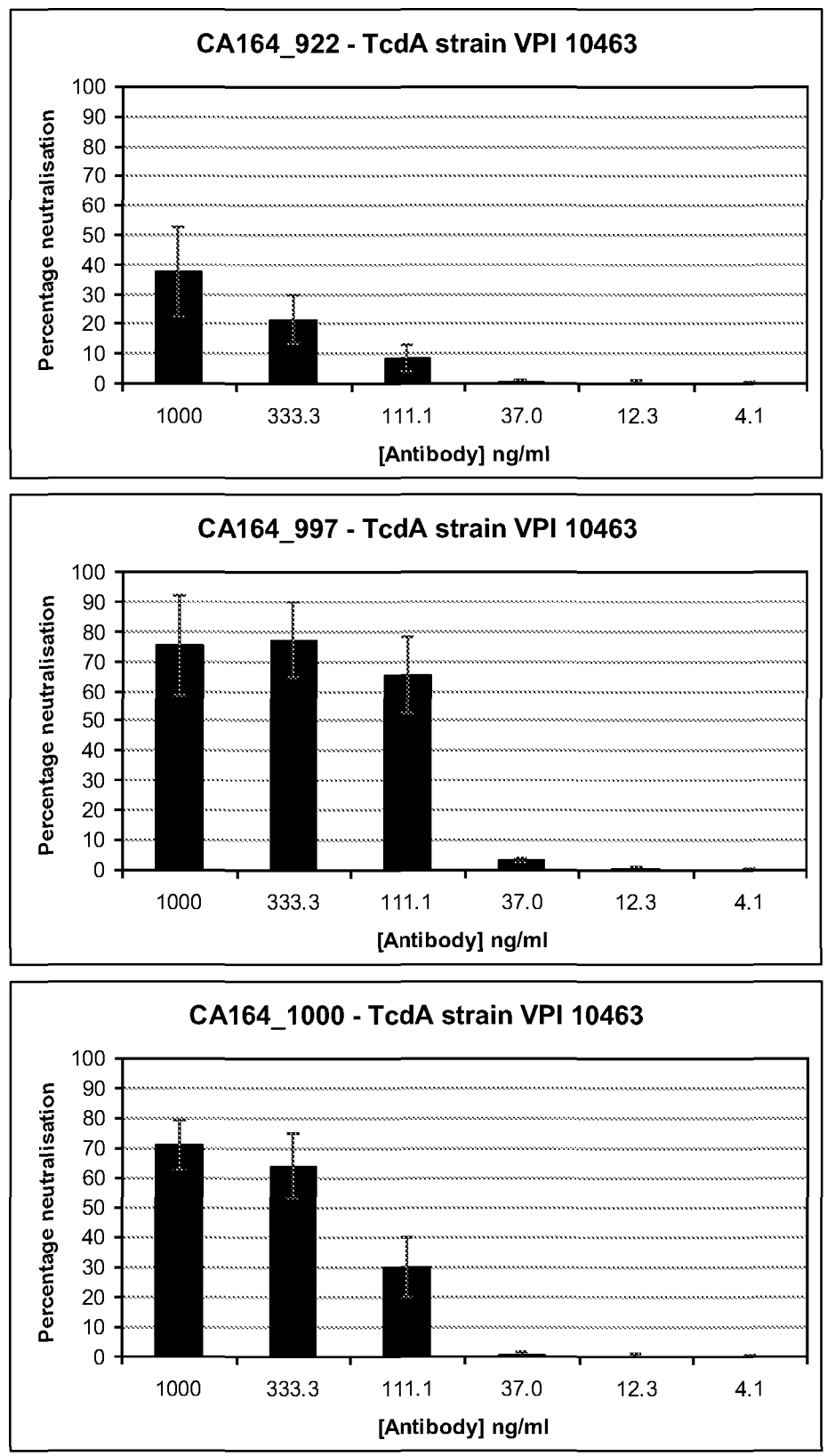

Figure 63
**Survival of hamsters after challenge with *Clostridium difficile*.
UCB high and low dose 3 Mab mixture: CA997.g1 (50%),
CA1125.g2 (25%) and CA1151.g4 (25%) vs controls**
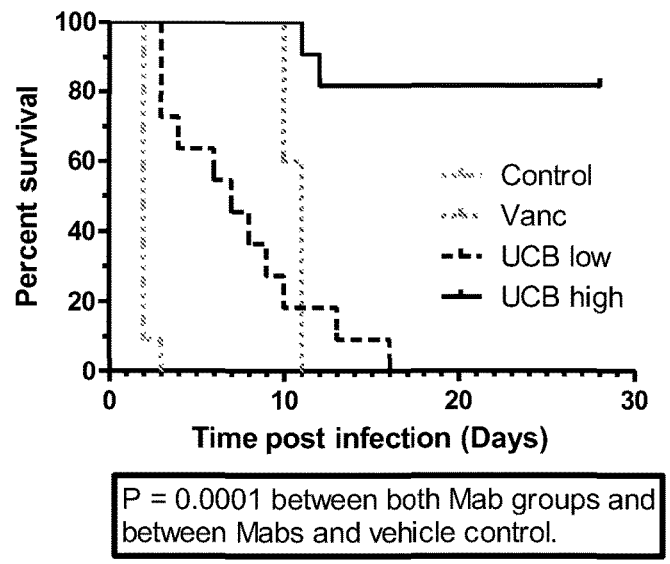
P = 0.0001 between both Mab groups and between Mabs and vehicle control.
Figure 64 Hamster body weight changes
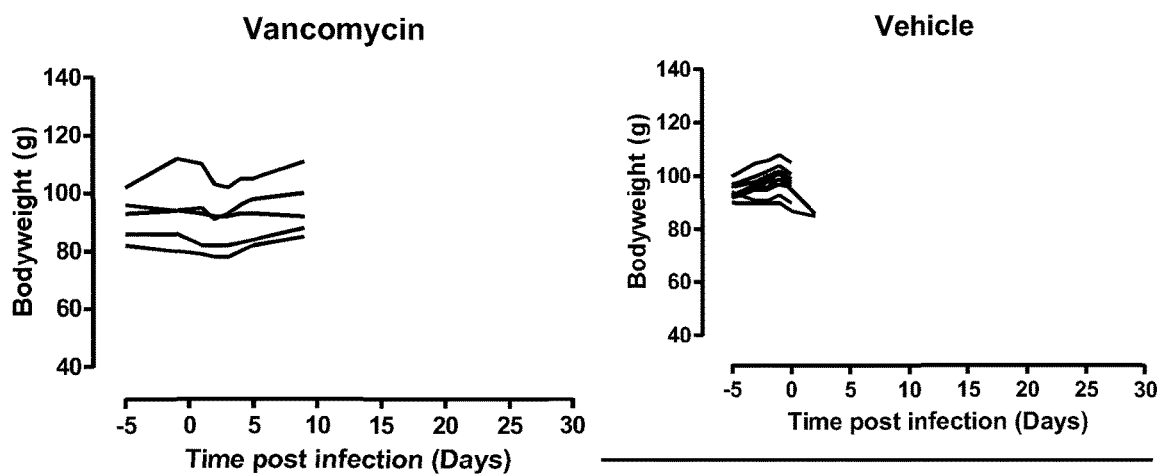

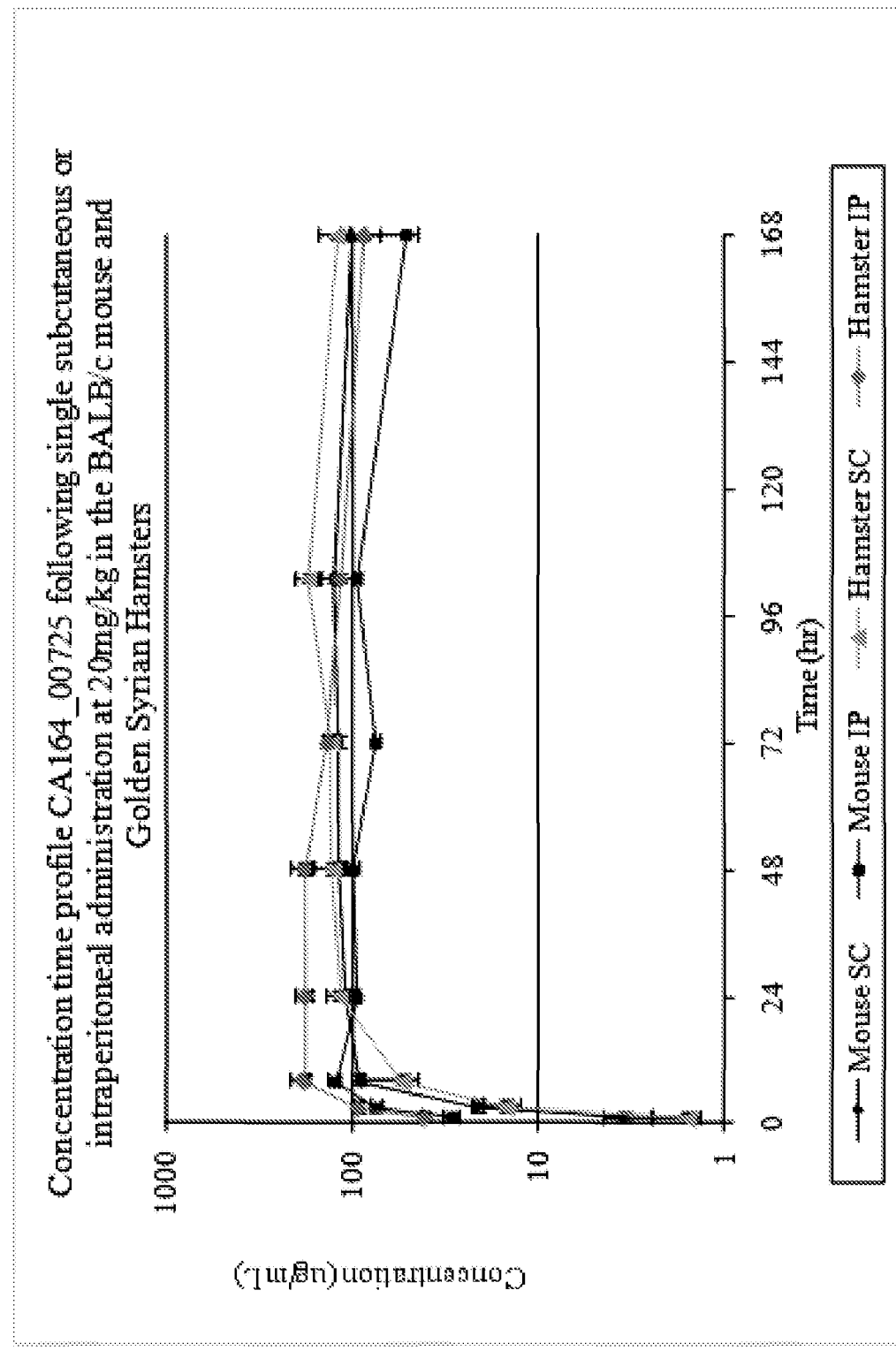
Figure 67 Serum pharmacokinetics of a human IgG1 in mice and hamsters Figure 68 Effect of Agitation *via* Vortexing on anti-TcdB IgG1 Molecules in PBS, pH 7.4 (n=3)

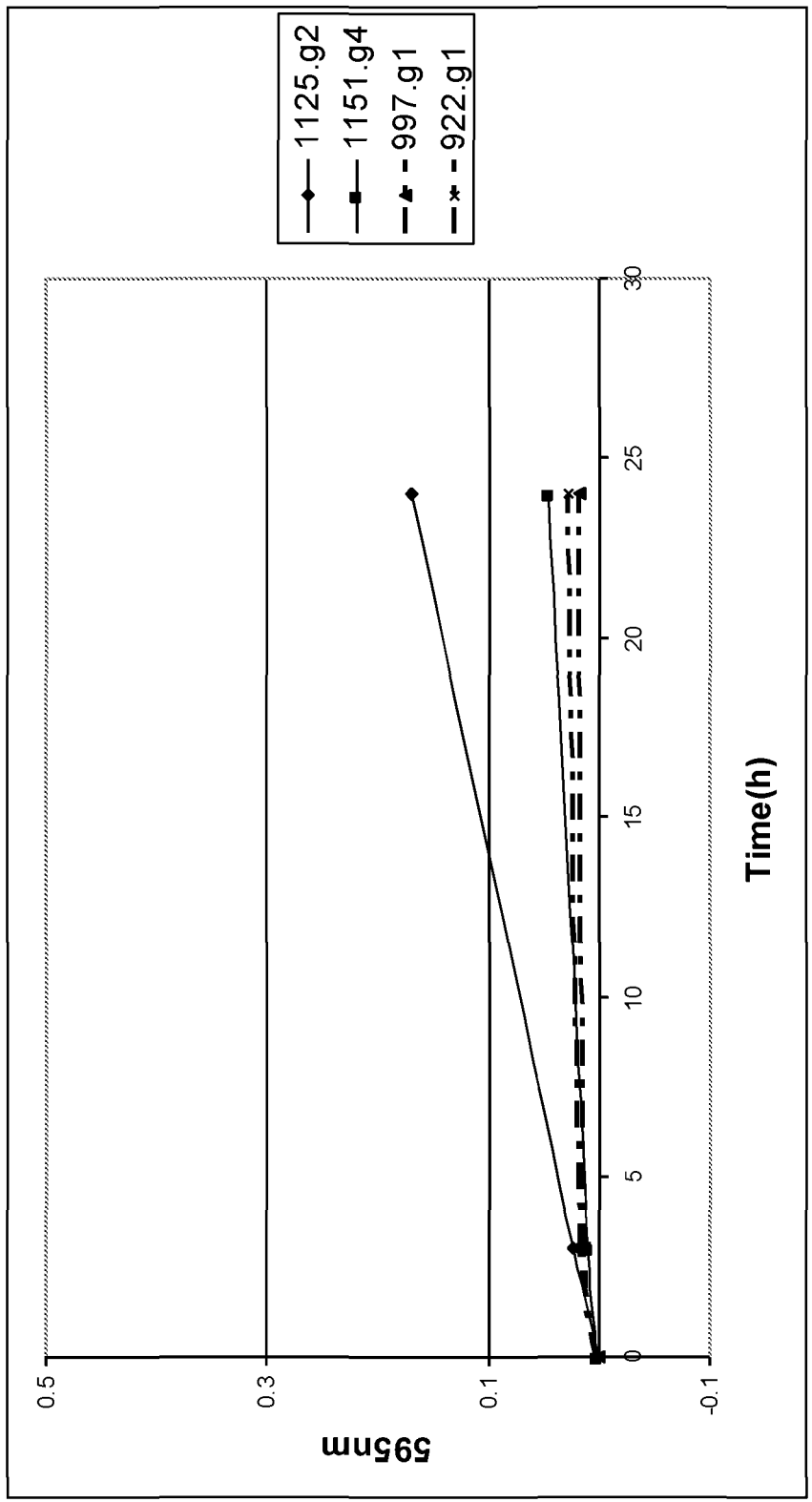
Figure 69 : Comparison of Aggregation Stability of anti-TcdA and anti-TcdB IgG1 Molecules in PBS pH 7.4

Figure 70 Neutralisation against ribotype 003
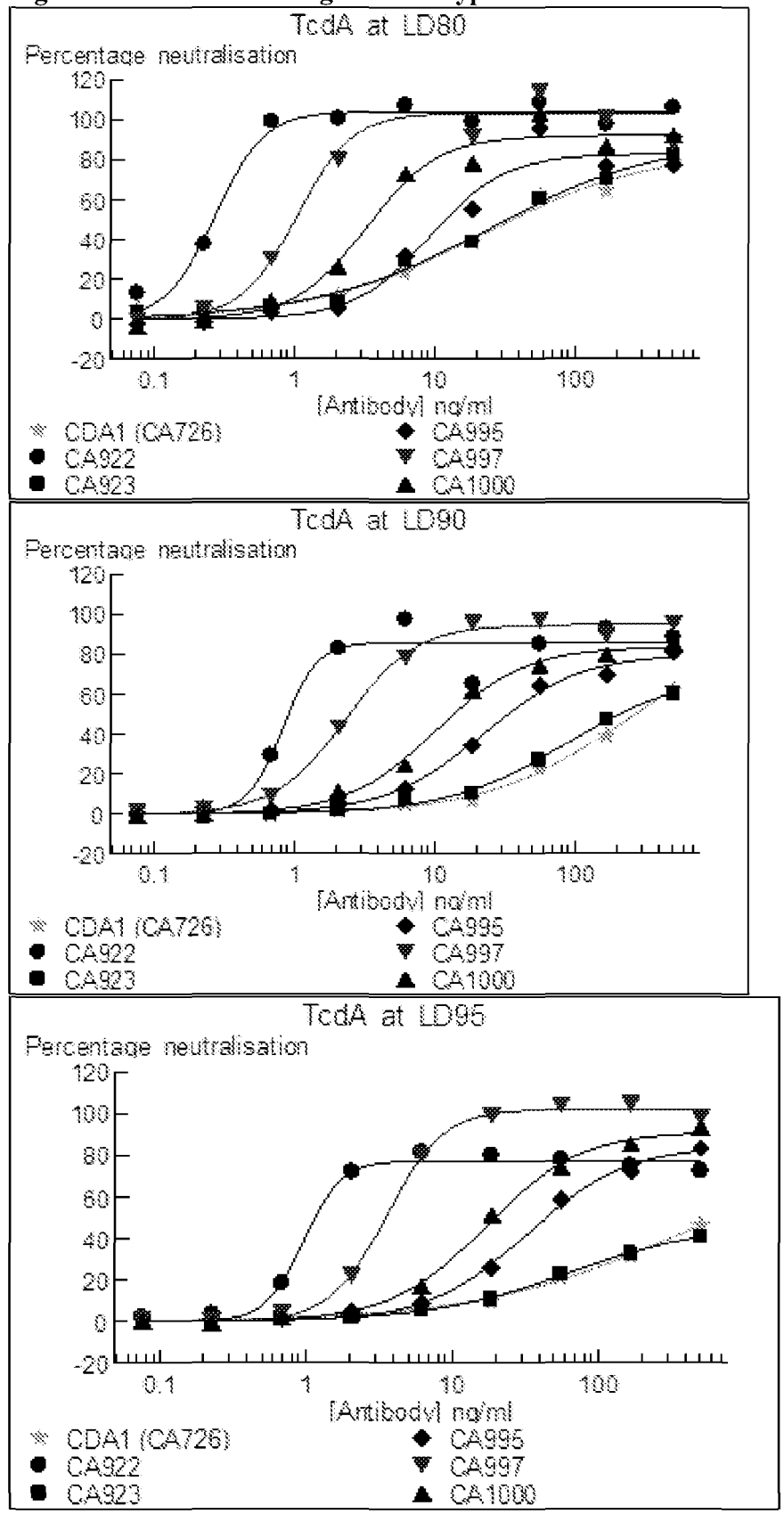

Figure 71 Neutralisation against ribotype 003
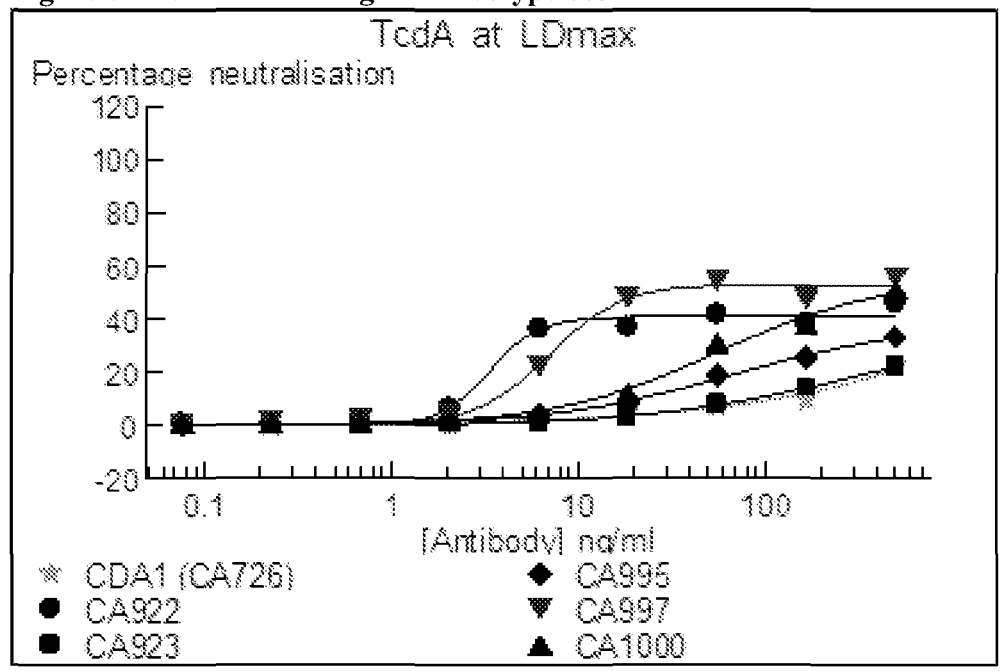
Figure 72 Neutralisation against ribotype 027
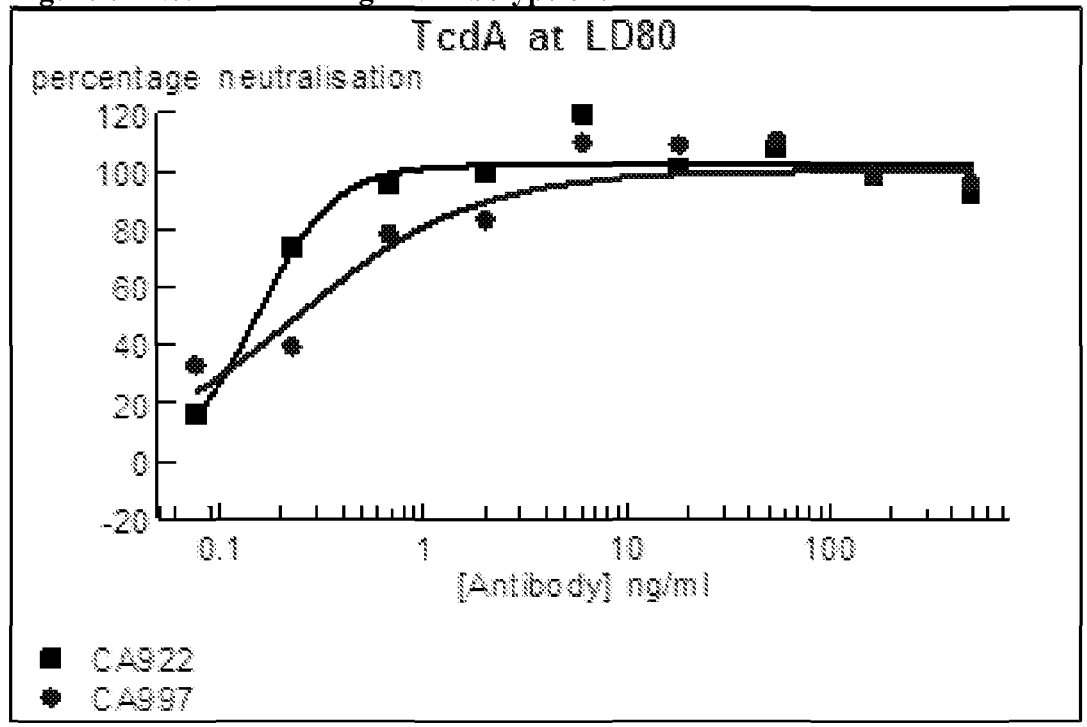

Figure 73 Neutralisation against ribotype 078
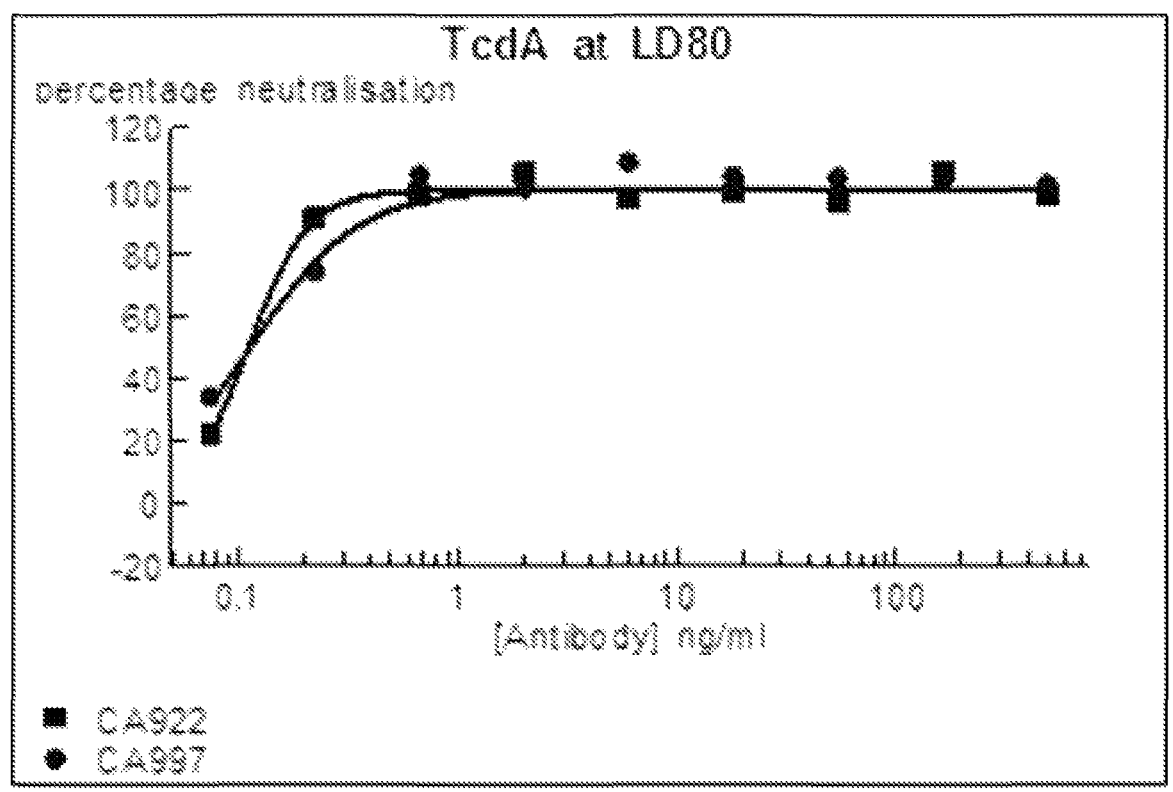

NEUTRALISING ANTIBODIES TO THE MAJOR EXOTOXINS TCDA AND TCDB OF CLOSTRIDIUM DIFFICILE

The present invention relates to antibodies to exotoxins of *Clostridium difficile*, for example TcdA and TcdB, pharmaceutical compositions comprising the same, processes of producing said antibodies and compositions and use of the antibodies and compositions in treatment and/or prophylaxis, in particular treatment or prophylaxis of *Clostridium difficile* infection, pseudomembranous colitis, fulminant colitis and/or toxic mega colon.

The two major exotoxins TcdA and TcdB have been established as the major pathogenicity determinants of *Clostridium difficile* in a large number of in vitro and in vivo studies. Non-toxigenic strains are not pathogenic to animals and man (1, 2). To date a clear understanding of the role of binary toxin has yet to be established (3).

Both toxins are entero- and cyto-toxic, but the balance of evidence suggests that TcdA is a more powerful enterotoxin than TcdB, whilst TcdB is typically observed to be ~1000× more cytotoxic than TcdA (4). Whilst both toxins are capable of inducing an inflammatory response, TcdA appears to aid the migration of the more inflammatory TcdB deeper into the gut mucosa (5).

In toto, a large collection of data generated for over 30 years support a model where both toxins are likely to be important in the human disease process. It is probable that TcdA initiates early (i.e. before TcdB) and rapid (i.e. 1-3 hours) gut damage through loss of tight junctions and destruction of villi tips and hence diarrhoea, probably through albumin driven fluid loss. This damage to the integrity of the gut lining enables TcdB to exert its superior molar potency (TcdB is typically cited as being 1000× more cytotoxic than TcdA) more rapidly and effectively (i.e. deeper into tissue, alternative cellular targets and damaging systemically accessed organs). Either toxin can be effective alone in vitro on human or animals cells and tissues. Either toxin can be effective alone in vivo in animals depending upon other eliciting factors such as mechanical damage, barrier overload and host specific sensitivities. It is now clear that in hamsters at least either TcdA or TcdB alone delivered by a *Clostridium difficile* gut infection can cause death (1). It is well established that A−B+ strains are capable of causing symptoms and death in humans (6,7). However, the majority (~95%) of clinical strains are A+B+ hence drugs aimed at treating *Clostridium difficile* infections (CDI) must be capable of neutralising the activities of and clearing both toxins effectively.

CDI is most typically a nosocomial infection of older patients or those with complicating co-morbidities. However, an increase in community acquired infections has been noted. Infection is almost always associated with or induced by use of broad spectrum antibiotics. Healthcare associated costs are estimated to be in excess of $1bn per annum in the US alone. These costs are primarily due to patients having longer hospitals stays. Current therapies involve the use of antibiotics such as clindamycin, vancomycin or fidaxomicin which kill the *Clostridium difficile* cells within the gut. Current therapies address the bacterial infection but do not deal with or prevent directly the significant pathogenesis caused by TcdA and TcdB which are major contributors to CDI symptoms and mortality.

CDI symptoms in humans include mild to severe diarrhoea, pseudomembranous colitis (PMC) and fulminant colitis or so called toxic mega colon. Death results in 5-15% of patients receiving current best care. Thus at the present time there is no specific therapy available to patients to prevent the damage and injury caused by *C. difficile* toxins after infection.

Raising an antibody response through vaccination and parenteral administration of polyclonal and monoclonal antibodies have all been shown to be capable of protecting animals from symptoms of diarrhoea and death (8-15). Early studies in hamsters suggested that antibodies against TcdA alone were all that was necessary for protection. However, use of strains functionally deleted for TcdA or TcdB demonstrate that either toxin is capable of causing disease in hamsters, but that both toxins together are more effective (1).

For therapeutic applications, monoclonal antibodies (Mabs) can offer efficacy, safety, manufacturing and regulatory advantages over serum derived polyclonal antibodies or serum derived hyper-immune sera. For these reasons Mabs are usually the preferred option for therapeutic products.

There have been a number of attempts to generate protective Mabs against TcdA and TcdB. The most advanced of these in the clinic is a mixture of 2 IgG1 Mabs, one against each TcdA and TcdB originally called CDA1 and MDX1388 developed by MBL and Medarex. They were demonstrated to be unable to fully protect hamsters in models of acute or relapse infections (15). This Mab combination is now being developed as MK3415A by Merck Inc. In a human phase II trial MK3415A resulted in a statistically significant reduction in disease recurrence (p=0.006) (see also Lowy et al., NEJM (2010) 362: 197-205) but did not affect the duration/severity of diarrhoea or death rates (16). This may mean that these antibodies may only be useful for preventing recurrence of infection. Recurrence of infection results in approximately 25% of patients. Thus there likely to be a significant patient population in which these antibodies are not effective.

In order to be able to have a positive influence upon diarrhoea (for example as a result of acute damage to gut tight junctions due to TcdA) and death (for example resulting from prolonged poor nutritional status, dehydration stress and initiation of an inflammatory cascade, widespread anatomical damage to the gut lining and possibly damage to distant organs due to systemic toxin TcdB more so than TcdA) Mabs are required with superior affinity, toxin neutralisation, superior prevention of loss of TEER (transepithelial electrical resistance), antigen decoration and antigen immune clearance.

SUMMARY OF THE PRESENT INVENTION

The present invention provide a Mab(s) with a very high level of potency in vitro and in vivo which have the potential to have an impact upon duration and severity of diarrhoea and death rate in humans suffering from *Clostridium difficile* infection (CDI).

In one embodiment there is provided a monoclonal antibody specific to antigen TcdA or TcdB, wherein the antibody has high affinity for the target antigen and is suitable for reducing the duration and/or severity of diarrhoea and morbidity in a patient with *Clostridium difficile* infection or at risk of said infection.

In one embodiment there is provided a Mab specific to TcdA or TcdB, or a population of at least two Mabs at least one of which is specific to TcdA and at least one of which is specific to TcdB, wherein the $EC_{50}$ of the or each antibody or the combination of antibodies is 200 ng/ml or less, for example 150 ng/ml or less such as 100 ng/ml.

The antibodies of the present disclosure are useful because they are likely to provide a means of treating the severity and duration of symptoms of a primary infection such as diarrhoea in a patient or preventing death and not just prevent the reoccurrence of disease symptoms.

In at least some embodiments the antibodies according to the present disclosure show no reduction in potency in the presence of high concentrations of toxin.

DETAILED DESCRIPTION OF THE PRESENT INVENTION

Specific as employed herein is intended to refer to an antibody that only recognises the antigen to which it is specific or an antibody that has significantly higher binding affinity to the antigen to which is specific compared to binding to antigens to which it is non-specific, for example 5, 6, 7, 8, 9, 10 times higher binding affinity.

Binding affinity may be measured by standard assays such as surface plasmon resonance, such as BIAcore.

In one embodiment the $EC_{50}$ is less than 75, 70, 60, 65, 55, 50, 45, 40, 35, 30, 25, 20, 15, 10, 9, 8, 7, 6, 5, 4, 3, 2, 1.5 ng/ml *Clostridium difficile* infection in cell culture assays and the patient. This is significantly lower (more potent) than known antibodies and is thought to be a major factor as to why the antibodies of the present disclosure have a significant and positive impact on survival of subjects receiving treatment.

As employed herein potency is the ability of the antibody to elicit an appropriate biological response, for example neutralisation of the deleterious toxin effects, at a given dose or concentration. Examples of potency include the percent maximal neutralisation of toxin activity (extent of protection), the lowest relative concentration of Mab to antigen (e.g. $EC_{50}$), the speed and durability of neutralisation activity.

In cell culture assays neutralisation might be observed as one or more of the following: prevention of binding of toxin to cells, immunoprecipitation of toxin from solution, prevention of loss of cell form and shape, prevention of loss of cytoskeletal structures, prevention of loss of cell monolayer tight junctions and trans-epithelial electrical resistance, prevention of cell death, apoptosis and production of pro-inflammatory cytokines such as TNFα, IL-1β, IL-6 and MIP1α.

In tissue section and explant assays neutralisation may, for example be observed as prevention of necrosis and/or oedematous fluid accumulation.

In in vivo assays neutralisation may be observed as one or more of the following: prevention of fluid accumulation in ligated ileal loops and prevention of gut tissue necrosis, diarrhoea, pseudo-membrane formation of death of animals, Thus in one embodiment there is provided an antibody (for example an anti-toxin A antibody) comprising a CDR, such as 1, 2, 3, 4, 5 or 6 CDRs, selected from:

```
                                    SEQ ID NO: 1
QASQSISNALA

SEQ ID NO: 2
SASSLAS

SEQ ID NO: 3
QYTHYSHTSKNP

SEQ ID NO: 4
GFTISSYYMS
```

```
                                    SEQ ID NO: 5
IISSGGHFTWYANWAKG

SEQ ID NO: 6
AYVSGSSFNGYAL
```

In one embodiment sequences 1 to 3 are in a light chain of the antibody.

In one embodiment sequences 4 to 6 are in a heavy chain of the antibody.

In one embodiment SEQ ID NO: 1 is CDR L1, SEQ ID NO: 2 is CDR L2 and SEQ ID NO; 3 is CDR L3.

In one embodiment SEQ ID NO: 4 is CDR H1, SEQ ID NO: 5 is CDR H2 and SEQ ID NO; 6 is CDR H3.

In one embodiment SEQ ID NO: 1 is CDR L1, SEQ ID NO: 2 is CDR L2, SEQ ID NO; 3 is CDR L3, SEQ ID NO: 4 is CDR H1, SEQ ID NO: 5 is CDR H2 and SEQ ID NO; 6 is CDR H3.

In one embodiment there is provided a variable region, such as a light chain variable region with the following sequence (Antibody 922 anti-toxin A antibody; Light chain Variable region sequence) SEQ ID NO: 7:

```
DPVMTQSPSTLSASVGDRVTITCQASQSISNALAWYQQKPGKAPKLLIYS
ASSLASGVPSRFKGSGSGTEFTLTISSLQPDDFATYYCQYTHYSHTSKNP
FGGGTKVEIK
``` wherein the CDRs are underlined and construct is referred to herein as 922.g1 VK (gL1).

The polynucleotide sequence encoding SEQ ID NO: 7 is shown in FIG. 1 and SEQ ID NO: 8 therein.

In one embodiment there is provided a variable region, such as a heavy chain variable region with the following sequence (Antibody 922 anti-toxin A antibody heavy chain variable region sequence) SEQ ID NO: 9:

```
EVQLVESGGGLVQPGGSLRLSCAASGFTISSYYMSWVRQAPGKGLEWIGI
ISSGGHFTWYANWAKGRFTISSDSTTVYLQMNSLRDEDTATYFCARAYVS
GSSFNGYALWGQGTLVTVS
``` wherein the CDRs are underlined and construct is referred to herein as 922.g1 VH (gH1)

The polynucleotide sequence encoding SEQ ID NO: 9 is shown in FIG. 1 and SEQ ID NO: 10 therein.

In one embodiment the antibody comprises the variable regions shown in SEQ ID NO: 7 and 9.

Thus in one embodiment there is provided an antibody (for example an anti-toxin A antibody) comprising a CDR, such as 1, 2, 3, 4, 5 or 6 CDRs, selected from:

```
                                    SEQ ID NO: 11
QASQSISNYLA

SEQ ID NO: 12
SASTLAS

SEQ ID NO: 13
QYSHYGTGVFGA

SEQ ID NO: 14
AFSLSNYYMS
```

-continued

IISSGSNALKWYASWPKG
SEQ ID NO: 15

NYVGSGSYYGMDL
SEQ ID NO: 16

In one embodiment sequences 11 to 13 are in a light chain of the antibody.

In one embodiment sequences 14 to 16 are in a heavy chain of the antibody.

In one embodiment SEQ ID NO: 11 is CDR L1, SEQ ID NO: 12 is CDR L2 and SEQ ID NO: 13 is CDR L3.

In one embodiment SEQ ID NO: 14 is CDR H1, SEQ ID NO: 15 is CDR H2 and SEQ ID NO; 16 is CDR H3.

In one embodiment SEQ ID NO: 11 is CDR L1, SEQ ID NO: 12 is CDR L2, SEQ ID NO: 13 is CDR L3, SEQ ID NO: 14 is CDR H1, SEQ ID NO: 15 is CDR H2 and SEQ ID NO; 16 is CDR H3.

In one embodiment there is provided a variable region, such as a light chain variable region with the following sequence (Antibody 923 anti-toxin A antibody; Light chain Variable region sequence) SEQ ID NO: 17:

DVVMTQSPSSLSASVGDRVTITCQASQSISNYLAWYQQKPGKVPKLLIYS

ASTLASGVPSRFKGSGSGTQFTLTISSLQPEDVATYYCQYSHYGTGVFGA

FGGGTKVEIK wherein the CDRs are underlined and construct is referred to herein as CA923.g1 gL1

The polynucleotide sequence encoding SEQ ID NO: 17 is shown in FIG. 1 and SEQ ID NO: 18 therein.

In one embodiment there is provided a variable region, such as a heavy chain variable region with the following sequence (Antibody 923 anti-toxin A antibody heavy chain variable region sequence) SEQ ID NO: 19:

EVQLVESGGGLVQPGGSLRLSCAASAFSLSNYYMSWVRQAPGKGLEWIGI

ISSGSNALKWYASWPKGRFTISKDSTTVYLQMNSLRAEDTATYFCARNYV

GSGSYYGMDLWGQGTLVTVS wherein the CDRs are underlined and construct is referred to herein as CA923.g1 gH1

The polynucleotide sequence encoding SEQ ID NO: 19 is shown in FIG. 2 and SEQ ID NO: 20 therein.

In one embodiment an antibody according to the invention comprises variable regions shown in SEQ ID NO 17: and SEQ ID NO: 19.

In one embodiment there is provided an antibody (for example an anti-toxin A antibody) comprising a CDR, such as 1, 2, 3, 4, 5 or 6 CDRs, selected from:

QASQSISSYFS
SEQ ID NO: 21

GASTLAS
SEQ ID NO: 22

QCTDYSGIYFGG
SEQ ID NO: 23

GFSLSSYYMS
SEQ ID NO: 24

IISSGSSTTFTWYASWAKG
SEQ ID NO: 25

AYVGSSSYYGFDP
SEQ ID NO: 26

In one embodiment sequences 21 to 23 are in a light chain of the antibody.

In one embodiment sequences 24 to 26 are in a heavy chain of the antibody.

In one embodiment SEQ ID NO: 21 is CDR L1, SEQ ID NO: 22 is CDR L2 and SEQ ID NO; 23 is CDR L3.

In one embodiment SEQ ID NO: 24 is CDR H1, SEQ ID NO: 25 is CDR H2 and SEQ ID NO; 26 is CDR H3.

In one embodiment SEQ ID NO: 21 is CDR L1, SEQ ID NO: 22 is CDR L2, SEQ ID NO; 23 is CDR L3, SEQ ID NO: 24 is CDR H1, SEQ ID NO: 25 is CDR H2 and SEQ ID NO; 26 is CDR H3.

In one embodiment there is provided a variable region, such as a light chain variable region with the following sequence (Antibody 993 anti-toxin A antibody; Light chain Variable region sequence) SEQ ID NO: 27:

DVVMTQSPSTLSASVGDRVTITCQASQSISSYFSWYQQKP

GKAPQLLIYGASTLASGVPSRFKGSGSGTELTLTISSLQP

DDFATYYCQCTDYSGIYFGGFGGGTKVEIK wherein the CDRs are underlined and construct is referred to herein as CA993.g1 gL1

The polynucleotide sequence encoding SEQ ID NO: 27 is shown in FIG. 2 and SEQ ID NO: 28 therein.

In one embodiment there is provided a variable region, such as a heavy chain variable region with the following sequence (Antibody 993 anti-toxin A antibody heavy chain variable region sequence) SEQ ID NO: 29:

EVQLVESGGGLVQPGGSLKLSCTASGFSLSSYYMSWVRQAP

GKGLEWIGIISSGSSTTFTWYASWAKGRFTISKTSTTVYLQ

MNSLKTEDTATYFCARAYVGSSSYYGFDPWGQGTLVTVS wherein the CDRs are underlined and construct is referred to herein as CA993.g1 gH1

The polynucleotide sequence encoding SEQ ID NO: 29 is shown in FIG. 2 and SEQ ID NO: 30 therein.

In one embodiment an antibody according to the invention comprises variable regions shown in SEQ ID NO: 27 and SEQ ID NO: 29.

In one embodiment there is provided an antibody (for example an anti-toxin A antibody) comprising a CDR, such as 1, 2, 3, 4, 5 or 6 CDRs, selected from:

QASQSINNYFS
SEQ ID NO: 31

GAANLAS
SEQ ID NO: 32

QNNYGVHIYGAA
SEQ ID NO: 33

GFSLSNYDMI
SEQ ID NO: 34

```
                                        SEQ ID NO: 35
            FINTGGITYYASWAKG

SEQ ID NO: 36
            VDDYIGAWGAGL
```

In one embodiment sequences 31 to 33 are in a light chain of the antibody.

In one embodiment sequences 34 to 36 are in a heavy chain of the antibody.

In one embodiment SEQ ID NO: 31 is CDR L1, SEQ ID NO: 32 is CDR L2 and SEQ ID NO; 33 is CDR L3.

In one embodiment SEQ ID NO: 34 is CDR H1, SEQ ID NO: 35 is CDR H2 and SEQ ID NO: 36 is CDR H3.

In one embodiment SEQ ID NO: 31 is CDR L1, SEQ ID NO: 32 is CDR L2, SEQ ID NO; 33 is CDR L3, SEQ ID NO: 34 is CDR H1, SEQ ID NO: 35 is CDR H2 and SEQ ID NO; 36 is CDR H3.

In one embodiment there is provided a variable region, such as a light chain variable region with the following sequence (Antibody 995 anti-toxin A antibody; Light chain Variable region sequence) SEQ ID NO: 37:

```
            DVVMTQSPSTLSASVGDRVTITCQASQSINNYFSWYQQKP

GKAPKLLIYGAANLASGVPSRFKGSGSGTEYTLTISSLQP

DDFATYSCQNNYGVHIYGAAFGGGTKVEIK
``` wherein the CDRs are underlined

The polynucleotide sequence encoding SEQ ID NO: 37 is shown in FIG. 3 and SEQ ID NO: 38 therein.

In one embodiment there is provided a variable region, such as a heavy chain variable region with the following sequence (Antibody 995 anti-toxin A antibody heavy chain variable region sequence) SEQ ID NO: 39

```
            EVQLVESGGGLVQPGGSLRLSCTASGFSLSNYDMIWVRQAP

GKGLEYIGFINTGGITYYASWAKGRFTISRDSSTVYLQMNS

LRAEDTATYFCARVDDYIGAWGAGLWGQGTLVTVS
``` wherein the CDRs are underlined

The polynucleotide sequence encoding SEQ ID NO: 39 is shown in FIG. 3 and SEQ ID NO: 40 therein.

In one embodiment an antibody according to the invention comprises variable regions shown in SEQ ID NO: 37 and SEQ ID NO: 39.

In one embodiment there is provided an antibody (for example an anti-toxin A antibody) comprising a CDR, such as 1, 2, 3, 4, 5 or 6 CDRs, selected from:

```
                                        SEQ ID NO: 41
            QASQSISSYLS

SEQ ID NO: 42
            RASTLAS

SEQ ID NO: 43
            LGVYGYSNDDGIA

SEQ ID NO: 44
            GIDLSSHHMC
```

```
                                        SEQ ID NO: 45
            VIYHFGSTYYANWATG

SEQ ID NO: 46
            ASIAGYSAFDP
```

In one embodiment sequences 41 to 43 are in a light chain of the antibody.

In one embodiment sequences 44 to 46 are in a heavy chain of the antibody.

In one embodiment SEQ ID NO: 41 is CDR L1, SEQ ID NO: 42 is CDR L2 and SEQ ID NO; 43 is CDR L3.

In one embodiment SEQ ID NO: 44 is CDR H1, SEQ ID NO: 45 is CDR H2 and SEQ ID NO: 46 is CDR H3.

In one embodiment SEQ ID NO: 41 is CDR L1, SEQ ID NO: 42 is CDR L2, SEQ ID NO; 43 is CDR L3, SEQ ID NO: 44 is CDR H1, SEQ ID NO: 45 is CDR H2 and SEQ ID NO; 46 is CDR H3.

In one embodiment there is provided a variable region, such as a light chain variable region with the following sequence (Antibody 997 anti-toxin A antibody; Light chain Variable region sequence) SEQ ID NO: 47:

```
            ALVMTQSPSSFSASTGDRVTITCQASQSISSYLSWYQQKP

GKAPKLLIYRASTLASGVPSRFSGSGSGTEYTLTISCLQS

EDFATYYCLGVYGYSNDDGIAFGGGTKVEIK
``` wherein the CDRs are underlined

The polynucleotide sequence encoding SEQ ID NO: 47 is shown in FIG. 3 and SEQ ID NO: 48 therein.

In one embodiment there is provided a variable region, such as a heavy chain variable region with the following sequence (Antibody 997 anti-toxin A antibody heavy chain variable region sequence) SEQ ID NO: 49:

```
            EVQLVESGGGLVQPGGSLRLSCTVSGIDLSSHHMCWVRQAP

GKGLEYIGVIYHFGSTYYANWATGRFTISKDSTTVYLQMNS

LRAEDTATYFCARASIAGYSAFDPWGQGTLVTVS
``` wherein the CDRs are underlined

The polynucleotide sequence encoding SEQ ID NO: 49 is shown in FIG. 4 and SEQ ID NO: 50 therein.

In one embodiment an antibody according to the invention comprises variable regions shown in SEQ ID NO: 47 and SEQ ID NO: 49.

In one embodiment there is provided an antibody (for example an anti-toxin A antibody) comprising a CDR, such as 1, 2, 3, 4, 5 or 6 CDRs, selected from:

```
                                        SEQ ID NO: 51
            QASQSIYSYLA

SEQ ID NO: 52
            DASTLAS

SEQ ID NO: 53
            QGNAYTSNSHDNA

SEQ ID NO: 54
            GIDLSSDAVG

SEQ ID NO: 55
            IIATFDSTYYASWAKG

SEQ ID NO: 56
            TGSWYYISGWGSYYYGMDL
```

In one embodiment sequences 51 to 53 are in a light chain of the antibody.

In one embodiment sequences 54 to 56 are in a heavy chain of the antibody.

In one embodiment SEQ ID NO: 51 is CDR L1, SEQ ID NO: 52 is CDR L2 and SEQ ID NO: 53 is CDR L3.

In one embodiment SEQ ID NO: 54 is CDR H1, SEQ ID NO: 55 is CDR H2 and SEQ ID NO; 56 is CDR H3.

In one embodiment SEQ ID NO: 51 is CDR L1, SEQ ID NO: 52 is CDR L2, SEQ ID NO; 53 is CDR L3, SEQ ID NO: 54 is CDR H1, SEQ ID NO: 55 is CDR H2 and SEQ ID NO: 56 is CDR H3.

In one embodiment there is provided a variable region, such as a light chain variable region with the following sequence (Antibody 1000 anti-toxin A antibody; Light chain Variable region sequence) SEQ ID NO: 57:

```
EIVMTQSPSTLSASVGDRVTITCQASQSIYSYLAWYQQKP

GKAPKLLIYDASTLASGVPSRFKGSGSGTEFTLTISSLQP

DDFATYYCQGNAYTSNSHDNAFGGGTKVEIK
``` wherein the CDRs are underlined.

The polynucleotide sequence encoding SEQ ID NO: 57 is shown in FIG. 4 and SEQ ID NO: 58 therein.

In one embodiment there is provided a variable region, such as a heavy chain variable region with the following sequence (Antibody 1000 anti-toxin A antibody heavy chain variable region sequence) SEQ ID NO: 59:

```
EVQLVESGGGLIQPGGSLRLSCTVSGIDLSSDAVGWVRQAPG

KGLEYIGIIATFDSTYYASWAKGRFTISKASSTTVYLQMNSL

RAEDTATYFCARTGSWYYISGWGSYYYGMDLWGQGTLVTVS
``` wherein the CDRs are underlined.

The polynucleotide sequence encoding SEQ ID NO: 59 is shown in FIG. 4 and SEQ ID NO: 60 therein.

In one embodiment an antibody according to the invention comprises variable regions shown in SEQ ID NO: 57 and SEQ ID NO: 59.

In one embodiment there is provided an antibody (for example an anti-toxin B antibody) comprising a CDR, such as 1, 2, 3, 4, 5 or 6 CDRs, selected from:

```
RASKSVSTLMH              SEQ ID NO: 61

LASNLES                  SEQ ID NO: 62

QQTWNDPWT                SEQ ID NO: 63

GFTFSNYGMA               SEQ ID NO: 64

SISSSGGSTYYRDSVKG        SEQ ID NO: 65

VIRGYVMDA                SEQ ID NO: 66
```

In one embodiment sequences 61 to 63 are in a light chain of the antibody.

In one embodiment sequences 64 to 66 are in a heavy chain of the antibody.

In one embodiment SEQ ID NO: 61 is CDR L1, SEQ ID NO: 62 is CDR L2 and SEQ ID NO: 63 is CDR L3.

In one embodiment SEQ ID NO: 64 is CDR H1, SEQ ID NO: 65 is CDR H2 and SEQ ID NO: 66 is CDR H3.

In one embodiment SEQ ID NO: 61 is CDR L1, SEQ ID NO: 62 is CDR L2, SEQ ID NO; 63 is CDR L3, SEQ ID NO: 64 is CDR H1, SEQ ID NO: 65 is CDR H2 and SEQ ID NO: 66 is CDR H3.

In one embodiment there is provided a variable region, such as a light chain variable region with the following sequence (Antibody 926 anti-toxin B antibody; Light chain Variable region sequence) SEQ ID NO: 67:

```
DTVLTQSPATLSLSPGERATLSCRASKSVSTLMHWFQQKP

GQAPKLLIYLASNLESGVPARFSGSGSGTDFTLTISSLEP

EDFAVYYCQQTWNDPWTFGGGTKVEIK
``` wherein the CDRs are underlined.

The polynucleotide sequence encoding SEQ ID NO: 67 is shown in FIG. 5 and SEQ ID NO: 68 therein.

In one embodiment there is provided a variable region, such as a heavy chain variable region with the following sequence (Antibody 926 anti-toxin B antibody heavy chain variable region sequence) SEQ ID NO: 69:

```
EVELLESGGGLVQPGGSLRLSCEASGFTFSNYGMAWVRQAP

TKGLEWVTSISSSGGSTYYRDSVKGRFTISRDNAKSSLYLQ

MNSLRAEDTATYYCTTVIRGYVMDAWGQGTLVTVS
``` wherein the CDRs are underlined.

The polynucleotide sequence encoding SEQ ID NO: 69 is shown in FIG. 5 and SEQ ID NO: 70 therein.

In one embodiment there is provided an antibody (for example an anti-toxin B antibody) comprising a CDR, such as 1, 2, 3, 4, 5 or 6 CDRs, selected from:

```
RASGSVSTLMH              SEQ ID NO: 71

KASNLAS                  SEQ ID NO: 72

HQSWNSDT                 SEQ ID NO: 73

GFTFSNYGMA               SEQ ID NO: 74

TINYDGRTTHYRDSVKG        SEQ ID NO: 75

ISRSHYFDC                SEQ ID NO: 76
```

In one embodiment sequences 71 to 73 are in a light chain of the antibody.

In one embodiment sequences 74 to 76 are in a heavy chain of the antibody.

In one embodiment SEQ ID NO: 71 is CDR L1, SEQ ID NO: 72 is CDR L2 and SEQ ID NO: 73 is CDR L3.

In one embodiment SEQ ID NO: 74 is CDR H1, SEQ ID NO: 75 is CDR H2 and SEQ ID NO: 76 is CDR H3.

In one embodiment SEQ ID NO: 71 is CDR L1, SEQ ID NO: 72 is CDR L2, SEQ ID NO; 73 is CDR L3, SEQ ID NO: 74 is CDR H1, SEQ ID NO: 75 is CDR H2 and SEQ ID NO: 76 is CDR H3.

In one embodiment there is provided a variable region, such as a light chain variable region with the following sequence (Antibody 927 anti-toxin B antibody; Light chain Variable region sequence) SEQ ID NO: 77:

DTQMTQSPSTLSASVGDRVTITC<u>RASGSVSTLMH</u>WYQQKPGKAPKLLIY<u>K</u>

<u>ASNLAS</u>GVPSRFSGSGSGTEFTLTISSLQPDDFATYYC<u>HQSWNSDT</u>FGQG

TRLEIK wherein the CDRs are underlined

The polynucleotide sequence encoding SEQ ID NO: 77 is shown in FIG. 5 and SEQ ID NO: 78 therein.

In one embodiment there is provided a variable region, such as a heavy chain variable region with the following sequence (Antibody 927 anti-toxin B antibody heavy chain variable region sequence) SEQ ID NO: 79:

EVQLVESGGGVVQPGRSLRLSCAAS<u>GFTFSNYGMA</u>WVRQAPGKGLEWVA<u>T</u>

<u>INYDGRTTHYRDSVKG</u>RFTISRDNSKSTLYLQMNSLRAEDTAVYYCTS<u>IS</u>

<u>RSHYFDC</u>WGQGTLVTVS wherein the CDRs are underlined.

The polynucleotide sequence encoding SEQ ID NO: 79 is shown in FIG. 5 and SEQ ID NO: 80 therein.

In one embodiment an antibody according to the invention comprises variable regions shown in SEQ ID NO: 77 and SEQ ID NO: 79.

In one embodiment there is provided an antibody (for example an anti-toxin B antibody) comprising a CDR, such as 1, 2, 3, 4, 5 or 6 CDRs, selected from:

KASKSISNHLA SEQ ID NO: 81

SGSTLQS SEQ ID NO: 82

QQYDEYPYT SEQ ID NO: 83

GFSLQSYTIS SEQ ID NO: 84

AISGGGSTYYNLPLKS SEQ ID NO: 85

PRWYPRSYFDY SEQ ID NO: 86

In one embodiment sequences 81 to 83 are in a light chain of the antibody.

In one embodiment sequences 84 to 86 are in a heavy chain of the antibody.

In one embodiment SEQ ID NO: 81 is CDR L1, SEQ ID NO: 82 is CDR L2 and SEQ ID NO: 83 is CDR L3.

In one embodiment SEQ ID NO: 84 is CDR H1, SEQ ID NO: 85 is CDR H2 and SEQ ID NO: 86 is CDR H3.

In one embodiment SEQ ID NO: 81 is CDR L1, SEQ ID NO: 82 is CDR L2, SEQ ID NO; 83 is CDR L3, SEQ ID NO: 84 is CDR H1, SEQ ID NO: 85 is CDR H2 and SEQ ID NO: 86 is CDR H3.

In one embodiment there is provided a variable region, such as a light chain variable region with the following sequence (Antibody 1099 anti-toxin B antibody; Light chain Variable region sequence) SEQ ID NO: 87:

DVQLTQSPSFLSASVGDRVTITC<u>KASKSISNHLA</u>WYQEKPGKANKLLIH<u>S</u>

<u>GSTLQS</u>GTPSRFSGSGSGTEFTLTISSLQPEDFATYYC<u>QQYDEYPYT</u>

FGQGTRLEIKRT wherein the CDRs are underlined.

In one embodiment the last two amino acids (RT) of SEQ ID NO: 87 are omitted.

The polynucleotide sequence encoding SEQ ID NO: 87 is shown in FIG. 6 and SEQ ID NO: 88 therein. In one embodiment the codons encoding the last two amino acids (RT) are omitted.

In one embodiment there is provided a variable region, such as a heavy chain variable region with the following sequence (Antibody 1099 anti-toxin B antibody heavy chain variable region sequence) SEQ ID NO: 89:

EVQLQESGPGLVKPSETLSLTCTVS<u>GFSLQSYTIS</u>WVRQPPGKGLEWIA<u>A</u>

<u>ISGGGSTYYNLPLKS</u>RVTISRDTSKSQVSLKLSSVTAADTAVYYCTR<u>PRW</u>

<u>YPRSYFDY</u>WGRGTLVTVS wherein the CDRs are underlined

The polynucleotide sequence encoding SEQ ID NO: 89 is shown in FIG. 6 and SEQ ID NO: 90 therein.

In one embodiment an antibody according to the invention comprises variable regions shown in SEQ ID NO 87: and SEQ ID NO: 89.

In one embodiment there is provided an antibody (for example an anti-toxin B antibody) comprising a CDR, such as 1, 2, 3, 4, 5 or 6 CDRs, selected from:

RASQRISTSIH SEQ ID NO: 91

YASQSIS SEQ ID NO: 92

QQSYSSLYT SEQ ID NO: 93

GFTFSDSYMA SEQ ID NO: 94

SISYGGTIIQYGDSVKG SEQ ID NO: 95

RQGTYARYLDF SEQ ID NO: 96

In one embodiment sequences 91 to 93 are in a light chain of the antibody.

In one embodiment sequences 94 to 96 are in a heavy chain of the antibody.

In one embodiment SEQ ID NO: 91 is CDR L1, SEQ ID NO: 92 is CDR L2 and SEQ ID NO; 93 is CDR L3.

In one embodiment SEQ ID NO: 94 is CDR H1, SEQ ID NO: 95 is CDR H2 and SEQ ID NO: 96 is CDR H3.

In one embodiment SEQ ID NO: 91 is CDR L1, SEQ ID NO: 92 is CDR L2, SEQ ID NO; 93 is CDR L3, SEQ ID NO: 94 is CDR H1, SEQ ID NO: 95 is CDR H2 and SEQ ID NO: 96 is CDR H3.

In one embodiment there is provided a variable region, such as a light chain variable region with the following sequence (Antibody 1102 anti-toxin B antibody; Light chain Variable region sequence) SEQ ID NO: 97:

NIVLTQSPATLSLSPGERATLSCRASQRISTSIHWYQQKPGQAPRLLIKY

ASQSISGIPARFSGSGSGTDFTLTISSLEPEDFAVYYCQQSYSSLYTFGQ

GTKLEIK wherein the CDRs are underlined

The polynucleotide sequence encoding SEQ ID NO: 97 is shown in FIG. 6 and SEQ ID NO: 98 therein.

In one embodiment there is provided a variable region, such as a heavy chain variable region with the following sequence (Antibody 1102 anti-toxin B antibody heavy chain variable region sequence) SEQ ID NO: 99:

EVQLVESGGGLVQPGGSLRLSCAVSGFTFSDSYMAWVRQAPGKGLEWIAS

ISYGGTIIQYGDSVKGRFTISRDNAKSSLYLQMNSLRAEDTAVYYCARRQ

GTYARYLDFWGQGTLVTVS wherein the CDRs are underlined.

The polynucleotide sequence encoding SEQ ID NO: 99 is shown in FIG. 7 and SEQ ID NO: 100 therein.

In one embodiment an antibody according to the invention comprises variable regions shown in SEQ ID NO 97: and SEQ ID NO: 99.

In one embodiment there is provided an antibody (for example an anti-toxin B antibody) comprising a CDR, such as 1, 2, 3, 4, 5 or 6 CDRs, selected from:

RASESVSTLLH     SEQ ID NO: 101

KASNLAS         SEQ ID NO: 102

HQSWNSPPT       SEQ ID NO: 103

GFTFSNYGMA      SEQ ID NO: 104

IINYDASTTHYRDSVKG   SEQ ID NO: 105

YGRSHYFDY       SEQ ID NO: 106

In one embodiment sequences 101 to 103 are in a light chain of the antibody.

In one embodiment sequences 104 to 106 are in a heavy chain of the antibody.

In one embodiment SEQ ID NO: 101 is CDR L1, SEQ ID NO: 102 is CDR L2 and SEQ ID NO: 103 is CDR L3.

In one embodiment SEQ ID NO: 104 is CDR H1, SEQ ID NO: 105 is CDR H2 and SEQ ID NO: 106 is CDR H3.

In one embodiment SEQ ID NO: 101 is CDR L1, SEQ ID NO: 102 is CDR L2, SEQ ID NO; 103 is CDR L3, SEQ ID NO: 104 is CDR H1, SEQ ID NO: 105 is CDR H2 and SEQ ID NO; 106 is CDR H3.

In one embodiment there is provided a variable region, such as a light chain variable region with the following sequence (Antibody 1114 anti-toxin B antibody; Light chain Variable region sequence) SEQ ID NO: 107:

ATQMTQSPSSLSASVGDRVTITCRASESVSTLLHWYQQKPGKAPKLLIYK

ASNLASGVPSRFSGSGSGTDFTLTISSLQPEDFATYYCHQSWNSPPTFG

QGTKLEIK wherein the CDRs are underlined.

The polynucleotide sequence encoding SEQ ID NO: 107 is shown in FIG. 7 and SEQ ID NO: 108 therein.

In one embodiment there is provided a variable region, such as a heavy chain variable region with the following sequence (Antibody 1114 anti-toxin B antibody heavy chain variable region sequence) SEQ ID NO: 109:

EVQLVESGGGLVQPGGSLRLSCAASGFTFSNYGMAWVRQAPGKGLEWVAI

INYDASTTHYRDSVKGRFTISRDNAKSSLYLQMNSLRAEDTAVYYCTRYG

RSHYFDYWGQGTLVTVS wherein the CDRs are underlined.

The polynucleotide sequence encoding SEQ ID NO: 109 is shown in FIG. 7 and SEQ ID NO: 110 therein.

In one embodiment an antibody according to the invention comprises variable regions shown in SEQ ID NO: 107 and SEQ ID NO: 109.

In one embodiment there is provided an antibody (for example an anti-toxin B antibody) comprising a CDR, such as 1, 2, 3, 4, 5 or 6 CDRs, selected from:

RASESVSTLLH     SEQ ID NO: 111

KASNLAS         SEQ ID NO: 112

HQSWNSPPT       SEQ ID NO: 113

GFTFSNYGMA      SEQ ID NO: 114

IINYDASTTHYRDSVK    SEQ ID NO: 115

YGRSHYFDY       SEQ ID NO: 116

In one embodiment sequences 111 to 113 are in a light chain of the antibody.

In one embodiment sequences 114 to 116 are in a heavy chain of the antibody.

In one embodiment SEQ ID NO: 111 is CDR L1, SEQ ID NO: 112 is CDR L2 and SEQ ID NO: 113 is CDR L3.

In one embodiment SEQ ID NO: 114 is CDR H1, SEQ ID NO: 115 is CDR H2 and SEQ ID NO: 116 is CDR H3.

In one embodiment SEQ ID NO: 111 is CDR L1, SEQ ID NO: 112 is CDR L2, SEQ ID NO; 113 is CDR L3, SEQ ID NO: 114 is CDR H1, SEQ ID NO: 115 is CDR H2 and SEQ ID NO: 116 is CDR H3.

In one embodiment there is provided a variable region, such as a light chain variable region with the following sequence (Antibody 1114 graft 8 anti-toxin B antibody; Light chain Variable region sequence) SEQ ID NO: 117:

DTVLTQSPSSLSASVGDRVTITC<u>RASESVSTLLH</u>WYQQKPGKAPKLLIY<u>K

ASNLAS</u>GVPSRFSGSGSGTDFTLTISSLQPEDFATYYC<u>HQSWNSPPT</u>FGQ

GTKLEIK wherein the CDRs are underlined.

The polynucleotide sequence encoding SEQ ID NO: 117 is shown in FIG. 8 and SEQ ID NO: 118 therein.

In one embodiment there is provided a variable region, such as a heavy chain variable region with the following sequence (Antibody 1114 graft 8 anti-toxin B antibody heavy chain variable region sequence) SEQ ID NO: 119:

EVQLVESGGGLVQPGGSLRLSCAAS<u>GFTFSNYGMA</u>WVRQAPGKGLEWVA<u>I

INYDASTTHYRD</u>SVKGRFTISRDNAKSSLYLQMNSLRAEDTAVYYCTR<u>YG

RSHYFDY</u>WGQGTLVTVS wherein the CDRs are underlined.

The polynucleotide sequence encoding SEQ ID NO: 119 is shown in FIG. 8 and SEQ ID NO: 120 therein.

In one embodiment an antibody according to the invention comprises variable regions shown in SEQ ID NO: 117 and SEQ ID NO: 119.

In one embodiment there is provided an antibody (for example an anti-toxin B antibody) comprising a CDR, such as 1, 2, 3, 4, 5 or 6 CDRs, selected from:

KASQNIYMYLN SEQ ID NO: 121

NTNKLHT SEQ ID NO: 122

LQHKSFPYT SEQ ID NO: 123

GFTFRDSFMA SEQ ID NO: 124

SISYEGDKTYYGDSVKG SEQ ID NO: 125

LTITTSGDS SEQ ID NO: 126

In one embodiment sequences 121 to 123 are in a light chain of the antibody.

In one embodiment sequences 124 to 126 are in a heavy chain of the antibody.

In one embodiment SEQ ID NO: 121 is CDR L1, SEQ ID NO: 122 is CDR L2 and SEQ ID NO: 123 is CDR L3.

In one embodiment SEQ ID NO: 124 is CDR H1, SEQ ID NO: 125 is CDR H2 and SEQ ID NO: 126 is CDR H3.

In one embodiment SEQ ID NO: 121 is CDR L1, SEQ ID NO: 122 is CDR L2, SEQ ID NO: 123 is CDR L3, SEQ ID NO: 124 is CDR H1, SEQ ID NO: 125 is CDR H2 and SEQ ID NO: 126 is CDR H3.

In one embodiment there is provided a variable region, such as a light chain variable region with the following sequence (Antibody 1125 anti-toxin B antibody; Light chain Variable region sequence) SEQ ID NO: 127:

DIQMTQSPSSLSASVGDRVTITC<u>KASQNIYMYLN</u>WYQQKPGKAPKRLIY

<u>NTNKLH</u>TGVPSRFSGSGSGTEYTLTISSLQPEDFATYYC<u>LQHKSFPYT</u>

GQGTKLEIK wherein the CDRs are underlined.

The polynucleotide sequence encoding SEQ ID NO: 127 is shown in FIG. 8 and SEQ ID NO: 128 therein.

In one embodiment there is provided a variable region, such as a heavy chain variable region with the following sequence (Antibody 1125 anti-toxin B antibody heavy chain variable region sequence) SEQ ID NO: 129:

EVQLVESGGGLVQPGGSLRLSCAAS<u>GFTFRDSFMA</u>WVRQAPGKGLEWVA

<u>SISYEGDKTYYGDSVKG</u>RFTISRDNAKNSLYLQMNSLRAEDTAVYYCAR

<u>LTITTSGDS</u>WGQGTMVTVSS wherein the CDRs are underlined.

In one embodiment the last amino acid (S) of SEQ ID NO: 129 is omitted.

The polynucleotide sequence encoding SEQ ID NO: 129 is shown in FIG. 9 and SEQ ID NO: 130 therein. In one embodiment the codon AGC encoding the last amino acid S is omitted.

In one embodiment an antibody according to the invention comprises variable regions shown in SEQ ID NO: 127 and SEQ ID NO: 129.

In one embodiment there is provided antibody (for example an anti-toxin B antibody) comprising a CDR, such as 1, 2, 3, 4, 5 or 6 CDRs, selected from:

KASQHVGTNVD SEQ ID NO: 131

GASIRYT SEQ ID NO: 132

LQYNYNPYT SEQ ID NO: 133

GFIFSNFGMS SEQ ID NO: 134

SISPSGGNAYYRDSVKG SEQ ID NO: 135

RAYSSPFAF SEQ ID NO: 136

In one embodiment sequences 131 to 133 are in a light chain of the antibody.

In one embodiment sequences 134 to 136 are in a heavy chain of the antibody.

In one embodiment SEQ ID NO: 131 is CDR L1, SEQ ID NO: 132 is CDR L2 and SEQ ID NO: 133 is CDR L3.

In one embodiment SEQ ID NO: 134 is CDR H1, SEQ ID NO: 135 is CDR H2 and SEQ ID NO: 136 is CDR H3.

In one embodiment SEQ ID NO: 131 is CDR L1, SEQ ID NO: 132 is CDR L2, SEQ ID NO: 133 is CDR L3, SEQ ID NO: 134 is CDR H1, SEQ ID NO: 135 is CDR H2 and SEQ ID NO: 136 is CDR H3.

In one embodiment there is provided a variable region, such as a light chain variable region with the following sequence (Antibody 1129 anti-toxin B antibody; Light chain Variable region sequence) SEQ ID NO: 137:

DTQMTQSPSSLSASVGDRVTITC<u>KASQHVGTNVD</u>WYQQKPGKVPKLLIY

<u>GASIRYT</u>GVPDRFTGSGSGTDFTLTISSLQPEDVATYYC<u>LQYNYNPYT</u>F

GQGTKLEIK wherein the CDRs are underlined.

The polynucleotide sequence encoding SEQ ID NO: 137 is shown in FIG. 8 and SEQ ID NO: 138 therein.

In one embodiment there is provided a variable region, such as a heavy chain variable region with the following sequence (Antibody 1129 anti-toxin B antibody heavy chain variable region sequence) SEQ ID NO: 139:

EVQLVESGGGVVQPGRSLRLSCATS<u>GFIFSNFGMS</u>WVRQAPGKGLEWVA<u>SISPSGGNAYYRDSVKG</u>RFTISRDNSKTTLYLQMNSLRAEDTAVYYCTR<u>RAYSSPFAF</u>WGQGTLVTVSS wherein the CDRs are underlined.

In one embodiment the last amino acid (S) of SEQ ID NO: 139 is omitted.

The polynucleotide sequence encoding SEQ ID NO: 139 is shown in FIG. 8 and SEQ ID NO: 140 therein. In one embodiment the codon AGC encoding the last amino acid S is omitted.

In one embodiment an antibody according to the invention comprises variable regions shown in SEQ ID NO: 137 and SEQ ID NO: 139.

In one embodiment there is provided an antibody (for example an anti-toxin B antibody) comprising a CDR, such as 1, 2, 3, 4, 5 or 6 CDRs, selected from:

KASKSISNHLA  SEQ ID NO: 141

SGSTLQP  SEQ ID NO: 142

QQYDEYPYT  SEQ ID NO: 143

GFSLNSYTIT  SEQ ID NO: 144

AISGGGSTYFNSALKS  SEQ ID NO: 145

PRWYPRSYFDY  SEQ ID NO: 146

In one embodiment sequences 141 to 143 are in a light chain of the antibody.

In one embodiment sequences 144 to 146 are in a heavy chain of the antibody.

In one embodiment SEQ ID NO: 141 is CDR L1, SEQ ID NO: 142 is CDR L2 and SEQ ID NO: 143 is CDR L3.

In one embodiment SEQ ID NO: 144 is CDR H1, SEQ ID NO: 145 is CDR H2 and SEQ ID NO: 146 is CDR H3.

In one embodiment SEQ ID NO: 141 is CDR L1, SEQ ID NO: 142 is CDR L2, SEQ ID NO: 143 is CDR L3, SEQ ID NO: 144 is CDR H1, SEQ ID NO: 145 is CDR H2 and SEQ ID NO: 146 is CDR H3.

In one embodiment there is provided a variable region, such as a light chain variable region with the following sequence (Antibody 1134 anti-toxin B antibody; Light chain Variable region sequence):

SEQ ID NO: 147
DVQLTQSPSFLSASVGDRVTITC<u>KASKSISNHLA</u>WYQEKPGKANKLLIH<u>SGSTLQP</u>GTPSRFSGSGSGTEFTLTISSLQPEDFATYYC<u>QQYDEYPYT</u>FGQGTRLEIK wherein the CDRs are underlined.

The polynucleotide sequence encoding SEQ ID NO: 147 is shown in FIG. 9 and SEQ ID NO: 148 therein.

In one embodiment there is provided a variable region, such as a heavy chain variable region with the following sequence (Antibody 1134 anti-toxin B antibody heavy chain variable region sequence) SEQ ID NO: 149:

EVQLQESGPGLVKPSETLSLTCTVS<u>GFSLNSYTIT</u>WVRQPPGKGLEWIA<u>AISGGGSTYFNSALKS</u>RVTISRDTSKSQVSLKLSSVTAADTAVYYCTR<u>PRWYPRSYFDY</u>WGRGTLVTVS wherein the CDRs are underlined The polynucleotide sequence encoding SEQ ID NO: 149 is shown in FIG. 9 and SEQ ID NO: 150 therein.

In one embodiment an antibody according to the invention comprises variable regions shown in SEQ ID NO 147: and SEQ ID NO: 149.

In one embodiment there is provided antibody (for example an anti-toxin B antibody) comprising a CDR, such as 1, 2, 3, 4, 5 or 6 CDRs, selected from:

KASQNVGNNVA  SEQ ID NO: 151

YASNRFT  SEQ ID NO: 152

QRVYQSTWT  SEQ ID NO: 153

GFSLTSYYVH  SEQ ID NO: 154

CIRTGGNTEYQSEFKS  SEQ ID NO: 155

GNYGFAY  SEQ ID NO: 156

In one embodiment sequences 151 to 153 are in a light chain of the antibody.

In one embodiment sequences 154 to 156 are in a heavy chain of the antibody.

In one embodiment SEQ ID NO: 151 is CDR L1, SEQ ID NO: 152 is CDR L2 and SEQ ID NO: 153 is CDR L3.

In one embodiment SEQ ID NO: 154 is CDR H1, SEQ ID NO: 155 is CDR H2 and SEQ ID NO: 156 is CDR H3.

In one embodiment SEQ ID NO: 151 is CDR L1, SEQ ID NO: 152 is CDR L2, SEQ ID NO; 153 is CDR L3, SEQ ID NO: 154 is CDR H1, SEQ ID NO: 155 is CDR H2 and SEQ ID NO; 156 is CDR H3.

In one embodiment there is provided a variable region, such as a light chain variable region with the following sequence (Antibody 1151 anti-toxin B antibody; Light chain Variable region sequence) SEQ ID NO: 157:

AIQMTQSPSSLSASVGDRVTITC<u>KASQNVGNNVA</u>WYQHKPGKAPKLLIY<u>YASNRFT</u>GVPSRFTGGGYGTDFTLTISSLQPEDFATYYC<u>QRVYQSTWT</u>FGQGTKVEIK wherein the CDRs are underlined.

The polynucleotide sequence encoding SEQ ID NO: 157 is shown in FIG. 9 and SEQ ID NO: 158 therein.

In one embodiment there is provided a variable region, such as a heavy chain variable region with the following sequence (Antibody 1151 anti-toxin B antibody heavy chain variable region sequence) SEQ ID NO: 159:

EVQLQESGPGLVKPSETLSLTCTVS<u>GFSLTSYYVH</u>WVRQPPGKGLEWMG<u>CIRTGGNTEYQSEFKS</u>RVTISRDTSKNQVSLKLSSVTAADTAVYYCAR<u>GNYGFAY</u>WGQGTLVTVS wherein the CDRs are underlined.

The polynucleotide sequence encoding SEQ ID NO: 159 is shown in FIG. 9 and SEQ ID NO: 160 therein.

In one embodiment an antibody according to the invention comprises variable regions shown in SEQ ID NO: 157 and SEQ ID NO: 159.

In one embodiment there is provided an antibody (for example an anti-toxin B antibody) comprising a CDR, such as 1, 2, 3, 4, 5 or 6 CDRs, selected from:

| | |
|---|---|
| KASQNINKYLD | SEQ ID NO: 161 |
| NIQSLHT | SEQ ID NO: 162 |
| FQHNSGW | SEQ ID NO: 163 |
| GFTFTQAAMF | SEQ ID NO: 164 |
| RISTKSNNFATYYPDSVKG | SEQ ID NO: 165 |
| PAYYYDGTVPFAY | SEQ ID NO: 166 |

In one embodiment sequences 161 to 163 are in a light chain of the antibody.

In one embodiment sequences 164 to 166 are in a heavy chain of the antibody.

In one embodiment SEQ ID NO: 161 is CDR L1, SEQ ID NO: 162 is CDR L2 and SEQ ID NO: 163 is CDR L3.

In one embodiment SEQ ID NO: 164 is CDR H1, SEQ ID NO: 165 is CDR H2 and SEQ ID NO: 166 is CDR H3.

In one embodiment SEQ ID NO: 161 is CDR L1, SEQ ID NO: 162 is CDR L2, SEQ ID NO: 163 is CDR L3, SEQ ID NO: 164 is CDR H1, SEQ ID NO: 165 is CDR H2 and SEQ ID NO: 166 is CDR H3.

In one embodiment there is provided a variable region, such as a light chain variable region with the following sequence (Antibody 1153 anti-toxin B antibody; Light chain Variable region sequence) SEQ ID NO: 167:

DIQMTQSPSSLSASVGDRVTITC<u>KASQNINKYLD</u>WYQQKPGKVPKLLIY<u>NIQSLHT</u>GIPSRFSGSGSGTDFTLTISSLQPEDVATYYC<u>FQHNSGW</u>TFGQGTRLEIK wherein the CDRs are underlined.

The polynucleotide sequence encoding SEQ ID NO: 167 is shown in FIG. 10 and SEQ ID NO: 168 therein.

In one embodiment there is provided a variable region, such as a heavy chain variable region with the following sequence (Antibody 1153 anti-toxin B antibody heavy chain variable region sequence) SEQ ID NO: 169:

EVQLVESGGGLVQPGGSLKLSCAAS<u>GFTFTQAAMF</u>WVRQASGKGLEGIA<u>RISTKSNNFATYYPDSVKG</u>RFTISRDDSKNTVYLQMNSLKTEDTAVYYCTAP<u>AYYYDGTVPFAY</u>WGQGTLVTVS wherein the CDRs are underlined.

The polynucleotide sequence encoding SEQ ID NO: 169 is shown in FIG. 10 and SEQ ID NO: 170 therein.

In one embodiment an antibody according to the invention comprises variable regions shown in SEQ ID NO: 167 and SEQ ID NO: 169.

In one embodiment there is provided antibody comprising 6 CDRs independently selected from SEQ ID NOs 1, 2, 3, 4, 5, 6, 11, 12, 13, 14, 15, 16, 21, 22, 23, 24, 25, 26, 31, 32, 33, 34, 35, 36, 41, 42, 43, 44, 45, 46, 51, 52, 53, 54, 55, 56, 61, 62, 63, 64, 65, 66, 71, 72, 73, 74, 75, 76, 81, 82, 83, 84, 85, 86, 91, 92, 93, 94, 95, 96, 101, 102, 103, 104, 105, 106, 111, 112, 113, 114, 115, 116, 121, 122, 123, 124, 125, 126, 131, 132, 133, 134, 135, 136, 141, 142, 143, 144, 145, 146, 151, 152, 153, 154, 155, 156, 161, 162, 163, 164, 165 and 166.

In one embodiment there is provided an anti-TcdA antibody comprising 6 CDRs independently selected from SEQ ID NOs 1, 2, 3, 4, 5, 6, 11, 12, 13, 14, 15, 16, 21, 22, 23, 24, 25, 26, 31, 32, 33, 34, 35, 36, 41, 42, 43, 44, 45, 46, 51, 52, 53, 54, 55 and 56.

In one embodiment there is provided an anti-TcdB antibody comprising 6 CDRs independently selected from SEQ ID NOs 61, 62, 63, 64, 65, 66, 71, 72, 73, 74, 75, 76, 81, 82, 83, 84, 85, 86, 91, 92, 93, 94, 95, 96, 101, 102, 103, 104, 105, 106, 111, 112, 113, 114, 115, 116, 121, 122, 123, 124, 125, 126, 131, 132, 133, 134, 135, 136, 141, 142, 143, 144, 145, 146, 151, 152, 153, 154, 155, 156, 161, 162, 163, 164, 165 and 166.

In one embodiment there is provided an antibody which comprises two variable regions independently selected from SEQ ID NOs: 7, 9, 17, 19, 27, 29, 37, 39, 47, 49, 57, 59, 67, 69, 77, 79, 87, 89, 97, 99, 107, 109, 117, 119, 127, 129, 137, 139, 147, 149, 157 and 159.

In one embodiment there is provided an antibody which comprises two variable regions independently selected from SEQ ID NOs: 7, 9, 17, 19, 27, 29, 37, 39, 47, 49, 57 and 59.

In one embodiment there is provided an antibody which comprises two variable regions independently selected from SEQ ID NOs: 67, 69, 77, 79, 87, 89, 97, 99, 107, 109, 117, 119, 127, 129, 137, 139, 147, 149, 157 and 159.

In one embodiment the antibodies according to the invention are humanized.

In one embodiment the antibody or antibodies are directed to the C terminal "cell binding" portion of the TcdA and/or TcdB toxin.

In one embodiment an antibody according to the invention is suitable for neutralising toxin A or toxin B.

Neutralising as employed herein is intended to refer to the elimination or reduction of harmful/deleterious effects of the target toxin, for example at least a 50% reduction in the relevant harmful effect.

The inventors have established by using internal comparisons between antibodies discovered in this application and by comparison against antibodies well described in the art (Babcock et al. 2006; Lowy et al., 2010) that some antibodies have the desirable characteristic of maintaining effective neutralization (for example low $EC_{50}$ and high % protection) even at high toxin concentrations. Other antibodies including those described in the art do not maintain effective toxin neutralization at high toxin concentrations.

Effective toxin concentrations can be defined as a 'lethal dose' (LD) in titration studies in the absence of neutralizing antibodies. Neutralisation assays are typically conducted at an LD of 50% of complete cell killing (i.e. an $LD_{50}$) but may be more rigorously conducted at an $LD_{80}$.

Assays may also be performed under considerably more challenging conditions such as $LD_{90}$, $LD_{95}$ and/or $LD_{max}$ ($LD_{max}$ is the maximal toxin quantity which can be included in an assay as constrained by assay volume and maximum toxin concentration/solubility). Such assays aim to mimic the early stages of infection of humans when *C. difficile* growth in the bowel is rampant and diarrhea and other symptoms lead one to hypothesise that toxin concentrations are at their highest. Antibodies which effectively neutralize damaging toxin activities under high toxin concentration conditions are thought by the present inventors to have special clinical value for the control of symptoms in human infections. In one embodiment the antibody or antibodies of the present disclosure have useful, for example low $EC_{50}$ values and/or high % protection from cell death for one or more the $LD_{80}$, $LD_{90}$, $LD_{95}$ and/or $LD_{max}$. In one embodiment the $EC_{50}$ in the one or more of the latter situations is 15 ng/ml or less, for example 10 ng/ml or less, such as 5 ng/ml or less, in particular 1 ng/ml or less. In one embodiment the % protection from cell death is >90%, or >75% or >50%.

Thus in one embodiment the present disclosure provides an antibody or a combination of antibodies which maintain toxin neutralization even in the presence of high levels of toxin, for example as measured in an assay provided herein.

The harmful effect of toxin may, for example be measured in a suitable in vitro assay. In one embodiment the neutralization is measured in an assay given in Example 1 below. Also provided is an antibody or antibodies identified in a neutralization assay, for example wherein the potency of the antibody is maintained in the presence of high levels of toxin.

Toxin A is used interchangeably with TcdA.

Toxin B is used interchangeably with TcdB.

In one embodiment an antibody according to the invention is a monoclonal antibody or binding fragment thereof.

In one embodiment a monoclonal antibody according to the invention is capable of neutralising TcdA with very high potency and affinity.

In one embodiment a monoclonal antibody according to the invention is capable of neutralising TcdA with very high potency and affinity and high avidity.

Avidity as employed herein refers to the combined strength of multiple binding affinities.

In one embodiment a monoclonal antibody according to the invention is capable of neutralising TcdA with very high potency and affinity and high avidity and high valency of binding.

Valency of binding as employed herein refers to the ability for a monoclonal antibody to bind to an antigen multiple times. High valency of binding hence results in high levels of decoration of antigen with antibodies and/or high levels of cross-linking of toxin molecules, which is thought to be advantageous.

Anti-TcdA Mabs according to the present disclosure may be suitable for neutralising the early effects of TcdA, for example on cells such as loss of tight junctions.

Tight junction as employed herein is intended to refer to impermeable zone of connection between cells within a monolayer or anatomical tissue structure. Fluid loss does not occur when tight junctions retain their structural and functional integrity. Loss of tight junctions is an indication that the cell has been compromised by toxin and is well documented as being an early step in the toxic effects of TcdA and TcdB (25) and results in loss of fluid containing serum, immunoglobulin and ions (26, 3). Loss of tight junctions is thought to be a first step on the onset of diarrhoea in humans.

The TEER assay system, can be used to measure the loss of tight junction in vitro. TEER is an acronym for trans epithelial electric resistance assay and it is generally employed to measure the permeability of a differentiated cell layer representative of a gut endothelial lining. However, in the context of screening for antibodies TEER loss can be employed to identify antibodies that slow or prevent damage to the tight junctions and hence is a surrogate for protection against tissue damage leading to diarrhoea.

Often Caco-2 cells are employed since they are derived from human colon cells and are known to form differentiated monolayers with cells connected by tight junctions. A kit is commercially available from Becton-Dickinson named the Caco-2 BioCoat HTS plate system (BD Biosciences/ 354802). The instructions in the kit are suitable for testing in the present context. The resistance of the membrane changes when the membrane has been compromised.

Generally the antibody will be pre-incubated with the toxin before addition to the TEER system to establish if the antibody can prevent or slow the damage to the membrane caused by the toxin. The assay may be performed over a suitable period, for example 24 hours taking measurements at certain time-points. The present inventors have established that the 4 hour time point is particularly discriminating for therapeutically useful antibodies. The concentration of toxin employed in the TEER assay is generally in the range 100-200 ng/ml, most preferably 125 ng/ml The concentration of antibody (for example IgG1) employed in the TEER assay is generally in the range of 4 to 2000 ng/ml, for example 50 to 1000 ng/ml, such as 100 to 500 ng/ml.

In one embodiment the $EC_{50}$ of the antibody in the TEER assay employed in said condition is at least 200 ng/ml, for example less than 100 ng/ml, such as about 60-80 ng/ml.

In one embodiment there is provided an anti-TcdA antibody or an anti-TcdB antibody suitable for use as a therapeutic agent in the treatment or prevention of *C. difficile* infection, wherein said antibody was screened and selected employing a TEER assay.

In one aspect there is provided a method of screening an antibody in a TEER assay for the ability to slow or prevent loss of tight junctions. In one embodiment the antibody or antibodies screened are anti-TcdA antibodies. In one embodiment the antibody or antibodies screened are anti-TcdB antibodies. In one embodiment the antibody or antibodies screened are a combination of anti-TcdA and anti-TcdB antibodies. In one embodiment the method comprises the step of identifying an appropriate antibody or antibodies and expressing suitable quantities of same. In one embodiment the method comprises the further step of formulating said antibody or antibodies in a pharmaceutical formulation. In one embodiment the method comprises the further step of administering said antibody or antibodies or said formulation to a patient in need thereof.

In one embodiment multiple antibodies of the disclosure may be capable of binding to the target toxin (TcdA or TcdB), which may aid immune clearance of the toxin.

Multiple antibodies as employed herein is intended to refer to multiple copies of an antibody with the same sequence or an antibody with the same amino acid sequence or an antibody specific to the same target antigen but with a different amino acid sequence.

In one embodiment the antibodies according to the invention are specific to the target antigen, for example specific to an epitope in the target antigen.

In one embodiment the antibodies of the invention are able to bind to the target antigen in two or more locations, for example two or three locations, such as four, five, six, seven, eight, nine, ten or more locations, for example the toxin may comprise repeating domains and thus an antibody may be specific to an epitope and in fact that epitope may be present in the antigen several times i.e. in more than one location. Thus given antibodies may bind the same epitope multiple times in different locations in the antigen.

In one embodiment the antibody binds to the given antigen multiple times, for example 2 to 20 times such as 3, 4, 5, 6, 7, 8, 9, 10, 11, 12, 13, 14, 15 or 16 times. In one embodiment the antibody binds the given antigen at least 3 times. This multiple binding is thought to be important in neutralisation and/or clearance of the toxin. Whilst not wishing to be bound by theory it is thought that multiple binding, for example 3 more times, i.e. by decoration with 3 or more Fc fragments is important in triggering rapid clearance of the toxin (24) primarily via the liver and spleen (27, 28).

In one embodiment the anti-TcdA antibody binds 3 or more times, for example 3 to 16 times.

In one embodiment the anti-TcdA antibody binds 12 times.

In one embodiment the anti-TcdA antibody binds 2 times.

In one embodiment an anti-TcdA antibody binds in the catalytic-terminal cell binding domain of TcdA.

In one embodiment the anti-Tcd B antibody binds 2 or more times, for example 2 times.

In one embodiment an anti-TcdB antibody binds in the catalytic-terminal cell binding domain of TcdB.

In one embodiment the antibody or antibodies according to disclosure are capable of cross-linking toxin molecules, for example one arm of the antibody molecule binds one toxin molecule and another of the antibody binds a epitope in a different toxin molecule, thereby forming a sort of immune complex. The formation of the latter may also facilitate activation of the immune system to clear the relate toxin and thereby minimise the deleterious in vivo effects of the same.

In one embodiment an innate immune response, such as complement is activated.

In one embodiment the antibody or antibodies of the disclosure have high potency against toxins derived from strains of different ribotypes, for example 003, 027, 078.

In one embodiment antibodies against TcdA may have an $EC_{50}$ in the range of 0.1-100 ng/ml, such as 1 to 10 ng/ml and a maximal inhibition in the range of 50-100% at toxin concentrations of $LD_{80-95}$, for example against toxins from strains of ribotypes 003, 027 and 078.

In one embodiment antibodies against TcdA may have an $EC_{50}$ in the range of 0.1-100 ng/ml, such as 1 to 10 ng/ml and a maximal inhibition in the range of 60-100%, 70-100%, 80-100% or 90-100% at toxin concentrations of $LD_{80-95}$, for example against toxins from strains of ribotypes 003, 027 and 078.

In one embodiment antibodies against TcdB may have $EC_{50}$ in the range of 0.1-100 ng/ml, such as 1 to 10 ng/ml and a maximal inhibition in the range of 50-100% at toxin concentrations of $LD_{80-95}$, for example against toxins from strains of ribotype 003.

In one embodiment antibodies against TcdB may have $EC_{50}$ in the range of 0.1-100 ng/ml, such as 1 to 10 ng/ml and a maximal inhibition in the range of 60-100%, 70-100%, 80-100% or 90-100% at toxin concentrations of $LD_{80-95}$, for example against toxins from strains of ribotype 003.

In one embodiment there are provided combinations of antibodies according to the invention, for example combinations of antibodies specific to TcdA, combinations of antibodies specific to TcdB or combinations of antibodies to specific to TcdA and antibodies specific to TcdB.

Combinations of antibodies specific to TcdA will generally refer to combinations of antibodies directed to different epitopes on the target antigen TcdA, or at least with different binding properties.

Combinations of antibodies specific to TcdB will generally refer to combinations of antibodies directed to different epitopes on the target antigen TcdB, or at least with different binding properties.

The combinations may comprise 2, 3, 4, 5, 6, 7, 8, 9, 10, 11, 12, 13, 14 or 15 distinct antibodies, for example 2, 3, 4 or 5 antibodies.

In one embodiment there is provided a combination of one anti-TcdA antibody and two anti-TcdB, for example wherein the anti-TcdA antibody is 997 and where the anti-TcdB antibodies are 1125 and 1151

In particular there is provided a combination of one anti-TcdA antibody comprising a heavy variable region with a sequence as shown in SEQ ID NO:49 and a light variable region with a sequence shown in SEQ ID NO: 47 and two anti-TcdB antibodies the first with a heavy variable region shown in SEQ ID NO: 129 and a light variable region shown in SEQ ID NO: 127, and the second with a heavy variable region shown in SEQ ID NO: 159 and light variable region shown in SEQ ID NO: 157.

Distinct antibodies as employed herein is intended to refer to antibodies with different amino acid sequences, which may bind the same epitope or different epitopes on the target antigen.

Also provided by the present invention is a specific region or epitope of TcdA which is bound by an antibody provided by the present invention, in particular an antibody comprising the heavy chain sequence given in SEQ ID NO:49 and the light chain sequence given in SEQ ID NO:47.

Also provided by the present invention is a specific region or epitope of TcdB which is bound by an antibody provided by the present invention, in particular an antibody comprising the heavy chain sequence given in SEQ ID NO:129 and the light chain sequence given in SEQ ID NO:127 or an antibody comprising the heavy chain sequence given in SEQ ID NO:159 and the light chain sequence given in SEQ ID NO:157.

This specific region or epitope of the TcdA or TcdB toxins can be identified by any suitable epitope mapping method known in the art in combination with any one of the antibodies provided by the present invention. Examples of such methods include screening peptides of varying lengths derived from the toxins for binding to the antibody of the present invention with the smallest fragment that can specifically bind to the antibody containing the sequence of the epitope recognised by the antibody. The peptides may be produced synthetically or by proteolytic digestion of the toxin polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antagonistic antibodies which bind the same epitope.

Antibodies which cross-block the binding of an antibody according to the present invention may be similarly useful in neutralizing toxin activity. Accordingly, the present invention also provides a neutralizing antibody having specificity for TcdA or TcdB, which cross-blocks the binding of any one of the antibodies described above to TcdA or TcdB and/or is cross-blocked from binding these toxins by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore assays where binding of the cross blocking antibody to TcdA or TcdB prevents the binding of an antibody of the present invention or vice versa.

In one embodiment there is provided a method of generating an anti-TcdA or anti-TcdB antibody, in particular a neutralizing antibody and/or an antibody which cross-blocks the binding of an antibody described herein, said method comprising the steps of immunizing a host with a suitable antigen, for example an antigen shown in any one of SEQ ID Nos 173 to 194 or a combination thereof. The said method may also comprise one or more the following steps, for example identifying an antibody of interest (in particular using a functional assay such as TEER assay), expressing the antibody of interest, and optionally formulating the antibody as a pharmaceutically acceptable composition.

Thus in one aspect the present disclosure provides a method of immunizing a host with an amino acid sequence shown in SEQ ID Nos 173 to 194 or a combination thereof.

In one embodiment the antibodies according to the invention have an affinity to the target antigen of 10 nM or less, for example 1 nM or less such as 900 pM, in particular 800 pM, 700 pM, 600 pM or 500 pM, such as 60 pM.

In one embodiment the affinity is for TcdA or TcdB or a fragment thereof. In one example the fragment is TcdA123 corresponding to residues S1827-D2249 of TcdA. In one example the fragment is TcdA456 corresponding to residues G2205-R2608. In one embodiment the fragment is TcdB1234 corresponding to residues S1833-E2366 of TcdB.

In one embodiment antibodies according to the invention or a combination thereof have an $EC_{50}$ of 200 ng/ml or less, for example 150 ng/ml or less such as 100 ng/ml or less, such as in the range 0.1 to 10 ng/ml.

The individual component antibodies of mixtures are not required to have an $EC_{50}$ in said range provided that when they are used in combination with one or more antibodies the combination has an $EC_{50}$ in said range.

Advantageously, the antibodies of the invention are stable, for example are thermally stable at temperatures above 50° C. such as 60 or 70° C.

The antibodies and combinations according to the present invention also have one or more of the following advantageous properties: slow off rate, high affinity, high potency, the ability to bind multiple times to the target antigen, to neutralise the toxin by a mechanism which reduces the loss of measurable TEER activity, to stimulate or assist the hosts natural immune response, to catalyse or assist in immune clearance of the pathogen (or toxin) and/or to educate the immune system to respond appropriately to the pathogen (or toxin).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies for use in the present invention may be obtained using any suitable method known in the art. The toxin A and/or toxin B polypeptide/protein including fusion proteins, for example toxin-Fc fusions proteins or cells (recombinantly or naturally) expressing the polypeptide (such as activated T cells) can be used to produce antibodies which specifically recognise the target toxins. The toxin polypeptide may be the full length polypeptide or a biologically active fragment or derivative thereof.

Polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The sequence for TcdA from ribotype 027 is given in SEQ ID NO: 171 (Uniprot accession number C9YJ37) and the sequence for TcdB from ribotype 027 is given is SEQ ID NO: 172 (Uniprot accession number C9YJ35).

The antigen polypeptide may in some instances be part of a larger protein such as a fusion protein for example fused to an affinity tag.

Antibodies generated against the antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler &

Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term 'humanised antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Thus, provided in one embodiment is a humanised antibody which binds toxin A or toxin B wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

Also, in a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Generally the antibody sequences disclosed in the present specification are humanised.

The invention also provides sequences which are 80%, 90%, 91%, 92%, 93% 94%, 95% 96%, 97%, 98% or 99% similar to a sequence or antibody disclosed herein.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

The antibody molecules of the present invention include a complete antibody molecule having full length heavy and light chains or a fragment thereof and may be, but are not limited to Fab, modified Fab, Fab', modified Fab', F(ab')2, Fv, Fab-Fv, Fab-dsFv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853 and WO05/113605). Bispecific and multispecific antibody variants are especially considered in this example since the aim is to neutralise two independent target proteins: TcdA and TcdB. Variable regions from antibodies disclosed herein may be configured in such a way as to produce a single antibody variant which is capable of binding to and neutralising TcdA and TcdB.

In one embodiment the antibody according to the present disclosure is provided as TcdA or TcdB binding antibody fusion protein which comprises an immunoglobulin moiety, for example a Fab or Fab' fragment, and one or two single domain antibodies (dAb) linked directly or indirectly thereto, for example as described in WO2009/040562.

In one embodiment the fusion protein comprises two domain antibodies, for example as a variable heavy (VH) and variable light (VL) pairing, optionally linked by a disulphide bond, for example as described in WO2010/035012.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

In one embodiment the multivalent fusion protein according to the invention binds TcdA and TcdB.

In one embodiment the multivalent fusion protein according to the invention binds TcdB in multiple positions, for example has distinct binding regions specific for two different epitopes.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply neutralising or agonising an antigen. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705:129-134, 1995).

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised antibody engineered to have an isoelectric point different to that of the originally identified antibody from which it is derived. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY www.expasy.ch/tools/pi_tool.html, and www.iut-arles.up.univ-mrs.fr/w3bb/d_abim/compo-p.html, may be used to predict the isoelectric point of the antibody or fragment.

It will be appreciated that the affinity of antibodies provided by the present invention may be altered using any suitable method known in the art. The affinity of the antibodies or variants thereof may be measured using any suitable method known in the art, including BIAcore, using an appropriate isolated natural or recombinant protein or a suitable fusion protein/polypeptide.

The present invention therefore also relates to variants of the antibody molecules of the present invention, which have an improved affinity for TcdA or TcdB, as appropriate. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

Improved affinity as employed herein in this context refers to an improvement refers to an improvement over the starting molecule.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, $\alpha$-interferon, $\beta$-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,677,425; WO98/25971, WO2008/038024). In one example the antibody molecule of the present invention is a modified Fab fragment wherein the modification is the addition to the C-terminal end of its heavy chain one or more amino acids to allow the attachment of an effector molecule.

Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly (ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

m is 2 or 5

That is to say each PEG is about 20,000 Da.
Further alternative PEG effector molecules of the following type:

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

In one embodiment one certain antibodies according to the present disclosure have the following properties:

| Antibody | Affinity (pM) | | Valency of binding | |
| | $TcdA_{123}$ | $TcdA_{456}$ | TcdA, est. | $EC_{50}$ (ng/ml) |
| --- | --- | --- | --- | --- |
| CA922 | 4.06 | 2.59 | 16 | 1.21 |
| CA923 | 64.7 | 312 | 12 | 160.42 |
| CA995 | nil | 119 | 1 | 37.64 |
| CA997 | 132 | 66.8 | 12 | 6.25 |
| CA1000 | 73.3 | 84.1 | 2 | 19.73 |

The present invention also provides compositions such as a pharmaceutical composition of antibody or combination of antibodies defined herein.

The present invention also provides a composition that comprises at least two antibodies according to the invention, for example wherein at least one antibody therein is specific to TcdA and at least one antibody therein is specific to TcdB or alternatively at least two antibodies specific to TcdA or at least two antibodies specific to TcdB.

In one embodiment there is provided a composition that comprises multiple antibodies specific to TcdA and optionally one or more antibodies specific to TcdB.

In one embodiment there is provided a composition that comprises multiple antibodies specific to TcdB and optionally one or more antibodies specific to TcdA.

Thus in one embodiment there is provided a composition comprising 2, 3, 4, 5, 6, 7, 8, 9, 10, 11, 12, 13, 14 or 15 antibodies according to the invention i.e. distinct antibodies.

The invention describes one particular mixture comprising 3 Mabs, one Mab of which is specific for TcdA and two Mabs of which are specific for TcdB. This mixture demonstrated very high levels of protection from death and gut inflammation from a lethal infective oral dose of *Clostridium difficile* in hamsters.

In particular there is provided a composition comprising a combination of one anti-TcdA antibody comprising a heavy variable region with a sequence as shown in SEQ ID NO:49 and a light variable region with a sequence shown in SEQ ID NO: 47 and two anti-TcdB the first with a heavy variable region shown in SEQ ID NO: 129 and a light variable region shown in SEQ ID NO: 127, and the second with a heavy variable region shown in SEQ ID NO: 159 and light variable region shown in SEQ ID NO: 157.

In one embodiment wherein the composition comprises 3 antibodies, such as one anti-TcdA and two anti-TcdB antibodies the antibodies are in the ratio of 50%, 25% and 25% respectively of the total antibody content thereof.

In one embodiment there is provided a composition comprising 2, 3, 4 or 5 antibodies specific to TcdA and optionally 1, 2, 3, 4 or 5 antibodies specific to TcdB.

In one embodiment the compositions provided according to the invention are well defined, for example are mixtures of monoclonal antibodies rather than simply polyclonal compositions derived from an immunised or immune competent host.

In one embodiment the composition of antibodies has an $EC_{50}$ of 200 ng/ml or less, for example 150 ng/ml or less, such as 100 ng/ml or less, such as 0.1 to 10 ng/ml.

Advantageously the antibodies described herein have very high levels of biophysical stability and so are suitable for inclusion in mixtures of antibodies.

In one aspect a pharmaceutical formulation or composition according to the invention further comprises a pharmaceutically acceptable excipient.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one embodiment the composition or formulation of the present disclosure comprises 1-200 mg/mL of antibodies, that this to say the combined antibody content, for example 150 mg/mL or less, such as 100 mg/mL or less, in particular 90, 80, 70, 60, 50, 40, 30, 20, 10 mg/mL or less.

In one embodiment a composition or formulation according to the present disclosure comprises 20 mg/mL of each antibody therein.

In one embodiment there is provided a formulation comprising:
33 mg/mL or less of one anti-TcdA antibody comprising a heavy variable region with a sequence as shown in SEQ ID NO: 49 and a light variable region with a sequence shown in SEQ ID NO: 47, and
28 mg/mL or less of a first anti-TcdB with a heavy variable region shown in SEQ ID NO: 129 and a light variable region shown in SEQ ID NO: 127, and
25 mg/mL of a second anti-TcdB with a heavy variable region shown in SEQ ID NO: 159 and light variable region shown in SEQ ID NO: 157.

In one embodiment the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant,
a) 10 to 500 mM of a stabiliser,
b) 5 to 500 mM of a tonicity agent, or
c) 10 to 500 mM of a stabiliser and 5 to 500 mM of a tonicity agent.

In one embodiment the composition or formulation according to the present disclosure comprises the buffer phosphate buffered saline.

For example the formulation at approximately pH6 may comprise 1 to 50 mg/mL of antibody, 20 mM L-histidine HCl, 240 mM trehalose and 0.02% polysorbate 20. Alternatively a formulation at approximately pH 5.5 may comprise 1 to 50 mg/mL of antibody, 20 mM citrate buffer, 240 mM sucrose, 20 mM arginine, and 0.02% polysorbate 20.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue.

The compositions can also be administered into a lesion or directly into the gastrointestinal tract by for examples, encapsulated oral dosage for swallowing, through a nasogastric tube to the stomach or ileum, through a rectal tube or enema solutions or by rectal capsule. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

The present invention also provides an antibody or antibody combination or a composition comprising the same, as described herein, for treatment, for example for the treatment or prophylaxis of *C. difficile* infection or complications associated with the same such as diarrhoea, colitis in particular pseudomembranous colitis, bloating, abdominal pain and toxic megacolon.

Prophylaxis can also be achieved by the administration of pre-formed complexes of inactivated toxin antigen (toxoid) and antibody in order to create a vaccine.

In one embodiment the antibodies, combinations thereof and compositions comprising the same according to the invention are suitable for treating infection with so-called super strains of *C. difficile*, i.e. hypervirulent strains such as ribotype 027.

The antibodies and compositions according to the present invention are suitable for use in the treatment or prophylaxis of acute and/or chronic effects of the relevant *C. difficile* toxins during primary infection.

The antibodies and compositions according to the present invention are suitable for use in the treatment or prophylaxis of effects of the relevant *C. difficile* toxins during secondary infection or re-infection. International guidelines enshrine time intervals after a primary infection which hence defines a secondary (or recurrent) infection as being distinct from a continuation of existing symptoms sometimes described as a relapse (29). Research has shown that secondary infections can be the result of the same strain or ribotype as the primary infection. In such cases recurrence rather than relapse relies on agreed temporal constraints. However, research also clearly shows that secondary infection can also be the result of infection of a strain or ribotype distinct from that of the primary infection. In one study, 48% of disease recurrences were the result of a second strain distinct from that having caused the first infection (30). In another study, more than 56% of disease recurrences were the result of a second strain distinct from that having caused the first infection (31).

In one embodiment the antibodies, combinations thereof and compositions comprising the same according to the invention are suitable for use in the prevention of damage, for example long term structural damage to the epithelium of the colon.

In one embodiment the antibodies, combinations and composition are suitable for preventing *C. difficile* infection including recurrence of infection, in particular nosocomial infection.

In one embodiment the antibodies, combinations thereof and compositions comprising the same according to the invention are suitable for reducing the risk of recurrence of *C. difficile* infection.

Advantageously, the antibodies of the present disclosure can be administered prophylactically to prevent infection or re-infection because in the absence of toxin to which the antibody is specific the antibody is simply to be cleared from the body without causing adverse interactions with the subjects body tissues.

Advantageously the antibodies of the present disclosure seem to elicit a rapid response after administration, for example within one or two days of administration rapid clearance of the target toxin is invoked, this may prevent vital organs such as the lungs, heart and kidneys being damaged. This is the first time that agents have been made available with can be employed to prevent damage or injury to a patient by toxins A and/or B in the acute *C. difficile* infection stage.

Thus in one embodiment the antibodies, combinations thereof and compositions comprising the same according to the invention are suitable for preventing damage to vital organs.

In one embodiment the antibody, combinations or formulations described herein are suitable for preventing death of an infected patient, if administered within an appropriate time frame before irreparable damage has been done by the toxins.

The antibodies of the present disclosure have fast on-rates, which facilitates the rapid effect in vivo.

In one embodiment the patient population is over 60, such as over 65 years of age.

In one embodiment the patient population is 5 years old or less.

The antibodies according the invention may be employed in combination with antibiotic treatment for example metronidazole, vancomycin or fidaxomicin.

A range of in vitro data exemplify the properties of the Mabs and Mab mixtures. We show that one mixture of 3 Mabs (50% molar quantities of anti-TcdA and 50% molar quantities of anti-TcdB components) was able to protect hamsters from a lethal CDI.

In one embodiment there is provided a method of treating a patient in need thereof by administering a therapeutically effective amount of an antibody as described herein or antibody combination or a composition comprising the same, for example in the treatment or prophylaxis of *C. difficile* infection or complications associated with the same such as diarrhoea, colitis in particular pseudomembranous colitis, bloating, abdominal pain and toxic megacolon.

In one embodiment the antibody, combination or formulation is administered by a parenteral route, for example subcutaneously, intraperitoneally, intravenously or intramuscularly. The data in the Examples generated in hamsters indicates that the doses administered by this route reach the gut and thus are able to generate a therapeutic effect.

In one embodiment the antibody, combination or formulation is administered orally, for example an enterically coated formulation.

In one embodiment there is provided use of an antibody, combination or formulation as described herein for the manufacture of a medicament for the treatment or prophylaxis of *C. difficile* infection.

In one embodiment the dose administered is in the range 1 to 1000 mg/Kg, for example 10 to 75 mg/Kg, such 20 to 50 mg/Kg.

In one embodiment the half-life of the antibody or antibodies in mice and hamsters in vivo is in the range 6 to 8 days in healthy (uninfected) animals and hence are expected to have half-lives in humans in the range of 14-28 days.

In one embodiment the antibody or antibodies are given as one dose only.

In one embodiment the antibody or antibodies are given as a weekly or biweekly dose.

In one embodiment the antibody or antibodies are given as once daily doses.

In one embodiment there is provided complex comprising TcdA or an immunogenic fragment thereof, complexed with one or more anti-TcdA antibodies defined herein. The complex may be employed as the antigen in a vaccine formulation, for example suitable for generating protective antibodies to toxin A in vivo after administration to a human.

In one embodiment there is provided complex comprising TcdB or an immunogenic fragment thereof, complexed with one or more anti-TcdB antibodies defined herein. The complex may be employed as the antigen in a vaccine formulation, for example suitable for generating protective antibodies to toxin B in vivo after administration to a human.

Th1-type immunostimulants which may be formulated to produce adjuvants suitable for use in the present invention include and are not restricted to the following.

In one embodiment there is provided a complex comprising TcdA or an immunogenic fragment thereof and TcdB or an immunogenic fragment thereof, wherein each toxin or fragment is complexed with one or more antibodies specific thereto, wherein the complex is suitable for administration as a vaccine formulation.

Antibody:antigen complexes are known to be taken up by the immune system in an Fc receptor mediated process (27, 28) and pre-formed complexes of antibody:antigen complexes have been successfully use as vaccines in human clinical trials (22).

In one or more embodiments the vaccine formulation further comprises an adjuvant as an immunostimulant.

Monophosphoryl lipid A, in particular 3-de-O-acylated monophosphoryl lipid A (3D-MPL), is a preferred Th1-type immunostimulant for use in the invention. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al., 1986, *Int.Arch.Allergy.Immunol.*, 79(4):392-6; Hilgers et al., 1987, Immunology, 60(1):141-6; and EP 0 549 074 B1). A preferred form of 3D-MPL is in the form of a particulate formulation having a small particle size less than 0.2 mm in diameter, and its method of manufacture is disclosed in EP 0 689 454.

Saponins are also preferred Th1 immunostimulants in accordance with the invention. Saponins are well known adjuvants and are taught in: Lacaille-Dubois, M and Wagner H. (1996. A review of the biological and pharmacological activities of saponins Phytomedicine vol 2 pp 363-386). For example, Quil A (derived from the bark of the South American tree Quillaja Saponaria Molina), and fractions thereof, are described in U.S. Pat. No. 5,057,540 and "Saponins as vaccine adjuvants", Kensil, C. R., *Crit Rev Ther Drug Carrier Syst,* 1996, 12 (1-2):1-55; and EP 0 362 279 B1. The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. One such system is known as an Iscorn and may contain one or more saponins.

Another preferred immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 96/02555, EP 468520, Davis et al., *J. Immunol,* 1998, 160(2):870-876; McCluskie and Davis, *J. Immunol.,* 1998, 161(9):4463-6). Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequences containing oligonucleotides can activate various immune subsets, including natural killer cells (which produce interferon g and have cytolytic activity) and macrophages (Wooldrige et al Vol 89 (no. 8), 1977). Other unmethylated CpG containing sequences not having this consensus sequence have also now been shown to be immunomodulatory.

CpG when formulated into vaccines, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., *Proc. Natl. Acad. Sci.*, USA, 1998, 95(26), 15553-8).

Such immunostimulants as described above may be formulated together with carriers, such as for example liposomes, oil in water emulsions, and or metallic salts, including aluminium salts (such as aluminium hydroxide). For example, 3D-MPL may be formulated with aluminium hydroxide (EP 0 689 454) or oil in water emulsions (WO 95/17210); QS21 may be advantageously formulated with cholesterol containing liposomes (WO 96/33739), oil in water emulsions (WO 95/17210) or alum (WO 98/15287); CpG may be formulated with alum (Davis et al. supra; Brazolot-Millan supra) or with other cationic carriers.

Combinations of immunostimulants are also preferred, in particular a combination of a monophosphoryl lipid A and a saponin derivative (WO 94/00153; WO 95/17210; WO 96/33739; WO 98/56414; WO 99/12565; WO 99/11241), more particularly the combination of QS21 and 3D-MPL as disclosed in WO 94/00153. Alternatively, a combination of CpG plus a saponin such as QS21 also forms a potent adjuvant for use in the present invention. Alternatively the saponin may be formulated in a liposome or in an Iscorn and combined with an immunostimulatory oligonucleotide.

Thus, suitable adjuvant systems include, for example, a combination of monophosphoryl lipid A, preferably 3D-MPL, together with an aluminium salt.

Thus is one embodiment the adjuvant is a combination of QS21 and 3D-MPL in an oil in water or liposomal formulation.

An enhanced system involves the combination of a monophosphoryl lipid A and a saponin derivative particularly the combination of QS21 and 3D-MPL as disclosed in WO 94/00153, or a less reactogenic composition where the QS21 is quenched in cholesterol containing liposomes (DQ) as disclosed in WO 96/33739. This combination may additionally comprise an immunostimulatory oligonucleotide.

A particularly potent adjuvant formulation involving QS21, 3D-MPL & tocopherol in an oil in water emulsion is described in WO 95/17210 and is another preferred formulation for use in the invention.

Another preferred formulation comprises a CpG oligonucleotide alone or together with an aluminium salt.

In a further aspect of the present invention there is provided a method of manufacture of a vaccine formulation as herein described, wherein the method comprises admixing a polypeptide according to the invention with a suitable adjuvant.

Particularly suitable adjuvant combinations for use in the formulations according to the invention are as follows:
i) 3D-MPL+QS21 in a liposome
ii) Alum+3D-MPL
iii) Alum+QS21 in a liposome+3D-MPL
iv) Alum+CpG
v) 3D-MPL+QS21+oil in water emulsion
vi) CpG As used herein, the term "comprising" in context of the present specification should be interpreted as "including".

Embodiments and preferences may be combined as technically appropriate.

The disclosure herein describes embodiments comprising certain integers. The disclosure also extends to the same embodiments consisting or consisting essentially of said integers.

FIGURES

FIG. 1-10 shows various antibody and fragment sequences

Figure 62A:
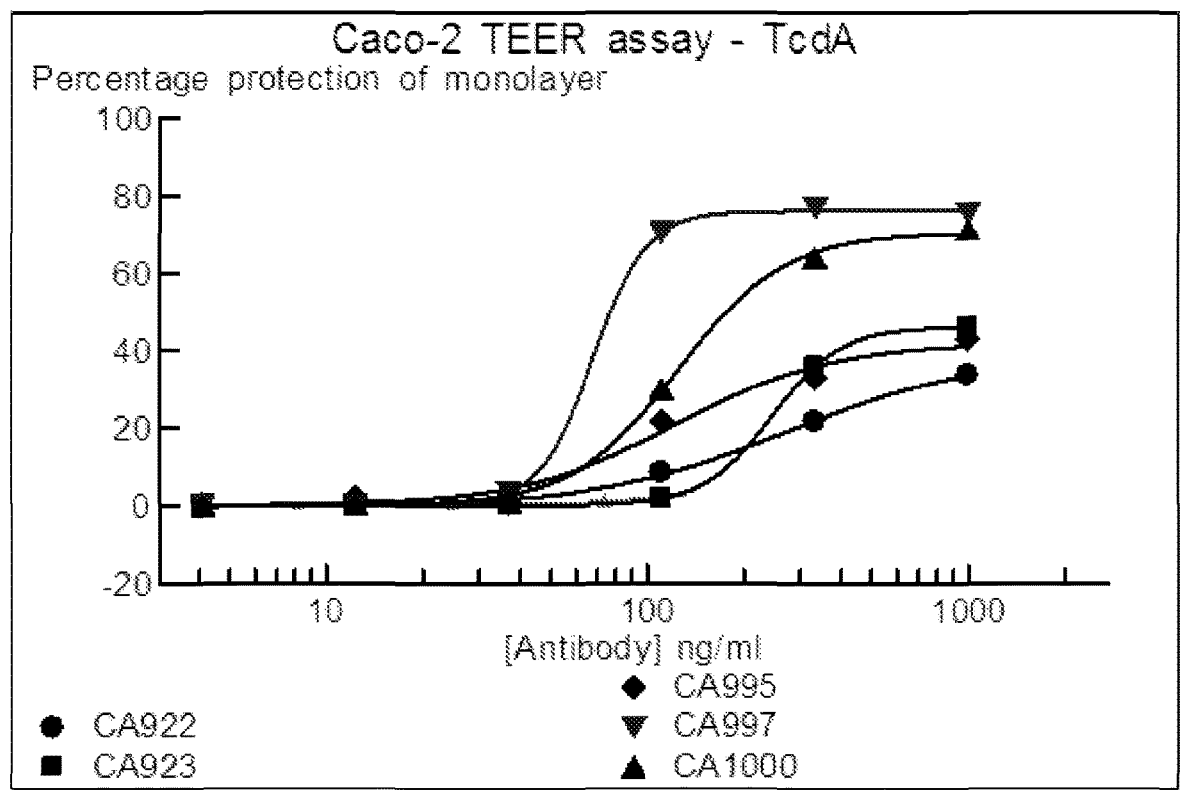

FIG. 12 shows anti TcdA (Ribotype 003) in-vitro neutralization data for single Mabs FIG. 13 shows anti TcdA (Ribotype 003) in-vitro neutralization data for single and paired Mabs FIG. 14-15 shows anti TcdA (Ribotype 003) in-vitro neutralization data for paired Mabs FIG. 16-18 shows anti TcdA (Ribotype 003) in-vitro neutralization data for three Mab mixtures FIG. 19-20 shows anti TcdA (Ribotype 003) in-vitro neutralization data for four and five Mab mixtures FIG. 21-22 shows anti TcdA (Ribotype 003) in-vitro neutralization data for single and paired Mabs at different TcdA concentrations FIG. 23-24 shows anti TcdA (Ribotype 003) in-vitro neutralization data for single and to five Mab mixtures at different TcdA concentrations FIG. 25-26 shows anti TcdB (Ribotype 003) in-vitro neutralization data for single Mabs FIG. 27-30 shows anti TcdB (Ribotype 003) in-vitro neutralization data for paired Mabs FIG. 31-33 shows anti TcdB (Ribotype 003) in-vitro neutralization data for three Mab mixtures FIG. 34-40 shows anti TcdB (Ribotype 003) in-vitro neutralization data for two Mab mixtures at different toxin concentrations FIG. 41-45 shows anti TcdB (Ribotype 003) in-vitro neutralization data for two Mab mixtures at different relative Mab ratios and different toxin concentrations FIG. 46-59 shows TcdB neutralisation data for single antibodies and pairs of antibodies FIG. 60 shows the amino acid sequence for TcdA FIG. 61 shows the amino acid sequence for TcdB FIG. 62 shows TEER assay data for TcdA in a histogram format FIG. 62A shows TEER assay data for TcdA in line graph format FIG. 63 shows a meier-kaplan curve for the combination of antibodies 997, 1125 and 1151, high concentration is 50 mg/Kg and low concentration is 5 mg/Kg 50 mg/kg' dose gave 100% protection to day 11, ~82% protection to day 28. 5 mg/kg' dose resulted in non-durable and incomplete protection.

FIG. 64 shows bodyweight changes for vancomycin and vehicle treated hamsters

Figure 65:
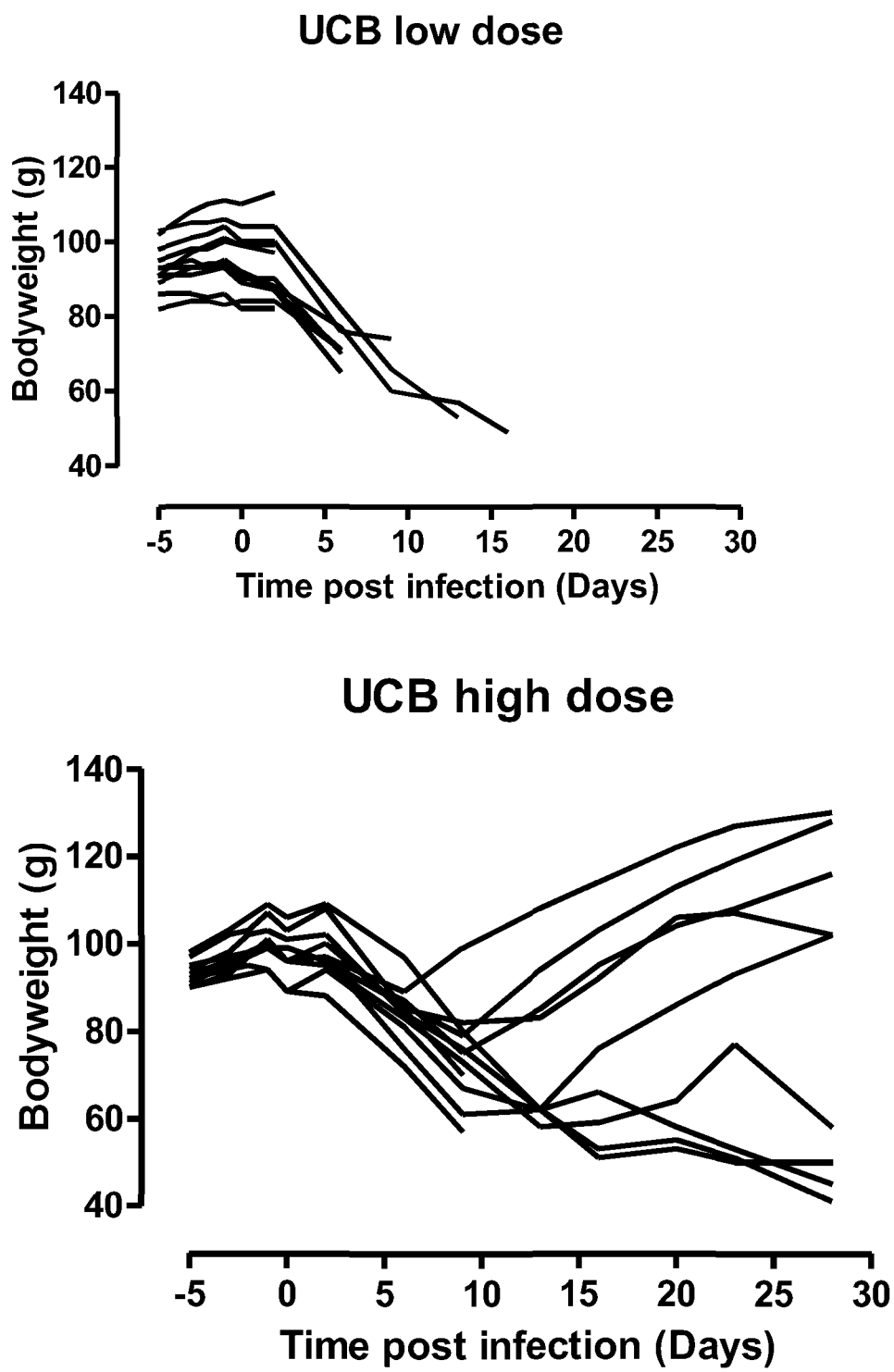
Figure 66:
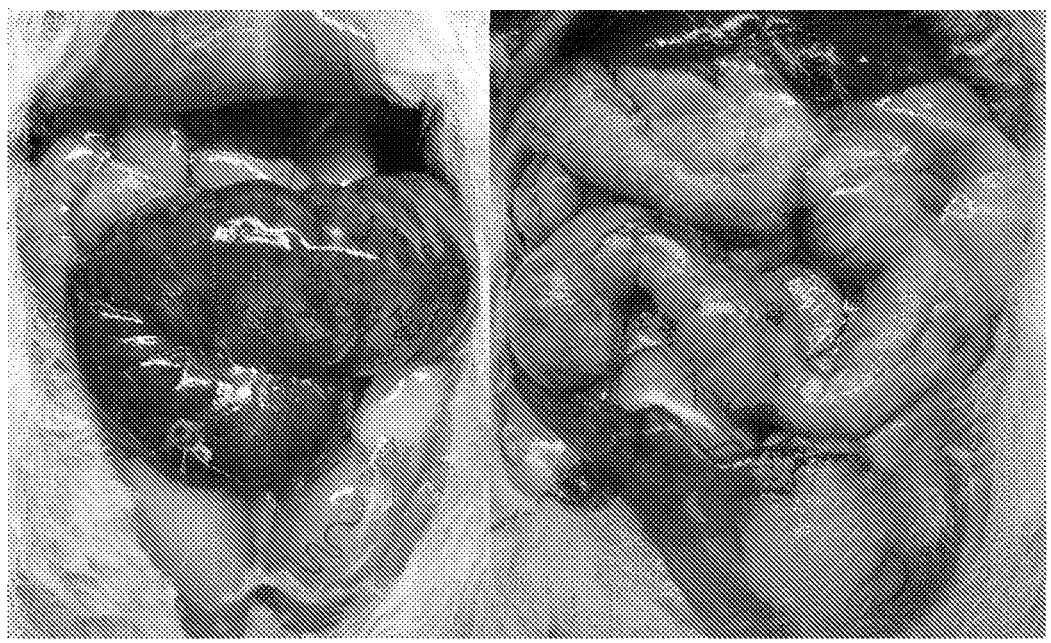

FIG. 65 shows the bodyweight for low dose antibodies 5 mg/Kg and high dose antibodies 50 mg/Kg FIG. 66 shows photographs of a colon where the animal received treatment with antibodies according to the present disclosure vs a control FIG. 67-68 show effects of vortexing on antibody stability FIG. 69 shows a comparison of aggregation stability for various antibodies FIG. 70-73 show neutralisation of TcdA for various ribotypes

EXAMPLES

Antibody Generation

A range of different immunogens and screening reagents were either purchased or produced by conventional *E. coli* expression techniques in order to provide a diverse and broad immune response and to facilitate identification and characterisation of monoclonal antibodies (listed in Table 1). In cases where recombinant proteins or peptides were generated, sequences were based on ribotype 027. The sequence for TcdA from ribotype 027 is given in SEQ ID NO: 171 (Uniprot accession number C9YJ37) and the sequence for TcdB from ribotype 027 is given is SEQ ID NO: 172 (Uniprot accession number C9YJ35).

Figure 11:
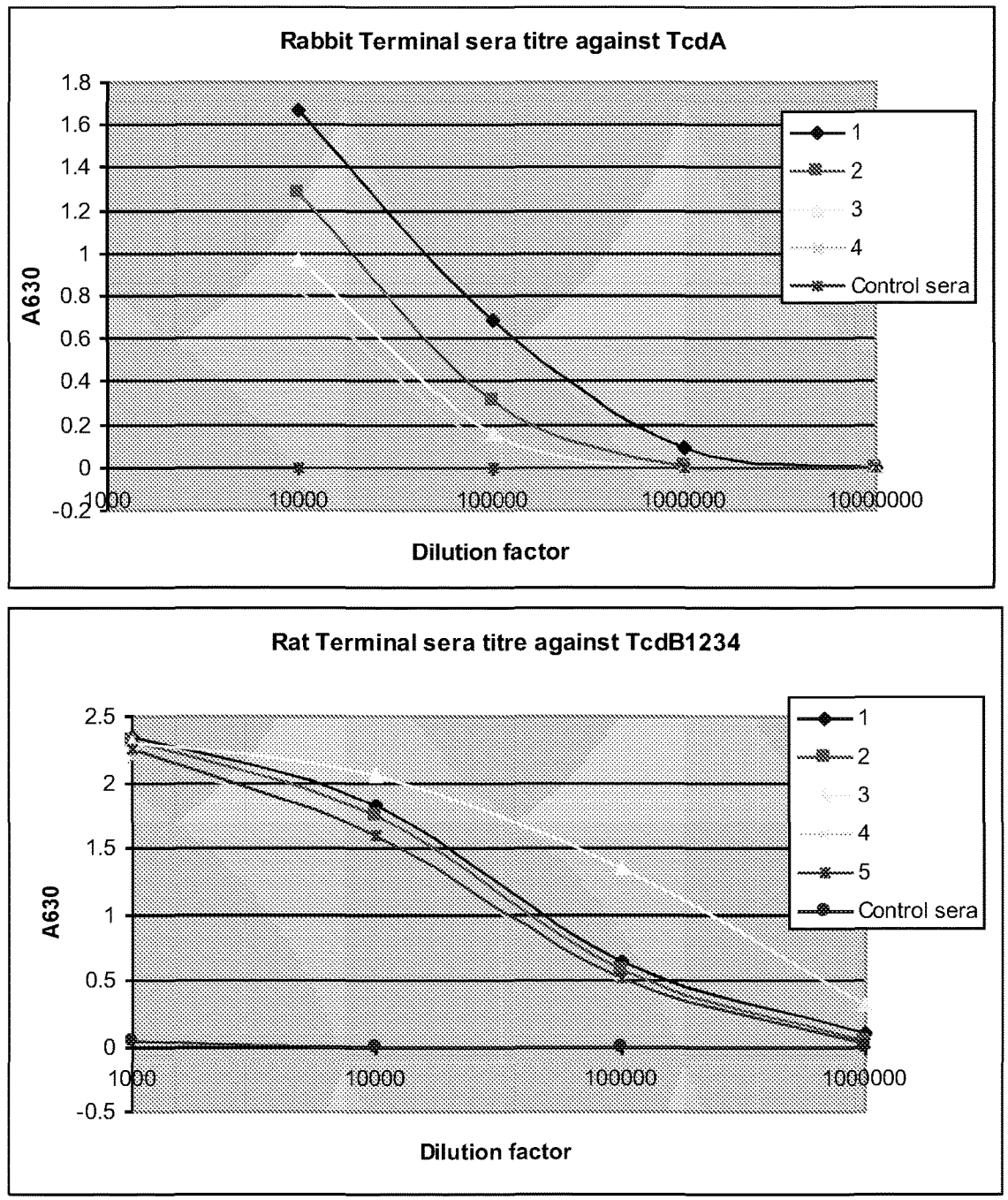
FIG. 11 shows sera titres for TcdA and TcdB

Sprague Dawley rats and half-lop rabbits were immunised with either synthetic peptides mapping to regions common to both TcdA and TdcdB full-length toxin, formaldehyde-inactivated toxoid A, binding domain fragments of Toxin A (CROPs1,2,3 or CROPs4,5,6) or binding domain fragment of Toxin B (CROPs1,2,3,4), or in some cases, a combination of the above. Following 2 to 6 immunisations, animals were sacrificed and PBMC, spleen and bone marrow harvested. Sera were monitored for binding to Toxin A domains, toxin B domains, toxin or toxoid by ELISA. Sera titres of 2 such immunisations are shown in FIG. 11. UCB SLAM was used as a means to generate monoclonal antibodies. B cells were cultured directly from immunised animals (Zubler et al., 1985). This step enabled sampling of a large percentage of the B cell repertoire. By incorporating the selected lymphocyte antibody method (SLAM) (Babcook et al., 1996) it was possible to deconvolute positive culture wells and identify antigen-specific antibody-secreting cells. Here we used a modified version of SLAM (UCB SLAM (Tickle et al. 2009)) that utilises a fluorescence-based method to identify antigen-specific B cells from culture wells. B cell cultures were set up and supernatants were first screened for their ability to bind a relevant purified toxin domain (binding, translocation or catalytic) in a bead-based assay using an Applied Biosystem 8200 cellular detection system. This was a homogeneous assay using B cell culture supernatant containing IgG, biotinylated toxin domains coated onto streptavidin beads and a goat anti-rat/rabbit Fc-Cy5 conjugate. Cell cultures positive for binding to TcdA or TcdB components from this assay were selected for use in cell-based functional assays to identify neutralisers of toxin-induced cytotoxicity. Approximately 12,000 toxin-specific positives were identified in the primary binding screen from a total of 40×50-plate experiments. This equated to the screening of approximately 0.5 billion B cells. Heavy and light variable region gene pairs were isolated from single cells harvested by micromanipulation from approximately 100 toxin-neutralising wells following reverse transcription (RT)-PCR. These V-region genes were then cloned as mouse IgG1/kappa full-length antibodies for rat variable regions and rabbit IgG/kappa full-length antibodies for rabbit variable regions. Antibodies were re-expressed in a HEK-293 transient expression system. These recombinant antibodies were then retested for their ability to neutralise toxin in cell based assays. Recombinant antibodies were also screened by BIAcore to determine affinity for a given toxin domain and to also determine the specificity and approximate the number of binding events of antibody to toxin. Based on in vitro activity in cell based assays and affinity measurements, lead candidates were selected for humanisation. Unless otherwise stated, all the data herein was generated using the humanised antibodies.

A panel of recombinant, *E. coli*-produced toxin fragments (TcdA), *C. difficile*-derived toxin or toxoid (A) and synthetic peptides (B) were generated or purchased from commercial sources.

TABLE 1

Toxin A (TcdA) sequence related reagents for screening and immunizations.

| Fragment | Residue number | Source |
|---|---|---|
| TcdA catalytic | M1-E659 | UCB *E. coli* expression |
| TcdA translocation | K577-D1350 | UCB *E. coli* expression |
| TcdA $CROPS_{123}$ (TcdA123) | S1827-D2249 | UCB *E. coli* expression |
| TcdA $CROPS_{456}$ (TcdA456) | G2205-R2608 | UCB *E. coli* expression |
| TcdA $CROP_1$ | S1827-N1978 | UCB *E. coli* expression |
| TcdA $CROP_2$ | G1966-N2133 | UCB *E. coli* expression |
| TcdA $CROP_3$ | G2100-D2249 | UCB *E. coli* expression |
| TcdA $CROP_4$ | G2213-N2381 | UCB *E. coli* expression |
| TcdA $CROP_5$ | G2328-N2494 | UCB *E. coli* expression |
| TcdA $CROP_6$ | G2462-N2609 | UCB *E. coli* expression |
| TcdA $CROP_7$ | R2554-D2701 | UCB *E. coli* expression |
| TcdB catalytic | M1-A593 | UCB *E. coli* expression |
| TcdB translocation | R576-D1349 | UCB *E. coli* expression |
| TcdB binding (TcdB1234) | S1833-E2366 | UCB *E. coli* expression |
| TcdB $CROP_1$ | S1833-S1981 | UCB *E. coli* expression |
| TcdB $CROP_2$ | G1968-D2113 | UCB *E. coli* expression |
| TcdB $CROP_3$ | G2100-E2247 | UCB *E. coli* expression |
| TcdB $CROP_4$ | G2234-E2366 | UCB *E. coli* expression |
| Toxin A | Full length | purchased |
| Toxin B | Full length | purchased |
| Toxoid A | Full length | purchased |

TABLE 2

Toxin B (TcdB) sequence related reagents for screening and immunizations.

| Toxin Domain | Amino acid Sequence |
|---|---|
| Catalytic | SPVEKNLHFVWIGGEVSD<br>SEQ ID NO: 173 |
| Catalytic | NLAAASDIVRL<br>SEQ ID NO: 174 |
| Catalytic | CGGVYLDVDMLPGIH<br>SEQ ID NO: 175 |
| Catalytic | CGGVYLDVDMLPGIHSDLFK<br>SEQ ID NO: 176 |
| Catalytic | CWEMIKLEAIMKYK<br>SEQ ID NO: 177 |
| Catalytic | CTNLVIEQVKNR<br>SEQ ID NO: 178 |
| Catalytic | PEARSTISLSGP<br>SEQ ID NO: 179 |
| Catalytic | CSNLIVKQIENR<br>SEQ ID NO: 180 |
| Catalytic | TEQEINSLWSFDQA<br>SEQ ID NO: 181 |
| Catalytic | TEQEINSLWSFDPEARSTISLSGPC<br>SEQ ID NO: 182 |
| Translocation | NVEETYPGKLLLC<br>SEQ ID NO: 183 |
| Translocation | Acetyl-CANQYEVRINSEGR<br>SEQ ID NO: 184 |
| Translocation | VNTLNAAFFIQSLIC<br>SEQ ID NO: 185 |
| Translocation | YAQLFSTGLNTIC<br>SEQ ID NO: 186 |
| Translocation | CAGISAGIPSLVNNEL<br>SEQ ID NO: 187 |
| Translocation | DDLVISEIDFNNNSIC<br>SEQ ID NO: 188 |
| Translocation | MEGGSGHTVT<br>SEQ ID NO: 189 |
| Translocation | AVNDTINVLPTITEGIPIVSTILDGINLGAAIKEL<br>SEQ ID NO: 190 |
| Binding | CGFEYFAPANTDANNIEGQA<br>SEQ ID NO: 191 |
| Binding | CGYKYFAPANTVNDNIYGQA<br>SEQ ID NO: 192 |
| Binding | CKYYFNTNTAEA<br>SEQ ID NO: 193 |
| Binding | CKYYFDEDTAEA<br>SEQ ID NO: 194 |

Expression and Purification of *C. difficile* Anti-Toxin Mabs

Separate light chain and heavy chain mammalian expression plasmids were combined in equimolar ratios and used to transfect HEK-293 or CHO-S cells. For small scale expression studies lipofectamine and HEK-293 cells were used whereas for production of larger batches of IgG electroporation into CHO-S was preferred.

Culture supernatants were loaded onto a MabSelect SuRe column (in PBS pH 7.4). Antibody was eluted with 100% 0.1M Sodium Citrate pH 3.4 buffer. Samples were neutralized to pH7.4 with Tris.Cl pH8.0. Aggregate was removed by Superdex 200 Gel Filtration column in PBS pH 7.4.

TABLE 3

| Antibody | Cell type | Volume of Expression SN (L) | type | Amount purified (mg) |
|---|---|---|---|---|
| CA164_00997.g1_P3 | CHO | 10 | Transient | 755.93 |
| CA164_00922.g1_P3 | CHO | 0.5 | Transient | 129.36 |
| CA164_01125.g2_P3 | CHO | 10 | Transient | 498.96 |
| CA164_01151.g4_P3 | CHO | 5 | Transient | 262.43 |

Example 1 In-Vitro Neutralization of TcdA Activity by Purified Mabs

All neutralisation screening assays were run in 96 well polystyrene plates. The assay uses CACO-2 cells grown, and screened in MEM+20% FCS, 2 mM Q, and NEAA. Any antibody combinations are at equal molar ratios unless stated otherwise. Day 1: Cells were plated @ 3000 per well in 50 µl media, and incubated for 24 hrs; Day 2: Purified samples of humanised Mab were added to 96 well round bottomed polypropylene sterile plates; Spike PP plates with toxin A at a concentration sufficient to generated the appropriate lethal dose i.e. $LD_{80}$ or above and incubate for 1 hr, at 37oC; Add 50 µl of this mixture to cell plates and incubate for 96 hrs; Day 5: Add Methylene blue (0.5% Methylene Blue 50% ethanol); Incubate for 1 hr at room temperature; Lyse the cells with 1% N-Lauryl Sarcosine, and Read on the BIOTEK Synergy2 plate reader at 405 nm. The results are shown in FIGS. 12 to 24. $EC_{50}$ and % maximum neutralization of TcdA activity shown confirm that the selected antibodies have very high potencies as single agents. Combinations of 2 to 5 of these did not improve upon the best $EC_{50}$ or % maximum neutralization. Lack of any synergy when combining Mabs CA922, 923, 995, 997 and 1000 is an important observation and may be due to the fact the each antibody alone has exceptionally high levels of affinity and potency. Supporting data in Example 5 also show that some of the Mabs (e.g. CA997) are capable of binding to TcdA subdomains many times. Hence it seems probable that these 5 Mabs represent that the maximum affinity, potency and valency that is achievable when targeting the C-terminal cell binding domain of TcdA. The antibodies were also effective at neutralising very high toxin concentrations ranging from LD80 to greater than $LD_{95}$ ($LD_{max}$) but some modest increases in $EC_{50}$ (i.e. decreases in potency) were observed with very high levels of [TcdA]. These data are also surprising since others have shown substantial reductions in potency when testing elevated TcdA concentrations (20).

The high potency and affinity of the Mabs described here, e.g. for CA997; is not due solely to their high valency of binding. Others (20 and WO06/071877) describe anti-TcdA Mabs capable of binding up to 14 times. These Mabs only had affinities in the range 0.3 to 100 nM and showed incomplete protection against TcdA mediated cell killing, alone (26-63% protection) or in pairs (31-73% protection). Hence it has been demon-strated that high valency of binding to TcdA does not necessarily invoke either high affinity of binding to or neutralisation of TcdA. Neither the affinities nor valency of binding to TcdA were described for Mab CDA-1 (18 and U.S. Pat. No. 7,625,559). Thus Mabs described herein to have surprising affinity, potency and valency.

TABLE 4

Anti TcdA 1, 2 & 3 Mab combinations at a single TcdA conc. ($LD_{80}$)

| Antibody | Final (highest) Mab conc. ng/ml | $EC_{50}$ (ng/ml) |
|---|---|---|
| 922 | 500 | 1.21 |
| 923 | 500 | 160.42 |
| 995 | 500 | 37.64 |
| 997 | 500 | 6.25 |
| 1000 | 500 | 19.73 |
| 922 + 923 | 500 | 3.58 |
| 922 + 925 | 500 | 3.326 |
| 922 + 997 | 500 | 2.88 |
| 922 + 1000 | 500 | 2.64 |
| 923 + 995 | 500 | 60.23 |
| 923 + 997 | 500 | 7.54 |
| 923 + 1000 | 500 | 9.24 |
| 995 + 997 | 500 | 7.29 |
| 995 + 1000 | 500 | 19.63 |
| 997 + 1000 | 500 | 4.46 |
| 922 + 923 + 995 | 500 | 4.72 |
| 922 + 923 + 997 | 500 | 3.23 |
| 922 + 923 + 1000 | 500 | 3.21 |
| 922 + 995 + 997 | 500 | 2.22 |
| 922 + 995 + 1000 | 500 | 2.85 |
| 922 + 997 + 1000 | 500 | 2.22 |
| 923 + 995 + 997 | 500 | 5.04 |
| 923 + 995 + 1000 | 500 | 9.49 |
| 995 + 997 + 1000 | 500 | 5.84 |
| 922 + 923 + 995 + 997 | 500 | 2.75 |
| 922 + 923 + 995 + 1000 | 500 | 3.75 |
| 922 + 995 + 997 + 1000 | 500 | 3.46 |
| 923 + 995 + 997 + 1000 | 500 | 4.81 |
| 922 + 923 + 997 + 1000 | 500 | 3.06 |
| 922 + 923 + 995 + 997 + 1000 | 500 | 4.72 |

TABLE 5

Anti TcdA single, paired, and triplet Mab combinations at various TcdA concentrations, where TcdA is at its $LD_{80}$, $LD_{90}$, $LD_{95}$ and $LD_{max}$.

| Toxin TcdA | Sample | Final Mab conc. ng/ml | $EC_{50}$ (ng/ml) |
|---|---|---|---|
| @ 3000 pg/ml ($LD_{MAX}$) | 922 | 500 | 4.89 |
| | 997 | 500 | 10.99 |
| | 1000 | 500 | 50.17 |
| | 922 + 997 | 500 | 7.18 |
| | 922 + 1000 | 500 | 6.99 |
| | 997 + 1000 | 500 | 9.437 |
| | 922 + 997 + 1000 | 500 | 10.80 |
| | 922 + 997 + 1000 + 995 | 500 | 15.03 |
| | 922 + 997 + 1000 + 995 + 923 | 500 | 7.16 |
| @ 1000 pg/ml ($LD_{95}$) | 922 | 500 | 1.24 |
| | 997 | 500 | 3.42 |
| | 1000 | 500 | 9.60 |
| | 922 + 997 | 500 | 1.85 |
| | 922 + 1000 | 500 | 2.51 |
| | 997 + 1000 | 500 | 3.61 |
| | 922 + 997 + 1000 | 500 | 2.40 |
| | 922 + 997 + 1000 + 995 | 500 | 2.74 |
| | 922 + 997 + 1000 + 995 + 923 | 500 | 2.38 |
| @ 700 pg/ml ($LD_{90}$) | 922 | 500 | 0.84 |
| | 997 | 500 | 2.40 |
| | 1000 | 500 | 6.23 |
| | 922 + 997 | 500 | 1.19 |
| | 922 + 1000 | 500 | 1.33 |
| | 997 + 1000 | 500 | 2.68 |
| | 922 + 997 + 1000 | 500 | 1.84 |
| | 922 + 997 + 1000 + 995 | 500 | 2.17 |
| | 922 + 997 + 1000 + 995 + 923 | 500 | 2.06 |
| @ 350 pg/ml ($LD_{80}$) | 922 | 500 | 0.39 |
| | 997 | 500 | 1.18 |
| | 1000 | 500 | 2.76 |
| | 922 + 997 | 500 | 0.67 |

TABLE 5-continued

Anti TcdA single, paired, and triplet Mab combinations at various TcdA concentrations, where TcdA is at its $LD_{80}$, $LD_{90}$, $LD_{95}$ and $LD_{max}$.

| Toxin TcdA | Sample | Final Mab conc. ng/ml | $EC_{50}$ (ng/ml) |
|---|---|---|---|
| | 922 + 1000 | 500 | 0.85 |
| | 997 + 1000 | 500 | 2.06 |
| | 922 + 997 + 1000 | 500 | 0.83 |
| | 922 + 997 + 1000 + 995 | 500 | 0.97 |
| | 922 + 997 + 1000 + 995 + 923 | 500 | 0.98 |

Example 2 Anti TcdB In-Vitro Neutralization by Purified Mab

Assay Methods Description:

All neutralisation screening assays were run in 96 well polystyrene plates.

The assay uses CACO-2 cells grown, and screened in MEM+20% FCS, 2 mM Q, and NEAA. Unless stated all Ab combinations are in equal ratios.

Day 1: Cells are plated @ 3000 per well in 50 μl media, and incubated for 24 hrs Day 2: Purified samples of humanised Mab were added to 96 well round bottomed polypropylene sterile plates Spike PP plates with toxin B lot #031 and incubate for 1 hr, at 37oC Add 50 μl of this mixture to cell plates Incubate for 96 hrs Day 5: Add Methylene blue (0.5% Methylene Blue 50% ethanol)

Incubate for 1 hr at room temperature

Lyse the cells with 1% N-Lauryl Sarcosine

Read on the BIOTEK Synergy2 plate reader at 405 nm

The data in FIGS. 25 to 33 show that single Mabs alone were relatively ineffective at neutralizing TcdB, both in terms of % maximum neutralization and activity ($EC_{50}$). However, when the antibodies were combined in two's and three's considerable improvements in both % maximum neutralization and activity ($EC_{50}$) were observed. 1125 and 1151 were selected as a best pairing, although other good pairings were observed: 1125+1153, 1125+1134.

The most effective pairs of Mabs were selected empirically and were found retrospectively to make unexpected and surprising combinations when regarding the individual potencies of each Mab. For example, in Table 6 only CA927 had a TcdB neutralisation potential which could result in a defined $EC_{50}$ whilst the TcdB neutralisation potential of both CA1125 and CA1151 were insufficient under these assay conditions to result in a defined $EC_{50}$. However, CA927 was not found to be the most effective Mab to use within a combination. The best CA927 containing combination had an $EC_{50}$ of 13.5 ng/ml whereas other two Mab combinations had $EC_{50}$'s as low as 2.59 and 4.71 ng/ml. In another example, in Table 8 CA1099 had the lowest TcdB neutralisation $EC_{50}$ under the assay conditions used. However, CA1099 was not found to be the most effective Mab to use within a combination. The best CA1099 containing combination had an $EC_{50}$ of 6 ng/ml whereas other two Mab combinations had $EC_{50}$'s as low as 2 and 1 ng/ml. We might speculate that the most effective pairings of Mabs are defined by their cooperative binding modalities especially as defined by having non-overlapping epitopes.

TABLE 6

Anti-TcdB Mab combinations and relative Mab ratios at constant toxin concentration.

| Sample | Final Mab conc. ng/ml | $EC_{50}$(ng/ml) |
|---|---|---|
| 1125.g2 | 1000 | >1000 |
| 1134.g5 | 1000 | >1000 |
| 927.g2 | 1000 | 12.89 |
| 1153.g8 | 1000 | >1000 |
| 1102.g4 | 1000 | >1000 |
| 927 + 1099 | 1000 | >1000 |
| 927 + 1102 | 1000 | >1000 |
| 927 + 1114 | 1000 | >111.111 |
| 927 + 1125 | 1000 | 13.55 |
| 927 + 1134 | 1000 | 51.58 |
| 1099 + 1114 | 1000 | >1000 |
| 1102 + 1114 | 1000 | >333.333 |
| 1102 + 1125 | 1000 | 15.51 |
| 1114 + 1134 | 1000 | 19.70 |
| 1114 + 1151 | 1000 | 25.69 |
| 1114 + 1153 | 1000 | 27.48 |
| 1125 + 1134 | 1000 | 2.59 |
| 1125 + 1151 | 1000 | 4.71 |
| 1125 + 1153 | 1000 | 21.23 |
| 1125 + 1134 + 1114 | 1000 | 3.77 |
| 1125 + 1134 + 927 | 1000 | 2.63 |
| 1125 + 1151 + 1114 | 1000 | 4.90 |
| 1125 + 1151 + 927 | 1000 | 5.69 |
| 1125.g2 + 1134.g5 + 927.g2 | 1000 | 5.83 |
| 1125.g2 + 1134.g5 + 1153.g8 | 1000 | 9.89 |
| 1125.g2 + 1134.g5 + 1102.g4 | 1000 | 2.72 |

Example 3 Neutralisation of TcdB by Combinations of Purified Mab

All neutralisation screening assays were run in 96 well polystyrene plates.

The assay uses CACO-2 cells grown, and screened in MEM+20% FCS, 2 mM Q, and NEAA.

Day 1: Cells are plated @ 3000 per well in 50 μl media, and incubated for 24 hrs Day 2: Purified samples of humanised Mab were added to 96 well round bottomed polypropylene sterile plates Spike PP plates with toxin B (VPI 10463) and incubate for 1 hr, at 37oC Add 50 μl of this mixture to cell plates Incubate for 72 hrs Day 5: Add Methylene blue (0.5% Methylene Blue 50% ETOH)

Incubate for 1 hr at room temperature

Lyse the cells with 1% N-Lauryl Sarcosine

Read on the BIOTEK Synergy2 plate reader at 405 nm

The results are shown in FIGS. 34 to 45.

These data show that the best pair of Mabs for neutralizing TcdB at a range of toxin concentrations was CA1125 and CA1151. Moreover, the 1125+1151 combination was largely unaffected by changes in the relative molar ratios which is in contrast to 1125+1153.

TABLE 7

Anti-TcdB Mab combinations and relative Mab ratios at 3 different toxin concs.

| Antibody combination | EC50 values (ng/ml) | | |
|---|---|---|---|
| | TcdB LD60 | TcdB LD77 | TcdB LD85 |
| 1125.g2 + 927.g2 (50:50) | 2.8 | 6 | 11.3 |
| 1125.g2 + 1102.g4 (50:50) | 4 | 13 | 44 |

TABLE 7-continued

Anti-TcdB Mab combinations and relative
Mab ratios at 3 different toxin concs.

| Antibody combination | EC50 values (ng/ml) | | |
|---|---|---|---|
| | TcdB LD60 | TcdB LD77 | TcdB LD85 |
| 1125.g2 + 1114.g8 (50:50) | 3.5 | 7.1 | 25.4 |
| 1125.g2 + 1134.g5 (50:50) | 0.48 | 1.4 | 4 |
| 1125.g2 + 1151.g4 (50:50) | 0.85 | 0.85 | 1.5 |
| 1125.g2 + 1153.g8 (50:50) | 2.7 | 5.2 | 25.2 |
| 1125.g2 + 1134.g5 (25:75) | <0.15 | 0.84 | 7.2 |
| 1125.g2 + 1151.g4 (25:75) | 0.73 | 1 | 2.1 |
| 1125.g2 + 1153.g8 (25:75) | 7 | 10 | 27 |
| 1125.g2 + 1134.g5 (75:25) | 0.66 | 1.2 | 2.5 |
| 1125.g2 + 1151.g4 (75:25) | 1.4 | 1.2 | 8.3 |
| 1125.g2 + 1153.g8 (75:25) | 2.9 | 7.5 | 30 |

The data show that even the most active specific paired combinations have surprisingly and non-predictably different properties relative to each other. The $EC_{50}$ of the preferred combination of CA1125 and CA1151 in equimolar ratios is largely unaffected by an increasing [TcdB]. The three relative molar ratios of Mabs tested (i.e. 25:75 vs 50:50 vs 75:25) have very similar $EC_{50}$'s to each other, suggesting that CA1125 and CA1151 have especially complementary modes of action. This is in contrast to the combination of CA1125 with CA1134 where the increase in $EC_{50}$ (i.e. reduction of potency) with higher [TcdB] is more substantial and where the three Mab molar ratios are not equally effective: The CA1125:CA1134 ratio of 25:75 is notably less potent than 50:50 and 75:25. This suggests that the combined potency of CA1125+CA1134 is more dependent upon the CA1125 component. The $EC_{50}$ of all three molar combinations of CA1125 and CA1153 is substantially affected by increasing [TcdB] suggesting that CA1153 is a less suitable partner for combination with CA1125. In toto, these data show that CA1125 and CA1151 are a particularly favourable combination since the highest potency is maintained across a range of Mab and TcdB molar ratios.

TABLE 8

TcdB neutralisation - 1 or 2 anti-TcdB
Mabs at constant toxin dose ($LD_{80}$).

| Antibody | IC50 (ng/ml) |
|---|---|
| 1099 | 2 |
| 1102 | N/A |
| 1114 | 103 |
| 1125 | N/A |
| 1134 | 8 |
| 1151 | 182 |
| 1153 | 260 |
| 926 | N/A |
| 927 | N/A |
| 1099 + 1125 | 6 |
| 1114 + 1125 | 7 |
| 1151 + 1125 | 2 |
| 1134 + 1125 | 1 |
| 1102 + 1125 | 6 |
| 1125 + 1153 | 12 |
| 926 + 1125 | 42 |
| 927 + 1125 | 4 |

TABLE 9

TcdB neutralisation - 1 or 2 anti-TcdB Mabs at various TcdB doses.

| Antibody combination | EC50 values (ng/ml) | | | Maximum neutralisation | | |
|---|---|---|---|---|---|---|
| | TcdB LD75 | TcdB LD86 | TcdB LD90 | TcdB LD75 | TcdB LD86 | TcdB LD90 |
| 1125.g2 | n/a | n/a | n/a | 40% | 25% | 15% |
| 1114.g8 | n/a | n/a | n/a | 45% | 25% | 15% |
| 1134.g5 | n/a | n/a | n/a | 45% | 25% | 15% |
| 1151.g4 | n/a | n/a | n/a | 45% | 25% | 20% |
| 1153.g8 | 28.3 | n/a | n/a | 65% | 35% | 28% |
| 1125.g2 + 1114.g8 (50:50) | 10.1 | 243.8 | n/a | 85% | 65% | 40% |
| 1125.g2 + 1134.g5 (50:50) | 1.7 | 22.6 | n/a | 87% | 60% | 40% |
| 1125.g2 + 1153.g8 (50:50) | 6.1 | 32.2 | n/a | 95% | 75% | 48% |
| 1125.g2 + 1151.g4 (50:50) | 0.8 | 2.8 | 19.1 | 85% | 80% | 55% |
| 1125.g2 + 1151.g4 (25:75) | 1.2 | 2.8 | 47.2 | 85% | 75% | 60% |
| 1125.g2 + 1151.g4 (75:25) | 2.9 | 3.8 | 2.6 | 75% | 70% | 60% |

These data show that combination of Mabs, especially CA1125 and CA1151 improve both the potency as measured by $EC_{50}$ but also as measured by % maximum protection. The % maximum protection is of particular relevance in this assay method since the Mab:TcdB mixture is incubated with cells for a long time (72 h). Since TcdB is toxic to Caco-2 cells in the range of pg/ml in 2-4 h this measure may be considered to be a very difficult test of Mab neutralisation ability and may reflect the ability of Mab mixture with regard to their binding kinetics or modalities. In turn this may reflect the ability of Mab mixtures to protect against the effects of TcdB during an established infection when there may be substantial quantities of TcdB within tissues for many hours. Selected data from Tables 6-9 are further illustrated in FIGS. 46-59.

Example 4 Valency of Binding of Mabs to TcdB Sub-Domains

The number of moles of binding events of anti-*C. difficile* TcdB antibodies to $TcdB_{1234}$ was determined by Surface Plasmon Resonance (SPR) on a Biacore 3000 (GE Healthcare). Streptavidin was immobilized on a CM5 sensor chip (GE Healthcare) to a level of ~4000 RU via amine coupling and biotinylated $TcdB_{1234}$ was bound at 500-600 RU. Two 20 μl injections of the same anti-TcdB antibody mixtures (final concentration of each antibody was 500 nM) were injected over this surface at 10 µl/min and the saturating binding response recorded. The surface was regenerated after every cycle using HCl. All the data was corrected for background binding using the response to the streptavidin only reference flowcell.

TABLE 10

Surface plasmon resonance analysis of the number of IgG binding sites on TcdB$_{1234}$

| Antibody combination | No. of binding cycle repeats | Binding Response (RU) | Binding relative to CA927 average response |
|---|---|---|---|
| CA1125.g2 | 10 | 750 | 0.9 |
| CA1151.g4 | 10 | 1232 | 1.6 |
| CA1125_CA1151 | 4 | 1941 | 2.5 |
| CA1125_CA927 | 3 | 1570 | 2.0 |
| CA1151_CA927 | 3 | 1959 | 2.5 |
| CA927 | 8 | 791 | 1.0 |

All responses have been expressed relative to a multiple of CA927 average response (final column table 10) since CA927 appears to be representative of a Mab which binds to TcdB$_{1234}$ once only.

Immobilized CA1125, when bound to TcdB$_{1234}$, does not allow CA1125 to bind further supporting the idea that CA1125 has one binding site on TcdB$_{1234}$ and that after this has been saturated that no other binding site for CA1125 can be found. However, when TcdB$_{1234}$ has been saturated by CA1125, CA1151 can still bind. This demonstrates that CA1151 binds at alternative sites to that occupied by CA1125. Together these data show that CA1125 is a single binder of TcdB$_{1234}$ whereas 1151 IgG binds to TcdB$_{1234}$ more than once, most likely twice. Hence a mixture of CA1125 and CA1151 can bind to TcdB$_{1234}$ approximately 3 times.

All antibodies combinations have an additive binding response showing that there are 2 or more non-competitive sites on TcdB$_{1234}$ bound by these combinations.

Example 5 Valency of Binding of Mabs to TcdA Sub-Domains

The number of moles of binding events of anti-C. difficile TcdA antibodies to TcdA$_{123}$ and A$_{456}$ were determined by Surface Plasmon Resonance (SPR) on a Biacore 3000 (GE Healthcare). Streptavidin was immobilized on a CM5 sensor chip (GE Healthcare) via amine coupling to a level of ~4000 RU and biotinylated TcdA$_{123}$ was bound to one flowcell and TcdA$_{456}$ was bound to a different flowcell to a response of ~500 RU. Two 30 µl injections of the same anti-TcdA antibody at 1 µM were injected over both flowcells at 10 µl/min and the saturating binding response recorded. The surface was regenerated after every cycle using HCl. All the data was corrected for background binding using the response to the streptavidin only reference flowcell.

TABLE 11

SPR analysis of the binding responses of IgGs to immobilised TcdA$_{123}$ and TcdA$_{456}$

|  | CA997 | CA1000 | CA997/CA1000 ratio |
|---|---|---|---|
| TcdA123 | 1069 | 166 | 6 |
| TcdA456 | 1285 | 407 | 3 |

Antibodies CA997 and CA1000 bind to TcdA$_{123}$ in a ratio of six CA997's to one CA1000 whereas they bind to TcdA$_{456}$ in a ratio of three CA997's to one CA1000 (Table 2).

The maximum antibody response for CA997, corrected for molecular weight and immobilized toxin level is similar for TcdA$_{123}$ and TcdA$_{456}$. This suggests that CA997 binds TcdA$_{456}$ six times and CA1000 binds twice to TcdA$_{456}$. Hence antibody CA997 likely binds to TcdA whole toxin (TcdA) approximately 12 times.

Overall CA997 binds six times or more to A$_{123}$ and six times or more to A$_{456}$, whereas CA1000 binds at least once to A$_{123}$ and twice to A$_{456}$.

Increased valency of binding to TcdA and TcdB may have two important effects in vivo. The first is that any Mab or Mab mixture which is capable of binding TcdB more than once will have increased potential to form inter-toxin binding events and hence immunoprecipitation. Immunoprecipitation can contribute to potency by reducing the solubility of toxin and forming very large macromolecular complexes which hence reduce the effective working concentration of toxin. Such large protein complexes may be taken up by macrophages and monocytes resident in the tissue and may contribute to an augmented host immune respone. Antigen: antibody complexes bearing Fc fragments have been specifically shown to be capable of priming a host immune respone against a gut pathogen (21). Also, soluble antigen: antibody complexes have been successfully used as a vaccine directed against the antigen in human clinical trials (22). In addition, immune decoration of toxin with Fc bearing IgG may contribute to immune clearance using normal mechanisms through the liver and spleen. In general, higher levels of Fc decoration of antigen lead to faster and more complete levels of clearance (23) Critically, it may be that presence of 2 or more Mab Fc domains per toxin, especially 3 Fc domains per toxin may represent a critical number of Fcs required for very rapid and substantial clearance of toxin (24). The anti-TcdA Mab CA997 is likely capable of binding to TcdA up to 12 times and the combination of CA1125 and CA1151 is likely capable of binding to TcdB 3 times. Hence the 3 Mab mixture is very likely to be capable of providing for these kinds of additional potency mechanisms in vivo.

Example 6 Mab Neutralisation of Loss of TEER Caused by TcdA

C. difficile monolayer integrity assay is performed using the Becton-Dickinson (BD) Caco-2 BioCoat HTS plate system.

Day 1—Caco-2 cells seeded @ 2×10$^5$/ml per well of the plate insert in 500 µl Basal seeding medium (provided by BD). 35 ml of Basal seeding medium added to the feeder tray. Cells incubated for 24 hours at 37° C. Day 2—Basal seeding medium removed from inserts and feeder tray, and replaced with Entero-STIM differentiation medium (supplied by BD). 500 µl added per well insert and 35 ml to the feeder tray. Cells incubate for a further 72 hrs at 37° C. Day 5—Antibodies prepared at 2× concentration relative to that to be used in the assay well in a polypropylene plate and toxin A. Toxin A added to antibodies at a concentration of 125 ng/ml and plate incubated for 1 hr at 37° C. 1 ml of Caco-2 growth medium (MEM+20% FCS, 2 mM Q, NEAA) added to each well of a standard 24-well TC plate. BioCoat insert plate transferred to the 24-well TC plate. Entero-STIM medium removed from inserts and replaced with 400 µl of toxin:Ab mixture.

Loss of tight junctions between gut cells is the key early effect of TcdA on cell monolayers and gut tissue sections and is the primary cause of diarrhoea. Albumin and other serum proteins are lost into the gut lumen along with accompanying serum fluid. The loss of trans-epithelial electrical resistance in differentiated cultured cells which have formed a monolayer is a useful surrogate for the protection against the acute effects of TcdA. Three antibodies shown have good levels of protection against TEER loss, FIG. 62. It is notable and surprising that the abilities of these Mabs in TEER assays do not reflect those seen in toxin neutralization as measured in a cell proliferation assay. CA922 has the best performance in a cell proliferation assay ($EC_{50}$=1.21 ng/ml) and yet this is considerably out-performed in the TEER assay by an antibody (CA1000) which has >10× lower potency in a cell proliferation assay ($EC_{50}$=19.73 ng/ml). CA997 had the best performance in the TEER assay since it had both high levels of protection and maintained this at the lower Mab concs. CA997 had a substantial potential to neutralize TEER loss with maximal inhibition approaching 80% and an $EC_{50}$ of approximately 80 ng/ml at 4 h. These observations are unexpected since the Mabs in question all had high affinities for TcdA domains (CA922 ~4 pM, CA997 ~132 pM, CA1000 ~73 pM). These data suggest that CA997 and CA1000 recognise epitopes important in TEER loss or neutralize TcdA by different mechanism to other Mabs. Furthermore, since CA1000 is estimated to bind to holotoxin twice (once in $TcdA_{123}$ and once in $TcdA_{456}$) CA1000 may define 'TEER critical' epitopes within the TcdA cell binding regions which might have particular value for defining vaccine immunogens. Results are shown in FIG. 62.

Example 7 Affinity of Anti-*C. difficile* Toxin Antibodies for Sub-Domains of TcdA and TcdB: $TcdA_{123}$, $TcdA_{456}$ and $TcdB_{1234}$ Kinetic constants for the interactions of anti-*C. difficile* TcdA and TcdB antibodies were determined by surface plasmon resonance conducted on a BIAcore 3000 using CM5 sensor chips. All experiments were performed at 25° C. Affinipure F(ab')$_2$ fragment goat anti-human IgG, Fc fragment specific (Jackson ImmunoResearch) was immobilised on a CM5 Sensor Chip (GE) via amine coupling chemistry to a capture level of ≈7000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 μL/min A 10 μL injection of each antibody at 1 ug/ml or lower was used for capture by the immobilised anti-human IgG, Fc. TcdA123, TcdA456 or TcdB 1234 were titrated over captured purified antibodies at doubling dilutions from 12.5 nM at a flow rate of 30 μL/min. For antibodies present in culture supernatants, a single concentration of 12.5 nM of TcdA123 or TcdA456 and 50 nM of TcdB 1234 was passed over the antibodies at 30 ul/min Kinetics were calculated on n=2 The surface was regenerated at a flowrate of 10 uL/min by two 10 μL injections of 40 mM HCl, and a 5 μL injection of 5 mM NaOH.

Double referenced background subtracted binding curves were analysed using the BIAevaluation software (version 3.2) following standard procedures. Kinetic parameters were determined from the fitting algorithm

TABLE 12

Anti-TcdA Mab affinities and binding kinetics

|  | Antibody ID | ka (1/Ms) | kd (1/s) | KD (M) | KD(pM) | Material/Assay |
|---|---|---|---|---|---|---|
| TcdA123 | CA164_00922.g1 | 1.09E+06 | 4.43E−06 | 4.06E−12 | 4.06 |  |
|  | CA164_00923.g1 | 5.36E+05 | 3.47E−05 | 6.47E−11 | 64.7 |  |
|  | CA164_00995.g1 | No binding |  |  | No binding | Purified Mab 5 point titration |
|  | CA164_00997.g1 | 7.84E+05 | 1.03E−04 | 1.32E−10 | 132 |  |
|  | CA164_01000.g1 | 1.33E+05 | 9.78E−06 | 7.33E−11 | 73.3 |  |
|  | CA164_00993.g1 | 9.00E+05 | 5.00E−06 | 5.56E−12 | 5.56 | Supernatant 2× 1point titration |
| TcdA456 | CA164_00922.g1 | 1.29E+06 | 3.33E−06 | 2.59E−12 | 2.59 |  |
|  | CA164_00923.g1 | 6.16E+05 | 1.92E−04 | 3.12E−10 | 312 | Purified Mab 5 point titration |
|  | CA164_00995.g1 | 2.87E+05 | 3.42E−05 | 1.19E−10 | 119 |  |
|  | CA164_00997.g1 | 9.21E+05 | 6.15E−05 | 6.68E−11 | 66.8 |  |
|  | CA164_01000.g1 | 3.55E+05 | 2.98E−05 | 8.41E−11 | 84.1 |  |
|  | CA164_00993.g1 | 1.25E+06 | 5.00E−06 | 4.00E−12 | 4.00 | Supernatant 2× 1point titration |

TABLE 13

Anti-TcdB Mab affinities and binding kinetics

|  | Antibody ID | ka (1/Ms) | kd (1/s) | KD(M) | KD (pM) | Material/Assay |
|---|---|---|---|---|---|---|
| TcdB1234 | CA164_1125.g2 | 2.64E+05 | 3.23E−05 | 1.22E−10 | 122 | Purified Mab 3 point titration |
|  | CA164_1151.g4 | 7.49E+05 | 4.13E−04 | 5.51E−10 | 551 | Purified Mab 3 point titration |
|  | CA164_926.g1 | 1.38E+05 | 7.12E−05 | 5.16E−10 | 516 | Supernatant 2× 1point titration |
|  | CA164_927.g2 | 3.97E+05 | 3.61E−05 | 9.11E−11 | 91 | Purified Mab 3 point titration |
|  | CA164_1099.g2 | 5.24E+35 | 1.63E−05 | 3.10E−11 | 31 | Purified Mab 3 point titration |

TABLE 13-continued

Anti-TcdB Mab affinities and binding kinetics

| Antibody ID | ka (1/Ms) | kd (1/s) | KD(M) | KD (pM) | Material/Assay |
|---|---|---|---|---|---|
| CA164_1102.g4 | 1.17E+05 | 3.78E−04 | 3.25E−09 | 3250 | Supernatant 2× 1point titration |
| CA164_1114.g2 | 2.87E+05 | 1.97E−03 | 6.87E−09 | 6870 | Supernatant 2× 1point titration |
| CA164_1114.g8 | 2.55E+05 | 1.85E−03 | 7.25E−09 | 7250 | Supernatant 2× 1point titration |
| CA164_1129.g1 | 1.89E+05 | 2.30E−04 | 1.22E−09 | 1220 | Supernatant 2× 1point titration |
| CA164_1134.g5 | 5.09E+05 | 2.45E−05 | 4.81E−11 | 48 | Purified Mab 3 point titration |
| CA164_1153.g8 | 1.43E+05 | 4.48E−05 | 3.14E−10 | 314 | Purified Mab 3 point titration |

The anti-TcdA affinities are particularly high compared to the published affinities of other Mabs. We demonstrate that affinities as low as 4 pM are achievable. The preferred CA997 has an affinity of 132 pM, CA1125 122 pM and CA115 551 pM. CA995 clearly shows that it does not bind to CROPs $A_{123}$ and hence that demonstrates that the Mab shown here have properties which are different from each other in surprising and unexpected ways. CA922, 923, 997 and 1000 do bind at least once to CROPs A123 and A456. Hence these 4 Mabs confirming that each must bind to holotoxin at least twice. We have been unable to derive affinities for the binding of these Mabs to holotoxin due to technical constraints. However, given the high affinities and valencies demonstrated for the anti-TcdA Mabs it is possible to speculate that the functional affinities against holotoxin may be even stronger than those illustrated for binding to toxin sub-domains.

The anti-TcdB Mabs also demonstrated strong affinities reaching as low as 31 pM. In particular CA1125, 1151, 927, 1099, 1134 and 1153 show affinities which surpass those demonstrated by others.

Example 8 Biophysical Characteristion of *C. difficile* Anti-Toxin Humanised IgG1 Molecules Molecules Analysed
Anti-TcdA IgG1:
CA164_00922.g1
CA164_0923.g1
CA164_0995.g1
CA164_0997.g1
CA164_01000.g1
Anti-TcdB IgG1
CA164_01125.g1
CA164_01125.g2
CA164_01134.g4
CA164_01134.g5
CA164_01134.g6
CA164_01102.g1
CA164_01102.g4
CA164_01151.g4

Antibody combinations need to be made up of Mabs having high levels of stability in order to mitigate potential risks of aggregation during long term storage. Thermal stability (Tm) is used as one measure. Of special value to Mab mixtures is measuring their propensity to aggregate due to physical stress such as agitation or shaking. Aggregates are undesirable components of drug compositions since they may reduce storage life time and may pose a safety risk to patients at certain levels. The Tm data show that all 5 anti-TcdA Mabs have high Tm stability, whilst three (CA922, 923 and 997) have very high Tm's in the range of 79-81° C. Of the anti-TcdB Mabs tested all but two have very high Tm's. Of note is that CA997, CA1125 and CA1151 which were tested in the hamster infection study (Example 9) had very high Tm's (79.2° C., 79.3° C. and 80.8° C. respectively) which makes them suitable for use in a Mab mixture.

In the shaking aggregation assay, CA997 and 922 had the lowest propensity to aggregate of the 5 anti-TcdA Mabs. Similarly, CA115 and 1151 had the lowest aggregation propensities of the anti-TcdB Mabs. Hence the use of CA997, 1125 and 1151 as a Mab mixture may have special value since they are more likely to survive co-formulation and storage at high protein concentrations.

Estimation of Isoelectric Point (pI) by Capillary IEF

Samples were prepared by mixing the following: 30 ul Protein sample at 2 mg/ml, 0.35% Methylcellulose, 4% pH3-10 ampholytes (Pharmalyte), synthetic pI markers (4.65 and 9.77), 1 ul of each stock solution, and HPLC grade water to make up the final volume to 200 ul. The mixture was then analysed using iCE280 IEF analyzer (pre-focusing at 1500V for 1 min followed by focusing at 3000V for 6 mins). The calibrated electropherograms were then integrated using Empower software (from Waters)

Thermal Stability (Tm) Measured Via Thermofluor Assay.

This method uses Sypro orange fluorescent dye to monitor the unfolding process of protein domains. The dye binds to exposed hydrophobic regions that become exposed as a consequence of unfolding which results in a change to the emission spectrum.

The sample (5 ul at 1 mg/ml) is mixed with a 5 ul of a stock solution of Sypro orange (30×) and the volume made up to 50 ul with PBS, pH 7.40.

10 ul aliquots of this solution is applied to wells in a 384 well plate (n=4).

The plate is placed in a 7900HT fast real-time PCR system containing a heating device for accurate temperature control. The temperature is increased from 20° C. to 99° C. (Ramp rate of 1.1° C./min). A CCD device simultaneously monitors the fluorescence changes in the wells. An algorithm is used to process intensity data and take into account multiple transitions.

Stressing of Samples by Agitation.

During manufacture antibody samples are subjected to mechanical stress generated by processes such as pumping and filtration. This may cause denaturation and consequently aggregation due to exposure of the protein to air-liquid interfaces and shear forces resulting in the ultimate loss of bioactivity. Stress by vortexing is a method to screen the robustness of the antibody samples for prediction of aggregation stability.

Both anti-TcdA and anti-TcdB IgG1 molecules were subjected to stress by agitation, by vortexing using an Eppendorf Thermomixer Comfort at 25° C., 1400 rpm. Sample size was 250 uL, (×3 per sample) in a 1.5 mL conical Eppendorf-style capped tube (plastic), in PBS pH 7.4. Each sample was brought to a concentration of 1 mg/ml (using extinction coefficient calculated from sequence) and aggregation was monitored by absorbance at 340 nm and/or 595 nm, by use of a Varian Cary 50-Bio spectrophotometer, measured at intervals for up to 24 hours.

Results Table 14 provides a summary of the measured pI and Tm data for both anti-TcdA and anti-TcdB IgG1 molecules.

TABLE 14

Compilation of pI and Tm Data

| | measured pI | Tm(Fab) in PBS | Tm(CH2) |
|---|---|---|---|
| Anti-TcdA IgG1 | | | |
| CA164_00922.g1 | 8.8 | 81 | 69.2 |
| CA164_0923.g1 | 9.2 | 79 | 69.3 |
| CA164_0995.g1 | 8.5 | 71 | no data* |
| CA164_0997.g1 | 8.3 | 79.2 | 68.4 |
| CA164_01000.g1 | 7.74 | 70.5 | no data* |
| Anti-TcdB IgG1 | | | |
| CA164_01125.g1 | 9.2 | 79.3 | 69.4 |
| CA164_01125.g2 | 9.2 | 79.5 | 69.3 |
| CA164_01134.g4 | 9.3 | 78.4 | 69.4 |
| CA164_01134.g5 | 9.2 | 76.4 | 69.2 |
| CA164_01134.g6 | 9.2 | 76.6 | 69.6 |
| CA164_01102.g1 | 9.1 | 69 | no data* |
| CA164_01102.g4 | 9.1 | 69.1 | no data* |
| CA164_01151.g4 | 9.2 | 80.8 | 69.8 |

*denotes that it was not possible to discern the Fab and CH2 domains.

Measured pI

The measured pI of the molecules were high (except for CA164_01000.g1_P3) and away from the pH of formulation buffers such as PBS, pH 7.4 and 50 m sodium acetate/125 mM sodium chloride, pH 5. This may mean that buffers with pH's suitable for co-formulation of two or more Mabs can be selected.

Thermal Stability (Tm) Measured Via Thermofluor Assay

Since all of the molecules are IgG1, the Tm of the Fc domain (Tm(CH2)) are the same. The difference in thermal stability between the molecules can be determined by the Tm of the Fab' domain (Tm(Fab)).

For the anti-TcdA molecules, the rank order (most stable first) was CA922≥997>923>995>1000 and for the anti-TcdB molecules (most stable first) was CA1151.g4>1125.g1, g4>1134.g4>1134.g5>1134.g6>1102.g1=1102.g4.

Stressing of Samples by Agitation

It was possible to determine different aggregation stability between the different antibodies, FIG. 67 shows the effect of agitation via vortexing on different anti-TcdA IgG1 molecules in PBS, pH 7.4.

It was possible to determine a ranking order (most aggregation stable first):

CA922≥997>923≥995>1000

FIG. 68 shows the effect of agitation via vortexing on different anti-TcdB molecules.

It was possible to rank the order of aggregation stability, such that the CA1125 grafts appeared more stable than the CA1134 molecules which were more stable than the CA1102 molecules.

A further study was performed to compare directly the aggregation stability of the anti-TcdB molecule (CA1151.g4) with the more stable molecule CA1125.g2 (see FIG. 2) and more aggregation stable anti-TcdA molecules (CA922.g1 and CA997.g1). The results can be seen in FIG. 69.

Further results for these 4 Mabs are also shown in FIGS. 67 and 68.

For the anti-TcdA molecules, CA922.g1 and CA977.g1, CA922 were preferable based on the analyses above, although apart from CA1000) all molecules could be considered suitable candidates for use as therapeutic IgG1.

For the anti-TcdB molecules, the biophysical characteristics could be grouped within the family of grafts based on the aggregation stability and Tm, such that the CA1125 grafts potentially proved more stable. The CA1102 grafts showed poorest Tm data and also showed the greatest tendency to aggregate via stress by agitation.

A study using CA1151.g4 showed that this molecule exhibited slightly increased aggregation stability relative to CA11125.g2 and seemed equivalent to the TcdA molecules (CA922.g1 and CA997.g1. All four molecules showed equivalent Tm values. CA997, CA1125 and CA1151 show very high levels of thermostability and very low levels of aggregate formation after agitation.

Example 9 Anti-*C. difficile* Toxin Mab Hamster Infection Study

The hamster infection study was performed by Ricerca Biosciences LLC, Cleveland, Ohio, USA. The study protocol was approved by the Ricerca IACUC committee. Active and control components (composition and dose) were blinded to Ricerca staff until after completion of the planned 28 day study period.

Golden Syrian male hamsters (weight 82-103 g, 54 days old) were individually housed in HEPA filtered disposable cages and fed Teklad Global Diet 2016 and water ad libitum. After acclimatisation, hamsters were pre-dosed (i.p.) with Mab mixtures or PBS (vehicle control) once a day for each of 4 days: days −3, −2, −1 and 0. Two doses of Mab were investigated: high dose=50 mg/kg each of anti-TcdA and anti-TcdB components and low dose 5 mg/kg each of anti-TcdA and anti-TcdB components.

The drug combination tested was composed of one anti-TcdA antibody (CA997.g1) which constituted 50% of the injected protein and two anti-TcdB antibodies (CA1125.g2 and CA1151.g4) which together constituted 50% of the injected protein but which alone constituted 25% of the injected protein. Hamsters were sensitised (day −1) with 50 mg/kg of Clindamycin phosphate in PBS (s.c.) before being challenged 1 day later (day 0) with 3.4×106 c.f.u. of vegetative cells from strain ATCC43596. Vancomycin was dosed at 5 mg/kg twice a day for 5 days (p.o.) on days 1, 2, 3, 4, 5.

Viability checks were performed on animals twice a day, animals found to be in extremis were euthanised and counted as dead. Body weights were determined on each day of dosing, then twice weekly and before euthanising survivors. Gross necropsy was performed on all animals. Survival curves were created by the method of Kaplan and Meier. Survival curves were analysed using the P value from the log rank test compared to the Bonferroni corrected threshold of P=0.005. The Vancomycin treated group were not included in the analysis. All statistical tests were done with Prism v5.04. All groups contained 11 animals, except the Vancomycin control group which contained 5 animals.

Survival curves can be seen in FIG. 63. Hamsters receiving PBS (control) all died on days +2 and +3, whilst those receiving vancomycin treatment for 5 days all died on days +10 and +11. Hamsters receiving the high dose of UCB Mab mixture all survived until day +11, thereafter only two animals died until the end of the 28 day study. Hamsters receiving the low dose of UCB Mab mixture all survived until day +3, thereafter animals were lost fairly steadily until day +16 when all had died. The data show exceptional levels and duration of protection when compared to published data for use of anti-toxin Mabs in hamsters (18). These in vivo data support the in vitro observations of very high level performance for neutralization and stability.

There is no apparent link between death and body weight during the acute phase (days 1-5) of the infection, FIGS. 64-65. Hence it may be supposed that hamsters die of overwhelming direct and indirect effects of TcdA and TcdB. Hamsters which survive the acute period due to partial protection (UCB low dose) of neutralizing Mabs lose weight, presumably due to gut damage and altered nutritional status. It was notable that many of the hamsters which went on to survive the 28 period of the study due to the protective effects of the UCB high dose Mabs recovered from weight loss and indeed even gained weight. This may be taken as evidence of the superior protective effects of the UCB Mabs enabling the gut to function as normal.

TABLE 15

Gross pathology scores

| Group | Black caecum | Dark red caecum | Red caecum | Pink caecum | Normal caecum | Anogenital staining 'wet-tail' | Red small intestine |
|---|---|---|---|---|---|---|---|
| PBS control | 1 | 9 | 1 | 0 | 0 | 1 | 1 |
| UCB low | 0 | 4 | 5 | 2 | 0 | 4 | 1 |
| UCB high | 0 | 0 | 1 | 1 | 9 | 3 | 0 |

It is clear that UCB Mabs were able to protect the large and small intestines from the bloody effusions caused by TcdA and TcdB.

The results are shown in FIGS. 63 to 66

The photographs in FIG. 66 show typical gross pathologies for the swelling and bloody effusions of caeca caused by TcdA and TcdB (left image, PBS control, animal death on day 2) and a normal stool filled caeca after protection by UCB high dose Mabs (right image, UCB high dose, animal surviving to day 28). These data show that after protection with a high dose of UCB Mabs the large intestine can return to normal morphology and function.

Example 10 Neutralisation of TcdA from Different Ribotyped Strains by Purified Mab Clinical infections are caused by a variety of different strains. Strain differences are characterized using a number of different methods of which ribotyping is a key one. Different ribotype strains are observed to have different pathogenicity, infection and sporulation properties. All of the TcdA neutralization shown above used TcdA purified from strain known as VPI10463. However, the predominant aggressively pathogenic strain associated with out-breaks is called ribotype 027. Other key ribotypes include 078, 001, 106 Amino acid sequence difference have been observed between toxins produced by different ribotypes and hence it is important that Mabs are capable of neutralizing toxin from a diverse set of clinical isolates. CA922, 997 and 1000 were tested for their ability to neutralize TcdA from strains 027 and 078 and compared to their abilities against TcdA from VPI10463. Mabs were tested at 4 [TcdA] and found to be capable of neutralizing all toxins without significant difference at $LD_{80}$, $LD_{90}$ and $LD_{95}$

TABLE 16

| | EC50 values (ng/ml) - TcdA strain VPI 10463 | | | |
|---|---|---|---|---|
| Antibody | LD80 | LD90 | LD95 | LDmax |
| CA164_922 | 0.27 | 0.9 | 1.2 | >500 |
| CA164_997 | 1 | 2.5 | 3.5 | 25.4 |
| CA164_1000 | 3.6 | 13.5 | 19.3 | >500 |

TABLE 17

| | EC50 values (ng/ml) - TcdA ribotype 027 | | | |
|---|---|---|---|---|
| Antibody | LD80 | LD90 | LD95 | LDmax |
| CA164_922 | 0.19 | 0.25 | 0.41 | 1.46 |
| CA164_997 | 0.92 | 1.27 | 1.75 | 7.19 |
| CA164_1000 | 2.25 | 2.49 | 3.52 | 16.32 |

TABLE 18

| | EC50 values (ng/ml) - TcdA ribotype 078 | | | |
|---|---|---|---|---|
| Antibody | LD80 | LD90 | LD95 | LDmax |
| CA164_922 | 0.11 | 0.12 | 0.25 | 0.68 |
| CA164_997 | 0.33 | 0.64 | 1.11 | 2.57 |
| CA164_1000 | 2.04 | 2.41 | 5.03 | 14.16 |

Example 11 PK Data

A PK study of a human IgG1 (20 mg/kg) in healthy hamsters. The hamster PK was found a half-life similar to Mabs in mice or rats. (t½ 6-8 days). i.p. and s.c. dosing were essentially the same.

The pharmacokinetics and distribution to the gut of a hIgG1 Mab was studied in 'normal' (non-infected) golden Syrian hamsters. Purified Mab was administered to male hamsters (120-135 g) by CARE Research LLC, Fort Collins, Colo., USA and samples were assayed by UCB Pharma.

The study was approved by the CARE IACUC committee. Eight animals each received a single dose of 20 mg/kg of IgG1, four were dosed i.p., four were dosed s.c. Blood was collected at 1, 3, 8, 24, 48, 72, 103 and 168 hours post-dose, serum was separated before storage at −80° C. Blood was also taken from two untreated hamsters in order to provide assay controls. Following euthanasia, a 2 cm length of colon was cut from the caeca junction onwards from each hamster. The colon section was flushed with wash buffer (50% (v/v) PBS containing 50% (v/v) Sigma protease inhibitor cocktail (P2714) before being opened and separation and removal of the mucosa from the underlying muscle. Mucosal samples were placed in 0.5 ml of wash buffer homogenized until visually uniform and stored at 4° C. before immediate shipping on wet ice. For the anti-human IgG1 ELISA Nunc maxisorp 96 well plates were coated overnight in 0.1M NaHCO$_3$ pH 8.3 with Goat F(ab')$_2$ anti-human IgG-Fcγ fragment (Jackson 109-006-098), plates were washed with PBS-Tween (PBS/0.1% (v/v) Tween 20) and then blocked with 1.0% (w/v) BSA & 0.1% (v/v) Tween in PBS. Serum samples were diluted in sample-conjugate buffer (1% (w/v) BSA, 0.2% Tween in PBS) and after washing were revealed with goat anti-human kappa-HRP (Cambridge Bioscience 2060-05) in sample-conjugate buffer and TMB with a 2.5M H$_2$SO$_4$ stop solution.

Gut, Mucosa and Serum Levels:

Serum samples collected from blood taken at 168 hour time point and colon samples were removed after this.

20 mg/kg IP at 168 hour

| Sample | ng/mL per cm mucosa | serum µg/mL |
| --- | --- | --- |
| 1001 | 23.2 | 75.0 |
| 1002 | 13.7 | 90.8 |
| 1003 | 21.8 | 70.5 |
| 1004 | 53.8 | 119.4 |

20 mg/kg SC at 168 hour

| Sample | ng/mL per cm mucosa | serum µg/mL |
| --- | --- | --- |
| 2001 | 41.4 | 108.7 |
| 2002 | 62.1 | 76.6 |
| 2003 | 35.6 | 163.7 |
| 2004 | 37.3 | 153.3 |

Serum Data

| | | Hamster i.p. | | Hamster s.c. | |
| --- | --- | --- | --- | --- | --- |
| | | Mean | SE of mean | Mean | SE of mean |
| $C_{max}$: | µg/mL | 202 | 12 | 186 | 21 |
| $T_{max}$: | hr | 36 | 7 | 76 | 16 |
| $AUC_{(last)}$: | hr · µg/mL | 22626 | 1378 | 22371 | 2258 |
| $AUC_{(inf)}$: | hr · µg/mL | 43287 | 7169 | 61290 | 17637 |
| % Extrapolation: | | 43.7 | 9.2 | 54 | 11.7 |
| CL/F | mL/hr/kg | 0.50 | 0.07 | 0.43 | 0.13 |
| $MRT_{inf}$ | h | 223 | 53 | 310 | 88 |
| $t_{1/2, z}$: | h | 149.2 | 36.9 | 188.5 | 61.9 |

The data is also shown in FIGS. 70 and 71

| Hamster ID | | Mean | SE |
| --- | --- | --- | --- |
| IP serum kinetics | | | |
| $C_{max}$: | µg/mL | 202 | 12 |
| $T_{max}$: | hr | 36 | 7 |
| $AUC_{(last)}$: | hr · µg/mL | 22626 | 1378 |
| $AUC_{(inf)}$: | hr · µg/mL | 43287 | 7169 |
| % Extrapolation: | | 43.7 | 9.2 |
| CL/F | mL/hr/kg | 0.50 | 0.07 |
| $MRT_{inf}$ | h | 223 | 53 |
| $t_{1/2, z}$: | h | 149.2 | 36.9 |
| SC serum kinetics | | | |
| $C_{max}$: | µg/mL | 186 | 21 |
| $T_{max}$: | hr | 76 | 16 |
| $AUC_{(last)}$: | hr · µg/mL | 22371 | 2258 |
| $AUC_{(inf)}$: | hr · µg/mL | 61290 | 17637 |
| % Extrapolation: | | 54 | 11.7 |
| CL/F | mL/hr/kg | 0.43 | 0.13 |
| $MRT_{inf}$ | h | 310 | 88 |
| $t_{1/2}$: | h | 188.5 | 61.9 |

It was also shown that hIgG1 could be found in 'scrapings' of the gut i.e that hIgG1 gets into the vasculature of healthy gut—and so could be protective in 'prophylactic dosing'. This effect would be even more profound in humans since they have a cognate hFcRn.

Example 12 Serum Levels in Hamsters with *C. difficile* Infection

This study was to determine the serum concentration of CA725.0, CA726.0, CA997.g1 CA1125.g2, and CA01151.g4 following i.p. administration (various doses detailed below) in the Golden Syrian Hamster.

Humanised Mabs were quantified using liquid chromatography tandem mass spectrometry (LC-MS/MS) analysis following tryptic digestion. Quantitation was achieved by comparison to authentic standard material spiked at known concentrations into blank matrix, with spiked horse myoglobin used as the internal standard.

A unique ("proteotypic") peptide common to all of the humanised Mabs investigated was selected (DTLMISR, a CH2 region peptide) and both samples and calibration samples were tryptically digested as outlined. Tryptic digest of 5 µl serum samples was performed overnight using sequencing grade modified Trypsin (Promega, Southampton, UK) following denaturation/reduction with acetonitrile/Tris(2-carboxyethyl)phosphine and carbamido-methylation with iodoacetamide (Sigma-Aldrich, Poole, UK).

The LC-MS/MS system consisted of a CTC HTS-x Autosampler (CTC Analytics, Zwingen, Switzerland), a Agilent 1290 LC system (Agilent Technologies, Stockport, UK) and a Sciex 5500 QTrap MS system (AB Sciex, Warrington, UK), equipped with a Turbo V ion source operated in electrospray mode. Analytes were separated using an Onyx Monolithic C18 column (100×4.6 mm, Phenomenex, Macclesfield, UK) with a gradient of 2 to 95% (v/v) water/acetonitrile (0.1% formic acid) delivered at 1.5 mL/min over 6 minutes. The injection volume was 10 µL; all of the eluent was introduced into the mass spectrometer source. The source temperature of the mass spectrometer was maintained at 600° C. and other source parameters (e.g. collision energy, declustering potential, curtain gas pressure etc.) were optimized to achieve maximum sensitivity for the peptide of interest. Selective transitions for each proteotypic peptide of interest were monitored.

Unique ("proteotypic") peptides were selected for all of the analytes of interest; samples were analysed following tryptic digestion.

Plasma concentrations calculated based on the peptides monitored are outlined below. For CA164_00997 and CA164_01151, interfering peaks were observed in the MRM traces. For this reason, these two analytes could not be quantified in the samples.

Total h-IgG was quantified in all samples using a peptide common to all analytes of interest. This was done using a combined standard curve of all five analytes. The validity of this approach is demonstrated by the fact that the sum of the concentrations observed for CA164_00725 and CA164_00726 are in good agreement (within experimental error) of the concentration observed for total h-IgG.

Using this approach, the total concentration of h-IgG in the samples of animals dosed with CA164_00997, CA164_01125 and CA164_01151 was determined.

Overall the data obtained indicate that the exposure of all five analytes of interest was similar for a given dose.

Study Groups

| Grp | Blinded labels Treatment | Actual Treatments | Dose days | Treatment components Anti-toxin A | | Anti-toxin B | |
|---|---|---|---|---|---|---|---|
| 4 | Treatment 3 | Vehicle PBS 5 mL/kg i.p. | 3, −2, −1, 0 | | | | |
| 2 | Vancomycin | Vancomycin 5 mg/kg b.i.d. p.o. | 1, 2, 3, 4, 5 | | | | |
| 1 | Treatment 1 | UCB LD* 5 mg/kg A 5 mg/kg i.p. | 3, −2, −1, 0 | CA997.g1_P3 5 mg/kg | CA1125.g2_P3 2.5 mg/kg | CA1151.g4_P3 2.5 mg/kg | |
| 5 | Treatment 4 | UCB HD* 50 mg/kg A 50 mg/kg i.p. | 3, −2, −1, 0 | CA997.g1_P3 50 mg/kg | CA1125.g2_P3 25 mg/kg | CA1151.g4_P3 25 mg/kg | |
| 6 | Treatment 5 | Competitor LD* 5 mg/kg A 5 mg/kg i.p. | 3, −2, −1, 0 | CA726_P3 5 mg/kg | CA725_P3 5 mg/kg | | |
| 3 | Treatment 2 | Competitor HD* 50 mg/kg A 50 mg/kg i.p. | 3, −2, −1, 0 | CA726_P3 50 mg/kg | CA725_P3 50 mg/kg | | |

TABLE 19

| Group/time | Day | Animal No | Dose | Serum conc μg/mL total h-IgG |
|---|---|---|---|---|
| 1 | 1 | 44 | 5 mg/kg 997, | 280 |
| | 1 | 45 | 2.5 mg/kg 1125, | 302 |
| | 1 | 46 | 2.5 mg/kg 1151 | 182 |
| | 6 | 45 | | 61 |
| | 6 | 47 | | 71 |
| | 6 | 49 | | 45 |
| 3 | 1 | 60 | 50 mg/kg 725, | 3040 |
| | 1 | 61 | 50 mg/kg 726 | 3330 |
| | 1 | 62 | | 2990 |
| | 6 | 62 | | 583 |
| | 6 | 63 | | 913 |
| | 6 | 64 | | 1240 |
| | 28 | 64 | | 199 |
| | 28 | 65 | | 36 |
| 4 | 1 | 71 | Vehicle | nd |
| | 1 | 72 | | nd |
| | 1 | 73 | | nd |
| 5 | 1 | 82 | 50 mg/kg 997, | 3050 |
| | 1 | 83 | 25 mg/kg 1125, | 2790 |
| | 1 | 84 | 25 mg/kg 1151 | 2370 |
| | 6 | 82 | | 838 |
| | 6 | 83 | | 645 |
| | 6 | 84 | | 855 |
| | 28 | 82 | | 116 |
| | 28 | 83 | | 65 |
| | 28 | 84 | | 66 |
| | 28 | 85 | | 44 |
| | 28 | 86 | | 101 |
| | 28 | 87 | | 89 |
| | 28 | 88 | | 27 |
| | 28 | 89 | | 31 |
| | 28 | 90 | | 66 |
| 6 | 1 | 93 | 5 mg/kg 725, | 335 |
| | 1 | 94 | 5 mg/kg 726 | 322 |
| | 1 | 95 | | 260 |
| | 6 | 200 | | 103 |
| | 6 | 202 | | 62 |
| | 6 | 203 | | 79 |
| | 28 | 203 | | nd | nd—not detected (LOQ = 2.5 μg/mL for all analytes
na—not analysed: interference in the sample was observed for 997 and 1151

TABLE 20

Antibody CA725 is prior art antibody MDX1388. Antibody CA726 is prior art antibody CDA1 as described (15) A summary of this data is presented in FIG. 72.

| | Caecal pathology | | | | | Small intestine pathology | |
|---|---|---|---|---|---|---|---|
| Group | Black | Dark Red | Red | Pink | Normal | Dark Red | Red |
| PBS control | 1 | 9 | 1 | 0 | 0 | 0 | 1 |
| MDX high 50 mg/Kg × 4 | 0 | 1 | 4 | 4 | 2 | 1 | 0 |
| UCB high 50 mg/Kg × 4 | 0 | 0 | 1 | 1 | 9 | 0 | 0 |

REFERENCES

1. Kuehne, S et al., "The role of toxin A and toxin B in *Clostridium difficile* Infection" Nature (2010) 467: 711-713.
2. Davies A H et al., "Super toxins from a super bug: structure and function of *Clostridium difficile* toxins" Biochem. J (2011) 436: 517-526.
3. Rothman, S et al., "Differential Cytotoxic Effects of Toxins A and B Isolated from *Clostridium difficile*" Infect. Imm. (1984) 46: 324-331.
4. Du, T and Alfa, M J "Translocation of *Clostridium difficile* toxin B across polarized Caco-2 cell monolayers is enhanced by toxin A" Can J Infect Dis. (2004) 15: 83-88.
5. Kim, Iaconis and Rolfe. "Immunization of Adult Hamsters against *Clostridium difficile*-Associated Ileocecitis and Transfer of Protection to Infant Hamsters" Infect. Imm (1987) 55:2984-2992
6. Rupnik J C M (2003) 41:1118-1125
7. Chaves-Olarte J B C (1999) 274:11046-11052.

8. Lylerly, D M et al., "Passive Immunization of Hamsters against Disease Caused by *Clostridium difficile* by Use of Bovine Immunoglobulin G Concentrate" Infection and Immunity (1991) 59:2215-2218.
9. Lylerly, D M et al., "Vaccination against Lethal *Clostridium difficile* Enterocolitis with a Nontoxic Recombinant Peptide of Toxin A" Current Microbiology (1990) 21:29-32.
10. Lylerly, D M et al., "Characterization of Toxins A and B of *Clostridium difficile* with Monoclonal Antibodies" Infect. Imm. (1986) 54:70-76.
11. Corthier et al., "Protection against Experimental Pseudomembranous Colitis in Gnotobiotic Mice by Use of Monoclonal Antibodies against *Clostridium difficile* Toxin A" Infect. Imm. (1991) 59: 1192-1195.
12. Kink J A and Williams J A, "Antibodies to Recombinant *Clostridium difficile* Toxins A and B Are an Effective Treatment and Prevent Relapse of *C. difficile*-Associated Disease in a Hamster Model of Infection" Infect. Imm. (1998) 66:2018-2025.
13. Ma D, et al., Progenics inc. ASM Poster 27 May 2010
14. Hansen, G and Demarest, S J. WO 2006/0718877 A2
15. Babcock G J, et al., "Human monoclonal antibodies directed against toxins A and B prevent *Clostridium difficile*-induced mortality in hamster" Infect. Imm. (2006) 74:6339-6347.
16. Lowy I et al., "Treatment with Monoclonal Antibodies against *Clostridium difficile* Toxins" NEJM (2010) 362: 197-205.
17. Zubler, R. H., Erard, F., Lees, R. K., Van, L. M., Mingari, C., Moretta, L. & MacDonald, H. R. (1985). Mutant E L-4 thymoma cells polyclonally activate murine and human B cells via direct cell interaction. J. Immunol. 134, 3662-3668
18. Babcook, J. S., Leslie, K. B., Olsen, O. A., Salmon, R. A. & Schrader, J. W. (1996). A novel strategy for generating monoclonal antibodies from single, isolated lymphocytes producing antibodies of defined specificities. Proc. Natl. Acad. Sci. U. S. A 93, 7843-7848
19. Tickle, S., Adams, R., Brown, D., Griffiths, M., Lightwood, D. & Lawson, A. (2010). High-Throughput Screening for High Affinity Antibodies, pp. 303-307.
20. Demarest et al., mAbs (2010) 2:190-198
21. Yoshida et al., J. Clin. Invest. (2006) 116: 2142-2151
22. Xu et al., Vaccine (2005) 23:2658-2664.
23. Yousaf et al., Clin. Exp. Immunol. (1986) 66:654-660
24. Mannik et al., J. Exp. Med. (1971) 133: 713-739
25. Nusrat et al., Infection and Immunity (2001) 69:1329-1336
26. Lima et al., Infect Immun (1988) 56:582-588
27. Ravichandran et al J of Pharmacology and Experimental Therapeutics. (2006) 318: 1343-1351
28. Takahashi et al., (2009) Vaccine 27:2616-2619
29. Cohen et al., Infect. Cont. and Hosp. Epidem. (2010) 31: 431-455
30. Barbut et al., J. Clin. Microbiol. (2000) 38: 2386-2388
31. Wilcox et al., J. Hospital Infection (1998) 38: 93-100.

The invention claimed is:

1. A pharmaceutical composition comprising an antibody molecule which binds specifically to antigen TcdA and wherein the anti-TcdA antibody comprises a heavy chain wherein the variable domain of the heavy chain comprises:
   (i) a CDR having the sequence given in SEQ ID NO: 44 for CDR-H1, a CDR having the sequence given in SEQ ID NO: 45 for CDR-H2 and a CDR having the sequence given in SEQ ID N O: 46 for CDR-H3;
   (ii) a CDR having the sequence given in SEQ ID NO: 54 for CDR-H1, a CDR having the sequence given in SEQ ID NO: 55 for CDR-H2 and a CDR having the sequence given in SEQ ID NO: 56 for CDR-H3;
   (iii) a CDR having the sequence given in SEQ ID NO: 4 for CDR-H1, a CDR having the sequence given in SEQ ID NO: 5 for CDR-H2 and a CDR having the sequence given in SEQ ID NO: 6 for CDR-H3; or
   (iv) a CDR having the sequence given in SEQ ID NO: 34 for CDR-H1, a CDR having the sequence given in SEQ ID NO: 35 for CDR-H2 and a CDR having the sequence given in SEQ ID NO: 36 for CDR-H3; and a light chain wherein the variable domain of the light chain comprises:
   (v) a CDR having the sequence given in SEQ ID NO: 41 for CDR-L1, a CDR having the sequence given in SEQ ID NO: 42 for CDR-L2 and a CDR having the sequence given in SEQ ID NO: 43 for CDR-L3;
   (vi) a CDR having the sequence given in SEQ ID NO: 51 for CDR-L1, a CDR having the sequence given in SEQ ID NO: 52 for CDR-L2 and a CDR having the sequence given in SEQ ID NO: 53 for CDR-L3;
   (vii) a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3; or
   (viii) a CDR having the sequence given in SEQ ID NO: 31 for CDR-L1, a CDR having the sequence given in SEQ ID NO: 32 for CDR-L2 and a CDR having the sequence given in SEQ ID NO: 33 for CDR-L3.

2. A pharmaceutical composition according to claim 1 wherein the antibody molecule binds specifically to antigen TcdA at epitope TcdA123 or TcdA456 with an affinity of 500 pM or less.

3. The pharmaceutical composition according to claim 2, wherein the anti-TcdA antibody binds 4, 5, 6, 7, 8, 9, 10, 11, 12, 13, 14, 15 times or more.

4. The pharmaceutical composition according to claim 3 wherein the maximal inhibition of toxin is between 50 and 100% when toxin is used at an $LD_{80}$ or higher.

5. The pharmaceutical composition according to claim 2, further comprising an antibody molecule which binds specifically to antigen TcdB at epitope TcdB1234, wherein said antibody molecule which binds specifically to antigen TcdB comprises a heavy chain wherein the variable domain of the heavy chain comprises:

(i) a CDR having the sequence given in SEQ ID NO: 124 for CDR-H1, a CDR having the sequence given in SEQ ID NO: 125 for CDR-H2, and a CDR having the sequence given in SEQ ID NO: 126 for CDR-H3; or (ii) a CDR having the sequence given in SEQ ID NO: 154 for CDR-H1, a CDR having the sequence given in SEQ ID NO: 155 for CDR-H2, and a CDR having the sequence given in SEQ ID NO: 156 for CDR-H3;

and a light chain wherein the variable domain of the light chain comprises:

(iii) a CDR having the sequence given in SEQ ID NO: 121 for CDR-L1, a CDR having the sequence given in SEQ ID NO: 122 for CDR-L2, and a CDR having the sequence given in SEQ ID NO: 123 for CDR-L3; or (iv) a CDR having the sequence given in SEQ ID NO: 151 for CDR-H1, a CDR having the sequence given in SEQ ID NO: 152 for CDR-L2, and a CDR having the sequence given in SEQ ID NO: 153 for CDR-L3.

6. The pharmaceutical composition according to claim 5, wherein the anti-TcdB antibody has an affinity in the range 600 pM or less.

7. The pharmaceutical composition according to claim 6, wherein the anti-TcdB antibody has an affinity in the range 50 to 600 pM.

8. The pharmaceutical composition according to claim 5, wherein one or more antibodies is a neutralizing antibody effective against ribotypes 003, 012, 027 and 078.

9. The pharmaceutical composition according to claim 2, wherein said antibody molecule which specifically binds TcdA comprises a heavy chain wherein the variable domain of the heavy chain comprises a CDR having the sequence given in SEQ ID NO:44 for CDR-H1, a CDR having the sequence given in SEQ ID NO:45 for CDR-H2 and a CDR having the sequence given in SEQ ID NO:46 for CDR-H3 and a light chain wherein the variable domain of the light chain comprises a CDR having the sequence given in SEQ ID NO:41 for CDR-L1, a CDR having the sequence given in SEQ ID NO:42 for CDR-L2 and a CDR having the sequence given in SEQ ID NO:43 for CDR-L3.

10. The pharmaceutical composition according to claim 9 wherein said antibody molecule has a heavy chain comprising the sequence given in SEQ ID NO:49 and a light chain comprising the sequence given in SEQ ID NO:47.

11. The pharmaceutical composition according to claim 2, wherein said antibody molecule comprises a heavy chain wherein the variable domain of the heavy chain comprises a CDR having the sequence given in SEQ ID NO:54 for CDR-H1, a CDR having the sequence given in SEQ ID NO:55 for CDR-H2 and a CDR having the sequence given in SEQ ID NO:56 for CDR-H3 and a light chain wherein the variable domain of the light chain comprises a CDR having the sequence given in SEQ ID NO:51 for CDR-L1, a CDR having the sequence given in SEQ ID NO:52 for CDR-L2 and a CDR having the sequence given in SEQ ID NO:53 for CDR-L3.

12. The pharmaceutical composition according to claim 11 wherein said antibody molecule has a heavy chain comprising the sequence given in SEQ ID NO:59 and a light chain comprising the sequence given in SEQ ID NO:57.

13. The pharmaceutical composition according to claim 2 further comprising an antibody molecule which binds specifically to antigen TcdB comprising a heavy chain wherein the variable domain of the heavy chain comprises a CDR having the sequence given in SEQ ID NO:124 for CDR-H1, a CDR having the sequence given in SEQ ID NO:125 for CDR-H2 and a CDR having the sequence given in SEQ ID NO:126 for CDR-H3 and a light chain wherein the variable domain of the light chain comprises a CDR having the sequence given in SEQ ID NO:121 for CDR-L1, a CDR having the sequence given in SEQ ID NO:122 for CDR-L2 and a CDR having the sequence given in SEQ ID NO:123 for CDR-L3.

14. The pharmaceutical composition according to claim 13 wherein said monoclonal antibody which binds specifically to antigen TcdB has a heavy chain comprising the sequence given in SEQ ID NO:129 and a light chain comprising the sequence given in SEQ ID NO:127.

15. The pharmaceutical composition according to claim 2 further comprising an antibody molecule which binds specifically to antigen TcdB comprising a heavy chain wherein the variable domain of the heavy chain comprises a CDR having the sequence given in SEQ ID NO:154 for CDR-H1, a CDR having the sequence given in SEQ ID NO:155 for CDR-H2 and a CDR having the sequence given in SEQ ID NO:156 for CDR-H3 and a light chain wherein the variable domain of the light chain comprises a CDR having the sequence given in SEQ ID NO:151 for CDR-L1, a CDR having the sequence given in SEQ ID NO:152 for CDR-L2 and a CDR having the sequence given in SEQ ID NO:153 for CDR-L3.

16. The pharmaceutical composition according to claim 15 wherein said antibody molecule which binds specifically to antigen TcdB has a heavy chain comprising the sequence given in SEQ ID NO:159 and a light chain comprising the sequence given in SEQ ID NO:157.

17. The pharmaceutical composition according to claim 2 wherein said antibody molecule has a heavy chain and a light chain wherein the heavy chain variable region comprises a sequence selected from the group consisting of SEQ ID NO:9, SEQ ID NO:49, SEQ ID NO:59, and SEQ ID NO:39 and the light chain variable region comprises a sequence selected from the group consisting of SEQ ID NO:7, SEQ ID NO: 47, SEQ ID NO: 57, and SEQ ID NO:37.

18. A pharmaceutical composition according to claim 6, comprising an antibody molecule which specifically binds TcdB having a heavy chain and a light chain wherein the heavy chain variable region comprises a sequence selected from the group consisting of SEQ ID NO:129 and SEQ ID NO:159 and the light chain variable region comprises a sequence selected from the group consisting of and SEQ ID NO:157.

19. A pharmaceutical composition according to claim 2, wherein at least one antibody in the composition is specific to TcdA and at least one antibody in the composition is specific to TcdB.

20. A pharmaceutical composition according to claim 19, wherein the composition further comprises at least a second antibody specific to TcdB.

21. A method for the treatment of *Clostridium difficile* infection or complications therefrom comprising administering a therapeutically effective amount of a composition of claim 2, to a patient in need thereof.

22. The pharmaceutical composition according to claim 1, wherein said antibody molecule which specifically binds TcdA comprises a heavy chain wherein the variable domain of the heavy chain comprises a CDR having the sequence given in SEQ ID NO: 4 for CDR-H1, a CDR having the sequence given in SEQ ID NO: 5 for CDR-H2 and a CDR having the sequence given in SEQ ID NO: 6 for CDR-H3 and a light chain wherein the variable domain of the light chain comprises a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3.

23. The pharmaceutical composition according to claim 1, wherein said antibody molecule which specifically binds TcdA comprises a heavy chain wherein the variable domain of the heavy chain comprises a CDR having the sequence given in SEQ ID NO: 34 for CDR-H1, a CDR having the sequence given in SEQ ID NO: 35 for CDR-H2 and a CDR having the sequence given in SEQ ID NO: 36 for CDR-H3 and a light chain wherein the variable domain of the light chain comprises a CDR having the sequence given in SEQ ID NO: 31 for CDR-L1, a CDR having the sequence given in SEQ ID NO: 32 for CDR-L2 and a CDR having the sequence given in SEQ ID NO: 33 for CDR-L3.

24. The pharmaceutical composition according to claim 1, wherein said antibody molecule which specifically binds TcdA comprises a heavy chain wherein the variable domain of the heavy chain comprises a CDR having the sequence given in SEQ ID NO: 44 for CDR-H1, a CDR having the sequence given in SEQ ID NO: 45 for CDR-H2 and a CDR having the sequence given in SEQ ID NO: 46 for CDR-H3 and a light chain wherein the variable domain of the light chain comprises a CDR having the sequence given in SEQ ID NO: 41 for CDR-L1, a CDR having the sequence given in SEQ ID NO: 42 for CDR-L2 and a CDR having the sequence given in SEQ ID NO: 43 for CDR-L3.

25. The pharmaceutical composition according to claim 1, wherein said antibody molecule which specifically binds TcdA comprises a heavy chain wherein the variable domain of the heavy chain comprises a CDR having the sequence given in SEQ ID NO: 54 for CDR-H1, a CDR having the sequence given in SEQ ID NO: 55 for CDR-H2 and a CDR having the sequence given in SEQ ID NO: 56 for CDR-H3 and a light chain wherein the variable domain of the light chain comprises a CDR having the sequence given in SEQ ID NO: 51 for CDR-L1, a CDR having the sequence given in SEQ ID NO: 52 for CDR-L2 and a CDR having the sequence given in SEQ ID NO: 53 for CDR-L3.

26. The pharmaceutical composition according to claim 22, wherein said antibody molecule has a heavy chain comprising the sequence given in SEQ ID NO: 9 and a light chain comprising the sequence given in SEQ ID NO: 7.

27. The pharmaceutical composition according to claim 23, wherein said antibody molecule has a heavy chain comprising the sequence given in SEQ ID NO:39 and a light chain comprising the sequence given in SEQ ID NO:37.

28. The pharmaceutical composition according to claim 24, wherein said antibody molecule has a heavy chain comprising the sequence given in SEQ ID NO:49 and a light chain comprising the sequence given in SEQ ID NO:47.

29. The pharmaceutical composition according to claim 25, wherein said antibody molecule has a heavy chain comprising the sequence given in SEQ ID NO:59 and a light chain comprising the sequence given in SEQ ID NO:57.

30. The pharmaceutical composition according to claim 1, wherein said antibody molecule is a complete antibody molecule having full length heavy and light chains or a fragment thereof.

31. The pharmaceutical composition according to claim 30, wherein the fragment thereof is independently selected from a Fab, a modified Fab, Fab', a modified Fab', a F(ab')2, a Fv, a Fab-Fv, a Fab-dsFv, a single domain antibodies, a scFv, a bi, tri or tetra-valent antibody, a Bis-scFv, a diabody, a triabody, a tetrabody or an epitope-binding fragment.

32. The pharmaceutical composition according to claim 1, wherein said antibody molecule is attached to a poly(ethyleneglycol) (PEG) moiety.

33. The pharmaceutical composition according to claim 1, further comprising a pharmaceutically acceptable excipient.

34. The pharmaceutical composition according to claim 1, further comprising a compound selected from the group comprising metronidazole, vancomycin, clindamycin, fidaxomicin and combinations thereof.

35. The pharmaceutical composition according to claim 2, wherein said antibody molecule comprises a heavy chain wherein the variable domain of the heavy chain comprises a CDR having the sequence given in SEQ ID NO: 4 for CDR-H1, a CDR having the sequence given in SEQ ID NO: 5 for CDR-H2 and a CDR having the sequence given in SEQ ID NO: 6 for CDR-H3 and a light chain wherein the variable domain of the light chain comprises a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3.

36. The pharmaceutical composition according to claim 35 wherein said antibody molecule has a heavy chain comprising the sequence given in SEQ ID NO:9 and a light chain comprising the sequence given in SEQ ID NO:7.

37. The pharmaceutical composition according to claim 2, wherein said antibody molecule comprises a heavy chain wherein the variable domain of the heavy chain a heavy chain wherein the variable domain of the heavy chain comprises a CDR having the sequence given in SEQ ID NO: 34 for CDR-H1, a CDR having the sequence given in SEQ ID NO: 35 for CDR-H2 and a CDR having the sequence given in SEQ ID NO: 36 for CDR-H3 and a light chain wherein the variable domain of the light chain comprises a CDR having the sequence given in SEQ ID NO: 31 for CDR-L1, a CDR having the sequence given in SEQ ID NO: 32 for CDR-L2 and a CDR having the sequence given in SEQ ID NO: 33 for CDR-L3.

38. The pharmaceutical composition according to claim 37 wherein said antibody molecule has a heavy chain comprising the sequence given in SEQ ID NO:39 and a light chain comprising the sequence given in SEQ ID NO:37.

39. The pharmaceutical composition according to claim 2, further comprising an antibody molecule which binds specifically to antigen TcdB at epitope TcdB1234, wherein said antibody molecule which binds specifically to antigen TcdB comprises a heavy chain wherein the variable domain of the heavy chain comprises:
  (i) a CDR having the sequence given in SEQ ID NO: 144 for CDR-H1, a CDR having the sequence given in SEQ ID NO: 145 for CDR-H2, and a CDR having the sequence given in SEQ ID NO: 146 for CDR-H3; or
  (ii) a CDR having the sequence given in SEQ ID NO: 164 for CDR-H1, a CDR having the sequence given in SEQ ID NO: 165 for CDR-H2, and a CDR having the sequence given in SEQ ID NO: 166 for CDR-H3; and a light chain wherein the variable domain of the light chain comprises:
  (iii) a CDR having the sequence given in SEQ ID NO: 141 for CDR-L1, a CDR having the sequence given in SEQ ID NO: 142 for CDR-L2, and a CDR having the sequence given in SEQ ID NO: 143 for CDR-L3; or
  (iv) a CDR having the sequence given in SEQ ID NO: 161 for CDR-H1, a CDR having the sequence given in SEQ ID NO: 162 for CDR-L2, and a CDR having the sequence given in SEQ ID NO: 163 for CDR-L3.

40. The pharmaceutical composition according to claim 2, further comprising an antibody molecule which binds specifically to antigen TcdB comprising a heavy chain wherein the variable domain of the heavy chain comprises a CDR having the sequence given in SEQ ID NO: 144 for CDR-H1, a CDR having the sequence given in SEQ ID NO: 145 for CDR-H2, and a CDR having the sequence given in SEQ ID NO: 146 for CDR-H3, and a light chain wherein the variable domain of the light chain comprises a CDR having the sequence given in SEQ ID NO: 141 for CDR-L1, a CDR having the sequence given in SEQ ID NO: 142 for CDR-L2, and a CDR having the sequence given in SEQ ID NO: 143 for CDR-L3.

41. The pharmaceutical composition according to claim 40, wherein said monoclonal antibody which binds specifically to antigen TcdB has a heavy chain comprising the sequence given in SEQ ID NO: 149 and a light chain comprising the sequence given in SEQ ID NO: 147.

42. The pharmaceutical composition according to claim 2, further comprising an antibody molecule which binds specifically to antigen TcdB comprising a heavy chain wherein the variable domain of the heavy chain comprises a CDR having the sequence given in SEQ ID NO: 164 for CDR-H1, a CDR having the sequence given in SEQ ID NO: 165 for CDR-H2, and a CDR having the sequence given in SEQ ID NO: 166 for CDR-H3, and a light chain wherein the variable domain of the light chain comprises a CDR having the sequence given in SEQ ID NO: 161 for CDR-L1, a CDR having the sequence given in SEQ ID NO: 162 for CDR-L2, and a CDR having the sequence given in SEQ ID NO: 163 for CDR-L3.

43. The pharmaceutical composition according to claim 42, wherein said monoclonal antibody which binds specifically to antigen TcdB has a heavy chain comprising the sequence given in SEQ ID NO: 169 and a light chain comprising the sequence given in SEQ ID NO: 167.

* * * * *

SEQUENCE LISTING

```
<160> NUMBER OF SEQ ID NOS: 194

<210> SEQ ID NO 1
<211> LENGTH: 11
<212> TYPE: PRT
<213> ORGANISM: Artificial
<220> FEATURE:
<223> OTHER INFORMATION: Antibody CDR

<400> SEQUENCE: 1

Gln Ala Ser Gln Ser Ile Ser Asn Ala Leu Ala
1               5                   10

<210> SEQ ID NO 2
<211> LENGTH: 7
<212> TYPE: PRT
<213> ORGANISM: Artificial
<220> FEATURE:
<223> OTHER INFORMATION: Antibody CDR

<400> SEQUENCE: 2

Ser Ala Ser Ser Leu Ala Ser
1               5

<210> SEQ ID NO 3
<211> LENGTH: 12
<212> TYPE: PRT
<213> ORGANISM: Artificial
<220> FEATURE:
<223> OTHER INFORMATION: Antibody CDR

<400> SEQUENCE: 3

Gln Tyr Thr His Tyr Ser His Thr Ser Lys Asn Pro
1               5                   10
```

```
<210> SEQ ID NO 4
<211> LENGTH: 10
<212> TYPE: PRT
<213> ORGANISM: Artificial
<220> FEATURE:
<223> OTHER INFORMATION: Antibody CDR

<400> SEQUENCE: 4

Gly Phe Thr Ile Ser Ser Tyr Tyr Met Ser
1               5                   10

<210> SEQ ID NO 5
<211> LENGTH: 17
<212> TYPE: PRT
<213> ORGANISM: Artificial
<220> FEATURE:
<223> OTHER INFORMATION: Antibody CDR

<400> SEQUENCE: 5

Ile Ile Ser Ser Gly Gly His Phe Thr Trp Tyr Ala Asn Trp Ala Lys
1               5                   10                  15

Gly

<210> SEQ ID NO 6
<211> LENGTH: 13
<212> TYPE: PRT
<213> ORGANISM: Artificial
<220> FEATURE:
<223> OTHER INFORMATION: Antibody CDR

<400> SEQUENCE: 6

Ala Tyr Val Ser Gly Ser Ser Phe Asn Gly Tyr Ala Leu
1               5                   10

<210> SEQ ID NO 7
<211> LENGTH: 110
<212> TYPE: PRT
<213> ORGANISM: Artificial
<220> FEATURE:
<223> OTHER INFORMATION: Antibody variable region

<400> SEQUENCE: 7

Asp Pro Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Asn Ala
            20                  25                  30

Leu Ala Trp Tyr Gln Gln Lys Pro Gly Lys Ala Pro Lys Leu Leu Ile
        35                  40                  45

Tyr Ser Ala Ser Ser Leu Ala Ser Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Tyr Thr His Tyr Ser His Thr
                85                  90                  95

Ser Lys Asn Pro Phe Gly Gly Gly Thr Lys Val Glu Ile Lys
            100                 105                 110

<210> SEQ ID NO 8
<211> LENGTH: 330
<212> TYPE: DNA
<213> ORGANISM: Artificial
<220> FEATURE:
<223> OTHER INFORMATION: Polynucleotide encoding variable region of
      anti-TcdA antibody 922.g1
```

<400> SEQUENCE: 8

```
gaccctgtga tgacccagag tccgagcact ctttctgcct ccgtgggaga ccgcgtgacc    60
attacatgtc aggcttcaca aagtatctcc aatgctctgg cctggtatca gcagaaaccc   120
ggcaaagccc ctaagctgct catctactct gcatcaagcc tggctagcgg cgtgccaagc   180
cgattcaagg ggagcggttc tggcactgag tttacgctga ccatcagtag cttgcagcct   240
gacgattttg caacctatta ctgccagtac acacactact cccatacatc taaaaaccca   300
ttcggagggg gtactaaggt cgaaataaag                                    330
```

```
<210> SEQ ID NO 9
<211> LENGTH: 119
<212> TYPE: PRT
<213> ORGANISM: Artificial
<220> FEATURE:
<223> OTHER INFORMATION: Antibody variable region for anti-TcdA antibody
      922
```

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Tyr Met Ser Trp Val Arg Gln Ala Pro Gly Lys Gly Leu Glu Trp Ile
        35                  40                  45

Gly Ile Ile Ser Ser Gly Gly His Phe Thr Trp Tyr Ala Asn Trp Ala
    50                  55                  60

Lys Gly Arg Phe Thr Ile Ser Ser Asp Ser Thr Thr Val Tyr Leu Gln
65                  70                  75                  80

Met Asn Ser Leu Arg Asp Glu Asp Thr Ala Thr Tyr Phe Cys Ala Arg
                85                  90                  95

Ala Tyr Val Ser Gly Ser Ser Phe Asn Gly Tyr Ala Leu Trp Gly Gln
            100                 105                 110

Gly Thr Leu Val Thr Val Ser
        115
```

```
<210> SEQ ID NO 10
<211> LENGTH: 357
<212> TYPE: DNA
<213> ORGANISM: Artificial
<220> FEATURE:
<223> OTHER INFORMATION: Polynucleotide encoding variable region of
      anti-TcdA antibody 922 (heavy chain variable region)
```

<400> SEQUENCE: 10

```
gaagtgcaat tggtggaaag tggcggagga ctggtgcaac cgggggtag tctgcgactg     60
agctgtgctg cctccggctt taccattagc tcctactata tgagctgggt tcgacaggcc   120
cctggaaaag gactcgaatg gatcggcatc atatcttccg gtgggcattt cacctggtac   180
gcaaactggg ctaaggggag attcacgatt agcagcgact ccacaaccgt gtacctgcaa   240
atgaacagcc tgagggatga ggacactgcc acatatttct gcgcacgcgc ttacgtgagc   300
ggaagctcat ttaatggcta tgcactgtgg gggcaaggaa cactcgtgac tgtctcg      357
```

```
<210> SEQ ID NO 11
<211> LENGTH: 11
<212> TYPE: PRT
<213> ORGANISM: Artificial
<220> FEATURE:
```

```
<223> OTHER INFORMATION: Antibody CDR

<400> SEQUENCE: 11

Gln Ala Ser Gln Ser Ile Ser Asn Tyr Leu Ala
1               5                   10

<210> SEQ ID NO 12
<211> LENGTH: 7
<212> TYPE: PRT
<213> ORGANISM: Artificial
<220> FEATURE:
<223> OTHER INFORMATION: Antibody CDR

<400> SEQUENCE: 12

Ser Ala Ser Thr Leu Ala Ser
1               5

<210> SEQ ID NO 13
<211> LENGTH: 12
<212> TYPE: PRT
<213> ORGANISM: Artificial
<220> FEATURE:
<223> OTHER INFORMATION: Antibody CDR

<400> SEQUENCE: 13

Gln Tyr Ser His Tyr Gly Thr Gly Val Phe Gly Ala
1               5                   10

<210> SEQ ID NO 14
<211> LENGTH: 10
<212> TYPE: PRT
<213> ORGANISM: Artificial
<220> FEATURE:
<223> OTHER INFORMATION: Antibody CDR

<400> SEQUENCE: 14

Ala Phe Ser Leu Ser Asn Tyr Tyr Met Ser
1               5                   10

<210> SEQ ID NO 15
<211> LENGTH: 18
<212> TYPE: PRT
<213> ORGANISM: Artificial
<220> FEATURE:
<223> OTHER INFORMATION: Antibody CDR

<400> SEQUENCE: 15

Ile Ile Ser Ser Gly Ser Asn Ala Leu Lys Trp Tyr Ala Ser Trp Pro
1               5                   10                  15

Lys Gly

<210> SEQ ID NO 16
<211> LENGTH: 13
<212> TYPE: PRT
<213> ORGANISM: Artificial
<220> FEATURE:
<223> OTHER INFORMATION: Antibody CDR

<400> SEQUENCE: 16

Asn Tyr Val Gly Ser Gly Ser Tyr Tyr Gly Met Asp Leu
1               5                   10

<210> SEQ ID NO 17
<211> LENGTH: 110
<212> TYPE: PRT
<213> ORGANISM: Artificial
```

```
<220> FEATURE:
<223> OTHER INFORMATION: Anitbody ariable region of anti-TcdA antibody
      923

<400> SEQUENCE: 17

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Val Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Gln Phe Thr Leu Thr Ile Ser Ser Leu Gln Pro
65                  70                  75                  80

Glu Asp Val Ala Thr Tyr Tyr Cys Gln Tyr Ser His Tyr Gly Thr Gly
                85                  90                  95

Val Phe Gly Ala Phe Gly Gly Gly Thr Lys Val Glu Ile Lys
            100                 105                 110

<210> SEQ ID NO 18
<211> LENGTH: 330
<212> TYPE: DNA
<213> ORGANISM: Artificial
<220> FEATURE:
<223> OTHER INFORMATION: Polynucleotide encoding antibody variable
      region for anti-TcdA antibody 923.g1

<400> SEQUENCE: 18
gacgtcgtga tgactcagag cccatctagt ctgagcgcta gcgtcggaga ccgagtcaca     60
attacctgtc aagcctccca gagcatctcc aactacctgg cctggtacca acagaaacct   120
ggcaaggtgc ccaagctgct gatctatagt gcttccacac tcgcaagcgg cgttccgtca   180
cgctttaagg gatctggctc tggcactcag ttcaccttga cgatctcaag cctgcagcca   240
gaagatgtgg ccacctatta ctgccagtat tcccactacg ggactggggt gttcggtgcc   300
tttggaggtg ggaccaaagt ggagataaag                                     330

<210> SEQ ID NO 19
<211> LENGTH: 120
<212> TYPE: PRT
<213> ORGANISM: Artificial
<220> FEATURE:
<223> OTHER INFORMATION: Antibody variable region for anti-TcdA antibody
      923

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Ala Phe Ser Leu Ser Asn Tyr
            20                  25                  30

Tyr Met Ser Trp Val Arg Gln Ala Pro Gly Lys Gly Leu Glu Trp Ile
        35                  40                  45

Gly Ile Ile Ser Ser Gly Ser Asn Ala Leu Lys Trp Tyr Ala Ser Trp
50                  55                  60

Pro Lys Gly Arg Phe Thr Ile Ser Lys Asp Ser Thr Thr Val Tyr Leu
65                  70                  75                  80

Gln Met Asn Ser Leu Arg Ala Glu Asp Thr Ala Thr Tyr Phe Cys Ala
                85                  90                  95
```

Arg Asn Tyr Val Gly Ser Gly Ser Tyr Tyr Gly Met Asp Leu Trp Gly
                100                 105                 110

Gln Gly Thr Leu Val Thr Val Ser
        115                 120

<210> SEQ ID NO 20
<211> LENGTH: 360
<212> TYPE: DNA
<213> ORGANISM: Artificial
<220> FEATURE:
<223> OTHER INFORMATION: Polynucleotide encoding antibody variable
      region for anti-TcdA antibody 923.g1

<400> SEQUENCE: 20
gaagttcaac ttgtggaatc tggaggcggg ctcgtgcagc ctggtggaag ccttagactg    60
agctgcgctg catccgcatt ttccctgtcc aactactaca tgagctgggt gcgacaagca   120
ccaggcaagg gactggaatg gattggcatc ataagctccg gttccaatgc cctgaaatgg   180
tacgcatcat ggccgaaagg ccgctttacc ataagcaagg actccaccac cgtctatctg   240
cagatgaact cattgcgtgc cgaggacact gcaacgtact tctgtgctcg caactacgtg   300
ggaagcggat cttattatgg catggatctg tggggacaag gtacactcgt gaccgtctcg   360

<210> SEQ ID NO 21
<211> LENGTH: 11
<212> TYPE: PRT
<213> ORGANISM: Artificial
<220> FEATURE:
<223> OTHER INFORMATION: Antibody CDR

<400> SEQUENCE: 21

Gln Ala Ser Gln Ser Ile Ser Ser Tyr Phe Ser
1               5                   10

<210> SEQ ID NO 22
<211> LENGTH: 7
<212> TYPE: PRT
<213> ORGANISM: Artificial
<220> FEATURE:
<223> OTHER INFORMATION: Antibody CDR

<400> SEQUENCE: 22

Gly Ala Ser Thr Leu Ala Ser
1               5

<210> SEQ ID NO 23
<211> LENGTH: 12
<212> TYPE: PRT
<213> ORGANISM: Artificial
<220> FEATURE:
<223> OTHER INFORMATION: Antibody CDR

<400> SEQUENCE: 23

Gln Cys Thr Asp Tyr Ser Gly Ile Tyr Phe Gly Gly
1               5                   10

<210> SEQ ID NO 24
<211> LENGTH: 10
<212> TYPE: PRT
<213> ORGANISM: Artificial
<220> FEATURE:
<223> OTHER INFORMATION: Antibody CDR

<400> SEQUENCE: 24

Gly Phe Ser Leu Ser Ser Tyr Tyr Met Ser

<210> SEQ ID NO 25
<211> LENGTH: 19
<212> TYPE: PRT
<213> ORGANISM: Artificial
<220> FEATURE:
<223> OTHER INFORMATION: Antibody CDR

<400> SEQUENCE: 25

Ile Ile Ser Ser Gly Ser Ser Thr Thr Phe Thr Trp Tyr Ala Ser Trp
1               5                   10                  15

Ala Lys Gly

<210> SEQ ID NO 26
<211> LENGTH: 13
<212> TYPE: PRT
<213> ORGANISM: Artificial
<220> FEATURE:
<223> OTHER INFORMATION: Antibody CDR

<400> SEQUENCE: 26

Ala Tyr Val Gly Ser Ser Ser Tyr Tyr Gly Phe Asp Pro
1               5                   10

<210> SEQ ID NO 27
<211> LENGTH: 110
<212> TYPE: PRT
<213> ORGANISM: Artificial
<220> FEATURE:
<223> OTHER INFORMATION: Antibody variable region for anti-TcdA antibody
      993

<400> SEQUENCE: 27

Asp Val Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Tyr
            20                  25                  30

Phe Ser Trp Tyr Gln Gln Lys Pro Gly Lys Ala Pro Gln Leu Leu Ile
        35                  40                  45

Tyr Gly Ala Ser Thr Leu Ala Ser Gly Val Pro Ser Arg Phe Lys Gly
    50                  55                  60

Ser Gly Ser Gly Thr Glu Leu Thr Leu Thr Ile Ser Ser Leu Gln Pro
65                  70                  75                  80

Asp Asp Phe Ala Thr Tyr Tyr Cys Gln Cys Thr Asp Tyr Ser Gly Ile
                85                  90                  95

Tyr Phe Gly Gly Phe Gly Gly Gly Thr Lys Val Glu Ile Lys
            100                 105                 110

<210> SEQ ID NO 28
<211> LENGTH: 330
<212> TYPE: DNA
<213> ORGANISM: Artificial
<220> FEATURE:
<223> OTHER INFORMATION: Polynucleotide encoding antibody variable
      region for anti-TcdA antibody 933.g1

<400> SEQUENCE: 28
gatgtcgtga tgactcagtc cccctctaca ttgagtgcct ctgtcggtga tcgagttacc      60
atcacctgtc aagcaagcca gagcatcagc tcctacttct cttggtacca gcaaaagccg     120
ggaaaagccc ctcaactgct gatttatggg gcctcaaaca tggcttctgg cgtgccatca     180

```
agattcaagg gatctggctc cggcactgag cttacactga ccattagctc cctgcaacct      240
gacgattttg ctacctacta ctgccagtgc accgactata gtgggatata tttcggcgga      300
tttgggggag ggacgaaagt ggaaatcaag                                       330
```

```
<210> SEQ ID NO 29
<211> LENGTH: 121
<212> TYPE: PRT
<213> ORGANISM: Artificial
<220> FEATURE:
<223> OTHER INFORMATION: Antibody variable region for anti-TcdA antibody
      993 (heavy chain)

<400> SEQUENCE: 29
```

```
Glu Val Gln Leu Val Glu Ser Gly Gly Gly Leu Val Gln Pro Gly Gly
1               5                   10                  15

Ser Leu Lys Leu Ser Cys Thr Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Ile Ile Ser Ser Gly Ser Ser Thr Thr Phe Thr Trp Tyr Ala Ser
    50                  55                  60

Trp Ala Lys Gly Arg Phe Thr Ile Ser Lys Thr Ser Thr Thr Val Tyr
65                  70                  75                  80

Leu Gln Met Asn Ser Leu Lys Thr Glu Asp Thr Ala Thr Tyr Phe Cys
                85                  90                  95

Ala Arg Ala Tyr Val Gly Ser Ser Ser Tyr Tyr Gly Phe Asp Pro Trp
            100                 105                 110

Gly Gln Gly Thr Leu Val Thr Val Ser
        115                 120
```

```
<210> SEQ ID NO 30
<211> LENGTH: 363
<212> TYPE: DNA
<213> ORGANISM: Artificial
<220> FEATURE:
<223> OTHER INFORMATION: Polynucleotide encoding antibody variable
      region for anti-TcdA antibody 993.g1

<400> SEQUENCE: 30
```

```
gaagttcagc tggtcgagag cggaggcgga ctggtgcaac ctggtggtag cctgaaactc       60
tcttgtactg cctccgggtt ttccctgagc tcttactata tgtcatgggt gagacaggct      120
cccgggaaag gattgaatgg atcgggatt atctcctccg gctcttccac cactttcaca      180
tggtacgcct catgggcaaa ggggaggttt accataagca agacaagcac gaccgtgtat      240
cttcagatga actccctgaa gacggaggat actgccacct actttttgcgc tcgggcctat      300 gtgggctcaa gctcttacta tggcttcgac ccatgggac agggcacact tgtgaccgtc      360
tcg                                                                    363
```

```
<210> SEQ ID NO 31
<211> LENGTH: 11
<212> TYPE: PRT
<213> ORGANISM: Artificial
<220> FEATURE:
<223> OTHER INFORMATION: Antibody CDR

<400> SEQUENCE: 31
```

```
Gln Ala Ser Gln Ser Ile Asn Asn Tyr Phe Ser
1               5                   10
```

```
<210> SEQ ID NO 32
<211> LENGTH: 7
<212> TYPE: PRT
<213> ORGANISM: Artificial
<220> FEATURE:
<223> OTHER INFORMATION: Antibody CDR

<400> SEQUENCE: 32

Gly Ala Ala Asn Leu Ala Ser
1               5

<210> SEQ ID NO 33
<211> LENGTH: 12
<212> TYPE: PRT
<213> ORGANISM: Artificial
<220> FEATURE:
<223> OTHER INFORMATION: Antibody CDR

<400> SEQUENCE: 33

Gln Asn Asn Tyr Gly Val His Ile Tyr Gly Ala Ala
1               5                   10

<210> SEQ ID NO 34
<211> LENGTH: 10
<212> TYPE: PRT
<213> ORGANISM: Artificial
<220> FEATURE:
<223> OTHER INFORMATION: Antibody CDR

<400> SEQUENCE: 34

Gly Phe Ser Leu Ser Asn Tyr Asp Met Ile
1               5                   10

<210> SEQ ID NO 35
<211> LENGTH: 16
<212> TYPE: PRT
<213> ORGANISM: Artificial
<220> FEATURE:
<223> OTHER INFORMATION: Antibody CDR

<400> SEQUENCE: 35

Phe Ile Asn Thr Gly Gly Ile Thr Tyr Tyr Ala Ser Trp Ala Lys Gly
1               5                   10                  15

<210> SEQ ID NO 36
<211> LENGTH: 12
<212> TYPE: PRT
<213> ORGANISM: Artificial
<220> FEATURE:
<223> OTHER INFORMATION: Antibody CDR

<400> SEQUENCE: 36

Val Asp Asp Tyr Ile Gly Ala Trp Gly Ala Gly Leu
1               5                   10

<210> SEQ ID NO 37
<211> LENGTH: 110
<212> TYPE: PRT
<213> ORGANISM: Artificial
<220> FEATURE:
<223> OTHER INFORMATION: Antibody variable region for anti-TcdA antibody
      995

<400> SEQUENCE: 37

Asp Val Val Met Thr Gln Ser Pro Ser Thr Leu Ser Ala Ser Val Gly
1               5                   10                  15
```

```
Asp Arg Val Thr Ile Thr Cys Gln Ala Ser Gln Ser Ile Asn Asn Tyr
            20                  25                  30

Phe Ser Trp Tyr Gln Gln Lys Pro Gly Lys Ala Pro Lys Leu Leu Ile
        35                  40                  45

Tyr Gly Ala Ala Asn Leu Ala Ser Gly Val Pro Ser Arg Phe Lys Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Ser Cys Gln Asn Asn Tyr Gly Val His Ile
                85                  90                  95

Tyr Gly Ala Ala Phe Gly Gly Gly Thr Lys Val Glu Ile Lys
            100                 105                 110
```

<210> SEQ ID NO 38
<211> LENGTH: 330
<212> TYPE: DNA
<213> ORGANISM: Artificial
<220> FEATURE:
<223> OTHER INFORMATION: Poly nucleotide encoding antibody variable
      region for anti-TcdA antibody 995. g1

<400> SEQUENCE: 38

```
gacgtcgtga tgacacagag cccttcaaca ctgtctgcaa gcgtgggcga tagggtcacc    60
ataacgtgcc aggcctctca atccatcaac aactatttta gctggtacca gcagaagcca   120
ggcaaggctc cgaaacttct gatctacgga gctgccaacc tggcaagtgg cgtgccatca   180
cggttcaagg gatccgggag cggtactgag tataccctga ccatttcatc tctccaaccc   240
gacgatttcg ccacctactc ctgccagaat aattacggcg tgcacatcta tggagctgcc   300
tttggcggtg ggacaaaagt ggaaattaag                                    330
```

<210> SEQ ID NO 39
<211> LENGTH: 117
<212> TYPE: PRT
<213> ORGANISM: Artificial
<220> FEATURE:
<223> OTHER INFORMATION: Antibody variable region for anti-TcdA antibody
      995 (heavy chain)

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Asn Tyr
            20                  25                  30

Asp Met Ile Trp Val Arg Gln Ala Pro Gly Lys Gly Leu Glu Tyr Ile
        35                  40                  45

Gly Phe Ile Asn Thr Gly Gly Ile Thr Tyr Tyr Ala Ser Trp Ala Lys
    50                  55                  60

Gly Arg Phe Thr Ile Ser Arg Asp Ser Ser Thr Val Tyr Leu Gln Met
65                  70                  75                  80

Asn Ser Leu Arg Ala Glu Asp Thr Ala Thr Tyr Phe Cys Ala Arg Val
                85                  90                  95

Asp Asp Tyr Ile Gly Ala Trp Gly Ala Gly Leu Trp Gly Gln Gly Thr
            100                 105                 110

Leu Val Thr Val Ser
            115
```

<210> SEQ ID NO 40
<211> LENGTH: 351

<212> TYPE: DNA
<213> ORGANISM: Artificial
<220> FEATURE:
<223> OTHER INFORMATION: Polynucleotide encoding antibody variable
    region for anti-TcdA antibody

<400> SEQUENCE: 40

```
gaagttcagc tggtcgagag tgggggaggg cttgtgcaac ctggtggctc cctccgtctg      60
agctgtactg cttctggatt ctcactgagc aattacgaca tgatctgggt gcgacaggca     120
cccggcaaag gactggagta cattggcttc atcaacaccg ggggtataac gtactatgcc     180
tcatgggcta aggggcgctt tacaattagt agggattcct ctaccgtgta cctgcagatg     240
aactcactga gagccgagga cactgccaca tatttctgcg ctcgggtgga tgactatatc     300
ggggcctggg gcgccggatt gtggggccaa ggaacactgg tcaccgtctc g              351
```

<210> SEQ ID NO 41
<211> LENGTH: 11
<212> TYPE: PRT
<213> ORGANISM: Artificial
<220> FEATURE:
<223> OTHER INFORMATION: Antibody CDR

<400> SEQUENCE: 41

Gln Ala Ser Gln Ser Ile Ser Ser Tyr Leu Ser
1               5                   10

<210> SEQ ID NO 42
<211> LENGTH: 7
<212> TYPE: PRT
<213> ORGANISM: Artificial
<220> FEATURE:
<223> OTHER INFORMATION: Antibody CDR

<400> SEQUENCE: 42

Arg Ala Ser Thr Leu Ala Ser
1               5

<210> SEQ ID NO 43
<211> LENGTH: 13
<212> TYPE: PRT
<213> ORGANISM: Artificial
<220> FEATURE:
<223> OTHER INFORMATION: Antibody CDR

<400> SEQUENCE: 43

Leu Gly Val Tyr Gly Tyr Ser Asn Asp Asp Gly Ile Ala
1               5                   10

<210> SEQ ID NO 44
<211> LENGTH: 10
<212> TYPE: PRT
<213> ORGANISM: Artificial
<220> FEATURE:
<223> OTHER INFORMATION: Antibody CDR

<400> SEQUENCE: 44

Gly Ile Asp Leu Ser Ser His His Met Cys
1               5                   10

<210> SEQ ID NO 45
<211> LENGTH: 16
<212> TYPE: PRT
<213> ORGANISM: Artificial
<220> FEATURE:
<223> OTHER INFORMATION: Antibody CDR

<400> SEQUENCE: 45

Val Ile Tyr His Phe Gly Ser Thr Tyr Tyr Ala Asn Trp Ala Thr Gly
1               5                   10                  15

<210> SEQ ID NO 46
<211> LENGTH: 11
<212> TYPE: PRT
<213> ORGANISM: Artificial
<220> FEATURE:
<223> OTHER INFORMATION: Antibody CDR

<400> SEQUENCE: 46

Ala Ser Ile Ala Gly Tyr Ser Ala Phe Asp Pro
1               5                   10

<210> SEQ ID NO 47
<211> LENGTH: 111
<212> TYPE: PRT
<213> ORGANISM: Artificial
<220> FEATURE:
<223> OTHER INFORMATION: Antibody variable region for anti-TcdA antibody
      997

<400> SEQUENCE: 47

Ala Leu Val Met Thr Gln Ser Pro Ser Ser Phe Ser Ala Ser Thr Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Tyr Thr Leu Thr Ile Ser Cys Leu Gln Ser
65                  70                  75                  80

Glu Asp Phe Ala Thr Tyr Tyr Cys Leu Gly Val Tyr Gly Tyr Ser Asn
                85                  90                  95

Asp Asp Gly Ile Ala Phe Gly Gly Gly Thr Lys Val Glu Ile Lys
            100                 105                 110

<210> SEQ ID NO 48
<211> LENGTH: 333
<212> TYPE: DNA
<213> ORGANISM: Artificial
<220> FEATURE:
<223> OTHER INFORMATION: Polynucleotide sequence encoding antibody
      variable region for anti-TcdA antibody 997.g1

<400> SEQUENCE: 48
gcactcgtga tgacacagag cccgagtagc tttagtgctt caaccggtga tagggtcact      60
attacttgcc aagcctctca gagtatatct agctatctga ctggtacca gcaaaagccc     120 gggaaggctc ctaaactgct gatctaccgg gcttccacat tggcctccgg cgttccctca     180
cgctttagcg gctccggatc cggaaccgag tacaccctga ctatctcttg cctgcaatct     240
gaggacttcg caacctacta ttgtctgggc gtctacggat atagcaacga tgacgggatc     300
gccttcggcg gcggtaccaa agtggaaatt aag                                  333

<210> SEQ ID NO 49
<211> LENGTH: 116
<212> TYPE: PRT
<213> ORGANISM: Artificial

```
<220> FEATURE:
<223> OTHER INFORMATION: Antibody variable region for anti-TcdA antibody
      997 (heavy chain)

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Ser His
            20                  25                  30

His Met Cys Trp Val Arg Gln Ala Pro Gly Lys Gly Leu Glu Tyr Ile
        35                  40                  45

Gly Val Ile Tyr His Phe Gly Ser Thr Tyr Tyr Ala Asn Trp Ala Thr
    50                  55                  60

Gly Arg Phe Thr Ile Ser Lys Asp Ser Thr Val Tyr Leu Gln Met
65                  70                  75                  80

Asn Ser Leu Arg Ala Glu Asp Thr Ala Thr Tyr Phe Cys Ala Arg Ala
                85                  90                  95

Ser Ile Ala Gly Tyr Ser Ala Phe Asp Pro Trp Gly Gln Gly Thr Leu
            100                 105                 110

Val Thr Val Ser
        115

<210> SEQ ID NO 50
<211> LENGTH: 348
<212> TYPE: DNA
<213> ORGANISM: Artificial
<220> FEATURE:
<223> OTHER INFORMATION: Polynucleotide sequence encoding antibody
      variable region for anti-TcdA anitbody 997.g1 (heavy chain)

<400> SEQUENCE: 50
gaggtgcaac ttgtggaaag cggggagga ctggtgcagc ctggggctc attgagactg        60 agctgcaccg tttctggtat tgacctgagc tccatcata tgtgctgggt gcgccaggca      120
cccggaaaag gactggaata catcggcgtc atataccact ttggctctac atactatgcc    180
aactgggcaa ctgggcgatt cacaattagc aaggactcaa ctaccgttta cctgcaaatg    240
aatagcctga gggctgagga tactgccacc tatttctgtg cccgggcttc aatcgccggc    300
tattctgcct ttgatccatg ggggcaagga acactcgtga ccgtctcg                  348

<210> SEQ ID NO 51
<211> LENGTH: 11
<212> TYPE: PRT
<213> ORGANISM: Artificial
<220> FEATURE:
<223> OTHER INFORMATION: Antibody CDR

<400> SEQUENCE: 51

Gln Ala Ser Gln Ser Ile Tyr Ser Tyr Leu Ala
1               5                   10

<210> SEQ ID NO 52
<211> LENGTH: 7
<212> TYPE: PRT
<213> ORGANISM: Artificial
<220> FEATURE:
<223> OTHER INFORMATION: Antibody CDR

<400> SEQUENCE: 52

Asp Ala Ser Thr Leu Ala Ser
1               5
```

<210> SEQ ID NO 53
<211> LENGTH: 13
<212> TYPE: PRT
<213> ORGANISM: Artificial
<220> FEATURE:
<223> OTHER INFORMATION: Antibody CDR

<400> SEQUENCE: 53

Gln Gly Asn Ala Tyr Thr Ser Asn Ser His Asp Asn Ala
1               5                   10

<210> SEQ ID NO 54
<211> LENGTH: 10
<212> TYPE: PRT
<213> ORGANISM: Artificial
<220> FEATURE:
<223> OTHER INFORMATION: Antibody CDR

<400> SEQUENCE: 54

Gly Ile Asp Leu Ser Ser Asp Ala Val Gly
1               5                   10

<210> SEQ ID NO 55
<211> LENGTH: 16
<212> TYPE: PRT
<213> ORGANISM: Artificial
<220> FEATURE:
<223> OTHER INFORMATION: Antibody CDR

<400> SEQUENCE: 55

Ile Ile Ala Thr Phe Asp Ser Thr Tyr Tyr Ala Ser Trp Ala Lys Gly
1               5                   10                  15

<210> SEQ ID NO 56
<211> LENGTH: 19
<212> TYPE: PRT
<213> ORGANISM: Artificial
<220> FEATURE:
<223> OTHER INFORMATION: Antibody CDR

<400> SEQUENCE: 56

Thr Gly Ser Trp Tyr Tyr Ile Ser Gly Trp Gly Ser Tyr Tyr Tyr Gly
1               5                   10                  15

Met Asp Leu

<210> SEQ ID NO 57
<211> LENGTH: 111
<212> TYPE: PRT
<213> ORGANISM: Artificial
<220> FEATURE:
<223> OTHER INFORMATION: Antibody variable region for anti-TcdA antibody
      1000

<400> SEQUENCE: 57

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Ala Ser Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Asn Ala Tyr Thr Ser Asn
                85                  90                  95

Ser His Asp Asn Ala Phe Gly Gly Gly Thr Lys Val Glu Ile Lys
            100                 105                 110

<210> SEQ ID NO 58
<211> LENGTH: 333
<212> TYPE: DNA
<213> ORGANISM: Artificial
<220> FEATURE:
<223> OTHER INFORMATION: Polynucleotide encoding antibody variable
      region for anti-TcdA antibody 1000.g1

<400> SEQUENCE: 58
gaaatcgtga tgacgcagtc accaagcaca ctgagcgctt ctgtgggaga tcgggtcaca      60
ataacctgtc aggcctccca gagcatctac tcttatctgg catggtacca gcagaagcca     120
gggaaagctc ccaagctgct gatttatgac gccagcactt tggcttccgg tgttcctagt     180
aggttcaaag gctccggaag cggtaccgag tttacccctg acatctcatc tctgcaaccc     240
gatgactttg ccacatacta ttgccagggg aatgcctaca cttccaactc acacgacaac     300
gcattcgggg gaggcaccaa agtcgaaatt aag                                   333

<210> SEQ ID NO 59
<211> LENGTH: 125
<212> TYPE: PRT
<213> ORGANISM: Artificial
<220> FEATURE:
<223> OTHER INFORMATION: Antibody variable region for anti-TcdA antibody
      1000 (heavy chain)

<400> SEQUENCE: 59

Glu Val Gln Leu Val Glu Ser Gly Gly Gly Leu Ile Gln Pro Gly Gly
1               5                   10                  15

Ser Leu Arg Leu Ser Cys Thr Val Ser Gly Ile Asp Leu Ser Ser Asp
            20                  25                  30

Ala Val Gly Trp Val Arg Gln Ala Pro Gly Lys Gly Leu Glu Tyr Ile
        35                  40                  45

Gly Ile Ile Ala Thr Phe Asp Ser Thr Tyr Tyr Ala Ser Trp Ala Lys
    50                  55                  60

Gly Arg Phe Thr Ile Ser Lys Ala Ser Ser Thr Thr Val Tyr Leu Gln
65                  70                  75                  80

Met Asn Ser Leu Arg Ala Glu Asp Thr Ala Thr Tyr Phe Cys Ala Arg
                85                  90                  95

Thr Gly Ser Trp Tyr Tyr Ile Ser Gly Trp Gly Ser Tyr Tyr Tyr Gly
            100                 105                 110

Met Asp Leu Trp Gly Gln Gly Thr Leu Val Thr Val Ser
        115                 120                 125

<210> SEQ ID NO 60
<211> LENGTH: 375
<212> TYPE: DNA
<213> ORGANISM: Artificial
<220> FEATURE:
<223> OTHER INFORMATION: Polynucleotide encoding antibody variable
      region for anti-TcdA antibody 1000.g1 (heavy chain)

<400> SEQUENCE: 60
gaagttcagc tggtcgagag cggaggggggt tgattcagc ccggtggctc acttagattg      60
agctgcaccg tgtccggaat cgatctgtca tctgatgccg tgggctgggt gcgacaggca     120

```
cctgggaaag gactggagta tatagggatc atcgccacct tcgactccac atactacgct    180
agctgggcaa aagggcgctt tacgattagc aaggcctcct ctactaccgt gtacctccaa    240
atgaactcac tgagggccga ggacactgcc acttatttct gtgctcggac cggtagctgg    300
tactacatct ctggctgggg ctcctactat tatggcatgg acctgtgggg acaggggaca    360
ctcgtgaccg tctcg                                                     375
```

<210> SEQ ID NO 61
<211> LENGTH: 11
<212> TYPE: PRT
<213> ORGANISM: Artificial
<220> FEATURE:
<223> OTHER INFORMATION: Antibody CDR

<400> SEQUENCE: 61

Arg Ala Ser Lys Ser Val Ser Thr Leu Met His
1               5                   10

<210> SEQ ID NO 62
<211> LENGTH: 7
<212> TYPE: PRT
<213> ORGANISM: Artificial
<220> FEATURE:
<223> OTHER INFORMATION: Antibody CDR

<400> SEQUENCE: 62

Leu Ala Ser Asn Leu Glu Ser
1               5

<210> SEQ ID NO 63
<211> LENGTH: 9
<212> TYPE: PRT
<213> ORGANISM: Artificial
<220> FEATURE:
<223> OTHER INFORMATION: Antibody CDR

<400> SEQUENCE: 63

Gln Gln Thr Trp Asn Asp Pro Trp Thr
1               5

<210> SEQ ID NO 64
<211> LENGTH: 10
<212> TYPE: PRT
<213> ORGANISM: Artificial
<220> FEATURE:
<223> OTHER INFORMATION: Antibody CDR

<400> SEQUENCE: 64

Gly Phe Thr Phe Ser Asn Tyr Gly Met Ala
1               5                   10

<210> SEQ ID NO 65
<211> LENGTH: 17
<212> TYPE: PRT
<213> ORGANISM: Artificial
<220> FEATURE:
<223> OTHER INFORMATION: Antibody CDR

<400> SEQUENCE: 65

Ser Ile Ser Ser Ser Gly Gly Ser Thr Tyr Tyr Arg Asp Ser Val Lys
1               5                   10                  15

Gly

```
<210> SEQ ID NO 66
<211> LENGTH: 9
<212> TYPE: PRT
<213> ORGANISM: Artificial
<220> FEATURE:
<223> OTHER INFORMATION: Antibody CDR

<400> SEQUENCE: 66

Val Ile Arg Gly Tyr Val Met Asp Ala
1               5

<210> SEQ ID NO 67
<211> LENGTH: 107
<212> TYPE: PRT
<213> ORGANISM: Artificial
<220> FEATURE:
<223> OTHER INFORMATION: Antibody variable region for anti-TcdB antibody
      926

<400> SEQUENCE: 67

Asp Thr Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Leu
            20                  25                  30

Met His Trp Phe Gln Gln Lys Pro Gly Gln Ala Pro Lys Leu Leu Ile
        35                  40                  45

Tyr Leu Ala Ser Asn Leu Glu Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Thr Trp Asn Asp Pro Trp
                85                  90                  95

Thr Phe Gly Gly Gly Thr Lys Val Glu Ile Lys
            100                 105

<210> SEQ ID NO 68
<211> LENGTH: 321
<212> TYPE: DNA
<213> ORGANISM: Artificial
<220> FEATURE:
<223> OTHER INFORMATION: Polynucleotide encoding antibody variable
      region for anti-TcdB antibody 926.g1

<400> SEQUENCE: 68
gataccgtgc tgacccagag ccctgctaca ttgtcactga gccccgggga gagggccaca      60
ttgagctgcc gggcttcaaa atccgtgtcc accctcatgc actggtttca gcaaaagccc     120
gggcaggccc caaaactgct gatctacctc gcatctaacc ttgaatctgg cgtgccggcc     180
cgctttagtg gctccggaag cggaaccgac ttcacactga cgattagctc cctggagcct     240
gaggatttcg ccgtgtacta ttgccagcaa acttggaatg acccttggac tttcggggc      300 ggtactaagg tcgaaataaa g                                               321

<210> SEQ ID NO 69
<211> LENGTH: 117
<212> TYPE: PRT
<213> ORGANISM: Artificial
<220> FEATURE:
<223> OTHER INFORMATION: Antibody variable region for anti-TcdB antibody
      926 (heavy chain)

<400> SEQUENCE: 69

Glu Val Glu Leu Leu Glu Ser Gly Gly Gly Leu Val Gln Pro Gly Gly
```

```
1               5                   10                  15
Ser Leu Arg Leu Ser Cys Glu Ala Ser Gly Phe Thr Phe Ser Asn Tyr
                20                  25                  30

Gly Met Ala Trp Val Arg Gln Ala Pro Thr Lys Gly Leu Glu Trp Val
            35                  40                  45

Thr Ser Ile Ser Ser Gly Gly Ser Thr Tyr Tyr Arg Asp Ser Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Thr Tyr Tyr Cys
                85                  90                  95

Thr Thr Val Ile Arg Gly Tyr Val Met Asp Ala Trp Gly Gln Gly Thr
            100                 105                 110

Leu Val Thr Val Ser
        115
```

<210> SEQ ID NO 70
<211> LENGTH: 351
<212> TYPE: DNA
<213> ORGANISM: Artificial
<220> FEATURE:
<223> OTHER INFORMATION: Polynucleotide encoding antibody variable
      region for anti-TcdBantibody 926.g1 (heavy chain)

<400> SEQUENCE: 70

```
gaggtggaac tgctcgaatc tggtggtggg ctggtgcagc ccggtggatc tctgagattg    60
tcatgcgagg catccggctt tacctttcc aactacggaa tggcctgggt gagacaggcc   120
ccaacgaagg ggctcgaatg ggttacaagc atcagctctt ctgggggatc tacttactat   180
cgcgatagcg tcaaaggccg gtttaccatt agccgagata tgccaaatc aagcctgtat    240 ctgcaaatga acagcctgag ggctgaggac accgccacat actattgtac aaccgtgata    300 agggctacg tgatggacgc atggggacag gggacattgg ttaccgtctc g             351
```

<210> SEQ ID NO 71
<211> LENGTH: 11
<212> TYPE: PRT
<213> ORGANISM: Artificial
<220> FEATURE:
<223> OTHER INFORMATION: Antibody CDR

<400> SEQUENCE: 71

```
Arg Ala Ser Gly Ser Val Ser Thr Leu Met His
1               5                   10
```

<210> SEQ ID NO 72
<211> LENGTH: 7
<212> TYPE: PRT
<213> ORGANISM: Artificial
<220> FEATURE:
<223> OTHER INFORMATION: Antibody CDR

<400> SEQUENCE: 72

```
Lys Ala Ser Asn Leu Ala Ser
1               5
```

<210> SEQ ID NO 73
<211> LENGTH: 8
<212> TYPE: PRT
<213> ORGANISM: Artificial
<220> FEATURE:
<223> OTHER INFORMATION: Antibody CDR

<400> SEQUENCE: 73

His Gln Ser Trp Asn Ser Asp Thr
1               5

<210> SEQ ID NO 74
<211> LENGTH: 10
<212> TYPE: PRT
<213> ORGANISM: Artificial
<220> FEATURE:
<223> OTHER INFORMATION: Antibody CDR

<400> SEQUENCE: 74

Gly Phe Thr Phe Ser Asn Tyr Gly Met Ala
1               5                  10

<210> SEQ ID NO 75
<211> LENGTH: 17
<212> TYPE: PRT
<213> ORGANISM: Artificial
<220> FEATURE:
<223> OTHER INFORMATION: Antibody CDR

<400> SEQUENCE: 75

Thr Ile Asn Tyr Asp Gly Arg Thr Thr His Tyr Arg Asp Ser Val Lys
1               5                   10                  15

Gly

<210> SEQ ID NO 76
<211> LENGTH: 9
<212> TYPE: PRT
<213> ORGANISM: Artificial
<220> FEATURE:
<223> OTHER INFORMATION: Antibody CDR

<400> SEQUENCE: 76

Ile Ser Arg Ser His Tyr Phe Asp Cys
1               5

<210> SEQ ID NO 77
<211> LENGTH: 106
<212> TYPE: PRT
<213> ORGANISM: Artificial
<220> FEATURE:
<223> OTHER INFORMATION: Antibody variable region for anti-TcdB antibody
      927

<400> SEQUENCE: 77

Asp Thr Gln Met Thr Gln Ser Pro Ser Thr Leu Ser Ala Ser Val Gly
1               5                   10                  15

Asp Arg Val Thr Ile Thr Cys Arg Ala Ser Gly Ser Val Ser Thr Leu
            20                  25                  30

Met His Trp Tyr Gln Gln Lys Pro Gly Lys Ala Pro Lys Leu Leu Ile
        35                  40                  45

Tyr Lys Ala Ser Asn Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Ser Trp Asn Ser Asp Thr
                85                  90                  95

Phe Gly Gln Gly Thr Arg Leu Glu Ile Lys
            100                 105

<210> SEQ ID NO 78
<211> LENGTH: 318
<212> TYPE: DNA
<213> ORGANISM: Artificial
<220> FEATURE:
<223> OTHER INFORMATION: Polynucleotide sequence encoding antbody
      variable region for anti-TcdB antibody 927.g2

<400> SEQUENCE: 78
gacacacaga tgacccagag cccatccact ttgtctgcat ccgtgggcga ccgagtgaca      60
atcacctgta gagcaagcgg ttccgtgagc acactgatgc attggtacca gcagaagcct    120
gggaaggctc ccaagctgct gatctacaaa gccagcaacc ttgcctccgg cgttccaagc    180
cggtttagcg gttccggatc tggaaccgag ttcaccctga ccatatcaag cctgcaaccc    240
gacgacttcg ccacctacta ttgccaccag agctggaata gcgacacgtt cgggcaaggc    300
acaaggctgg aaatcaaa                                                  318

<210> SEQ ID NO 79
<211> LENGTH: 117
<212> TYPE: PRT
<213> ORGANISM: Artificial
<220> FEATURE:
<223> OTHER INFORMATION: Antibody variable region for anti-TcdB antibody
      927 (heavy chain)

<400> SEQUENCE: 79

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Thr Ile Asn Tyr Asp Gly Arg Thr Thr His Tyr Arg Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Ser Ile Ser Arg Ser His Tyr Phe Asp Cys Trp Gly Gln Gly Thr
            100                 105                 110

Leu Val Thr Val Ser
        115

<210> SEQ ID NO 80
<211> LENGTH: 351
<212> TYPE: DNA
<213> ORGANISM: Artificial
<220> FEATURE:
<223> OTHER INFORMATION: Polynucleotide encoding antibody variable
      region for anti-TcdB antibody 927.g2 (heavy chain)

<400> SEQUENCE: 80
gaggtgcaac ttgtggaaag cggagggggc gtggtccaac ccggaagaag tctccgtctt      60
tcttgcgccg caagtggctt cacctttcc aactacggaa tggcctgggt cgacaagct     120 cctgggaaag gattggagtg ggtggccact atcaactatg acggacgcac gacacactac    180
cgagactctg ttaaggggcg ctttacgatt tcccgcgaca atagcaagag caccctctac    240
ctgcaaatga atagcctccg ggccgaggat actgctgtgt actattgtac ctccatctca    300
cggagccact acttcgattg ctggggacaa ggcacactcg tgactgtctc g        351

<210> SEQ ID NO 81
<211> LENGTH: 11
<212> TYPE: PRT
<213> ORGANISM: Artificial
<220> FEATURE:
<223> OTHER INFORMATION: Antibody CDR

<400> SEQUENCE: 81

Lys Ala Ser Lys Ser Ile Ser Asn His Leu Ala
1               5                   10

<210> SEQ ID NO 82
<211> LENGTH: 7
<212> TYPE: PRT
<213> ORGANISM: Artificial
<220> FEATURE:
<223> OTHER INFORMATION: Antibody CDR

<400> SEQUENCE: 82

Ser Gly Ser Thr Leu Gln Ser
1               5

<210> SEQ ID NO 83
<211> LENGTH: 9
<212> TYPE: PRT
<213> ORGANISM: Artificial
<220> FEATURE:
<223> OTHER INFORMATION: Antibody CDR

<400> SEQUENCE: 83

Gln Gln Tyr Asp Glu Tyr Pro Tyr Thr
1               5

<210> SEQ ID NO 84
<211> LENGTH: 10
<212> TYPE: PRT
<213> ORGANISM: Artificial
<220> FEATURE:
<223> OTHER INFORMATION: Antibody CDR

<400> SEQUENCE: 84

Gly Phe Ser Leu Gln Ser Tyr Thr Ile Ser
1               5                   10

<210> SEQ ID NO 85
<211> LENGTH: 16
<212> TYPE: PRT
<213> ORGANISM: Artificial
<220> FEATURE:
<223> OTHER INFORMATION: Antibody CDR

<400> SEQUENCE: 85

Ala Ile Ser Gly Gly Gly Ser Thr Tyr Tyr Asn Leu Pro Leu Lys Ser
1               5                   10                  15

<210> SEQ ID NO 86
<211> LENGTH: 11
<212> TYPE: PRT
<213> ORGANISM: Artificial
<220> FEATURE:
<223> OTHER INFORMATION: Antibody CDR

<400> SEQUENCE: 86

Pro Arg Trp Tyr Pro Arg Ser Tyr Phe Asp Tyr
1               5                   10

```
<210> SEQ ID NO 87
<211> LENGTH: 109
<212> TYPE: PRT
<213> ORGANISM: Artificial
<220> FEATURE:
<223> OTHER INFORMATION: Antibody variable region for anti-TcdB antibody
      1099

<400> SEQUENCE: 87

Asp Val Gln Leu Thr Gln Ser Pro Ser Phe Leu Ser Ala Ser Val Gly
1               5                   10                  15

Asp Arg Val Thr Ile Thr Cys Lys Ala Ser Lys Ser Ile Ser Asn His
            20                  25                  30

Leu Ala Trp Tyr Gln Glu Lys Pro Gly Lys Ala Asn Lys Leu Leu Ile
        35                  40                  45

His Ser Gly Ser Thr Leu Gln Ser Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asp Glu Tyr Pro Tyr
                85                  90                  95

Thr Phe Gly Gln Gly Thr Arg Leu Glu Ile Lys Arg Thr
            100                 105

<210> SEQ ID NO 88
<211> LENGTH: 327
<212> TYPE: DNA
<213> ORGANISM: Artificial
<220> FEATURE:
<223> OTHER INFORMATION: Polynucleotide encoding antibody variable
      region for anti-TcdB antibody 1099.g2

<400> SEQUENCE: 88
gacgtccagc tcactcaatc tccctccttt ctgtctgctt ctgtgggcga tcgcgtgaca       60
ataacctgca aggcctccaa atcaattagc aaccatctgg catggtatca ggagaagcct      120
ggcaaagcca ataagctgct gatccactcc ggctcaactc tgcaatccgg taccccaagc      180
cgatttagcg gatctgggag cggaaccgag ttcacactta ccattagctc cctgcaaccg      240
gaggacttcg ccacctatta ctgccagcaa tacgacgaat accccctatac gttcggccaa      300 gggacaagat tggaaatcaa gcgtacg                                          327

<210> SEQ ID NO 89
<211> LENGTH: 118
<212> TYPE: PRT
<213> ORGANISM: Artificial
<220> FEATURE:
<223> OTHER INFORMATION: Antibody variable region for anti-TcdB antibody
      1099 (heavy chain)

<400> SEQUENCE: 89

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gln Ser Tyr
            20                  25                  30

Thr Ile Ser Trp Val Arg Gln Pro Pro Gly Lys Gly Leu Glu Trp Ile
        35                  40                  45

Ala Ala Ile Ser Gly Gly Gly Ser Thr Tyr Tyr Asn Leu Pro Leu Lys
    50                  55                  60
```

```
Ser Arg Val Thr Ile Ser Arg Asp Thr Ser Lys Gln Val Ser Leu
 65                  70                  75                  80

Lys Leu Ser Ser Val Thr Ala Ala Asp Thr Ala Val Tyr Tyr Cys Thr
                 85                  90                  95

Arg Pro Arg Trp Tyr Pro Arg Ser Tyr Phe Asp Tyr Trp Gly Arg Gly
             100                 105                 110

Thr Leu Val Thr Val Ser
        115
```

<210> SEQ ID NO 90
<211> LENGTH: 354
<212> TYPE: DNA
<213> ORGANISM: Artificial
<220> FEATURE:
<223> OTHER INFORMATION: Polynucleotide encoding antibody variable
      region for anti-TcdB antibody 1099.g2 (heavh chain)

<400> SEQUENCE: 90

```
gaagttcagc tgcaggaatc tggacctggc ttggtgaaac caagcgagac acttagtctc      60
acttgcaccg tttccggctt ctcccttcaa tcctacacga tctcttgggt gcggcaacca     120
cccgggaaag gactggaatg gatcgcagcc attagcgggg agggagcac  ctattacaac     180 ttgcctctca agagccgcgt gaccatatcc cgtgacacaa gcaagagcca ggtttccctg     240
aagctgagct ccgtgactgc tgccgatacg gctgtttact attgcacccg acctcgctgg     300
tatccccgtt cctatttcga ctactgggga agaggcacac tggttaccgt ctcg           354
```

<210> SEQ ID NO 91
<211> LENGTH: 11
<212> TYPE: PRT
<213> ORGANISM: Artificial
<220> FEATURE:
<223> OTHER INFORMATION: Antibody CDR

<400> SEQUENCE: 91

```
Arg Ala Ser Gln Arg Ile Ser Thr Ser Ile His
 1               5                   10
```

<210> SEQ ID NO 92
<211> LENGTH: 7
<212> TYPE: PRT
<213> ORGANISM: Artificial
<220> FEATURE:
<223> OTHER INFORMATION: Antibody CDR

<400> SEQUENCE: 92

```
Tyr Ala Ser Gln Ser Ile Ser
 1               5
```

<210> SEQ ID NO 93
<211> LENGTH: 9
<212> TYPE: PRT
<213> ORGANISM: Artificial
<220> FEATURE:
<223> OTHER INFORMATION: Antibody CDR

<400> SEQUENCE: 93

```
Gln Gln Ser Tyr Ser Ser Leu Tyr Thr
 1               5
```

<210> SEQ ID NO 94
<211> LENGTH: 10
<212> TYPE: PRT
<213> ORGANISM: Artificial

<220> FEATURE:
<223> OTHER INFORMATION: Antibody CDRs

<400> SEQUENCE: 94

Gly Phe Thr Phe Ser Asp Ser Tyr Met Ala
1               5                   10

<210> SEQ ID NO 95
<211> LENGTH: 17
<212> TYPE: PRT
<213> ORGANISM: Artificial
<220> FEATURE:
<223> OTHER INFORMATION: Antibody CDR

<400> SEQUENCE: 95

Ser Ile Ser Tyr Gly Gly Thr Ile Ile Gln Tyr Gly Asp Ser Val Lys
1               5                   10                  15

Gly

<210> SEQ ID NO 96
<211> LENGTH: 11
<212> TYPE: PRT
<213> ORGANISM: Artificial
<220> FEATURE:
<223> OTHER INFORMATION: Antibody CDR

<400> SEQUENCE: 96

Arg Gln Gly Thr Tyr Ala Arg Tyr Leu Asp Phe
1               5                   10

<210> SEQ ID NO 97
<211> LENGTH: 107
<212> TYPE: PRT
<213> ORGANISM: Artificial
<220> FEATURE:
<223> OTHER INFORMATION: Antibody variable region for anti-TcdB antibody
      1102

<400> SEQUENCE: 97

Asn Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Ile Ser Thr Ser
            20                  25                  30

Ile His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Ser Leu Tyr
                85                  90                  95

Thr Phe Gly Gln Gly Thr Lys Leu Glu Ile Lys
            100                 105

<210> SEQ ID NO 98
<211> LENGTH: 321
<212> TYPE: DNA
<213> ORGANISM: Artificial
<220> FEATURE:
<223> OTHER INFORMATION: Polynucleotide encoding antibody variable
      region for anti-TcdB antibody 1102.g4

<400> SEQUENCE: 98

```
aacatcgtgc tgacacagtc tcctgcaacc ctttcactgt ctccaggtga acgagcaacc    60
ctgagttgta gagccagtca gaggatctcc acgagcattc actggtatca gcaaaagcct   120
gggcaagctc ccagactctt gatcaagtac gcctctcaga gcataagtgg cattccagct   180
aggtttagcg gctcaggctc aggaacagac ttcactctga ccatcagctc cctggaaccg   240
gaggactttg ccgtctatta ctgccagcaa tcctactcca gtctgtacac cttcgggcag   300
ggtactaaac tggagataaa g                                             321
```

```
<210> SEQ ID NO 99
<211> LENGTH: 119
<212> TYPE: PRT
<213> ORGANISM: Artificial
<220> FEATURE:
<223> OTHER INFORMATION: Antibody variabl region for anti-TcdB antibody
      1102 (heavy chain)

<400> SEQUENCE: 99
```

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Ser
            20                  25                  30

Tyr Met Ala Trp Val Arg Gln Ala Pro Gly Lys Gly Leu Glu Trp Ile
        35                  40                  45

Ala Ser Ile Ser Tyr Gly Gly Thr Ile Ile Gln Tyr Gly Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gln Gly Thr Tyr Ala Arg Tyr Leu Asp Phe Trp Gly Gln
            100                 105                 110

Gly Thr Leu Val Thr Val Ser
        115

```
<210> SEQ ID NO 100
<211> LENGTH: 357
<212> TYPE: DNA
<213> ORGANISM: Artificial
<220> FEATURE:
<223> OTHER INFORMATION: Polynucleotide encoding antibody variable
      region for anti-TcdB antibody 1002.g4 (heavy chain)

<400> SEQUENCE: 100
gaagtgcagc tggtcgaatc cggggaggt tggtgcaac caggtggctc actgagactg     60
agctgtgccg tttccggctt tacgttctca gacagttata tggcctgggt cgtcaagca   120 cctggaaaag ggctggagtg gattgccagt atcagctatg gtgggaccat aatccagtac   180
ggcgatagcg tcaagggcag gtttactatc tccaggaca acgccaagtc aagcctttac   240
ctgcagatga attctctccg cgcagaggat accgctgtgt attactgcgc tagacggcag   300
ggaacctacg ctcgatacct ggacttctgg ggtcaggaa cactcgttac agtctcg      357
```

```
<210> SEQ ID NO 101
<211> LENGTH: 11
<212> TYPE: PRT
<213> ORGANISM: Artificial
<220> FEATURE:
<223> OTHER INFORMATION: Antibody CDR

<400> SEQUENCE: 101
```

Arg Ala Ser Glu Ser Val Ser Thr Leu Leu His
1               5                   10

<210> SEQ ID NO 102
<211> LENGTH: 7
<212> TYPE: PRT
<213> ORGANISM: Artificial
<220> FEATURE:
<223> OTHER INFORMATION: Antibody CDR

<400> SEQUENCE: 102

Lys Ala Ser Asn Leu Ala Ser
1               5

<210> SEQ ID NO 103
<211> LENGTH: 9
<212> TYPE: PRT
<213> ORGANISM: Artificial
<220> FEATURE:
<223> OTHER INFORMATION: Antibody CDR

<400> SEQUENCE: 103

His Gln Ser Trp Asn Ser Pro Pro Thr
1               5

<210> SEQ ID NO 104
<211> LENGTH: 10
<212> TYPE: PRT
<213> ORGANISM: Artificial
<220> FEATURE:
<223> OTHER INFORMATION: Anitbody CDR

<400> SEQUENCE: 104

Gly Phe Thr Phe Ser Asn Tyr Gly Met Ala
1               5                   10

<210> SEQ ID NO 105
<211> LENGTH: 17
<212> TYPE: PRT
<213> ORGANISM: Artificial
<220> FEATURE:
<223> OTHER INFORMATION: Antibody CDR

<400> SEQUENCE: 105

Ile Ile Asn Tyr Asp Ala Ser Thr Thr His Tyr Arg Asp Ser Val Lys
1               5                   10                  15

Gly

<210> SEQ ID NO 106
<211> LENGTH: 9
<212> TYPE: PRT
<213> ORGANISM: Artificial
<220> FEATURE:
<223> OTHER INFORMATION: Antibody CDR

<400> SEQUENCE: 106

Tyr Gly Arg Ser His Tyr Phe Asp Tyr
1               5

<210> SEQ ID NO 107
<211> LENGTH: 107
<212> TYPE: PRT
<213> ORGANISM: Artificial
<220> FEATURE:
<223> OTHER INFORMATION: Antibody variable region for anti-TcdB anitbody
      1114

<400> SEQUENCE: 107

Ala Thr Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ser Thr Leu
            20                  25                  30

Leu His Trp Tyr Gln Gln Lys Pro Gly Lys Ala Pro Lys Leu Leu Ile
        35                  40                  45

Tyr Lys Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Ser Trp Asn Ser Pro Pro
                85                  90                  95

Thr Phe Gly Gln Gly Thr Lys Leu Glu Ile Lys
            100                 105

<210> SEQ ID NO 108
<211> LENGTH: 321
<212> TYPE: DNA
<213> ORGANISM: Artificial
<220> FEATURE:
<223> OTHER INFORMATION: Polynucleotide sequence encoding antibody
      variable region for anti-TcdB antibody 1114.g2

<400> SEQUENCE: 108
gcgacgcaaa tgactcagtc gccctcatcg cttagcgcgt ccgtcggaga tagagtgacg      60
atcacctgcc gcgcatcaga gtcggtgtcc acactcctcc actggtatca gcagaaaccg     120
gggaaggcac caaaactctt gatctacaaa gccagcaacc ttgcgtccgg tgtcccgtca     180
aggttctccg ggagcggttc ggggacagac tttactttga ccatttcgtc gcttcagccg     240
gaggacttcg ccacctatta ctgtcatcag tcatggaact cacctcccac atttggccag     300
ggaacgaaac tcgaaatcaa g                                                321

<210> SEQ ID NO 109
<211> LENGTH: 117
<212> TYPE: PRT
<213> ORGANISM: Artificial
<220> FEATURE:
<223> OTHER INFORMATION: Antibody variable region for anti-TcdB antibody
      1114 (heavy chain)

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Ile Ile Asn Tyr Asp Ala Ser Thr Thr His Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Tyr Gly Arg Ser His Tyr Phe Asp Tyr Trp Gly Gln Gly Thr
            100                 105                 110

Leu Val Thr Val Ser
        115

<210> SEQ ID NO 110
<211> LENGTH: 351
<212> TYPE: DNA
<213> ORGANISM: Artificial
<220> FEATURE:
<223> OTHER INFORMATION: Polynucleotide encoding anitbody variable
      region for anti-TcdB antibody 1114.g2 (heavy chain)

<400> SEQUENCE: 110
gaagtacaac tcgtagagtc aggggggtggg ctggtccaac ctggcggctc ccttcggctt     60
tcgtgtgccg cctcgggatt cacgtttagc aattacggta tggcctgggt gaggcaggca    120
ccagggaagg gtcttgagtg ggtagcgatc atcaactatg atgcaagcac cacccactac    180
agggatagcg tcaagggacg ctttactatc agccgggata atgcgaaatc ctcgctctat    240
ctgcagatga actccctcag agccgaggac accgcagtgt actattgcac acgatacgga    300
cgctcgcact atttcgacta ttggggacag gggacgctcg taactgtctc g              351

<210> SEQ ID NO 111
<211> LENGTH: 11
<212> TYPE: PRT
<213> ORGANISM: Artificial
<220> FEATURE:
<223> OTHER INFORMATION: Antibody CDR

<400> SEQUENCE: 111

Arg Ala Ser Glu Ser Val Ser Thr Leu Leu His
1               5                   10

<210> SEQ ID NO 112
<211> LENGTH: 7
<212> TYPE: PRT
<213> ORGANISM: Artificial
<220> FEATURE:
<223> OTHER INFORMATION: Anitbody CDR

<400> SEQUENCE: 112

Lys Ala Ser Asn Leu Ala Ser
1               5

<210> SEQ ID NO 113
<211> LENGTH: 9
<212> TYPE: PRT
<213> ORGANISM: Artificial
<220> FEATURE:
<223> OTHER INFORMATION: Antibody CDR

<400> SEQUENCE: 113

His Gln Ser Trp Asn Ser Pro Pro Thr
1               5

<210> SEQ ID NO 114
<211> LENGTH: 10
<212> TYPE: PRT
<213> ORGANISM: Artificial
<220> FEATURE:
<223> OTHER INFORMATION: Antibody CDR

<400> SEQUENCE: 114

Gly Phe Thr Phe Ser Asn Tyr Gly Met Ala
1               5                   10

```
<210> SEQ ID NO 115
<211> LENGTH: 16
<212> TYPE: PRT
<213> ORGANISM: Artificial
<220> FEATURE:
<223> OTHER INFORMATION: Antibody CDR

<400> SEQUENCE: 115

Ile Ile Asn Tyr Asp Ala Ser Thr Thr His Tyr Arg Asp Ser Val Lys
1               5                   10                  15

<210> SEQ ID NO 116
<211> LENGTH: 9
<212> TYPE: PRT
<213> ORGANISM: Artificial
<220> FEATURE:
<223> OTHER INFORMATION: Antibody CDR

<400> SEQUENCE: 116

Tyr Gly Arg Ser His Tyr Phe Asp Tyr
1               5

<210> SEQ ID NO 117
<211> LENGTH: 107
<212> TYPE: PRT
<213> ORGANISM: Artificial
<220> FEATURE:
<223> OTHER INFORMATION: Antibody variable region for anti-TcdB antibody
      1114 graft 8

<400> SEQUENCE: 117

Asp Thr Val Leu Thr Gln Ser Pro Ser Ser Leu Ser Ala Ser Val Gly
1               5                   10                  15

Asp Arg Val Thr Ile Thr Cys Arg Ala Ser Glu Ser Val Ser Thr Leu
                20                  25                  30

Leu His Trp Tyr Gln Gln Lys Pro Gly Lys Ala Pro L

<210> SEQ ID NO 119
<211> LENGTH: 117
<212> TYPE: PRT
<213> ORGANISM: Artificial
<220> FEATURE:
<223> OTHER INFORMATION: Antibody variable region for anti-TcdB antibody 1114 graft 8 (heavy chain)

<400> SEQUENCE: 119

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Ala Trp Val Arg Gln Ala Pro Gly Lys Gly Leu Glu Trp Val
        35                  40                  45
Ala Ile Ile Asn Tyr Asp Ala Ser Thr

```
<400> SEQUENCE: 122

Asn Thr Asn Lys Leu His Thr
1 5

<210> SEQ ID NO 123
<211> LENGTH: 9
<212> TYPE: PRT
<213> ORGANISM: Artificial
<220> FEATURE:
<223> OTHER INFORMATION: Antibody CDR

<400> SEQUENCE: 123

Leu Gln His Lys Ser Phe Pro Tyr Thr
1 5

<210> SEQ ID NO 124
<211> LENGTH: 10
<212> TYPE: PRT
<213> ORGANISM: Artificial
<220> FEATURE:
<223> OTHER INFORMATION: Antibody CDR

<400> SEQUENCE: 124

Gly Phe Thr Phe Arg Asp Ser Phe Met Ala
1 5 10

<210> SEQ ID NO 125
<211> LENGTH: 17
<212> TYPE: PRT
<213> ORGANISM: Artificial
<220> FEATURE:
<223> OTHER INFORMATION: Antibody CDR

<400> SEQUENCE: 125

Ser Ile Ser Tyr Glu Gly Asp Lys Thr Tyr Tyr Gly Asp Ser Val Lys
1 5 10 15

Gly

<210> SEQ ID NO 126
<211> LENGTH: 9
<212> TYPE: PRT
<213> ORGANISM: Artificial
<220> FEATURE:
<223> OTHER INFORMATION: Antibody CDR

<400> SEQUENCE: 126

Leu Thr Ile Thr Thr Ser Gly Asp Ser
1 5

<210> SEQ ID NO 127
<211> LENGTH: 107
<212> TYPE: PRT
<213> ORGANISM: Artificial
<220> FEATURE:
<223> OTHER INFORMATION: Antibody variable region for anti-TcdB antibody
1125

<400> SEQUENCE: 127

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Ile Tyr Met Tyr
20 25 30

Leu Asn Trp Tyr Gln Gln Lys Pro Gly Lys Ala Pro Lys Arg Leu Ile
35 40 45

```
Tyr Asn Thr Asn Lys Leu His Thr Gly Val Pro Ser Arg Phe Ser Gly
        50                  55                  60

Ser Gly Ser Gly Thr Glu Tyr Thr Leu Thr Ile Ser Ser Leu Gln Pro
 65              70                  75                  80

Glu Asp Phe Ala Thr Tyr Tyr Cys Leu Gln His Lys Ser Phe Pro Tyr
                85                  90                  95

Thr Phe Gly Gln Gly Thr Lys Leu Glu Ile Lys
            100                 105
```

<210> SEQ ID NO 128
<211> LENGTH: 321
<212> TYPE: DNA
<213> ORGANISM: Artificial
<220> FEATURE:
<223> OTHER INFORMATION: Polynucleotide sequence encoding antibody variable region for anti-TcdB antibody 1125.g2

<400> SEQUENCE: 128

```
gatatacaaa tgactcagag ccctagctca ctgagcgctt ctgtgggcga tcgtgtgaca    60
atcacttgca aagcaagcca gaacatctat atgtacctga attggtacca gcaaaaaccg   120
ggaaaagctc ccaagcgcct gatttacaac accaataagc tgcataccgg cgtgccaagc   180
cgttttagcg gatctggctc tggaaccgaa tatacactga ccataagctc cctgcaaccg   240
gaagactttg caacttacta ttgcctccag cacaaatcct tccctatac gttcggacaa   300 gggaccaaac tggaaatcaa a                                             321
```

<210> SEQ ID NO 129
<211> LENGTH: 118
<212> TYPE: PRT
<213> ORGANISM: Artificial
<220> FEATURE:
<223> OTHER INFORMATION: Antibody variable region for anti-TcdB antibody 1125 (heavy chain)

<400> SEQUENCE: 129

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Asp Ser
            20                  25                  30

Phe Met Ala Trp Val Arg Gln Ala Pro Gly Lys Gly Leu Glu Trp Val
        35                  40                  45

Ala Ser Ile Ser Tyr Glu Gly Asp Lys Thr Tyr Tyr Gly Asp Ser Val
    50                  55                  60

Lys Gly Arg Phe Thr Ile Ser Arg Asp Asn Ala Lys Asn Ser Leu Tyr
 65              70                  75                  80

Leu Gln Met Asn Ser Leu Arg Ala Glu Asp Thr Ala Val Tyr Tyr Cys
                85                  90                  95

Ala Arg Leu Thr Ile Thr Thr Ser Gly Asp Ser Trp Gly Gln Gly Thr
            100                 105                 110

Met Val Thr Val Ser Ser
        115
```

<210> SEQ ID NO 130
<211> LENGTH: 354
<212> TYPE: DNA
<213> ORGANISM: Artificial
<220> FEATURE:
<223> OTHER INFORMATION: Polynucleotide encoding antibody variable region for anti-TcdB antibody 1125.g2 (heavy chain)

<400> SEQUENCE: 130

```
gaagtgcagc tggtcgaaag cggcggagga ttggtgcaac ctggtggctc tcttcgcctg    60
tcttgcgctg caagcggctt tacgttccgc gatagcttta tggcttgggt gcgacaagct   120
cctgggaaag gctggaatg gtcgctagc ataagctacg aaggcgacaa gacttactat    180
ggggactctg tgaaaggccg attcaccatt agccgagaca acgcaaagaa ctccctgtac   240
ctgcagatga actccctgcg tgccgaagat accgccgtgt actattgcgc taggctgacg   300
atcactacaa gcggagatag ctggggacaa gggacaatgg tgaccgtctc gagc         354
```

<210> SEQ ID NO 131
<211> LENGTH: 11
<212> TYPE: PRT
<213> ORGANISM: Artificial
<220> FEATURE:
<223> OTHER INFORMATION: Antibody CDR

<400> SEQUENCE: 131

Lys Ala Ser Gln His Val Gly Thr Asn Val Asp
1               5                   10

<210> SEQ ID NO 132
<211> LENGTH: 7
<212> TYPE: PRT
<213> ORGANISM: Artificial
<220> FEATURE:
<223> OTHER INFORMATION: Antibody CDR

<400> SEQUENCE: 132

Gly Ala Ser Ile Arg Tyr Thr
1               5

<210> SEQ ID NO 133
<211> LENGTH: 9
<212> TYPE: PRT
<213> ORGANISM: Artificial
<220> FEATURE:
<223> OTHER INFORMATION: Antibody CDR

<400> SEQUENCE: 133

Leu Gln Tyr Asn Tyr Asn Pro Tyr Thr
1               5

<210> SEQ ID NO 134
<211> LENGTH: 10
<212> TYPE: PRT
<213> ORGANISM: Artificial
<220> FEATURE:
<223> OTHER INFORMATION: Antibody CDR

<400> SEQUENCE: 134

Gly Phe Ile Phe Ser Asn Phe Gly Met Ser
1               5                   10

<210> SEQ ID NO 135
<211> LENGTH: 17
<212> TYPE: PRT
<213> ORGANISM: Artificial
<220> FEATURE:
<223> OTHER INFORMATION: Antibody CDR

<400> SEQUENCE: 135

Ser Ile Ser Pro Ser Gly Gly Asn Ala Tyr Tyr Arg Asp Ser Val Lys
1               5                   10                  15

<210> SEQ ID NO 136
<211> LENGTH: 9
<212> TYPE: PRT
<213> ORGANISM: Artificial
<220> FEATURE:
<223> OTHER INFORMATION: Antibody CDR

<400> SEQUENCE: 136

Arg Ala Tyr Ser Ser Pro Phe Ala Phe
1               5

<210> SEQ ID NO 137
<211> LENGTH: 107
<212> TYPE: PRT
<213> ORGANISM: Artificial
<220> FEATURE:
<223> OTHER INFORMATION: Antibody variable region for anti-TcdB antibody
      1129

<400> SEQUENCE: 137

Asp Thr Gln Met Thr Gln Ser Pro Ser Ser Leu Ser Ala Ser Val Gly
1               5                   10                  15

Asp Arg Val Thr Ile Thr Cys Lys Ala Ser Gln His Val Gly Thr Asn
            20                  25                  30

Val Asp Trp Tyr Gln Gln Lys Pro Gly Lys Val Pro Lys Leu Leu Ile
        35                  40                  45

Tyr Gly Ala Ser Ile Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asn Tyr Asn Pro Tyr
                85                  90                  95

Thr Phe Gly Gln Gly Thr Lys Leu Glu Ile Lys
            100                 105

<210> SEQ ID NO 138
<211> LENGTH: 321
<212> TYPE: DNA
<213> ORGANISM: Artificial
<220> FEATURE:
<223> OTHER INFORMATION: Polynucleotide sequence encoding antibody
      variable region for anti-TcdB antibody 1129.g1

<400> SEQUENCE: 138
gacacccaga tgactcagtc tccgtcaagc ctttctgcct ctgttggaga tcgagtcaca     60
attacgtgca aggcaagcca acacgtgggt accaacgtgg actggtatca acagaagcca    120
gggaaggtcc ccaaactgct gatctacggt gccagtattc gctataccgg cgtgcctgat    180
cgcttcaccg gaagcgggtc agggaccgat ttcacactga caatcagctc cctgcaacct    240
gaagacgtgg ctacttacta ctgcctgcag tacaactata tccctacac ctttggccag    300 ggcaccaaac tggagataaa g                                              321

<210> SEQ ID NO 139
<211> LENGTH: 118
<212> TYPE: PRT
<213> ORGANISM: Artificial
<220> FEATURE:
<223> OTHER INFORMATION: Antibody variable region for anti-TcdB antibody
      1129 (heavy chain)

<400> SEQUENCE: 139

Glu Val Gln Leu Val Glu Ser Gly Gly Val Val Gln Pro Gly Arg
1               5                   10                  15

Ser Leu Arg Leu Ser Cys Ala Thr Ser Gly Phe Ile Phe Ser Asn Phe
            20                  25                  30

Gly Met Ser Trp Val Arg Gln Ala Pro Gly Lys Gly Leu Glu Trp Val
        35                  40                  45

Ala Ser Ile Ser Pro Ser Gly Gly Asn Ala Tyr Tyr Arg Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Thr Arg Arg Ala Tyr Ser Ser Pro Phe Ala Phe Trp Gly Gln Gly Thr
            100                 105                 110

Leu Val Thr Val Ser Ser
            115

<210> SEQ ID NO 140
<211> LENGTH: 354
<212> TYPE: DNA
<213> ORGANISM: Artificial
<220> FEATURE:
<223> OTHER INFORMATION: Polynucleotide sequence encoding antibody
      variable region for anti-TcdB antibody  1129.g1(heavy chain)

<400> SEQUENCE: 140
gaggtgcaac ttgtggaatc aggaggtggc gtggttcagc ccggtagatc acttcgtctg     60
agttgtgcaa caagcggctt tatcttctcc aacttcggga tgtcttgggt tagacaggct    120
cctggtaagg gcctcgaatg ggtggctagt attagcccaa gcggggggaaa cgcctactat   180
agggacagcg tgaaaggacg cttcactatc agccgagata actccaagac cacgctgtat   240
ctgcagatga atagtctgag ggccgaggat accgcagtgt actactgcac tcgacgggcc   300
tattcttccc cttttgcctt ttggggacag gggactctgg tgacagtctc gagc          354

<210> SEQ ID NO 141
<211> LENGTH: 11
<212> TYPE: PRT
<213> ORGANISM: Artificial
<220> FEATURE:
<223> OTHER INFORMATION: Antibody CDR

<400> SEQUENCE: 141

Lys Ala Ser Lys Ser Ile Ser Asn His Leu Ala
1               5                   10

<210> SEQ ID NO 142
<211> LENGTH: 7
<212> TYPE: PRT
<213> ORGANISM: Artificial
<220> FEATURE:
<223> OTHER INFORMATION: Antibody CDR

<400> SEQUENCE: 142

Ser Gly Ser Thr Leu Gln Pro
1               5

<210> SEQ ID NO 143
<211> LENGTH: 9

```
<212> TYPE: PRT
<213> ORGANISM: Artificial
<220> FEATURE:
<223> OTHER INFORMATION: Antibody CDR

<400> SEQUENCE: 143

Gln Gln Tyr Asp Glu Tyr Pro Tyr Thr
1               5

<210> SEQ ID NO 144
<211> LENGTH: 10
<212> TYPE: PRT
<213> ORGANISM: Artificial
<220> FEATURE:
<223> OTHER INFORMATION: Antibody CDR

<400> SEQUENCE: 144

Gly Phe Ser Leu Asn Ser Tyr Thr Ile Thr
1               5                   10

<210> SEQ ID NO 145
<211> LENGTH: 16
<212> TYPE: PRT
<213> ORGANISM: Artificial
<220> FEATURE:
<223> OTHER INFORMATION: Antibody CDR

<400> SEQUENCE: 145

Ala Ile Ser Gly Gly Gly Ser Thr Tyr Phe Asn Ser Ala Leu Lys Ser
1               5                   10                  15

<210> SEQ ID NO 146
<211> LENGTH: 11
<212> TYPE: PRT
<213> ORGANISM: Artificial
<220> FEATURE:
<223> OTHER INFORMATION: Antibody CDR

<400> SEQUENCE: 146

Pro Arg Trp Tyr Pro Arg Ser Tyr Phe Asp Tyr
1               5                   10

<210> SEQ ID NO 147
<211> LENGTH: 107
<212> TYPE: PRT
<213> ORGANISM: Artificial
<220> FEATURE:
<223> OTHER INFORMATION: Antibody variable region for anti-TcdB antibody
      1134

<400> SEQUENCE: 147

Asp Val Gln Leu Thr Gln Ser Pro Ser Phe Leu Ser Ala Ser Val Gly
1               5                   10                  15

Asp Arg Val Thr Ile Thr Cys Lys Ala Ser Lys Ser Ile Ser Asn His
                20                  25                  30

Leu Ala Trp Tyr Gln Glu Lys Pro Gly Lys Ala Asn Lys Leu Leu Ile
            35                  40                  45

His Ser Gly Ser Thr Leu Gln Pro Gly Thr Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asp Glu Tyr Pro Tyr
                85                  90                  95

Thr Phe Gly Gln Gly Thr Arg Leu Glu Ile Lys
            100                 105
```

<210> SEQ ID NO 148
<211> LENGTH: 321
<212> TYPE: DNA
<213> ORGANISM: Artificial
<220> FEATURE:
<223> OTHER INFORMATION: Polynucleotide encoding antibody variable
      region for anti-TcdB antibody 1134.g5

<400> SEQUENCE: 148

```
gacgtccagc tcactcaatc tccctccttt ctgtctgctt ctgtgggcga tcgcgtgaca      60
ataacctgca aggcctccaa atcaattagc aaccatctgg catggtatca ggagaagcct     120
ggcaaagcca ataagctgct gatccactcc ggctcaactc tgcaacccgg taccccaagc     180
cgatttagcg gatctgggag cggaaccgag ttcacactta ccattagctc cctgcaaccg     240
gaggacttcg ccacctatta ctgccagcaa tacgacgaat accccatata cgttcggcca     300
gggacaagat tggaaatcaa g                                               321
```

<210> SEQ ID NO 149
<211> LENGTH: 118
<212> TYPE: PRT
<213> ORGANISM: Artificial
<220> FEATURE:
<223> OTHER INFORMATION: Antibody variable region for anti-TcdB antibody
      1134 (heavy chain)

<400> SEQUENCE: 149

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Asn Ser Tyr
            20                  25                  30

Thr Ile Thr Trp Val Arg Gln Pro Pro Gly Lys Gly Leu Glu Trp Ile
        35                  40                  45

Ala Ala Ile Ser Gly Gly Gly Ser Thr Tyr Phe Asn Ser Ala Leu Lys
    50                  55                  60

Ser Arg Val Thr Ile Ser Arg Asp Thr Ser Lys Ser Gln Val Ser Leu
65                  70                  75                  80

Lys Leu Ser Ser Val Thr Ala Ala Asp Thr Ala Val Tyr Tyr Cys Thr
                85                  90                  95

Arg Pro Arg Trp Tyr Pro Arg Ser Tyr Phe Asp Tyr Trp Gly Arg Gly
            100                 105                 110

Thr Leu Val Thr Val Ser
        115

<210> SEQ ID NO 150
<211> LENGTH: 354
<212> TYPE: DNA
<213> ORGANISM: Artificial
<220> FEATURE:
<223> OTHER INFORMATION: Polynucleotide encoding antibody variable
      region for anti-TcdB antibody 1134.g5 (heavy chain)

<400> SEQUENCE: 150

```
gaagttcagc tgcaggaatc tggacctggc ttggtgaaac caagcgagac acttagtctc      60
acttgcaccg tttccggctt ctcccttaat tcctacacga tcacttgggt gcggcaacca     120
cccgggaaag gactggaatg gatcgcagcc attagcgggg gagggagcac ctatttcaac     180
tcggctctca agagccgcgt gaccatatcc cgtgacacag gcaagagcca ggtttccctg     240
```

```
aagctgagct ccgtgactgc tgccgatacg gctgtttact attgcacccg acctcgctgg    300
tatccccgtt cctatttcga ctactgggga agaggcacac tggttaccgt ctcg          354
```

<210> SEQ ID NO 151
<211> LENGTH: 11
<212> TYPE: PRT
<213> ORGANISM: Artificial
<220> FEATURE:
<223> OTHER INFORMATION: Antibody CDR

<400> SEQUENCE: 151

Lys Ala Ser Gln Asn Val Gly Asn Asn Val Ala
1               5                   10

<210> SEQ ID NO 152
<211> LENGTH: 7
<212> TYPE: PRT
<213> ORGANISM: Artificial
<220> FEATURE:
<223> OTHER INFORMATION: Antibody CDR

<400> SEQUENCE: 152

Tyr Ala Ser Asn Arg Phe Thr
1               5

<210> SEQ ID NO 153
<211> LENGTH: 9
<212> TYPE: PRT
<213> ORGANISM: Artificial
<220> FEATURE:
<223> OTHER INFORMATION: Antibody CDR

<400> SEQUENCE: 153

Gln Arg Val Tyr Gln Ser Thr Trp Thr
1               5

<210> SEQ ID NO 154
<211> LENGTH: 10
<212> TYPE: PRT
<213> ORGANISM: Artificial
<220> FEATURE:
<223> OTHER INFORMATION: Antibody CDR

<400> SEQUENCE: 154

Gly Phe Ser Leu Thr Ser Tyr Tyr Val His
1               5                   10

<210> SEQ ID NO 155
<211> LENGTH: 16
<212> TYPE: PRT
<213> ORGANISM: Artificial
<220> FEATURE:
<223> OTHER INFORMATION: Antibody CDR

<400> SEQUENCE: 155

Cys Ile Arg Thr Gly Gly Asn Thr Glu Tyr Gln Ser Glu Phe Lys Ser
1               5                   10                  15

<210> SEQ ID NO 156
<211> LENGTH: 7
<212> TYPE: PRT
<213> ORGANISM: Artificial
<220> FEATURE:
<223> OTHER INFORMATION: Antibody CDR

<400> SEQUENCE: 156

Gly Asn Tyr Gly Phe Ala Tyr
1               5

<210> SEQ ID NO 157
<211> LENGTH: 107
<212> TYPE: PRT
<213> ORGANISM: Artificial
<220> FEATURE:
<223> OTHER INFORMATION: Antibody variable region for anti-TcdB antibody
      1151

<400> SEQUENCE: 157

Ala Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln His Lys Pro Gly Lys Ala Pro Lys Leu Leu Ile
        35                  40                  45

Tyr Tyr Ala Ser Asn Arg Phe Thr Gly Val Pro Ser Arg Phe Thr Gly
    50                  55                  60

Gly Gly Tyr Gly Thr Asp Phe Thr Leu Thr Ile Ser Ser Leu Gln Pro
65                  70                  75                  80

Glu Asp Phe Ala Thr Tyr Tyr Cys Gln Arg Val Tyr Gln Ser Thr Trp
                85                  90                  95

Thr Phe Gly Gln Gly Thr Lys Val Glu Ile Lys
            100                 105

<210> SEQ ID NO 158
<211> LENGTH: 321
<212> TYPE: DNA
<213> ORGANISM: Artificial
<220> FEATURE:
<223> OTHER INFORMATION: Polynucleotide encoding antibody variable
      region for anti-TcdB antibody 1151.g1

<400> SEQUENCE: 158
gcgattcaaa tgactcagtc gccctcatcg cttagcgcgt ccgtcggaga tagagtgacg      60
atcacgtgca agcatcaca aaatgtcggg aacaatgtgg catggtatca gcataaaccg     120
gggaaggcac caaaactctt gatctactac gccagcaaca ggtttactgg tgtcccgtca     180
aggttcacgg gaggggggtta cgggacagac tttactttga ccatttcgtc gcttcagccg    240
gaggacttcg ccacctatta ctgtcagagg gtctaccagt caacgtggac atttggccag    300
ggaacgaaag tggaaatcaa g                                               321

<210> SEQ ID NO 159
<211> LENGTH: 114
<212> TYPE: PRT
<213> ORGANISM: Artificial
<220> FEATURE:
<223> OTHER INFORMATION: Antibody variable region for anti-TcdB antibody
      1151 (heavy chain)

<400> SEQUENCE: 159

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Tyr Val His Trp Val Arg Gln Pro Pro Gly Lys Gly Leu Glu Trp Met
        35                  40                  45

Gly Cys Ile Arg Thr Gly Gly Asn Thr Glu Tyr Gln Ser Glu Phe Lys

```
                 50                  55                  60
Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                     85                  90                  95

Arg Gly Asn Tyr Gly Phe Ala Tyr Trp Gly Gln Gly Thr Leu Val Thr
                100                 105                 110

Val Ser

<210> SEQ ID NO 160
<211> LENGTH: 342
<212> TYPE: DNA
<213> ORGANISM: Artificial
<220> FEATURE:
<223> OTHER INFORMATION: Polynucleotide sequence encoding antibody
      variable region for anti-TcdB antibody 1151.g4 (he <213> ORGANISM: Artificial
<220> FEATURE:
<223> OTHER INFORMATION: Antibody CDR

<400> SEQUENCE: 164

Gly Phe Thr Phe Thr Gln Ala Ala Met Phe
1               5                   10

<210> SEQ ID NO 165
<211> LENGTH: 19
<212> TYPE: PRT
<213> ORGANISM: Artificial
<220> FEATURE:
<223> OTHER INFORMATION: Antibody CDR

<400> SEQUENCE: 165

Arg Ile Ser Thr Lys Ser Asn Asn Phe Ala Thr Tyr Tyr Pro Asp Ser
1               5                   10                  15

Val Lys Gly

<210> SEQ ID NO 166
<211> LENGTH: 13
<212> TYPE: PRT
<213> ORGANISM: Artificial
<220> FEATURE:
<223> OTHER INFORMATION: Antibody CDR

<400> SEQUENCE: 166

Pro Ala Tyr Tyr Tyr Asp Gly Thr Val Pro Phe Ala Tyr
1               5                   10

<210> SEQ ID NO 167
<211> LENGTH: 106
<212> TYPE: PRT
<213> ORGANISM: Artificial
<220> FEATURE:
<223> OTHER INFORMATION: Antibody variable region for anti-TcdB antibody
      1153.g8

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Tyr
            20                  25                  30

Leu Asp Trp Tyr Gln Gln Lys Pro Gly Lys Val Pro Lys Leu Leu Ile
        35                  40                  45

Tyr Asn Ile Gln Ser Leu His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Phe Gln His Asn Ser Gly Trp Thr
                85                  90                  95

Phe Gly Gln Gly Thr Arg Leu Glu Ile Lys
            100                 105

<210> SEQ ID NO 168
<211> LENGTH: 318
<212> TYPE: DNA
<213> ORGANISM: Artificial
<220> FEATURE:
<223> OTHER INFORMATION: Polynucleotide sequence encoding antibody
      variable region for anti-TcdB antibody 1153.g8

<400> SEQUENCE: 168

```
gatatacaga tgactcagtc cccttctagc ctttcagctt ccgtgggcga tagagtgact      60
atcacgtgta aggctagtca gaacattaac aagtatctgg actggtacca gcagaaaccc     120
gggaaggttc ccaagctgct gatctacaac atccagtccc tgcatacagg cattcctagc     180
cggtttagcg gatctggttc agggaccgac ttcaccctga caatcagctc tctgcaacca     240
gaagacgtgg ccacctatta ctgcttccag cacaatagtg gctggacttt tggacaaggt     300
accaggctgg agatcaaa                                                   318
```

<210> SEQ ID NO 169
<211> LENGTH: 123
<212> TYPE: PRT
<213> ORGANISM: Artificial
<220> FEATURE:
<223> OTHER INFORMATION: Antibody variable region for anti-TcdB antibody
      1153 (graft 8 heavy chain)

<400> SEQUENCE: 169

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Thr Gln Ala
            20                  25                  30

Ala Met Phe Trp Val Arg Gln Ala Ser Gly Lys Gly Leu Glu Gly Ile
        35                  40                  45

Ala Arg Ile Ser Thr Lys Ser Asn Asn Phe Ala Thr Tyr Tyr Pro Asp
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Ala Pro Ala Tyr Tyr Asp Gly Thr Val Pro Phe Ala
            100                 105                 110

Tyr Trp Gly Gln Gly Thr Leu Val Thr Val Ser
        115                 120
```

<210> SEQ ID NO 170
<211> LENGTH: 369
<212> TYPE: DNA
<213> ORGANISM: Artificial
<220> FEATURE:
<223> OTHER INFORMATION: Polynucleotide sequence encoding antibody
      variable region for anti-TcdB antibody 1153.g8 (heavy chain)

<400> SEQUENCE: 170

```
gaggttcagc tggtggaatc aggaggggt ctggtgcaac caggaggctc cctgaaactg       60
tcttgcgccg caagcggctt tacgtttacc caggccgcta tgttctgggt taggcaggcc     120
agtgggaagg gtcttgaagg catcgcaaga atcagcacca gagcaacaa tttcgctacg      180 tactatccgg actccgtgaa aggccggttt accatttctc gcgatgacag caagaacacc     240
gtgtacctgc agatgaacag tctcaagacc gaggacacag ccgtgtacta ttgtactgct     300
cccgcctatt attacgatgg cacagtgcct ttcgcatact ggggacaggg tactttggtg     360
actgtctcg                                                            369
```

<210> SEQ ID NO 171
<211> LENGTH: 2710
<212> TYPE: PRT
<213> ORGANISM: Clostridia

```
<400> SEQUENCE: 171

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415
```

-continued

```
Ile Glu Ser Asp Asn Asn Phe Thr Asp Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
            485                 490                 495

Leu Ile Glu Phe Lys Phe Pro Glu Asn Asn Leu Ser Gln Leu Thr Glu
        500                 505                 510

Gln Glu Ile Asn Ser Leu Trp Ser Phe Asp Gln Ala Ser Ala Lys Tyr
    515                 520                 525

Gln Phe Glu Lys Tyr Val Arg Asp Tyr Thr Gly Gly Ser Leu Ser Glu
530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
            565                 570                 575

Lys Asn Tyr Val His Tyr Ile Ile Gln Leu Gln Gly Asp Asp Ile Ser
        580                 585                 590

Tyr Glu Ala Thr Cys Asn Leu Phe Ser Lys Asn Pro Lys Asn Ser Ile
    595                 600                 605

Ile Ile Gln Arg Asn Met Asn Glu Ser Ala Lys Ser Tyr Phe Leu Ser
        610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
            645                 650                 655

Lys Asp Glu Phe Asn Thr Ser Glu Phe Ala Arg Leu Ser Val Asp Ser
        660                 665                 670

Leu Ser Asn Glu Ile Ser Ser Phe Leu Asp Thr Ile Lys Leu Asp Ile
    675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
            725                 730                 735

Ile Thr Ile Gly Ala Asn Gln Tyr Glu Val Arg Ile Asn Ser Glu Gly
        740                 745                 750

Arg Lys Glu Leu Leu Ala His Ser Gly Lys Trp Ile Asn Lys Glu Glu
    755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
            805                 810                 815

Pro Asp Thr Lys Phe Ile Leu Asn Asn Leu Lys Leu Asn Ile Glu Ser
        820                 825                 830
```

```
Ser Ile Gly Asp Tyr Ile Tyr Glu Lys Leu Glu Pro Val Lys Asn
        835                 840                 845
Ile Ile His Asn Ser Ile Asp Asp Leu Ile Asp Glu Phe Asn Leu Leu
850                 855                 860
Glu Asn Val Ser Asp Glu Leu Tyr Glu Leu Lys Lys Leu Asn Asn Leu
865                 870                 875                 880
Asp Glu Lys Tyr Leu Ile Ser Phe Glu Asp Ile Ser Lys Asn Asn Ser
            885                 890                 895
Thr Tyr Ser Val Arg Phe Ile Asn Lys Ser Asn Gly Glu Ser Val Tyr
                900                 905                 910
Val Glu Thr Glu Lys Glu Ile Phe Ser Lys Tyr Ser Glu His Ile Thr
            915                 920                 925
Lys Glu Ile Ser Thr Ile Lys Asn Ser Ile Ile Thr Asp Val Asn Gly
        930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                965                 970                 975
Lys Asp Val Leu Asn Asp Leu Ser Thr Ser Val Lys Val Gln Leu Tyr
            980                 985                 990
Ala Gln Leu Phe Ser Thr Gly Leu Asn Thr Ile Tyr Asp Ser Ile Gln
            995                 1000                1005
Leu Val Asn Leu Ile Ser Asn Ala Val Asn Asp Thr Ile Asn Val
        1010                1015                1020
Leu Pro Thr Ile Thr Glu Gly Ile Pro Ile Val Ser Thr Ile Leu
        1025                1030                1035
Asp Gly Ile Asn Leu Gly Ala Ala Ile Lys Glu Leu Leu Asp Glu
        1040                1045                1050
His Asp Pro Leu Leu Lys Lys Glu Leu Glu Ala Lys Val Gly Val
        1055                1060                1065
Leu Ala Ile Asn Met Ser Leu Ser Ile Ala Ala Thr Val Ala Ser
        1070                1075                1080
Ile Val Gly Ile Gly Ala Glu Val Thr Ile Phe Leu Leu Pro Ile
        1085                1090                1095
Ala Gly Ile Ser Ala Gly Ile Pro Ser Leu Val Asn Asn Glu Leu
        1100                1105                1110
Ile Leu His Asp Lys Ala Thr Ser Val Val Asn Tyr Phe Asn His
        1115                1120                1125
Leu Ser Glu Ser Lys Lys Tyr Gly Pro Leu Lys Thr Glu Asp Asp
        1130                1135                1140
Lys Ile Leu Val Pro Ile Asp Asp Leu Val Ile Ser Glu Ile Asp
        1145                1150                1155
Phe Asn Asn Asn Ser Ile Lys Leu Gly Thr Cys Asn Ile Leu Ala
        1160                1165                1170
Met Glu Gly Gly Ser Gly His Thr Val Thr Gly Asn Ile Asp His
        1175                1180                1185
Phe Phe Ser Ser Pro Ser Ile Ser Ser His Ile Pro Ser Leu Ser
        1190                1195                1200
Ile Tyr Ser Ala Ile Gly Ile Glu Thr Glu Asn Leu Asp Phe Ser
        1205                1210                1215
Lys Lys Ile Met Met Leu Pro Asn Ala Pro Ser Arg Val Phe Trp
        1220                1225                1230
Trp Glu Thr Gly Ala Val Pro Gly Leu Arg Ser Leu Glu Asn Asp
```

```
            1235                1240                1245
Gly  Thr  Arg  Leu  Leu  Asp  Ser  Ile  Arg  Asp  Leu  Tyr  Pro  Gly  Lys
            1250                1255                1260

Phe  Tyr  Trp  Arg  Phe  Tyr  Ala  Phe  Phe  Asp  Tyr  Ala  Ile  Thr  Thr
            1265                1270                1275

Leu  Lys  Pro  Val  Tyr  Glu  Asp  Thr  Asn  Ile  Lys  Ile  Lys  Leu  Asp
            1280                1285                1290

Lys  Asp  Thr  Arg  Asn  Phe  Ile  Met  Pro  Thr  Ile  Thr  Thr  Asn  Glu
            1295                1300                1305

Ile  Arg  Asn  Lys  Leu  Ser  Tyr  Ser  Phe  Asp  Gly  Ala  Gly  Gly  Thr
            1310                1315                1320

Tyr  Ser  Leu  Leu  Leu  Ser  Ser  Tyr  Pro  Ile  Ser  Thr  Asn  Ile  Asn
            1325                1330                1335

Leu  Ser  Lys  Asp  Asp  Leu  Trp  Ile  Phe  Asn  Ile  Asp  Asn  Glu  Val
            1340                1345                1350

Arg  Glu  Ile  Ser  Ile  Glu  Asn  Gly  Thr  Ile  Lys  Lys  Gly  Lys  Leu
            1355                1360                1365

Ile  Lys  Asp  Val  Leu  Ser  Lys  Ile  Asp  Ile  Asn  Lys  Asn  Lys  Leu
            1370                1375                1380

Ile  Ile  Gly  Asn  Gln  Thr  Ile  Asp  Phe  Ser  Gly  Asp  Ile  Asp  Asn
            1385                1390                1395

Lys  Asp  Arg  Tyr  Ile  Phe  Leu  Thr  Cys  Glu  Leu  Asp  Asp  Lys  Ile
            1400                1405                1410

Ser  Leu  Ile  Ile  Glu  Ile  Asn  Leu  Val  Ala  Lys  Ser  Tyr  Ser  Leu
            1415                1420                1425

Leu  Leu  Ser  Gly  Asp  Lys  Asn  Tyr  Leu  Ile  Ser  Asn  Leu  Ser  Asn
            1430                1435                1440

Thr  Ile  Glu  Lys  Ile  Asn  Thr  Leu  Gly  Leu  Asp  Ser  Lys  Asn  Ile
            1445                1450                1455

Ala  Tyr  Asn  Tyr  Thr  Asp  Glu  Ser  Asn  Asn  Lys  Tyr  Phe  Gly  Ala
            1460                1465                1470

Ile  Ser  Lys  Thr  Ser  Gln  Lys  Ser  Ile  Ile  His  Tyr  Lys  Lys  Asp
            1475                1480                1485

Ser  Lys  Asn  Ile  Leu  Glu  Phe  Tyr  Asn  Asp  Ser  Thr  Leu  Glu  Phe
            1490                1495                1500

Asn  Ser  Lys  Asp  Phe  Ile  Ala  Glu  Asp  Ile  Asn  Val  Phe  Met  Lys
            1505                1510                1515

Asp  Asp  Ile  Asn  Thr  Ile  Thr  Gly  Lys  Tyr  Tyr  Val  Asp  Asn  Asn
            1520                1525                1530

Thr  Asp  Lys  Ser  Ile  Asp  Phe  Ser  Ile  Ser  Leu  Val  Ser  Lys  Asn
            1535                1540                1545

Gln  Val  Lys  Val  Asn  Gly  Leu  Tyr  Leu  Asn  Glu  Ser  Val  Tyr  Ser
            1550                1555                1560

Ser  Tyr  Leu  Asp  Phe  Val  Lys  Asn  Ser  Asp  Gly  His  His  Asn  Thr
            1565                1570                1575

Ser  Asn  Phe  Met  Asn  Leu  Phe  Leu  Asp  Asn  Ile  Ser  Phe  Trp  Lys
            1580                1585                1590

Leu  Phe  Gly  Phe  Glu  Asn  Ile  Asn  Phe  Val  Ile  Asp  Lys  Tyr  Phe
            1595                1600                1605

Thr  Leu  Val  Gly  Lys  Thr  Asn  Leu  Gly  Tyr  Val  Glu  Phe  Ile  Cys
            1610                1615                1620

Asp  Asn  Asn  Lys  Asn  Ile  Asp  Ile  Tyr  Phe  Gly  Glu  Trp  Lys  Thr
            1625                1630                1635
```

```
Ser  Ser  Ser  Lys  Ser  Thr  Ile  Phe  Ser  Gly  Asn  Gly  Arg  Asn  Val
     1640                1645                1650

Val  Val  Glu  Pro  Ile  Tyr  Asn  Pro  Asp  Thr  Gly  Glu  Asp  Ile  Ser
     1655                1660                1665

Thr  Ser  Leu  Asp  Phe  Ser  Tyr  Glu  Pro  Leu  Tyr  Gly  Ile  Asp  Arg
     1670                1675                1680

Tyr  Ile  Asn  Lys  Val  Leu  Ile  Ala  Pro  Asp  Leu  Tyr  Thr  Ser  Leu
     1685                1690                1695

Ile  Asn  Ile  Asn  Thr  Asn  Tyr  Tyr  Ser  Asn  Glu  Tyr  Tyr  Pro  Glu
     1700                1705                1710

Ile  Ile  Val  Leu  Asn  Pro  Asn  Thr  Phe  His  Lys  Lys  Val  Asn  Ile
     1715                1720                1725

Asn  Leu  Asp  Ser  Ser  Ser  Phe  Glu  Tyr  Lys  Trp  Ser  Thr  Glu  Gly
     1730                1735                1740

Ser  Asp  Phe  Ile  Leu  Val  Arg  Tyr  Leu  Glu  Glu  Ser  Asn  Lys  Lys
     1745                1750                1755

Ile  Leu  Gln  Lys  Ile  Arg  Ile  Lys  Gly  Ile  Leu  Ser  Asn  Thr  Gln
     1760                1765                1770

Ser  Phe  Asn  Lys  Met  Ser  Ile  Asp  Phe  Lys  Asp  Ile  Lys  Lys  Leu
     1775                1780                1785

Ser  Leu  Gly  Tyr  Ile  Met  Ser  Asn  Phe  Lys  Ser  Phe  Asn  Ser  Glu
     1790                1795                1800

Asn  Glu  Leu  Asp  Arg  Asp  His  Leu  Gly  Phe  Lys  Ile  Ile  Asp  Asn
     1805                1810                1815

Lys  Thr  Tyr  Tyr  Tyr  Asp  Glu  Asp  Ser  Lys  Leu  Val  Lys  Gly  Leu
     1820                1825                1830

Ile  Asn  Ile  Asn  Asn  Ser  Leu  Phe  Tyr  Phe  Asp  Pro  Ile  Glu  Phe
     1835                1840                1845

Asn  Leu  Val  Thr  Gly  Trp  Gln  Thr  Ile  Asn  Gly  Lys  Lys  Tyr  Tyr
     1850                1855                1860

Phe  Asp  Ile  Asn  Thr  Gly  Ala  Ala  Leu  Thr  Ser  Tyr  Lys  Ile  Ile
     1865                1870                1875

Asn  Gly  Lys  His  Phe  Tyr  Phe  Asn  Asn  Asp  Gly  Val  Met  Gln  Leu
     1880                1885                1890

Gly  Val  Phe  Lys  Gly  Pro  Asp  Gly  Phe  Glu  Tyr  Phe  Ala  Pro  Ala
     1895                1900                1905

Asn  Thr  Gln  Asn  Asn  Asn  Ile  Glu  Gly  Gln  Ala  Ile  Val  Tyr  Gln
     1910                1915                1920

Ser  Lys  Phe  Leu  Thr  Leu  Asn  Gly  Lys  Lys  Tyr  Tyr  Phe  Asp  Asn
     1925                1930                1935

Asn  Ser  Lys  Ala  Val  Thr  Gly  Trp  Arg  Ile  Ile  Asn  Asn  Glu  Lys
     1940                1945                1950

Tyr  Tyr  Phe  Asn  Pro  Asn  Asn  Ala  Ile  Ala  Ala  Val  Gly  Leu  Gln
     1955                1960                1965

Val  Ile  Asp  Asn  Asn  Lys  Tyr  Tyr  Phe  Asn  Pro  Asp  Thr  Ala  Ile
     1970                1975                1980

Ile  Ser  Lys  Gly  Trp  Gln  Thr  Val  Asn  Gly  Ser  Arg  Tyr  Tyr  Phe
     1985                1990                1995

Asp  Thr  Asp  Thr  Ala  Ile  Ala  Phe  Asn  Gly  Tyr  Lys  Thr  Ile  Asp
     2000                2005                2010

Gly  Lys  His  Phe  Tyr  Phe  Asp  Ser  Asp  Cys  Val  Val  Lys  Ile  Gly
     2015                2020                2025
```

```
Val Phe Ser Thr Ser Asn Gly Phe Glu Tyr Phe Ala Pro Ala Asn
    2030            2035            2040

Thr Tyr Asn Asn Asn Ile Glu Gly Gln Ala Ile Val Tyr Gln Ser
    2045            2050            2055

Lys Phe Leu Thr Leu Asn Gly Lys Lys Tyr Tyr Phe Asp Asn Asn
    2060            2065            2070

Ser Lys Ala Val Thr Gly Leu Gln Thr Ile Asp Ser Lys Lys Tyr
    2075            2080            2085

Tyr Phe Asn Thr Asn Thr Ala Glu Ala Ala Thr Gly Trp Gln Thr
    2090            2095            2100

Ile Asp Gly Lys Lys Tyr Tyr Phe Asn Thr Asn Thr Ala Glu Ala
    2105            2110            2115

Ala Thr Gly Trp Gln Thr Ile Asp Gly Lys Lys Tyr Tyr Phe Asn
    2120            2125            2130

Thr Asn Thr Ala Ile Ala Ser Thr Gly Tyr Thr Ile Ile Asn Gly
    2135            2140            2145

Lys His Phe Tyr Phe Asn Thr Asp Gly Ile Met Gln Ile Gly Val
    2150            2155            2160

Phe Lys Gly Pro Asn Gly Phe Glu Tyr Phe Ala Pro Ala Asn Thr
    2165            2170            2175

Asp Ala Asn Asn Ile Glu Gly Gln Ala Ile Leu Tyr Gln Asn Glu
    2180            2185            2190

Phe Leu Thr Leu Asn Gly Lys Lys Tyr Tyr Phe Gly Ser Asp Ser
    2195            2200            2205

Lys Ala Val Thr Gly Trp Arg Ile Ile Asn Asn Lys Lys Tyr Tyr
    2210            2215            2220

Phe Asn Pro Asn Asn Ala Ile Ala Ala Ile His Leu Cys Thr Ile
    2225            2230            2235

Asn Asn Asp Lys Tyr Tyr Phe Ser Tyr Asp Gly Ile Leu Gln Asn
    2240            2245            2250

Gly Tyr Ile Thr Ile Glu Arg Asn Asn Phe Tyr Phe Asp Ala Asn
    2255            2260            2265

Asn Glu Ser Lys Met Val Thr Gly Val Phe Lys Gly Pro Asn Gly
    2270            2275            2280

Phe Glu Tyr Phe Ala Pro Ala Asn Thr His Asn Asn Asn Ile Glu
    2285            2290            2295

Gly Gln Ala Ile Val Tyr Gln Asn Lys Phe Leu Thr Leu Asn Gly
    2300            2305            2310

Lys Lys Tyr Tyr Phe Asp Asn Asp Ser Lys Ala Val Thr Gly Trp
    2315            2320            2325

Gln Thr Ile Asp Gly Lys Lys Tyr Tyr Phe Asn Leu Asn Thr Ala
    2330            2335            2340

Glu Ala Ala Thr Gly Trp Gln Thr Ile Asp Gly Lys Lys Tyr Tyr
    2345            2350            2355

Phe Asn Leu Asn Thr Ala Glu Ala Ala Thr Gly Trp Gln Thr Ile
    2360            2365            2370

Asp Gly Lys Lys Tyr Tyr Phe Asn Thr Asn Thr Phe Ile Ala Ser
    2375            2380            2385

Thr Gly Tyr Thr Ser Ile Asn Gly Lys His Phe Tyr Phe Asn Thr
    2390            2395            2400

Asp Gly Ile Met Gln Ile Gly Val Phe Lys Gly Pro Asn Gly Phe
    2405            2410            2415

Glu Tyr Phe Ala Pro Ala Asn Thr Asp Ala Asn Asn Ile Glu Gly
```

```
                2420                2425                2430

Gln Ala Ile Leu Tyr Gln Asn Lys Phe Leu Thr Leu Asn Gly Lys
            2435                2440                2445

Lys Tyr Tyr Phe Gly Ser Asp Ser Lys Ala Val Thr Gly Leu Arg
            2450                2455                2460

Thr Ile Asp Gly Lys Lys Tyr Tyr Phe Asn Thr Asn Thr Ala Val
            2465                2470                2475

Ala Val Thr Gly Trp Gln Thr Ile Asn Gly Lys Lys Tyr Tyr Phe
            2480                2485                2490

Asn Thr Asn Thr Ser Ile Ala Ser Thr Gly Tyr Thr Ile Ile Ser
            2495                2500                2505

Gly Lys His Phe Tyr Phe Asn Thr Asp Gly Ile Met Gln Ile Gly
            2510                2515                2520

Val Phe Lys Gly Pro Asp Gly Phe Glu Tyr Phe Ala Pro Ala Asn
            2525                2530                2535

Thr Asp Ala Asn Asn Ile Glu Gly Gln Ala Ile Arg Tyr Gln Asn
            2540                2545                2550

Arg Phe Leu Tyr Leu His Asp Asn Ile Tyr Tyr Phe Gly Asn Asn
            2555                2560                2565

Ser Lys Ala Ala Thr Gly Trp Val Thr Ile Asp Gly Asn Arg Tyr
            2570                2575                2580

Tyr Phe Glu Pro Asn Thr Ala Met Gly Ala Asn Gly Tyr Lys Thr
            2585                2590                2595

Ile Asp Asn Lys Asn Phe Tyr Phe Arg Asn Gly Leu Pro Gln Ile
            2600                2605                2610

Gly Val Phe Lys Gly Ser Asn Gly Phe Glu Tyr Phe Ala Pro Ala
            2615                2620                2625

Asn Thr Asp Ala Asn Asn Ile Glu Gly Gln Ala Ile Arg Tyr Gln
            2630                2635                2640

Asn Arg Phe Leu His Leu Leu Gly Lys Ile Tyr Tyr Phe Gly Asn
            2645                2650                2655

Asn Ser Lys Ala Val Thr Gly Trp Gln Thr Ile Asn Gly Lys Val
            2660                2665                2670

Tyr Tyr Phe Met Pro Asp Thr Ala Met Ala Ala Ala Gly Gly Leu
            2675                2680                2685

Phe Glu Ile Asp Gly Val Ile Tyr Phe Phe Gly Val Asp Gly Val
            2690                2695                2700

Lys Ala Pro Gly Ile Tyr Gly
            2705                2710

<210> SEQ ID NO 172
<211> LENGTH: 2366
<212> TYPE: PRT
<213> ORGANISM: Clostridia

<400> SEQUENCE: 172

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60
```

-continued

```
Lys Ser Gly Arg Asn Lys Ala Leu Lys Lys Phe Lys Glu Tyr Leu Val
 65                  70                  75                  80

Thr Glu Val Leu Glu Leu Lys Asn Asn Asn Leu Thr Pro Val Glu Lys
                 85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
145         130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
```

```
                      485             490             495
Asp Leu Arg Asn Phe Glu Ile Ser Lys Thr Asn Ile Ser Gln Ser Thr
                500             505             510

Glu Gln Glu Met Ala Ser Leu Trp Ser Phe Asp Asp Ala Arg Ala Lys
            515                 520             525

Ala Gln Phe Glu Glu Tyr Lys Arg Asn Tyr Phe Glu Gly Ser Leu Gly
        530             535                 540

Glu Asp Asn Leu Asp Phe Ser Gln Asn Ile Val Val Asp Lys Glu
545             550             555                 560

Tyr Leu Leu Glu Lys Ile Ser Ser Leu Ala Arg Ser Ser Glu Arg Gly
                565             570             575

Tyr Ile His Tyr Ile Val Gln Leu Gln Gly Asp Lys Ile Ser Tyr Glu
                580             585             590

Ala Ala Cys Asn Leu Phe Ala Lys Thr Pro Tyr Asp Ser Val Leu Phe
            595                 600             605

Gln Lys Asn Ile Glu Asp Ser Glu Ile Ala Tyr Tyr Tyr Asn Pro Gly
        610             615                 620

Asp Gly Glu Ile Gln Glu Ile Asp Lys Tyr Lys Ile Pro Ser Ile Ile
625             630             635                 640

Ser Asp Arg Pro Lys Ile Lys Leu Thr Phe Ile Gly His Gly Lys Asp
                645             650             655

Glu Phe Asn Thr Asp Ile Phe Ala Gly Phe Asp Val Asp Ser Leu Ser
            660                 665             670

Thr Glu Ile Glu Ala Ala Ile Asp Leu Ala Lys Glu Asp Ile Ser Pro
        675             680             685

Lys Ser Ile Glu Ile Asn Leu Leu Gly Cys Asn Met Phe Ser Tyr Ser
690             695             700

Ile Asn Val Glu Glu Thr Tyr Pro Gly Lys Leu Leu Lys Val Lys
705             710             715             720

Asp Lys Ile Ser Glu Leu Met Pro Ser Ile Ser Gln Asp Ser Ile Ile
            725             730             735

Val Ser Ala Asn Gln Tyr Glu Val Arg Ile Asn Ser Glu Gly Arg Arg
        740             745             750

Glu Leu Leu Asp His Ser Gly Glu Trp Ile Asn Lys Glu Glu Ser Ile
            755             760             765

Ile Lys Asp Ile Ser Ser Lys Glu Tyr Ile Ser Phe Asn Pro Lys Glu
        770             775             780

Asn Lys Ile Thr Val Lys Ser Lys Asn Leu Pro Glu Leu Ser Thr Leu
785             790             795             800

Leu Gln Glu Ile Arg Asn Asn Ser Asn Ser Ser Asp Ile Glu Leu Glu
            805             810             815

Glu Lys Val Met Leu Thr Glu Cys Glu Ile Asn Val Ile Ser Asn Ile
            820             825             830

Asp Thr Gln Ile Val Glu Glu Arg Ile Glu Glu Ala Lys Asn Leu Thr
            835             840             845

Ser Asp Ser Ile Asn Tyr Ile Lys Asp Glu Phe Lys Leu Ile Glu Ser
850             855             860

Ile Ser Asp Ala Leu Cys Asp Leu Lys Gln Gln Asn Glu Leu Glu Asp
865             870             875             880

Ser His Phe Ile Ser Phe Glu Asp Ile Ser Glu Thr Asp Glu Gly Phe
            885             890             895

Ser Ile Arg Phe Ile Asn Lys Glu Thr Gly Glu Ser Ile Phe Val Glu
                900             905             910
```

```
Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr Ile Thr Asp Ala Ala Lys Val Val
            995                1000               1005

Glu Leu Val Ser Thr Ala Leu Asp Glu Thr Ile Asp Leu Leu Pro
    1010               1015               1020

Thr Leu Ser Glu Gly Leu Pro Ile Ile Ala Thr Ile Ile Asp Gly
    1025               1030               1035

Val Ser Leu Gly Ala Ala Ile Lys Glu Leu Ser Glu Thr Ser Asp
    1040               1045               1050

Pro Leu Leu Arg Gln Glu Ile Glu Ala Lys Ile Gly Ile Met Ala
    1055               1060               1065

Val Asn Leu Thr Thr Ala Thr Ala Ile Ile Thr Ser Ser Leu
    1070               1075               1080

Gly Ile Ala Ser Gly Phe Ser Ile Leu Leu Val Pro Leu Ala Gly
    1085               1090               1095

Ile Ser Ala Gly Ile Pro Ser Leu Val Asn Asn Glu Leu Val Leu
    1100               1105               1110

Arg Asp Lys Ala Thr Lys Val Val Asp Tyr Phe Lys His Val Ser
    1115               1120               1125

Leu Val Glu Thr Glu Gly Val Phe Thr Leu Leu Asp Asp Lys Ile
    1130               1135               1140

Met Met Pro Gln Asp Asp Leu Val Ile Ser Glu Ile Asp Phe Asn
    1145               1150               1155

Asn Asn Ser Ile Val Leu Gly Lys Cys Glu Ile Trp Arg Met Glu
    1160               1165               1170

Gly Gly Ser Gly His Thr Val Thr Asp Asp Ile Asp His Phe Phe
    1175               1180               1185

Ser Ala Pro Ser Ile Thr Tyr Arg Glu Pro His Leu Ser Ile Tyr
    1190               1195               1200

Asp Val Leu Glu Val Gln Lys Glu Glu Leu Asp Leu Ser Lys Asp
    1205               1210               1215

Leu Met Val Leu Pro Asn Ala Pro Asn Arg Val Phe Ala Trp Glu
    1220               1225               1230

Thr Gly Trp Thr Pro Gly Leu Arg Ser Leu Glu Asn Asp Gly Thr
    1235               1240               1245

Lys Leu Leu Asp Arg Ile Arg Asp Asn Tyr Glu Gly Glu Phe Tyr
    1250               1255               1260

Trp Arg Tyr Phe Ala Phe Ile Ala Asp Ala Leu Ile Thr Thr Leu
    1265               1270               1275

Lys Pro Arg Tyr Glu Asp Thr Asn Ile Arg Ile Asn Leu Asp Ser
    1280               1285               1290

Asn Thr Arg Ser Phe Ile Val Pro Ile Ile Thr Thr Glu Tyr Ile
    1295               1300               1305
```

-continued

Arg Glu Lys Leu Ser Tyr Ser Phe Tyr Gly Ser Gly Gly Thr Tyr
1310              1315              1320

Ala Leu Ser Leu Ser Gln Tyr Asn Met Gly Ile Asn Ile Glu Leu
1325              1330              1335

Ser Glu Ser Asp Val Trp Ile Ile Asp Val Asp Asn Val Val Arg
1340              1345              1350

Asp Val Thr Ile Glu Ser Asp Lys Ile Lys Lys Gly Asp Leu Ile
1355              1360              1365

Glu Gly Ile Leu Ser Thr Leu Ser Ile Glu Glu Asn Lys Ile Ile
1370              1375              1380

Leu Asn Ser His Glu Ile Asn Phe Ser Gly Glu Val Asn Gly Ser
1385              1390              1395

Asn Gly Phe Val Ser Leu Thr Phe Ser Ile Leu Glu Gly Ile Asn
1400              1405              1410

Ala Ile Ile Glu Val Asp Leu Leu Ser Lys Ser Tyr Lys Leu Leu
1415              1420              1425

Ile Ser Gly Glu Leu Lys Ile Leu Met Leu Asn Ser Asn His Ile
1430              1435              1440

Gln Gln Lys Ile Asp Tyr Ile Gly Phe Asn Ser Glu Leu Gln Lys
1445              1450              1455

Asn Ile Pro Tyr Ser Phe Val Asp Ser Glu Gly Lys Glu Asn Gly
1460              1465              1470

Phe Ile Asn Gly Ser Thr Lys Glu Gly Leu Phe Val Ser Glu Leu
1475              1480              1485

Pro Asp Val Val Leu Ile Ser Lys Val Tyr Met Asp Asp Ser Lys
1490              1495              1500

Pro Ser Phe Gly Tyr Tyr Ser Asn Asn Leu Lys Asp Val Lys Val
1505              1510              1515

Ile Thr Lys Asp Asn Val Asn Ile Leu Thr Gly Tyr Tyr Leu Lys
1520              1525              1530

Asp Asp Ile Lys Ile Ser Leu Ser Leu Thr Leu Gln Asp Glu Lys
1535              1540              1545

Thr Ile Lys Leu Asn Ser Val His Leu Asp Glu Ser Gly Val Ala
1550              1555              1560

Glu Ile Leu Lys Phe Met Asn Arg Lys Gly Asn Thr Asn Thr Ser
1565              1570              1575

Asp Ser Leu Met Ser Phe Leu Glu Ser Met Asn Ile Lys Ser Ile
1580              1585              1590

Phe Val Asn Phe Leu Gln Ser Asn Ile Lys Phe Ile Leu Asp Ala
1595              1600              1605

Asn Phe Ile Ile Ser Gly Thr Thr Ser Ile Gly Gln Phe Glu Phe
1610              1615              1620

Ile Cys Asp Glu Asn Asp Asn Ile Gln Pro Tyr Phe Ile Lys Phe
1625              1630              1635

Asn Thr Leu Glu Thr Asn Tyr Thr Leu Tyr Val Gly Asn Arg Gln
1640              1645              1650

Asn Met Ile Val Glu Pro Asn Tyr Asp Leu Asp Asp Ser Gly Asp
1655              1660              1665

Ile Ser Ser Thr Val Ile Asn Phe Ser Gln Lys Tyr Leu Tyr Gly
1670              1675              1680

Ile Asp Ser Cys Val Asn Lys Val Val Ile Ser Pro Asn Ile Tyr
1685              1690              1695

Thr Asp Glu Ile Asn Ile Thr Pro Val Tyr Glu Thr Asn Asn Thr

-continued

```
            1700                1705                1710
Tyr Pro Glu Val Ile Val Leu Asp Ala Asn Tyr Ile Asn Glu Lys
        1715                1720                1725
Ile Asn Val Asn Ile Asn Asp Leu Ser Ile Arg Tyr Val Trp Ser
        1730                1735                1740
Asn Asp Gly Asn Asp Phe Ile Leu Met Ser Thr Ser Glu Glu Asn
        1745                1750                1755
Lys Val Ser Gln Val Lys Ile Arg Phe Val Asn Val Phe Lys Asp
        1760                1765                1770
Lys Thr Leu Ala Asn Lys Leu Ser Phe Asn Phe Ser Asp Lys Gln
        1775                1780                1785
Asp Val Pro Val Ser Glu Ile Ile Leu Ser Phe Thr Pro Ser Tyr
        1790                1795                1800
Tyr Glu Asp Gly Leu Ile Gly Tyr Asp Leu Gly Leu Val Ser Leu
        1805                1810                1815
Tyr Asn Glu Lys Phe Tyr Ile Asn Asn Phe Gly Met Met Val Ser
        1820                1825                1830
Gly Leu Ile Tyr Ile Asn Asp Ser Leu Tyr Tyr Phe Lys Pro Pro
        1835                1840                1845
Val Asn Asn Leu Ile Thr Gly Phe Val Thr Val Gly Asp Asp Lys
        1850                1855                1860
Tyr Tyr Phe Asn Pro Ile Asn Gly Gly Ala Ala Ser Ile Gly Glu
        1865                1870                1875
Thr Ile Ile Asp Asp Lys Asn Tyr Tyr Phe Asn Gln Ser Gly Val
        1880                1885                1890
Leu Gln Thr Gly Val Phe Ser Thr Glu Asp Gly Phe Lys Tyr Phe
        1895                1900                1905
Ala Pro Ala Asn Thr Leu Asp Glu Asn Leu Glu Gly Glu Ala Ile
        1910                1915                1920
Asp Phe Thr Gly Lys Leu Ile Ile Asp Glu Asn Ile Tyr Tyr Phe
        1925                1930                1935
Asp Asp Asn Tyr Arg Gly Ala Val Glu Trp Lys Glu Leu Asp Gly
        1940                1945                1950
Glu Met His Tyr Phe Ser Pro Glu Thr Gly Lys Ala Phe Lys Gly
        1955                1960                1965
Leu Asn Gln Ile Gly Asp Tyr Lys Tyr Tyr Phe Asn Ser Asp Gly
        1970                1975                1980
Val Met Gln Lys Gly Phe Val Ser Ile Asn Asp Asn Lys His Tyr
        1985                1990                1995
Phe Asp Asp Ser Gly Val Met Lys Val Gly Tyr Thr Glu Ile Asp
        2000                2005                2010
Gly Lys His Phe Tyr Phe Ala Glu Asn Gly Glu Met Gln Ile Gly
        2015                2020                2025
Val Phe Asn Thr Glu Asp Gly Phe Lys Tyr Phe Ala His His Asn
        2030                2035                2040
Glu Asp Leu Gly Asn Glu Glu Gly Glu Glu Ile Ser Tyr Ser Gly
        2045                2050                2055
Ile Leu Asn Phe Asn Asn Lys Ile Tyr Tyr Phe Asp Asp Ser Phe
        2060                2065                2070
Thr Ala Val Val Gly Trp Lys Asp Leu Glu Asp Gly Ser Lys Tyr
        2075                2080                2085
Tyr Phe Asp Glu Asp Thr Ala Glu Ala Tyr Ile Gly Leu Ser Leu
        2090                2095                2100
```

```
Ile Asn Asp Gly Gln Tyr Tyr Phe Asn Asp Asp Gly Ile Met Gln
    2105                2110                2115

Val Gly Phe Val Thr Ile Asn Asp Lys Val Phe Tyr Phe Ser Asp
    2120                2125                2130

Ser Gly Ile Ile Glu Ser Gly Val Gln Asn Ile Asp Asp Asn Tyr
    2135                2140                2145

Phe Tyr Ile Asp Asp Asn Gly Ile Val Gln Ile Gly Val Phe Asp
    2150                2155                2160

Thr Ser Asp Gly Tyr Lys Tyr Phe Ala Pro Ala Asn Thr Val Asn
    2165                2170                2175

Asp Asn Ile Tyr Gly Gln Ala Val Glu Tyr Ser Gly Leu Val Arg
    2180                2185                2190

Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asn Pro Glu Thr Lys Lys Ala Cys Lys Gly Ile Asn Leu Ile
    2225                2230                2235

Asp Asp Ile Lys Tyr Tyr Phe Asp Glu Lys Gly Ile Met Arg Thr
    2240                2245                2250

Gly Leu Ile Ser Phe Glu Asn Asn Asn Tyr Tyr Phe Asn Glu Asn
    2255                2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 173
<211> LENGTH: 18
<212> TYPE: PRT
<213> ORGANISM: Artificial
<220> FEATURE:
<223> OTHER INFORMATION: Fragment from C. difficile toxin TcdB

<400> SEQUENCE: 173

Ser Pro Val Glu Lys Asn Leu His Phe Val Trp Ile Gly Gly Glu Val
1               5                   10                  15

Ser Asp

<210> SEQ ID NO 174
<211> LENGTH: 11
<212> TYPE: PRT
<213> ORGANISM: Artificial
<220> FEATURE:
<223> OTHER INFORMATION: Fragment from C. difficile toxin TcdB

<400> SEQUENCE: 174
```

```
Asn Leu Ala Ala Ala Ser Asp Ile Val Arg Leu
1               5                   10

<210> SEQ ID NO 175
<211> LENGTH: 15
<212> TYPE: PRT
<213> ORGANISM: Artificial
<220> FEATURE:
<223> OTHER INFORMATION: Fragment of C. difficile toxin TcdB

<400> SEQUENCE: 175

Cys Gly Gly Val Tyr Leu Asp Val Asp Met Leu Pro Gly Ile His
1               5                   10                  15

<210> SEQ ID NO 176
<211> LENGTH: 20
<212> TYPE: PRT
<213> ORGANISM: Artificial
<220> FEATURE:
<223> OTHER INFORMATION: Fragment from C. difficile toxin TcdB

<400> SEQUENCE: 176

Cys Gly Gly Val Tyr Leu Asp Val Asp Met Leu Pro Gly Ile His Ser
1               5                   10                  15

Asp Leu Phe Lys
            20

<210> SEQ ID NO 177
<211> LENGTH: 14
<212> TYPE: PRT
<213> ORGANISM: Artificial
<220> FEATURE:
<223> OTHER INFORMATION: Fragment of C. difficile toxin TcdB

<400> SEQUENCE: 177

Cys Trp Glu Met Ile Lys Leu Glu Ala Ile Met Lys Tyr Lys
1               5                   10

<210> SEQ ID NO 178
<211> LENGTH: 12
<212> TYPE: PRT
<213> ORGANISM: Artificial
<220> FEATURE:
<223> OTHER INFORMATION: Fragment of C. difficile toxin TcdB

<400> SEQUENCE: 178

Cys Thr Asn Leu Val Ile Glu Gln Val Lys Asn Arg
1               5                   10

<210> SEQ ID NO 179
<211> LENGTH: 12
<212> TYPE: PRT
<213> ORGANISM: Artificial
<220> FEATURE:
<223> OTHER INFORMATION: Fragment of C. difficile toxin TcdB

<400> SEQUENCE: 179

Pro Glu Ala Arg Ser Thr Ile Ser Leu Ser Gly Pro
1               5                   10

<210> SEQ ID NO 180
<211> LENGTH: 12
<212> TYPE: PRT
<213> ORGANISM: Artificial
<220> FEATURE:
<223> OTHER INFORMATION: Fragment of C. difficile toxin TcdB
```

```
<400> SEQUENCE: 180

Cys Ser Asn Leu Ile Val Lys Gln Ile Glu Asn Arg
1               5                   10

<210> SEQ ID NO 181
<211> LENGTH: 14
<212> TYPE: PRT
<213> ORGANISM: Artificial
<220> FEATURE:
<223> OTHER INFORMATION: Fragment of C. difficile toxin TcdB

<400> SEQUENCE: 181

Thr Glu Gln Glu Ile Asn Ser Leu Trp Ser Phe Asp Gln Ala
1               5                   10

<210> SEQ ID NO 182
<211> LENGTH: 25
<212> TYPE: PRT
<213> ORGANISM: Artificial
<220> FEATURE:
<223> OTHER INFORMATION: Fragment of C. difficile toxin TcdB

<400> SEQUENCE: 182

Thr Glu Gln Glu Ile Asn Ser Leu Trp Ser Phe Asp Pro Glu Ala Arg
1               5                   10                  15

Ser Thr Ile Ser Leu Ser Gly Pro Cys
            20                  25

<210> SEQ ID NO 183
<211> LENGTH: 13
<212> TYPE: PRT
<213> ORGANISM: Artificial
<220> FEATURE:
<223> OTHER INFORMATION: Fragment of C. difficile toxin TcdB

<400> SEQUENCE: 183

Asn Val Glu Glu Thr Tyr Pro Gly Lys Leu Leu Leu Cys
1               5                   10

<210> SEQ ID NO 184
<211> LENGTH: 14
<212> TYPE: PRT
<213> ORGANISM: Artificial
<220> FEATURE:
<223> OTHER INFORMATION: Fragment of C. difficile toxin TcdB

<400> SEQUENCE: 184

Cys Ala Asn Gln Tyr Glu Val Arg Ile Asn Ser Glu Gly Arg
1               5                   10

<210> SEQ ID NO 185
<211> LENGTH: 15
<212> TYPE: PRT
<213> ORGANISM: Artificial
<220> FEATURE:
<223> OTHER INFORMATION: Fragment of C. difficile toxin TcdB

<400> SEQUENCE: 185

Val Asn Thr Leu Asn Ala Ala Phe Phe Ile Gln Ser Leu Ile Cys
1               5                   10                  15

<210> SEQ ID NO 186
<211> LENGTH: 13
<212> TYPE: PRT
<213> ORGANISM: Artificial
```

```
<220> FEATURE:
<223> OTHER INFORMATION: Fragment of C. difficile toxin TcdB

<400> SEQUENCE: 186

Tyr Ala Gln Leu Phe Ser Thr Gly Leu Asn Thr Ile Cys
1               5                   10

<210> SEQ ID NO 187
<211> LENGTH: 16
<212> TYPE: PRT
<213> ORGANISM: Artificial
<220> FEATURE:
<223> OTHER INFORMATION: Fragment of C. difficile toxin TcdB

<400> SEQUENCE: 187

Cys Ala Gly Ile Ser Ala Gly Ile Pro Ser Leu Val Asn Asn Glu Leu
1               5                   10                  15

<210> SEQ ID NO 188
<211> LENGTH: 16
<212> TYPE: PRT
<213> ORGANISM: Artificial
<220> FEATURE:
<223> OTHER INFORMATION: Fragment of C. difficile toxin TcdB

<400> SEQUENCE: 188

Asp Asp Leu Val Ile Ser Glu Ile Asp Phe Asn Asn Asn Ser Ile Cys
1               5                   10                  15

<210> SEQ ID NO 189
<211> LENGTH: 10
<212> TYPE: PRT
<213> ORGANISM: Artificial
<220> FEATURE:
<223> OTHER INFORMATION: Fragment of C. difficile toxin TcdB

<400> SEQUENCE: 189

Met Glu Gly Gly Ser Gly His Thr Val Thr
1               5                   10

<210> SEQ ID NO 190
<211> LENGTH: 35
<212> TYPE: PRT
<213> ORGANISM: Artificial
<220> FEATURE:
<223> OTHER INFORMATION: Fragment of C. difficile toxin TcdB

<400> SEQUENCE: 190

Ala Val Asn Asp Thr Ile Asn Val Leu Pro Thr Ile Thr Glu Gly Ile
1               5                   10                  15

Pro Ile Val Ser Thr Ile Leu Asp Gly Ile Asn Leu Gly Ala Ala Ile
                20                  25                  30

Lys Glu Leu
        35

<210> SEQ ID NO 191
<211> LENGTH: 20
<212> TYPE: PRT
<213> ORGANISM: Artificial
<220> FEATURE:
<223> OTHER INFORMATION: Fragment of C. difficile toxin TcdB

<400> SEQUENCE: 191

Cys Gly Phe Glu Tyr Phe Ala Pro Ala Asn Thr Asp Ala Asn Asn Ile
1               5                   10                  15
```

```
<210> SEQ ID NO 192
<211> LENGTH: 20
<212> TYPE: PRT
<213> ORGANISM: Artificial
<220> FEATURE:
<223> OTHER INFORMATION: Fragment of C. difficile toxin TcdB

<400> SEQUENCE: 192

Cys Gly Tyr Lys Tyr Phe Ala Pro Ala Asn Thr Val Asn Asp Asn Ile
1               5                   10                  15

Tyr Gly Gln Ala
            20

<210> SEQ ID NO 193
<211> LENGTH: 12
<212> TYPE: PRT
<213> ORGANISM: Artificial
<220> FEATURE:
<223> OTHER INFORMATION: Fragment of C. difficile toxin TcdB

<400> SEQUENCE: 193

Cys Lys Tyr Tyr Phe Asn Thr Asn Thr Ala Glu Ala
1               5                   10

<210> SEQ ID NO 194
<211> LENGTH: 12
<212> TYPE: PRT
<213> ORGANISM: Artificial
<220> FEATURE:
<223> OTHER INFORMATION: Fragment of C. difficile toxin TcdB

<400> SEQUENCE: 194

Cys Lys Tyr Tyr Phe Asp Glu Asp Thr Ala Glu Ala
1               5                   10
```

UNITED STATES PATENT AND TRADEMARK OFFICE
CERTIFICATE OF CORRECTION

| | | |
|---|---|---|
| PATENT NO. | : 10,752,676 B2 | Page 1 of 1 |
| APPLICATION NO. | : 14/344637 | |
| DATED | : August 25, 2020 | |
| INVENTOR(S) | : Humphreys et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 797 days.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*